(12) United States Patent
Karchi et al.

(10) Patent No.: US 7,910,800 B2
(45) Date of Patent: Mar. 22, 2011

(54) METHODS OF INCREASING ABIOTIC STRESS TOLERANCE AND/OR BIOMASS IN PLANTS AND PLANTS GENERATED THEREBY

(75) Inventors: Hagai Karchi, Doar-Na Emek Soreq (IL); Gil Ronen, Emek Hefer (IL); Rodrigo Yelin, Zur-Yigal (IL); Larisa Rabinovich, Rishon-LeZion (IL)

(73) Assignee: Evogene Ltd., Rechovot (IL)

( * ) Notice: Subject to any disclaimer, the term of this patent is extended or adjusted under 35 U.S.C. 154(b) by 0 days.

(21) Appl. No.: 11/990,386

(22) PCT Filed: Aug. 15, 2006

(86) PCT No.: PCT/IL2006/000947
§ 371 (c)(1),
(2), (4) Date: Feb. 13, 2008

(87) PCT Pub. No.: WO2007/020638
PCT Pub. Date: Feb. 22, 2007

(65) Prior Publication Data
US 2009/0089898 A1 Apr. 2, 2009

Related U.S. Application Data

(60) Provisional application No. 60/707,957, filed on Aug. 15, 2005.

(51) Int. Cl.
*C12N 15/82* (2006.01)
*C12N 5/04* (2006.01)
*C12N 15/00* (2006.01)
*A01H 5/00* (2006.01)
*C07H 21/04* (2006.01)

(52) U.S. Cl. ..... 800/278; 800/289; 800/298; 435/320.1; 435/419; 536/23.6

(58) Field of Classification Search .......... None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 4,945,050 A | 7/1990 | Sanford et al. |
| 5,011,771 A | 4/1991 | Bellet et al. |
| 5,187,267 A | 2/1993 | Comai et al. |
| 5,192,659 A | 3/1993 | Simons |
| 5,268,463 A | 12/1993 | Jefferson |
| 5,272,057 A | 12/1993 | Smulson et al. |
| 5,281,521 A | 1/1994 | Trojanowski et al. |
| 5,296,462 A | 3/1994 | Thomashow |
| 5,316,931 A | 5/1994 | Donson et al. |
| 5,356,816 A | 10/1994 | Thomashow |
| 5,399,680 A | 3/1995 | Zhu et al. |
| 5,464,765 A | 11/1995 | Coffee et al. |
| 5,466,785 A | 11/1995 | De Framond |
| 5,495,070 A | 2/1996 | John |
| 5,569,597 A | 10/1996 | Grimsley et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,693,507 A | 12/1997 | Daniell et al. |
| 6,313,375 B1 | 11/2001 | Jung et al. |
| 6,313,376 B1 | 11/2001 | Jung et al. |
| 6,670,528 B1 | 12/2003 | Shinozaki et al. |
| 6,720,477 B2 | 4/2004 | da Costa e Silva et al. |
| 7,554,007 B2 | 6/2009 | Ronen et al. |
| 2002/0049999 A1 | 4/2002 | Allen et al. |
| 2002/0170088 A1 | 11/2002 | Wilkins |
| 2003/0233670 A1 | 12/2003 | Edgerton et al. |

(Continued)

FOREIGN PATENT DOCUMENTS

AU 2005229157 10/2005

(Continued)

OTHER PUBLICATIONS

Wells (Biochemistry 29:8509-8517, 1990).*
Guo et al. (PNAS, 101: 9205-9210, 2004).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Alcala et al. "Generation of ESTs From Tomato Fruit Tissue", Database GenBank on STIC, National Center for Biotechnology Information, Accession No. AW932839, 2001.
Apse et al. "Engineering Salt Tolerance in Plants", Current Opinion in Biotechnology, 13: 146-150, 2002.
Brandle et al. "Perspectives on the Production of Recombinant Proteins in Plants", AgBiotechNet, 3(ABN 070): 1-4, 2001. Abstract.
Hill et al. "Functional Analysis of Conserved Histidines in ADP-Glucose Pyrophosphorylase From *Escherichia coli*", Biochemical and Biophysical Research Communications, 244(2): 573-577, 1998.
In et al. "Panax Gingseng mRNA for Cytoplasmic Ribosomal Protein S13, Complete Cds", Database EMBL [Online], Retrieved From EBI Accession No. EMBL, Database Accession No. AB043974, 2000.

(Continued)

*Primary Examiner* — Vinod Kumar

(57) ABSTRACT

Isolated polynucleotides having a nucleic acid sequence at least 80% homologous to SEQ ID NO:1, 3, 5, 7, 9, 11, 158, 159, 160, 161, 162-204, 206-211, 214-287 and/or encoding polypeptides having an amino acid sequence at least 80% homologous to SEQ ID NO: 2, 4, 6, 8, 10, 12, 13-56, 58-63, 66-121, 141-156 or 157 are provided. Also provided are methods of utilizing same for increasing the tolerance of a plant to abiotic stresses and/or increasing the biomass, vigor and/or yield of a plant.

14 Claims, 2 Drawing Sheets
(2 of 2 Drawing Sheet(s) Filed in Color)

U.S. PATENT DOCUMENTS

| | | | |
|---|---|---|---|
| 2004/0006794 | A1 | 1/2004 | Wilkins |
| 2004/0031072 | A1 | 2/2004 | La Rosa et al. |
| 2004/0034888 | A1* | 2/2004 | Liu et al. .................. 800/289 |
| 2004/0123343 | A1 | 6/2004 | La Rosa et al. |
| 2004/0172684 | A1 | 9/2004 | Kovalic et al. |
| 2006/0123516 | A1* | 6/2006 | Ronen et al. ............... 800/289 |
| 2006/0260002 | A1 | 11/2006 | Ronen et al. |
| 2007/0044172 | A1 | 2/2007 | Schneeberger et al. |
| 2007/0061916 | A1 | 3/2007 | Kovalic et al. |
| 2008/0196120 | A1 | 8/2008 | Wu et al. |
| 2008/0301839 | A1 | 12/2008 | Ravanello |
| 2009/0126042 | A1 | 5/2009 | Ronen et al. |
| 2009/0260109 | A1 | 10/2009 | Ronen et al. |
| 2009/0293154 | A1 | 11/2009 | Yelin et al. |

FOREIGN PATENT DOCUMENTS

| | | |
|---|---|---|
| EP | 0905242 | 3/1999 |
| EP | 1033405 | 9/2000 |
| EP | 1225231 | 7/2002 |
| RU | 2350653 | 3/2009 |
| WO | WO 93/06710 | 4/1993 |
| WO | WO 93/07278 | 4/1993 |
| WO | WO 94/17194 | 8/1994 |
| WO | WO 95/08914 | 4/1995 |
| WO | WO 96/26639 | 9/1996 |
| WO | WO 96/40924 | 12/1996 |
| WO | WO 01/17333 | 3/2001 |
| WO | WO 02/16655 | 2/2002 |
| WO | WO 02/079403 | 10/2002 |
| WO | WO 02/090557 | 11/2002 |
| WO | WO 03/020025 | 3/2003 |
| WO | WO 03/087313 | 10/2003 |
| WO | WO 03/098186 | 11/2003 |
| WO | WO 2004/053055 | 6/2004 |
| WO | WO 2004/092367 | 10/2004 |
| WO | WO 2004/104162 | 12/2004 |
| WO | WO 2005/095614 | 10/2005 |
| WO | WO 2005/108422 | 11/2005 |
| WO | WO 2005/121364 | 12/2005 |
| WO | WO 2006/138012 | 12/2006 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |

OTHER PUBLICATIONS

Kim et al. "Molecular Cloning of Low-Temperature-Inducible Ribosomal Proteins From Soybean", Journal of Experimental Botany, 55(399): 1153-1155, 2004.
Park et al. "Glycine Max Ribosomal Protein S13 (RPS13) mRNA, Complete Cds", Database EMBL [Online], Retreieved From EBI Accession No. EMBL, Database Accession No. AY453393, 2004.
Sáez-Vásquez et al. "Accumulation and Nuclear Targeting of BnC24, A *Brassica napus* Ribosomal Protein Corresponding to A mRNA Accumulating in Response to Cold Treatment", Plant Science, 156(1): 35-46, 2000.
Smart et al. "MIP Genes Are Down-Regulated Under Drought Stress in *Nicotiana glauca*", Plant and Cell Physiology, 42(7): 686-693, 2001. Referenc to Database Entry AF290618 on p. 686, p. 692, 1-h col., § 2.
Smart et al. "*Nicotiana glauca* Putative Delta TIP (MIP2) mRNA, Complete Cds", Database EMBL [Online], Retrieved From EBI Accession No. EMBL: Af290618, Database Accession No. AF290618:, Jan. 2, 2001.
Tamura et al. "Osmotic Stress Tolerance of Transgenic Tobacco Expressing A Gene Encoding A Membrane-Located Receptor-Like Protein From Tobacco Plants", Plant Physiology, 131(2): 454-462, 2003.
Tanaka et al. "Enhanced Tolerance Against Salt-Stress and Freezing-Stress of *Escherichia coli* Cells Expressing Algal BBC1 Gene", Current Microbiology, 42(3): 173-177, 2001.
Van der Hoeven et al. "EST301294 Tomato Root During/After Fruit Set, Cornell University Lycopersicon Esculentum cDNA Clone cLEX1K11 Similar to *Vernicia fordii* Aquaporin, mRNA Sequence", Database EMBL [Online], Retrieved From EBI Accession No. EMBL: AW218814, Database Accession No. AW218814. Abstract:, Dec. 14, 1999.
Van der Hoeven et al. "EST301295 Tomato Root During/After Fruit Set, Cornell University Lycopersicon Esculentum cDNA Clone cLEX1K11 Similar to *Vernicia fordii* Aquaporin, mRNA Sequence", Database EMBL [Online], Retrieved From EBI Accession No. EMBL: AW218815, Database Accession No. AW218815. Abstract;, Dec. 14, 1999.
Van der Hoeven et al. "EST428934 Tomato Nutrient Deficient Roots Lycopersicon Esculentum cDNA Clone cLEW26B2 5' Sequence, mRNA Sequence", Database EMBL, Retrieved From EBI Accession No. EMBL, Database Accession No. BF098413, 2000.
Communication Pursuant to Article 94(3) EPC Dated Sep. 9, 2009 From the European Patent Office Re.: Application No. 04734072.4.
Communication Pursuant to Article 94(3) EPC Dated Dec. 8, 2008 From the European Patent Office Re.: Application No. 04734072.4.
International Preliminary Report on Patentability Dated Dec. 8, 2005 From the International Bureau of WIPO Re.: Application No. PCT/IL2004/000431.
International Preliminary Report on Patentability Dated Jan. 22, 2009 From the International Bureau of WIPO Re.: Application No. PCT/IL2006/000947.
Office Action Dated Jan. 9, 2009 From the State Intellectual Property Office of the People's Republic of China Re.: Application No. 200480020597.0.
Office Action Dated Apr. 27, 2009 From the Israeli Patent Office Re.: Application No. 172135 and Its Translation Into English.
Official Action Dated May 15, 2009 From the US Patent and Trademark Office Re.: U.S. Appl. No. 11/990,386.
Official Action Dated Oct. 18, 2007 From the US Patent and Trademark Office Re.: U.S. Appl. No. 11/284,236.
Official Action Dated Jul. 28, 2008 From the US Patent and Trademark Office Re.: U.S. Appl. No. 11/284,236.
Translation of the Office Action Dated Jan. 9, 2009 From the State Intellectual Property Office Re.: Application No. 2004800200597.0.
Office Action Dated Aug. 4, 2010 From the Israel Patent Office Re.: Application No. 172135 and Its Translation Into English.
Official Action Dated Aug. 18, 2010 From the US Patent and Trademark Office Re. U.S. Appl. No. 12/083,978.
Supplementary European Search Report and the European Search Opinion Dated Jul. 29, 2010 From the European Patent Office Re. Application No. 08776651.5.
Communication Pursuant to Article 94(3) EPC Dated Feb. 13, 2009 From the European Patent Office Re.: Application No. 05750089.4.
European Search Report and the European Search Opinion Dated Aug. 9, 2010 From the European Patent Office Re.: Application No. 09163033.5.
Examiner's Report Dated Dec. 17, 2009 From the Australian Patent Office Re.: Application No. 2005252469.
International Preliminary Report on Patentability Dated Jan. 14, 2010 From the International Bureau of WIPO Re.: Application No. PCT/iL2008/000489.
International Preliminary Report on Patentability Dated Jan. 21, 2010 From the International Bureau of WIPO Re.: Application No. PCT/IL2007/001590.
International Preliminary Report on Patentability Dated Mar. 29, 2007 From the International Bureau of WIPO Re.: Application No. PCT/IL2005/000627.
International Preliminary Report on Patentability Dated Jan. 30, 2007 From the International Bureau of WIPO Re.: Application No. PCT/IL05/00627.
International Search Report and the Written Opinion Dated Nov. 24, 2008 From the International Searching Authority Re.: Application No. PCT/1L08/00489.
International Search Report Dated Jul. 2, 2009 From the International Searching Authority Re.: Application No. PCT/IL07/01590.
International Search Report Dated Jan. 3, 2007 From the International Searching Authority Re.: Application No. PCT/IL2005/000627.
Invitation to Pay Additional Fees Dated Sep. 8, 2006 From the International Searching Authority Re.: Application No. PCT/1L05/00627.

Notice of Allowance Dated Apr. 16, 2010 From the US Patent and Trademark Office Re.: U.S. Appl. No. 11/629,411.
Office Action Dated May 13, 2010 From the Israel Patent Office Re. Application No. 180022 and Its Translation Into English.
Office Action Dated Jan. 22, 2010 From the State Intellectual Property Office of the People's Republic of China Re.: Application No. 200580027481.4 and Its Translation Into English.
Official Action Dated May 1, 2009 From the US Patent and Trademark Office Re.: U.S. Appl. No. 11/629,411.
Official Action Dated Sep. 2, 2009 From the US Patent and Trademark Office Re.: U.S. Appl. No. 11/629,411.
Official Action Dated Jun. 8, 2010 From the US Patent and Trademark Office Re.: U.S. Appl. No. 11/629,411.
Partial European Search Report Dated Apr. 19, 2010 From the European Patent Office Re.: Application No. 09163033.5.
Response Dated Jan. 4, 2010 to Official Action of Sep. 2, 2009 From the US Patent and Trademark Office Re.: U.S. Appl. No. 11/629,411.
Response Dated May 17, 2010 to Office Action of Jan. 22, 2010 From the State Intellectual Property Office of the People's Republic of China Re.: Application No. 200580027481.4.
Supplementary European Search Report and the European Search Opinion Dated Jul. 1, 2010 From the European Patent Office Re. Application No. 07849616.3.
Supplementary European Search Report and the European Search Opinion Dated Aug. 11, 2010 From the European Patent Office Re. Application No. 08738191.9.
Supplementary European Search Report Dated Apr. 23, 2008 From the European Patent Office Re.: Application No. 05750089.4.
Translation of Notice of Payment of the Restoration Fee for Unity of invention Dated Mar. 20, 2009 From the State Intellectual Property Office of the People's Republic of China Re.: Application No. 200580027481.4.
Written Opinion Dated Jul. 2, 2009 From the International Searching Authority Re.: Application No. PCT/IL07/01590.
Written Opinion Dated Jan. 3, 2007 From the International Searching Authority Re.: Application No. PCT/IL2005/000627.
Blewitt et al. "BNLGHi10083 Six-Day Cotton Fiber Gossypium Hirsutum cDNA 5' Similar to (AC004521) Unknown Protein [Arabidopsis Thaliana], mRNA Sequence", XP002576188, Retrieved Fron EBT Accession No. EMBL:AI728187, Database Accession No. AI728187, Jun. 12, 1999. Sequence.
Blewitt et al. "BNLGHi8081 Six-Day Cotton Fiber Gossypium Hirsutum cDNA 5' Similar to (AC004521) Unknown Protein [Arabidopsis Thalian], mRNA Sequence", XP002576189, Retrieved From EBI Accesion No. EMBL:AI730835, Database Accession No. AI730835, Jun. 12, 1999. Sequence.
Blewitt et al. "BNLGHi8396 Six-Day Cotton Fiber Gossypium Hirsutum cDNA 5' Similar to (AC004521) Unknown Protein [Arabidopsis Thaliana], mRNA Sequence", XP002576190, Retrieved From EBI Accession No. EMBL:AT27553, Database Accession No. A127553, Jun. 12, 1999. Sequence.
Bowie et al. "Deciphering the Message in Protein Sequences: Tolerance to Amino Acid Substitutions", Science, 247(4948): 1306-1310, Mar. 16, 1990.
Cheuk et al. "Arabidopsis Thaliana At2g46960/F14M4.21 mRNA, Complete CDS", Database EMBL [Online], XP002593835, Retrieved From EBI Accession No. EMBL:AY091688, Database Accession No. AY091688, Apr. 14, 2002.
François et al. "Overexpression of the VvLTP1 Gene Interferes With Somatic Embryo Development in Grapevine", Functional Plant Biology, 35(5): 394-402, 2008.
Ji et al. "Gossypium Hirsutum Expansin mRNA, Complete CDs", XP002474936, Retrieved From EBI Accession No. EMBL:AY189969, Database Accession No. AY189969.
Ji et al. "Isolation and Analyses of Genes Preferentially Expressed During Early Cotton Fiber Development by Subtractive PCR and cDNA Array", Nucleic Acids Research, XP002474935, 31(10): 2534-2543, May 15 2003.
Kim et al. "Arabidopsis Thaliana At2g46960/F14M4.21 mRNA, Complete CDS", Database EMBL [Online], XP002593834, Retrieved From EBI Accession No. EMBL:AF367329, Database Accession No. AF367329, Apr. 12, 2001.

Kirubakaran et al. "Characterization of A New Antifungal Lipid Transfer Protein From Wheat", Plant Physiology and Biochemistry, 46: 918-927, 2008.
McConnell et al. "Role of PHABULOSA and PHAVOLUTA in Determining Radial Patterning in Shoots", Nature, 411(6338): 709-713, Jun. 7, 2001.
Merriam-Webster "Exogenous Definition", Merrian-Webster On-Line Dictionary, 2010.
NCBI "Protein Sequence (588 Letters)", NCBI BLAST Basic Local Alignment Search Tool, 3 P., Retrieved From the Internet on Nov. 24, 2009.
Orford et al. "Specific Expression of An Expansin Gene During Elongation of Cotton Fibres", Biochimica et Biophysica Acta, XP000866032, 1398(3): 342-346, Jul. 9, 1998. Abstract, p. 343, Fig.1.
Orzaez et al. "Agroinjection of Tomato Fruits. A Tool for Rapid Functional Analysis of Transgenes Directly in Fruit", Plant Physiology, 140: 3-11, 2006.
Udall et al. "A Global Assembly of Cotton ESTs", Genome Research, 16(3): 441-450, 2006.
Wallace et al. "Oligonucleotide Probes for the Screening of Recombinant DNA Libraries", Methods in Enzymology, XP002957829, 152: 432-442, Jan. 1, 1987.
Wing et al. "An Integrated Analysis of the Genetics, Devlopment, and Evolution of Cotton Fiber", NBCI GenBank Accession No. BE052336, 2000.
Wing et al. "GA__Eb0023E09f Gossypium Arboreum 7-10 Dpa Fiber Library Gossypium Arboreum cDNA Clone GA_Eb0023F09f, mRNA Sequence", XP002576191, Retrieved From EBI Accession No. EMBL:BF275177, Database Accession No. BF275177, Nov. 20, 2000. Sequence.
Response Dated Sep.13, 2010 to Office Action Dated May 13, 2010 From the Israel Patent Office Re. Application No. 180022.
International Preliminary Report on Patentability Dated Jul. 8, 2010 From the International Bureau of WIPO Re.: Application No. PCT/IL2008/001657.
Office Action Dated Jun. 17, 2010 From the Israel Patent Office Re. Application No. 190918 and Its Translation Into English.
Response Dated Jun. 29, 2010 to Examination Report of Feb. 17, 2010 From the Instituto Mexicano de la Propriedad Industrial Re. Application No. PA/a/2005/012565.
Invitation to Pay Additional Fees Dated Dec. 18, 2008 From the International Searching Authority Re.: Application No. PCT/IL08/01024.
International Preliminary Report on Patentability Dated Feb. 4, 2010 From the International Bureau of WIPO Re.: Application No. PCT/IL2008/001024.
International Search Report Dated Mar. 4, 2009 From the International Searching Authority Re.: Application No. PCT/IL08/01024.
Office Action Dated Jan. 31, 2010 From the Israel Patent Office Re.: Application No. 172135 and Its Translation Into English.
Response Dated Jan. 7, 2010 to Communication Pursuant to Article 94(3) EPC of Sep. 9, 2009 From the European Patent Office Re.: Application No. 04734072.4.
Supplementary European Search Report and the European Search Opinion Dated Feb. 1, 2010 From the European Patent Office Re.: Application No. 06766224.7.
Written Opinion Dated Mar. 4, 2009 From the International Searching Authority Re.: Application No. PCT/IL08/01024.
Nuccio et al. "Metabolic Engineering of Plants for Osmotic Stress Resistance", Current Opinion in Plant Biology, XP002216348, 2(2): 128-134, Apr. 1, 1999.
International Preliminary Report on Patentability Dated Jan. 22, 2009 From the International Bureau of WIPO Re.: Application No. PCT/IL2006/001223.
Invitation to Pay Additional Fees Dated Feb. 7, 2008 From the International Searching Authority Re.: Application No. PCT/IL06/001223.
Communication Pursuant to Article 94(3) EPC Dated Nov. 27, 2009 From the European Patent Office Re.: Application No. 06809784.9.
International Search Report and the Written Opinion Dated Jul. 29, 2008 From the International Searching Authority Re.: Application No. PCT/IL06/001223.

Supplementary European Search Report and the European Search Opinion Dated Sep. 14, 2009 From the European Patent Office Re.: Application No. 06809784.9.

Gardiner et al. "Zea Mays PC0131392 mRNA Sequence", Database EMBL/GenBank/DDBJ, EBI Database Accession No. AY107021, XP002542347, May 28, 2002. 96,5% Identity in 1118 nt Overlap of AY107021 (1118 nt) With SEQ ID No. 68 (1348 nt) of the Present Application, Abstract.

Grover et al. "Understanding Molecular Alphabets of the Plant Abiotic Stress Responses", Current Science, 80(2): 206-216, Jan. 25, 2001.

Liu et al. "Root-Specific Expression of A Western White Pine PR10 Gene Is Mediated by Different Promoter Regions in Transgenic Tobacco", Plant Molecular Biology, 52: 103-120, 2003.

Examination Report Dated Feb. 17, 2010 From the Instituto Mexicano de la Propriedad Industrial Re. Application No. PA/a/2005/012565 and Its Summary in English.

Communication Pursuant to Article 94(3) EPC Dated May 12, 2010 From the European Patent Office Re.: Application No. 06766224.7.

Response Dated May 31, 2010 to Office Action of Jan. 31, 2010 From the Israel Patent Office Re.: Application No. 172135.

Communication Relating to the Results of the Partial International Search Dated Jul. 8, 2009 From the International Searching Authority Re.: Application No. PCT/IL2008/001657.

International Search Report and the Written Opinion Dated Oct. 30, 2009 From the International Searching Authority Re.: Application No. PCT/IL2008/001657.

Fray et al. "Nucleotide Sequence and Expression of A Ripening and Water Stress-Related cDNA From tomato With Homology to the MIP Class of Membrane Channel Proteins", Plant Molecular Biology [Online], XP009117320, 24(3): 539-543, 1994. Figs.1, 2. & Database UniProt, REcName: Full=Probable Aquaporin PIP-Type pTOM75; AltName: Full=Ripening-Associated Membrane Protein; Short=RAMP, Oct. 1, 1994.

Hachez et al. "Modulating the Expression of Aquaporin Genes in Planta: A Key to Understand Their Physiological Functions?", Biochimica et Biophysica Acta, XP005655605, 1758(8): 1142-1156, Aug. 1, 2006. p. 1151, Col. 1, § 2 - p. 1153, Col. 1, § 1, Table 1.

Kirkness et al. "Lycopersicon Esculentum Clone 133453R, mRNA Sequence", Database EMBL [Online], XP002529190, Retrieved From EBI Accession No. EMBL:BT014251, Database Accession No. BT014251, May 12, 2004.

Maurel "Plant Aquaporins: Novel Functions and Regulation Properties", FEBS Letters, XP022078418, 581(12): 2227-2236, May 25, 2007. p. 2230, Col. 2, Last § -p. 2231, Col. 1, § 2, Fig.1.

Wu et al. "SubName: Full=Major Intrinsic Protein", Database UniProt [Online], XP002529191, Retrieved From EBI Accession No. UNIPROT:AOFI89, Database Accession No. AOFI89, Nov. 28, 2006.

* cited by examiner

METHODS OF INCREASING ABIOTIC STRESS TOLERANCE AND/OR BIOMASS IN PLANTS AND PLANTS GENERATED THEREBY

RELATED APPLICATIONS

This Application is a National Phase of PCT Patent Application No. PCT/IL2006/000947 having International Filing Date of Aug. 15, 2006, which claims the benefit of U.S. Provisional Patent Application No. 60/707,957 filed on Aug. 15, 2005. The contents of the above Applications are all incorporated herein by reference.

FIELD AND BACKGROUND OF THE INVENTION

The present invention relates to methods of increasing abiotic stress tolerance and/or biomass in plants and, more particularly, to plants expressing exogenous abiotic stress-tolerance genes.

Abiotic stress (also referred to as "environmental stress") conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield of most crop plants are profound. Furthermore, most of the crop plants are very susceptible to abiotic stress (ABS) and thus necessitate optimal growth conditions for commercial crop yields. Continuous exposure to stress causes major alterations in the plant metabolism which ultimately lead to cell death and consequently yield losses. Thus, despite extensive research and the use of sophisticated and intensive crop-protection measures, losses due to abiotic stress conditions remain in the billions of dollars annually (1,2).

The following summarizes the implications of exemplary abiotic stress conditions.

Problems associated with drought. A drought is a period of abnormally dry weather that persists long enough to produce a serious hydrologic imbalance (for example crop damage, water supply shortage, etc.). While much of the weather that we experience is brief and short-lived, drought is a more gradual phenomenon, slowly taking hold of an area and tightening its grip with time. In severe cases, drought can last for many years and can have devastating effects on agriculture and water supplies. With burgeoning population and chronic shortage of available fresh water, drought is not only the number one weather related problem in agriculture, it also ranks as one of the major natural disasters of all time, causing not only economic damage, but also loss of human lives. For example, losses from the US drought of 1988 exceeded $40 billion, exceeding the losses caused by Hurricane Andrew in 1992, the Mississippi River floods of 1993, and the San Francisco earthquake in 1989. In some areas of the world, the effects of drought can be far more severe. In the Horn of Africa the 1984-1985 drought led to a famine that killed 750,000 people.

Problems for plants caused by low water availability include mechanical stresses caused by the withdrawal of cellular water. Drought also causes plants to become more susceptible to various diseases (Simpson (1981). "The Value of Physiological Knowledge of Water Stress in Plants", In Water Stress on Plants, (Simpson, G. M., ed.), Praeger, N.Y., pp. 235-265).

In addition to the many land regions of the world that are too arid for most if not all crop plants, overuse and over-utilization of available water is resulting in an increasing loss of agriculturally-usable land, a process which, in the extreme, results in desertification. The problem is further compounded by increasing salt accumulation in soils, as described above, which adds to the loss of available water in soils.

Problems associated with high salt levels. One in five hectares of irrigated land is damaged by salt, an important historical factor in the decline of ancient agrarian societies. This condition is only expected to worsen, further reducing the availability of arable land and crop production, since none of the top five food crops—wheat, corn, rice, potatoes, and soybean—can tolerate excessive salt.

Detrimental effects of salt on plants are a consequence of both water deficit resulting in osmotic stress (similar to drought stress) and the effects of excess sodium ions on critical biochemical processes. As with freezing and drought, high saline causes water deficit; the presence of high salt makes it difficult for plant roots to extract water from their environment (Buchanan et al. (2000) in Biochemistry and Molecular Biology of Plants, American Society of Plant Physiologists, Rockville, Md.). Soil salinity is thus one of the more important variables that determines where a plant may thrive. In many parts of the world, sizable land areas are uncultivable due to naturally high soil salinity. To compound the problem, salination of soils that are used for agricultural production is a significant and increasing problem in regions that rely heavily on agriculture. The latter is compounded by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. Thus, germination normally takes place at a salt concentration much higher than the mean salt level in the whole soil profile.

Problems associated with excessive heat. Germination of many crops is very sensitive to temperature. A gene that would enhance germination in hot conditions would be useful for crops that are planted late in the season or in hot climates. Seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function [Buchanan et al. (2000) in Biochemistry and Molecular Biology of Plants, American Society of Plant Physiologists, Rockville, Md. Heat shock may produce a decrease in overall protein synthesis, accompanied by expression of heat shock proteins. Heat shock proteins function as chaperones and are involved in refolding proteins denatured by heat.

Heat stress often accompanies conditions of low water availability. Heat itself is seen as an interacting stress and adds to the detrimental effects caused by water deficit conditions. Evaporative demand exhibits near exponential increases with increases in daytime temperatures and can result in high transpiration rates and low plant water potentials [Hall et al. (2000) Plant Physiol. 123: 1449-1458]. High-temperature damage to pollen almost always occurs in conjunction with drought stress, and rarely occurs under well-watered conditions. Thus, separating the effects of heat and drought stress on pollination is difficult. Combined stress can alter plant metabolism in novel ways; therefore understanding the interaction between different stresses may be important for the development of strategies to enhance stress tolerance by genetic manipulation.

Problems associated with excessive chilling conditions. The term "chilling sensitivity" has been used to describe many types of physiological damage produced at low, but above freezing, temperatures. Most crops of tropical origins, such as soybean, rice, maize, and cotton are easily damaged by chilling. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. For example, chilling may lead to yield losses and lower product quality through the delayed ripening of maize. Another consequence of poor growth is the rather poor ground cover of maize fields in spring, often resulting in soil erosion, increased occurrence of weeds, and reduced uptake of nutrients. A retarded uptake of mineral nitrogen could also lead to increased losses of nitrate into the ground water. By some estimates, chilling accounts for monetary losses in the United States (US) behind only to drought and flooding.

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson (1990) Trends Biotechnol. 8: 358-362).

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The pathway regulating ion homeostasis in response to salt stress has been reviewed recently by Xiong and Zhu (2002) Plant Cell Environ. 25: 131-139.

The osmotic component of salt stress involves complex plant reactions that overlap with drought and/or cold stress responses.

Common aspects of drought, cold and salt stress response have been reviewed recently by Xiong and Zhu (2002) supra. Those include:

(a) transient changes in the cytoplasmic calcium levels very early in the signaling event (Knight, (2000) Int. Rev. Cytol. 195: 269-324; Sanders et al. (1999) Plant Cell 11: 691-706);

(b) signal transduction via mitogen-activated and/or calcium dependent protein kinases (CDPKs; see Xiong et al., 2002) and protein phosphatases (Merlot et al. (2001) Plant J. 25: 295-303; Tahtiharju and Palva (2001) Plant J. 26: 461-470);

(c) increases in abscisic acid levels in response to stress triggering a subset of responses (Xiong et al. (2002) supra, and references therein);

(d) inositol phosphates as signal molecules (at least for a subset of the stress responsive transcriptional changes (Xiong et al. (2001) Genes Dev. 15: 1971-1984);

(e) activation of phospholipases which in turn generate a diverse array of second messenger molecules, some of which might regulate the activity of stress responsive kinases (phospholipase D functions in an ABA independent pathway, Frank et al. (2000) Plant Cell 12: 111-124); [0026] (f) induction of late embryogenesis abundant (LEA) type genes including the CRT/DRE responsive COR/RD genes (Xiong and Zhu (2002) supra);

(g) increased levels of antioxidants and compatible osmolytes such as proline and soluble sugars (Hasegawa et al. (2000) Annu. Rev. Plant Mol. Plant Physiol. 51: 463-499); and [0028] (h) accumulation of reactive oxygen species such as superoxide, hydrogen peroxide, and hydroxyl radicals (Hasegawa et al. (2000) supra).

Abscisic acid biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Based on the commonality of many aspects of cold, drought and salt stress responses, it can be concluded that genes that increase tolerance to cold or salt stress can also improve drought stress protection. In fact this has already been demonstrated for transcription factors (in the case of AtCBF/DREB 1) and for other genes such as OsCDPK7 (Saijo et al. (2000) Plant J. 23: 319-327), or AVP1 (a vacuolar pyrophosphatase-proton-pump, Gaxiola et al. (2001) Proc. Natl. Acad. Sci. USA 98: 11444-11449).

Developing stress-tolerant plants is a strategy that has the potential to solve or mediate at least some of these problems. However, traditional plant breeding strategies used to develop new lines of plants that exhibit tolerance to ABS are relatively inefficient since they are tedious, time consuming and of unpredictable outcome. Furthermore, limited germplasm resources for stress tolerance and incompatibility in crosses between distantly related plant species represent significant problems encountered in conventional breeding. Additionally, the cellular processes leading to ABS tolerance are complex in nature and involve multiple mechanisms of cellular adaptation and numerous metabolic pathways (4-7).

Genetic engineering efforts, aimed at conferring abiotic stress tolerance to transgenic crops, have been described in the prior art. Studies by Apse and Blumwald (Curr Opin Biotechnol. 13:146-150, 2002), Quesada et al. (Plant Physiol. 130:951-963, 2002), Holmström et al. (Nature 379: 683-684, 1996), Xu et al. (Plant Physiol 110: 249-257, 1996), Pilon-Smits and Ebskamp (Plant Physiol 107: 125-130, 1995) and Tarczynski et al. (Science 259: 508-510, 1993) have all attempted at generating stress tolerant plants.

In addition, several U.S. patents and patent applications also describe polynucleotides associated with stress tolerance and their use in generating stress tolerant plants. U.S. Pat. Nos. 5,296,462 and 5,356,816 describe transforming plants with polynucleotides encoding proteins involved in cold adaptation in *Arabidopsis thaliana*, to thereby promote cold tolerance in the transformed plants.

U.S. Pat. No. 6,670,528 describes transforming plants with polynucleotides encoding polypeptides binding to stress responsive elements, to thereby promote tolerance of the transformed plants to abiotic stress.

U.S. Pat. No. 6,720,477 describes transforming plants with a polynucleotide encoding a signal transduction stress-related protein, capable of increasing tolerance of the transformed plants to abiotic stress.

U.S. application Ser. Nos. 09/938,842 and 10/342,224 describe abiotic stress-related genes and their use to confer upon plants tolerance to abiotic stress.

U.S. application Ser. No. 10/231,035 describes overexpressing a molybdenum cofactor sulfurase in plants to thereby increase their tolerance to abiotic stress.

Although the above described studies were at least partially successful in generating stress tolerant plants, there remains a need for stress tolerant genes which can be utilized to generate plants tolerant of a wide range of abiotic stress conditions.

While reducing the present invention to practice, the present inventors have identified through bioinformatic and laboratory studies several novel abiotic stress-tolerance genes, which can be utilized to increase tolerance to abiotic stress and/or biomass, vigor and yield in plants.

SUMMARY OF THE INVENTION

According to one aspect of the present invention there is provided a method of increasing tolerance of a plant to an abiotic stress, comprising expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155 thereby increasing the tolerance of the plant to the abiotic stress.

According to still further features in the described preferred embodiments the abiotic stress is selected from the group consisting of salinity, water deprivation, low temperature, high temperature, heavy metal toxicity, anaerobiosis, nutrient deficiency, nutrient excess, atmospheric pollution and UV irradiation.

According to another aspect of the present invention there is provided a method of increasing biomass, vigor and/or yield of a plant, comprising expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155, thereby increasing biomass, vigor and/or yield of the plant.

According to still further features in the described preferred embodiments the expressing is effected by:

(a) transforming a cell of the plant with the exogenous polynucleotide;
(b) generating a mature plant from the cell; and
(c) cultivating the mature plant under conditions suitable for expressing the exogenous polynucleotide within the mature plant.

According to still further features in the described preferred embodiments the transforming is effected by introducing to the plant cell a nucleic acid construct including the exogenous polynucleotide and at least one promoter capable of directing transcription of the exogenous polynucleotide in the plant cell.

According to yet another aspect of the present invention there is provided a nucleic acid construct, comprising a nucleic acid sequence at least 90% identical to a nucleotide sequence selected from the group consisting of SEQ ID NOs: 1, 3, 5, 7, 9, 11, 156, 157, 158, 159, 160-202, 204-209, 212-285 and a promoter capable of directing transcription of the nucleic acid sequence in a host cell.

According to still further features in the described preferred embodiments the promoter is a constitutive promoter.

According to still further features in the described preferred embodiments the constitutive promoter is CaMV 35S promoter.

According to still further features in the described preferred embodiments the constitutive promoter is At6669 promoter.

According to still further features in the described preferred embodiments the promoter is an inducible promoter.

According to still further features in the described preferred embodiments the inducible promoter is an abiotic stress inducible promoter.

According to still further features in the described preferred embodiments the host cell is a plant cell.

According to still further features in the described preferred embodiments the plant cell forms a part of a dicotyledonous plant cell.

According to still further features in the described preferred embodiments the plant cell forms a part of a monocotyledonous plant cell.

According to still another aspect of the present invention there is provided an isolated polypeptide, comprising an amino acid sequence at least 90% homologous to the amino acid sequence encoded by a polynucleotide selected from the group consisting of SEQ ID NOs: 1, 3, 5, 7, 9, 11, 156, 157, 158, 159, 160-202, 204-209, 212-285.

According to still further features in the described preferred embodiments the amino acid sequence is at least 90% homologous to SEQ ID NO: 2, 4, 6, 8, 10, 12, 13-56, 58-63, 66-119, 139-154 or 155.

According to an additional aspect of the present invention there is provided a plant cell comprising an exogenous polynucleotide encoding a polypeptide having an amino acid sequence at least 90% homologous to SEQ ID NO: 2, 4, 6, 8, 10, 12, 13-56, 58-63, 66-119, 139-154 or 155 thereby increasing the tolerance of the plant to the abiotic stress.

According to still further features in the described preferred embodiments the plant cell forms a part of a plant.

The present invention successfully addresses the shortcomings of the presently known configurations by providing methods of utilizing novel abiotic stress-tolerance genes to increase plants tolerance to abiotic stress and/or biomass.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 2A—Plants grown under non-stressing conditions for 7-10 days were transferred to high osmoticum conditions and their growth was followed for 12 days using digital imaging. Processed images of pictures taken at Day 0, Day 5 and Day 12 are shown. Note the control plants in the upper center of each plate and the independent transgenic events surrounding the control plants. FIG. 2B is a graph that describes plant area growth as a function of time using the images shown in panel A. Four of the five events shown are able to grow significantly faster than the wild-type control plants under the same conditions. Statistical analysis of the results is shown further below in Table 5 rows 1-5.

DESCRIPTION OF THE PREFERRED EMBODIMENTS

Figure 1:
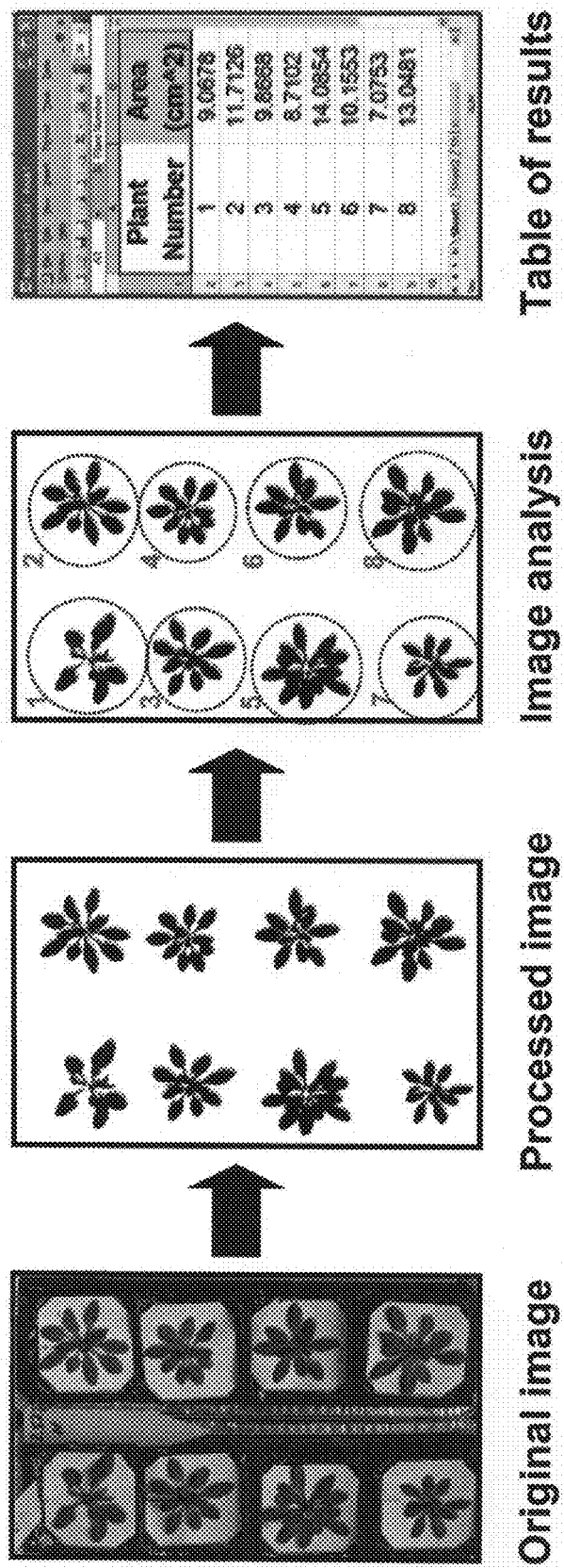
FIG. 1 is a schematic illustration of the methodology used to measure plants' size. Digital pictures are taken using uniform illumination and a tripod set a constant distance. The digital pictures obtained are processed using a "green-based" filter that removes the "non-green parts" of the picture leaving only the plant rosette area for quantification. Following quantification of the rosette area, results are exported to a spreadsheet and analyzed using statistical software.

The present invention is of methods of increasing plants tolerance to abiotic stress and/or biomass by utilizing novel abiotic stress tolerance genes and of plants exhibiting increased tolerance to stress conditions and/or increased capacity to accumulate biomass.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Whilst reducing the present invention to practice, the present inventors while employing bioinformatic techniques, identified polynucleotide sequences which encode putative abiotic-stress tolerance (ABST) proteins (Example 1). Selected sequences were isolated (Example 2), cloned into expression vectors (Example 3-4) and introduced into *Arabidopsis thaliana* plants (Example 5-6). These plants, were grown under salinity stress conditions, or under normal conditions, and checked for increased biomass as compared with similar control plants not carrying the exogenous ABST genes. As is evident from the results shown in Example 8, nucleic acid sequences selected according to the teachings of the present invention were shown to improve the tolerance of transgenic plants transfected therewith to abiotic stress as compared to control plants.

Thus, according to one aspect of the present invention, there is provided a method of increasing tolerance of a plant to an abiotic stress and/or plant biomass. The method includes expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155.

According to one preferred embodiment of this aspect of the present invention the isolated polynucleotide is as set forth is SEQ ID NO: 1, 3, 5, 7, 9, 11, 156, 157, 158, 159, 160-202, 204-209, 212-285.

Alternatively, the exogenous polynucleotide of the present invention encodes a polypeptide having an amino acid sequence as further described hereinbelow, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 2, 4, 6, 8, 10, 12, 13-56, 58-63, 66-119, 139-154 or 155.

The phrase "abiotic stress" used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability. Preferably, the genetically engineered plants of the present invention exhibit at least about 2% more, 5% more, 10% more, 20% more, 30% more, 40% more, 50% more, 60% more, 70% more, 80% more, 90% more or even higher tolerance to abiotic stress than non-transgenic plants.

As used herein, the term "exogenous polynucleotide" refers to a nucleic acid sequence which is not naturally expressed within the plant but which, when introduced into the plant either in a stable or transient manner, produces at least one polypeptide product.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

The polynucleotide of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences of the polypeptides of the present invention may be optimized for expression. Such optimized sequences are provided in SEQ ID NOs: 156, 157, 158 and 159. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[($X_n-Y_n$)/$Y_n$]2/N, where $X_n$ refers to the frequency of usage of codon n in highly expressed plant genes, where $Y_n$ to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (Hypertext Transfer Protocol:// World Wide Web (dot) kazusa (dot) or (dot) jp/codon/). The Codon Usage Database contains codon usage tables for a number of different species, with each codon usage table having been statistically determined based on the data present in Genbank By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The polynucleotides described above also encode previously uncharacterized polypeptides.

Thus the present invention provides a polypeptide having an amino acid sequence as further described hereinbelow, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 2, 4, 6, 8, 10, 12, 13-56, 58-63, 66-119, 139-154 or 155.

The present invention also encompasses fragments of the above described polypeptides and polypeptides having mutations, such as deletions, insertions or substitutions of one or more amino acids, either naturally occurring or man induced, either randomly or in a targeted fashion.

A suitable plant for use with the method of the present invention can be any monocotyledonous or dicotyledonous plant including, but not limited to, maize, wheat, barely, rye, oat, rice, soybean, peanut, pea, lentil and alfalfa, cotton, rapeseed, canola, pepper, sunflower, potato, tobacco, tomato, eggplant, eucalyptus, a tree, an ornamental plant, a perennial grass and a forage crop.

Expressing the exogenous polynucleotide of the present invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO: 120; Odell et al., Nature 313:810-812, 1985); *Arabidopsis* At6669 promoter (SEQ ID NO: 121, patent No WO2004/104162); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597; 5,466,785; 5,399,680; 5,268,463; and 5,608,142.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); and heat-inducible promoters such as heat tomato hsp80-promoter from tomato (U.S. Pat. No. 5,187,267).

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Preferably, mature transformed plants generated as described above are further selected for abiotic stress tolerance. Accordingly, transformed and non-transformed (wild type) plants are exposed to an abiotic stress condition, such as water depravation, suboptimal temperature, nutrient deficiency, or preferably a salt stress condition. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium (e.g., MS medium). Since different plants vary considerably in their tolerance to salinity, the salt concentration in the irrigation water, growth solution, or growth medium is preferably adjusted according to the specific characteristics of the specific plant cultivar or variety, so as to inflict a mild or moderate effect on the physiology and/or morphology of the plants (for guidelines as to appropriate concentration please see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein). Following exposure to the stress condition the plants are frequently monitored until substantial physiological and/or morphological effects appear in wild type plants. Subsequently, transformed plants not exhibiting substantial physiological and/or morphological effects, or exhibiting higher biomass than wild-type plants, are identified as abiotic stress tolerant plants.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990)269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since abiotic stress tolerance in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance and/or biomass traits, using conventional plant breeding techniques.

Hence, the present application provides methods of utilizing novel abiotic stress-tolerance genes to increase tolerance to abiotic stress and/or biomass in a wide range of economical plants, in a safe and cost effective manner.

Plants are subject to a range of environmental challenges. Several of these, including salt stress, general osmotic stress, drought stress and freezing stress, have the ability to impact whole plant and cellular water availability. Not surprisingly, then, plant responses to this collection of stresses are related. In a recent review, Zhu notes that "most studies on water stress signaling have focused on salt stress primarily because plant responses to salt and drought are closely related and the mechanisms overlap" (Zhu (2002) Ann. Rev. Plant Biol. 53: 247-273). Many examples of similar responses and pathways to this set of stresses have been documented. For example, the CBF transcription factors have been shown to condition resistance to salt, freezing and drought (Kasuga et al. (1999) Nature Biotech. 17: 287-291). The *Arabidopsis* rd29B gene is induced in response to both salt and dehydration stress, a process that is mediated largely through an ABA signal transduction process (Uno et al. (2000) Proc. Natl. Acad. Sci. USA 97: 11632-11637), resulting in altered activity of transcription factors that bind to an upstream element within the rd29B promoter. In *Mesembryanthemum crystallinum* (ice plant), Patharker and Cushman have shown that a calcium-dependent protein kinase (McCDPK1) is induced by exposure to both drought and salt stresses (Patharker and Cushman (2000) Plant J. 24: 679-691). The stress-induced kinase was also shown to phosphorylate a transcription factor, presumably altering its activity, although transcript levels of the target transcription factor are not altered in response to salt or drought stress. Similarly, Saijo et al. demonstrated that a rice salt/drought-induced calmodulin-dependent protein kinase (OsCDPK7) conferred increased salt and drought tolerance to rice when overexpressed (Saijo et al. (2000) Plant J. 23: 319-327).

Exposure to dehydration invokes similar survival strategies in plants as does freezing stress (see, for example, Yelenosky (1989) Plant Physiol 89: 444-451) and drought stress induces freezing tolerance (see, for example, Siminovitch et al. (1982) Plant Physiol 69: 250-255; and Guy et al. (1992) Planta 188: 265-270). In addition to the induction of cold-acclimation proteins, strategies that allow plants to survive in low water conditions may include, for example, reduced surface area, or surface oil or wax production.

It will be appreciated that some pathways involved in resistance to one stress (as described above), will also be involved in resistance to other stresses, regulated by the same or homologous genes. Of course, the overall resistance pathways are related, not identical, and therefore not all genes controlling resistance to one stress will control resistance to the other stresses. Nonetheless, if a gene conditions resistance to one of these stresses, it would be apparent to one skilled in the art to test for resistance to these related stresses. Methods of assessing stress resistance are further provided in the Examples section which follows.

Polynucleotide sequences of the present invention are capable of increasing a biomass of a plant. It will be appreciated that the ability of the polypeptides of the present invention to increase plant yield/biomass/vigor is inherent to their ability to promote the increase in plant cell-size (as shown in Example 8 and FIG. 2).

Thus, the present invention also envisages a method of increasing a biomass/vigor/yield of a plant (coniferous plants, moss, algae, monocot or dicot, as well as other plants listed in Hypertext Transfer Protocol://World Wide Web (dot) nationmaster (dot) com/encyclopedia/Plantae).

As used herein the phrase "plant biomass" refers to the amount or quantity of tissue produced from the plant in a growing season, which could also determine or affect the plant yield or the yield per growing area.

As used herein the phrase "plant vigor" refers to the amount or quantity of tissue produced from the plant in a given time. Hence increase vigor could determine or affect the plant yield or the yield per growing time or growing area.

As used herein the phrase "plant yield" refers to the amount or quantity of tissue produced and harvested as the plant produced product. Hence increase yield could affect the economic benefit one can obtain from the plant in a certain growing are and/or growing time.

Preferably, the genetically engineered plants of the present invention exhibit at least about 2% more, 5% more, 10% more, 20% more, 30% more, 40% more, 50% more, 60% more, 70% more, 80% more, 90% more or even greater biomass, vigor and/or yield than non-transgenic plants.

Methods of assaying plant vigor, yield and biomass are well known in the art (see Example 10).

Thus, the present invention is of high agricultural value for promoting the yield of commercially desired crops (e.g., biomass of vegetative organ such as poplar wood, or reproductive organ such as number of seeds or seed biomass).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Identifying Putative Abiotic Stress-Tolerance Genes from Monocots

Abiotic stress-tolerance (ABST) genes were identified and validated in vivo as previously described WO2004/104162 to the present assignee. A number of ABS genes and polypeptides encoded thereby were identified from dicot plants (SEQ ID NOs. 122-126 and 127-131, respectively). Screen for orthologous sequences was performed on monocot genomic databases, NCBI (Hypertext Transfer Protocol://World Wide Web (dot) ncbi (dot) nlm (dot) nih (dot) gov), and TIGR (Hypertext Transfer Protocol://World Wide Web (dot) tigr (dot) org/) databases of Maize, *Sorghum*, Rice and Barley.

The expressed sequence tags (ESTs) and cDNA sequences were clustered and assembled using the LEADS™ software (Compugen) and compared to the TIGR Hypertext Transfer Protocol://World Wide Web (dot) tigr (dot) org/) databases of the above monocots. Overall, clustering of 372,000 maize ESTs resulted in 41,990 clusters among them 19,870 singletones. In *Sorghum* about 190,000 ESTs were clustered into 39,000 clusters, while in barley 370,500 ESTs generated 50,000 different clusters each representing a different gene. Similar number of sequences and clustered genes were found in the rice genomic database.

A digital expression profile summary was compiled for each cluster according to all keywords included in the sequence records comprising the cluster. Digital expression, also known as electronic northern blot, is a tool that displays virtual expression profile based on the EST sequences forming the gene cluster. The tool can provide the expression profile of a cluster in terms of plant anatomy (in what tissues/organs is the gene expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations are taken into consideration: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

The concepts of orthology and paralogy have recently been applied to functional characterizations and classifications on the scale of whole-genome comparisons Orthologs and paralogs constitute two major types of homologs: The first evolved from a common ancestor by specialization, and the latter are related by duplication events. It is assumed that paralogs arising from ancient duplication events are likely to have diverged in function while true orthologs are more likely to retain identical function over evolutionary time.

To further investigate and identify the ABST putative ortholog genes from monocot species, two computational methods were integrated:

(i) Method for alignments of ortholog sequences—the method is effected by constructing ortholog groups across multiple eukaryotic taxa, using modifications on the Markov cluster algorithm to group putative orthologs and paralogs. These putative orthologs were further organized under Phylogram—a branching diagram (tree) assumed to be an estimate of a phylogeny of the genes.

(ii) Method for generating genes expression profile "Digital Expression"—The present inventors have performed considerable work aimed at annotating sequences. Expression data was analyzed and the EST libraries were classified using a fixed vocabulary of custom terms such as experimental treatments. The annotations from all the ESTs clustered to a gene were analyzed statistically by comparing their frequency in the cluster versus their abundance in the database, allowing to construct a numeric and graphic expression profile of that gene, which is termed "digital expression".

The rationale of using these two complementary methods is based on the assumption that true orthologs are likely to retain identical function over evolutionary time. These two methods (sequence and expression pattern) provide two different sets of indications on function similarities between two homologous genes, similarities in the sequence level—identical amino acids in the protein domains and similarity in expression profiles.

While comparing the sequences from monocots to the tomato ABST genes, homology levels between the tomato genes and their best orthologue gene from monocot differed dramatically, ranging from 45% to 88%. Moreover, the in-silico expression profile of the monocot genes does not always fit to a gene involved in ABS tolerance. Hence, an extensive search for the monocot functional orthologue of each tomato gene (SEQ ID NO: 122-131) was effected.

In attempt to identify the best orthologues of the tomato ABST genes, two sets of analyses were performed. First, the sequences of 5 tomato ABST genes (SEQ ID NO: 122-126) and their deduced polypeptide sequences (SEQ ID NO: 127-131) were compared to all monocot putative proteins, encoded by DNA sequences of gene clusters mentioned above. The comparison was done on the protein level looking for identity higher than 45% along the entire protein sequence.

Table 1 below shows the best homologous genes and their identity level to the tomato ABST proteins. Next, these monocot proteins originated from different monocot species (barley, *sorghum* and maize) were screened based on their expression pattern during the development of several monocot species. This screening was based on digital expression of the genes, as described above. The digital expression represents the distribution of the ESTs composing each in silico gene and the deviation of the actual distribution from random distribution. The genes were selected based on three criteria: genes with higher expression in roots, roots and leaves and/or induced by treatments representing soil stress conditions (drought, salinity, soil deficiencies). An increase in expression was considered only in cases were greater than 2 folds (relative to the random EST distribution) increase was evident with significance probability lower than 0.05. Table 2 below summarizes the expression profile of the genes in different organ or tissues and the treatments that set off significant elevation in their expression level.

TABLE 1

The level of homology between the tomato ABST genes and their homologes genes from monocot.

| Tomato gene SEQ ID NO | TIGR Name/ Acc No of Homologous gene | Plant origin | Level of homology (e value) | % Identity (Percentage from the entire protein sequence) |
|---|---|---|---|---|
| 122 | TC104838 SEQ ID NO 1 | Sorghum | 2E-70 | 88% |
| | TC103857 | Sorghum | 2E-70 | 88% |
| | TC258871 | Maize | 1E-69 | 86% |
| | TC139195 | Barley | 5E-69 | 86% |
| 123 | TC94284 SEQ ID NO 3 | Sorghum | 3E-43 | 45% |
| | TC132394 | Barley | 6E-40 | 44% |
| 124 | TC102291 SEQ ID NO 5 | Sorghum | 1E-72 | 54% |
| | TC146720 | Barley | 3E-99 | 58% |
| 125 | TC92953 SEQ ID NO 7 | Sorghum | 7E-59 | 47% |
| | TC91426 SEQ ID NO 9 | Sorghum | 4E-98 | 74% |
| | TC91474 | Sorghum | 5E-98 | 72% |
| | TC263205 | Maize | 2E-97 | 74% |
| 126 | TC103772 SEQ ID NO 11 | Sorghum | 1E-52 | 49% |
| | TC148356 | Barley | 1E-54 | 46% |
| | TC260731 | Maize | 1E-54 | 46% |

TABLE 2

The expression profile of the ABST homologous in silico genes as it represented by statistical analysis of their ESTs distribution

| Name of Homologous gene | Plant species | Organs/tissues with the highest gene expression | Fold increase (All results are significant in P value > 0.05) | Treatments that induce th expression level | Fold increase (all results are significant in P value > 0.05) |
|---|---|---|---|---|---|
| TC104838 SEQ ID NO 1 | Sorghum | Pollen pre anthesis stage | 3 | Ethylene, drought | 2 |
| TC103857 | Sorghum | Diverse expression | 2 | None* | None* |
| TC258871 | Maize | Diverse expression, preferentially in cell lignification region of leaves | 2 | None* | None* |
| TC139195 | Barley | In various grain tissues | 2-3.5 | None | None |
| TC94284 SEQ ID NO 3 | Sorghum | Leaves, roots during fruit loading | 4.5 2 | Drought, nitrogen deficiencies, soil acidity | 4 2 2 |
| TC132394 | Barley | Leaves, coleoptile mainly during fruit development | 2.5 3 | None | None |
| TC102291 SEQ ID NO 5 | Sorghum | Callus and cell suspension | 3 | Salinity and drought stress | 3 |
| TC146720 | Barley | Seeds preferentially in the embryo and scutellum during ripening | 2 | Cold stress, Fusarium infection | 3 3.5 |
| TC92953 SEQ ID NO 7 | Sorghum | Leaves during fruit loading | 2 | Drought, Nitrogen-deficiency, salinity (150 Mm) | 4 4 2.5 |
| TC91426 SEQ ID NO 9 | Sorghum | Young roots | 12 | Ethylene, etiolation, soil acidity | 4 3 12 |
| TC91474 | Sorghum | Entire seedling | 2 | Etiolation | 16 |
| TC263205 | Maize | Primary root system in seedling stage | 3 | Drought | 2 |
| TC103772 SEQ ID NO 11 | Sorghum | Young roots | 2 | Drought, soil acidity | 2 2 |
| TC148356 | Barley | Callus, leaves in the vetatative stage | 4, 2 | Infection by Blumeria graminis | 2 |

TABLE 2-continued

The expression profile of the ABST homologous in silico genes as it represented by statistical analysis of their ESTs distribution

| Name of Homologous gene | Plant species | Organs/tissues with the highest gene expression | Fold increase (All results are significant in P value > 0.05) | Treatments that induce th expression level | Fold increase (all results are significant in P value > 0.05) |
|---|---|---|---|---|---|
| TC260731 | Maize | Root preferntialy primary roots | 2.5 | None | None |

None* - None of the treatments with significant elevation in digital expression could be considered as soil stress treatment Combination of the above screening as it is described in Table 1 and in Table 2 above revealed the final list of five monocot genes that are predicted to be the most related to the tomato ABST genes (SEQ ID NOs. 1, 3, 5, 7, 9).

The selected polynucleotide sequences (Table 3 below) were analyzed for presence of ORFs using Vector NTI suite (InforMax, U.K.) version 6 (Hasting Software, Inc: World Wide Web (dot) generunner (dot) com/). ORFs identified in each of these polynucleotide sequences were compared to Genbank database sequences, using Blast (World Wide Web (dot) ncbi (dot) nlm (dot) nih (dot) gov/BLAST/); the ORF displaying the highest homology to a GenBank sequence or sequences, was mapped in order to identify an ATG start codon. The position of the ATG start codon of this ORF was then compared with that of the identified polynucleotide sequence in order to verify that each of the five sequences described herein includes a full length ORF and an ATG start codon (thus qualifies as a "putative monocot ABST gene").

TABLE 3

| Monocot ABST genes | | |
|---|---|---|
| Tomato ABST SEQ ID NO. | Artificially Homologous Monocot ABST Gene SEQ ID NO: | optimized ABST* Gene SEQ ID NO: |
| 122 | 1 | 156 |
| 123 | 3 | 157 |
| 124 | 5 | 158 |
| 125 | 7 | |
| 125 | 9 | |
| 126 | 11 | 159 |

*Further described in Example 2 below.

Polypeptides with significant homology to the Monocot ABST genes have been identified from the NCBI databases using BLAST software (Table 4).

TABLE 4

ABST homologues

| Monocot ABST Putative Gene SEQ ID No. | ABST Polypeptide Homologue, encoded by TIGR Acession No/SEQ ID NO: | Source Organism | ABST Polypeptide Homologue SEQ ID No. | Homology in Polypeptide sequence (%) |
|---|---|---|---|---|
| 1 | TC270110/160 | Zea mays | 13 | 100 |
| 1 | TC56855/161 | Saccharum officinarum | 14 | 100 |
| 1 | TC104838/162 | sorghum | 15 | 100 |
| 1 | TC57929/163 | Saccharum officinarum | 16 | 98 |
| 1 | TC103857/164 | sorghum | 17 | 98 |
| 1 | TC262554/165 | Oryza sativa | 18 | 98 |
| 1 | TC258871/166 | Zea mays | 19 | 97 |
| 1 | TC139195/167 | Hordeum vulgare | 20 | 96 |
| 1 | TC262556/168 | Oryza sativa | 21 | 95 |
| 1 | TC232174/169 | Triticum aestivum | 22 | 95 |
| 1 | TC232139/170 | Triticum aestivum | 23 | 95 |
| 1 | TC139194/171 | Hordeum vulgare | 24 | 95 |
| 1 | CA486561/172 | Triticum aestivum | 25 | 100 |
| 1 | TC258873/173 | Zea mays | 26 | 100 |
| 1 | CA187014/174 | Saccharum officinarum | 27 | 90 |
| 1 | TC233455/175 | Triticum aestivum | 28 | 96 |
| 1 | CF063450/176 | Zea mays | 29 | 98 |
| 1 | CA617041/177 | Triticum aestivum | 30 | 100 |
| 3 | TC94284/178 | sorghum | 31 | 100 |
| 3 | TC49791/179 | Saccharum officinarum | 32 | 95 |
| 180 | TC93449/180 | sorghum | 33 | 100 |
| 180 | TC49718/181 | Saccharum officinarum | 34 | 95 |
| 180 | TC49720/182 | Saccharum officinarum | 35 | 96 |
| 7 | TC92953/183 | sorghum | 36 | 100 |
| 7 | TC66617/184 | Saccharum officinarum | 37 | 90 |
| 7 | TC273860/185 | Zea mays | 38 | 91 |
| 7 | TC253191/186 | Zea mays | 39 | 90 |
| 11 | TC103772/187 | sorghum | 40 | 100 |
| 11 | TC272084/188 | Zea mays | 41 | 92 |

TABLE 4-continued

ABST homologues

| Monocot ABST Putative Gene SEQ ID No. | ABST Polypeptide Homologue, encoded by TIGR Acession No/SEQ ID NO: | Source Organism | ABST Polypeptide Homologue SEQ ID No. | Homology in Polypeptide sequence (%) |
|---|---|---|---|---|
| 11 | TC60928/189 | Saccharum officinarum | 42 | 94 |
| 1 | TC5422/190 | canola | 43 | 88 |
| 1 | TC904/191 | canola | 44 | 88 |
| 1 | TC121774/192 | Solanum tuberosum | 45 | 88 |
| 1 | TC40342/193 | Gossypium | 46 | 88 |
| 1 | TC40115/194 | Gossypium | 47 | 88 |
| 1 | TC155918/195 | Lycopersicon esculentum | 48 | 88 |
| 1 | TC154398/196 | Lycopersicon esculentum | 49 | 88 |
| 1 | TC154397/197 | Lycopersicon esculentum | 50 | 88 |
| 1 | TC153989/198 | Lycopersicon esculentum | 51 | 88 |
| 1 | TC120511/199 | Solanum tuberosum | 52 | 88 |
| 1 | TC113582/200 | Solanum tuberosum | 53 | 88 |
| 1 | TC112701/201 | Solanum tuberosum | 54 | 88 |
| 1 | TC111912/202 | Solanum tuberosum | 55 | 88 |
| 1 | TC4674/203 | Capsicum annum | 56 | 88 |
| 1 | TC270923/204 | arabidopsis | 57 | 87 |
| 1 | CD823817/205 | canola | 58 | 86 |
| 1 | TC526/206 | canola | 59 | 86 |
| 1 | TC525/207 | canola | 60 | 86 |
| 1 | BG442528/208 | Gossypium | 61 | 87 |
| 1 | TC33702/209 | Gossypium | 62 | 87 |
| 1 | TC32714/210 | Gossypium | 63 | 87 |
| 1 | TC270782/211 | arabidopsis | 64 | 87 |
| 1 | TC225449/212 | Glycine max | 65 | 87 |
| 1 | TC5255/213 | Capsicum annum | 66 | 88 |
| 1 | TC28221/214 | populus | 67 | 84 |
| 1 | TC108140/215 | medicago | 68 | 85 |
| 1 | TC28222/216 | populus | 69 | 84 |
| 1 | TC94402/217 | medicago | 70 | 84 |
| 1 | TC28223/218 | populus | 71 | 83 |
| 1 | TC102506/219 | medicago | 72 | 85 |
| 1 | NP890576/222 | Oryza sativa | 73 | 76 |
| 1 | TC280376/223 | Oryza sativa | 74 | 73 |
| 1 | CN009841/224 | Triticum aestivum | 75 | 75 |
| 1 | BI948270/225 | Hordeum vulgare | 76 | 75 |
| 1 | TC259334/226 | arabidopsis | 77 | 75 |
| 1 | BQ767154/227 | Hordeum vulgare | 78 | 73 |
| 1 | TC60345/228 | Saccharum officinarum | 79 | 73 |
| 1 | TC138474/229 | Hordeum vulgare | 80 | 85 |
| 1 | TC41472/230 | populus | 81 | 72 |
| 1 | BJ458177/231 | Hordeum vulgare | 82 | 72 |
| 1 | CB674176/232 | Oryza sativa | 83 | 82 |
| 1 | TC216405/233 | Glycine max | 84 | 88 |
| 1 | AJ777371/234 | populus | 85 | 70 |
| 1 | CV019213/235 | tobacco | 86 | 85 |
| 1 | CK215690/236 | Triticum aestivum | 87 | 80 |
| 1 | CD830784/237 | canola | 88 | 85 |
| 1 | CA624722/238 | Triticum aestivum | 89 | 85 |
| 1 | TC32906/239 | populus | 90 | 76 |
| 1 | CR285127/240 | Oryza sativa | 91 | 89 |
| 1 | TC251945/241 | Triticum aestivum | 92 | 72 |
| 3 | TC274823/242 | Oryza sativa | 93 | 77 |
| 3 | TC132394/243 | Hordeum vulgare | 94 | 75 |
| 3 | TC267180/244 | Triticum aestivum | 95 | 77 |
| 3 | TC261921/245 | Zea mays | 96 | 87 |
| 3 | TC267181/246 | Triticum aestivum | 97 | 74 |
| 3 | TC261922/247 | Zea mays | 98 | 81 |
| 3 | TC267182/248 | Triticum aestivum | 99 | 73 |
| 180 | TC249531/249 | Zea mays | 100 | 86 |
| 180 | TC232170/250 | Triticum aestivum | 101 | 85 |
| 180 | TC146720/251 | Hordeum vulgare | 102 | 85 |
| 180 | TC249329/252 | Oryza sativa | 103 | 84 |
| 180 | TC249532/253 | Zea mays | 104 | 88 |
| 180 | TC232150/254 | Triticum aestivum | 105 | 85 |
| 180 | TC249330/255 | Oryza sativa | 106 | 76 |
| 180 | CB672603/256 | Oryza sativa | 107 | 71 |
| 180 | TC32440/257 | Gossypium | 108 | 81 |
| 180 | TC119105/258 | Solanum tuberosum | 109 | 72 |
| 7 | TC247999/259 | Triticum aestivum | 110 | 78 |
| 7 | TC247359/260 | Triticum aestivum | 111 | 77 |

TABLE 4-continued

ABST homologues

| Monocot ABST Putative Gene SEQ ID No. | ABST Polypeptide Homologue, encoded by TIGR Acession No/SEQ ID NO: | Source Organism | ABST Polypeptide Homologue SEQ ID No. | Homology in Polypeptide sequence (%) |
|---|---|---|---|---|
| 7 | TC132566/261 | Hordeum vulgare | 112 | 77 |
| 7 | TC248676/262 | Triticum aestivum | 113 | 74 |
| 7 | TC249667/263 | Oryza sativa | 114 | 77 |
| 7 | TC66618/264 | Saccharum officinarum | 115 | 88 |
| 11 | TC253495/282 | Oryza sativa | 116 | 78 |
| 11 | TC267485/283 | Triticum aestivum | 117 | 77 |
| 11 | TC148621/284 | Hordeum vulgare | 118 | 76 |
| 11 | TC275474/285 | Oryza sativa | 119 | 85 |
| 9 | TC275473/265 | Oryza sativa | 139 | 89 |
| 9 | TC224823/266 | Glycine max | 140 | 75 |
| 9 | TC234990/267 | Triticum aestivum | 141 | 74 |
| 9 | TC266178/268 | Triticum aestivum | 142 | 73 |
| 9 | TC119051/266 | Solanum tuberosum | 143 | 64 |
| 9 | TC56409/270 | Saccharum officinarum | 144 | 75 |
| 9 | TC35873/271 | Populus | 145 | 80 |
| 9 | TC119052/272 | Solanum tuberosum | 146 | 82 |
| 9 | TC204518/273 | Glycine max | 147 | 85 |
| 9 | TC112169/274 | Solanum tuberosum | 148 | 84 |
| 9 | TC254696/275 | Zea mays | 149 | 70 |
| 9 | TC254696/276 | Zea mays | 150 | 70 |
| 9 | TC248906/277 | Oryza sativa | 151 | 75 |
| 9 | TC154007/278 | Lycopersicon esculentum | 152 | 82 |
| 9 | TC6466/279 | Capsicum annuum | 153 | 74 |
| 9 | TC131227/280 | Hordeum vulgare | 154 | 74 |
| 9 | TC27564/281 | Gossypium | 155 | 71 |

Example 2

Generating the Putative Monocot ABST Genes

DNA sequences of the monocot ABST genes were synthesized by GeneArt (Hypertext Transfer Protocol://World Wide Web (dot) geneart (dot) com/). Synthetic DNA was designed in silico, based on the encoded amino-acid sequences of the monocot ABST genes (SEQ ID Nos 2, 4, 6, 12) and using codon-usage tables calculated from plant transcriptomes (example of such tables can be found in the Codon Usage Database available online at Hypertext Transfer Protocol://World Wide Web (dot) kazusa (dot) or (dot) jp/codon/). The optimized coding sequences are designed in a way that no changes are introduced in the encoded amino acid sequence while using codons preferred for expression in dicotyledonous plants (mainly tomato and *Arabidopsis*) and monocotyledonous plants such as maize. At least one silent mutation per 20 nucleotide base pairs was introduced in the sequence compared to the orthologous monocot sequences to avoid possible silencing when over-expressing the gene in monocot species such as maize. To the optimized sequences the following restriction enzymes sites were added—SalI, XbaI, BamHI, SmaI at the 5' end and SacI at the 3' end. The sequences synthesized by the supplier (GeneArt, Gmbh) were cloned in the pCR-Script plasmid. The resulting sequences are SEQ ID Nos 158, 159, 160, 161; representing the original monocot ABST SEQ ID Nos 1, 3, 5, 11 respectively, as described in Table 3, above.

Example 3

Cloning the Putative ABST Genes

The PCR Script plasmids harboring the synthetic, monocot-based ABST genes were digested with the restriction endonucleases XbaI and SacI (Roche). The resulting fragment was purified using Gel extraction Kit (Qiagen, Germany) and ligated using T4 DNA ligase enzyme (Roche) into the plant expression vector pKG(NOSter), (SEQ ID NO 136), excised with the same enzymes. pKG plasmid is based on the PCR Script backbone, with several changes in the polylinker site to facilitate the cloning of genes of interest downstream to a promoter and upstream to a terminator suitable for expression in plant cells. As a result, the inserted gene, together with the promoter and the terminator can be easily moved to a binary vector.

The resulting pKG(NOSter) harboring putative monocot ABST genes were introduced to *E. coli* DH5 competent cells by electroporation, using a MicroPulser electroporator (Biorad), 0.2 cm cuvettes (Biorad) and EC-2 electroporation program (Biorad). The treated cells were cultured in LB liquid medium at 37° C. for 1 hr, then plated over LB agar supplemented with ampicillin (100 mg/L) and incubated at 37° C. for 16 hrs. Colonies that developed on the selective medium were analyzed by PCR using the primers of SEQ ID NO 132 and SEQ ID NO 133 which were designed to span the inserted sequence in the pKG plasmids. The resulting PCR products were separated on 1% agarose gels and "PCR-positive" colonies labeled and further grown. DNA from positive colonies was isolated using (Qiagen) and sequenced using the ABI 377 sequencer (Amersham Biosciences Inc) to verify the lack of mutations in the final sequence.

The At6669 promoter sequence (set forth in SEQ ID NO: 121) was inserted in all the pKG(NOSter) plasmids harboring putative Monocot ABST genes using the restriction enzymes HindIII and SalI (Roche). Colonies were analyzed by PCR using the primers SEQ ID NO: 138 and SEQ ID NO: 133. Positive plasmids were identified, isolated and sequenced as described above.

Example 4

Generating Binary Vectors Comprising Putative Monocot ABST Genes and Plant Promoters for Driving Expression Thereof Generating binary vectors comprising the At6669 promoter: The four pKG(At6669+NOSter) constructs harboring putative Monocot ABST genes downstream to At6669 promoter sequence (set forth in SEQ ID NO: 121), and upstream to the Nopaline Synthase (NOS) terminator, were digested with HindIII and EcoRI (Roche) in order to excise the expression cassettes that were ligated into pGI plasmid digested with the same restriction endonucleases. Altogether, four pGI constructs were generated, each comprising the At6669 promoter positioned upstream of a putative Monocot ABST gene having a sequence set forth in SEQ ID NO: 1,3,5, 11.

The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Acc. No. U12640). In some cases the backbone binary plasmid used was pGI which is similar to pPI but the GUS gene was replaced by the GUS-Intron gene (Vancanneyt. G, et al MGG 220, 245-50, 1990).

The At6669 promoter was isolated from *Arabidopsis thaliana* var Co10 genomic DNA by PCR amplification using the primers set forth in SEQ ID NOs: 134 and 135. The PCR product was purified (Qiagen, Germany) and digested with the restriction endonucleases HindIII and SalI (Roche). The resulting promoter sequence was introduced into the open binary pPI vector digested with the same enzymes, to produce pPI+At6669 plasmid.

Example 5

Transforming *Agrobacterium tumefaciens* Cells with Binary Vectors Harboring Putative Monocot ABST Genes Each of the binary vectors described in Example 4 above were used to transform *Agrobacterium* cells. Two additional binary constructs, having the Luciferase reporter gene replacing the Monocot ABST gene (positioned downstream of the 35S or At6669 promoter), were used as negative controls.

The binary vectors were introduced to *Agrobacterium tumefaciens* GV301, or LB4404 competent cells (about $10^9$ cells/mL) by electroporation. The electroporation was effected by using a MicroPulser electroporator (Biorad), 0.2 cm cuvettes (Biorad) and EC-2 electroporation program (Biorad). The treated cells were cultured in LB liquid medium at 28° C. for 3 hr, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hrs. *Agrobacterium* colonies which developed on the selective media were analyzed by PCR using the primers set forth in SEQ ID NOs: 132 and 138, which were designed to span the inserted sequence in the pPI plasmid. The resulting PCR products were isolated and sequenced as described in Example 4 above, to verify that the correct ABST sequences were properly introduced to the *Agrobacterium* cells.

Example 6

Transformation of *Arabidopsis thaliana* Plants with Putative Monocot ABST Genes

*Arabidopsis thaliana* Columbia plants ($T_0$ plants) were transformed using the Floral Dip procedure described by Clough and Bent (10) and by Desfeux et al. (11), with minor modifications. Briefly, $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hr light/dark cycles. The $T_0$ plants were ready for transformation six days before anthesis.

Single colonies of *Agrobacterium* carrying the binary constructs, were generated as described in Example 5 above. Colonies were cultured in LB medium supplemented with kanamycin (50 mg/L) and gentamycin (50 mg/L). The cultures were incubated at 28° C. for 48 hrs under vigorous shaking and then centrifuged at 4000 rpm for 5 minutes. The pellets comprising *Agrobacterium* cells were re-suspended in a transformation medium containing half-strength (2.15 g/L) Murashige-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was effected by inverting each plant into an *Agrobacterium* suspension, such that the above ground plant tissue was submerged for 3-5 seconds. Each inoculated $T_0$ plant was immediately placed in a plastic tray, then covered with clear plastic dome to maintain humidity and was kept in the dark at room temperature for 18 hrs, to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry. Seeds were harvested from plants and kept at room temperature until sowing.

For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ *Arabidopsis* plants were transferred to a fresh culture plates for another week of incubation. Following incubation the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 7

Evaluating Germination of Transgenic Plants Cultivated Under Abiotic Stress Conditions Tolerance to salinity or osmotic stress is aimed at identifying genes that confer better germination, seedling vigor or growth in high salt, drought or combination of these or other environmental stresses. Plants differ in their tolerance to salt (NaCl) depending on their stage of development, therefore seed germination, seedling vigor, and plant growth responses are evaluated.

A typical salinity tolerance test is effected by taking plants at different developmental stages and irrigating them with increasing concentrations of NaCl (for example 50 mM, 100 mM, 200 mM, 400 mM). Transgenic plants are compared to control plants in their external phenotypic appearance, degree of wilting, and overall success to reach maturity and yield progeny at concentrations inhibitory to control plants. Quantitative parameters of tolerance measured are as for the previous case, the average wet and dry weight, and the weight of the seeds yielded, the average seed size and the number of seeds produced per plant. Osmotic stress assays (including NaCl and mannitol assays) are conducted to determine if an osmotic stress tolerant phenotype is NaCl-specific or if it is a general osmotic stress related phenotype. Plants tolerant to osmotic stress are in general more tolerant to drought, salinity and freezing conditions and therefore are highly valuable in terms of agronomic traits.

Methods:

The method used to test the plants for improved abiotic stress tolerance includes the test of germination and seedling growth under adverse conditions such as high salinity and high osmoticum.

Germination assay—Germination tests compare the percentage of seeds from transgenic plants that could complete the germination process (radicle protrusion from the seed coat and complete opening of the cotyledons) to the percentage of seeds from control plants treated in the same manner. Evaluation of germination and seedling vigor is conducted for three weeks after planting. To measure germination and seedling growth, seeds from T2 plants are surface sterilized and individually sown on square agar plates containing for example, solidified basal media supplemented with high salinity (for example 50 mM, 100 mM, 200 mM, 400 mM) or high osmoticum (for example 50 mM, 100 mM, 200 mM, 400 mM mannitol). The basal media is 50% Murashige-Skoog medium (MS)+vitamins supplemented with 0.8% plant agar as solidifying agent. After sowing, plates are transferred for 2-3 days at 4° C. for stratification and then grown for three weeks.

To follow the germination and growth at adverse conditions plates are screened manually or automatically and plant size is determined. Five to ten independent transformation events can be analyzed from each construct. Plants expressing the genes from this invention are compared to control plants sown on the same plates under the same conditions or to the average measurement of all the constructs, seeds and events sown.

Example 8

Evaluating Transgenic Plant Growth Under Abiotic Stress Conditions

Methods:

Stress resistance and analysis—A complementary experiment performed with seedlings follows the tolerance of the plants to adverse conditions. Surface sterilized seeds are sown in basal media [50% Murashige-Skoog medium (MS)+vitamins supplemented with 0.8% plant agar as solidifying agent] in the presence of Kanamycin (for transgenic plants) or in its absence (for wild-type control plants). After sowing, plates were transferred for 2-3 days at 4° C. for stratification and then grown at 25° C. under 23-hour light 1-hour dark daily cycles for 7 to 10 days. At this time point, seedlings randomly chosen were carefully transferred to plates containing high salinity conditions (150 mM NaCl) or conditions resembling the high osmolarity found during drought (210 mM mannitol). Plant growth was followed as a function of time using digital imaging. To follow the plant growth at adverse conditions plants were photographed the day they were transferred to the stress conditions (Day 0). Pictures were subsequently taken every few days after transferring the plants to the stress condition and up to 12 days after the transfer. Plant size was determined from the digital pictures taken. ImageJ software was used for quantitate the plant size from the digital pictures (Hypertext Transfer Protocol://rsb (dot) info (dot) nih (dot) gov/ij/). Proprietary scripts were designed to analyze the size of individual plants as a function of time. FIG. 1 shows the methodology used for image area quantitation. Five to ten independent transformation events were analyzed from each construct and at least 6 randomly selected plants from each event were analyzed in each stress experiment. Plants expressing the genes from this invention were compared either to control plants sown on the same stress inducing plates (internal controls) or to the average measurement of all the control plants used in the same experiment (all controls).

Statistical analysis—To identify genes conferring tolerance to plants showing significant differences, plant area data was analyzed using the JMP statistics program (Version 5.2.1, SAS Institute Inc., Cary, N.C., USA). A one-way ANOVA (ANalysis Of VAriance) was used in order to detect the variation between the different genes (populations of independent events) and control plants and identify constructs and events showing statistically different outstanding performance. For gene versus control analysis a Students t-test was employed, using significance of p<0.05. In order to find significantly different independent transformation events with increased plant area the Tukey's HSD (Honestly Significantly Different) test was employed using significance of p<0.05. Two-way ANOVA was used to identify events that showed significant differences in plant area at certain day points compared to the mean area of control plants growing either in the same plates or in all plates of the same experiment. The Student's t-test was utilized to compare independent transformation events to control plants.

Results:

In order to identify genes providing tolerance to salinity or osmoticum, T2 plants were generated from 5 to 10 independent transgenic events from each construct. The seeds were collected from the T2 plants and plants produced therefrom were analyzed. As detailed above the plants were sown on a selective medium in which transgenic plants are able to strive (kanamycin) and after 7-10 days (4-6 leaves stage) the plants were transferred to a stress producing media: high salinity (150 mM) or high osmoticum (210 mM mannitol). Plants size was analyzed since the day of the transfer and up to 12 days thereon. Student's t-test and Tukey HSD test were used to identify the events that show outstanding performance compared to wild type plants.

The results of the transgenic plants expressing SEQ ID Nos 156, 157, 158, 159; representing the original monocot ABST SEQ ID Nos 1, 3, 5, 11 respectively, as described in Table 4 above under the At6669 promoter (Seq ID 121) are shown. Significant differences were found in the ability of the transgenic plants to grow in the presence of a high salinity stress and/or high osmoticum stress. Table 5 below summarizes the findings of outstanding events conferring tolerance to osmotic stress in comparison to control plants. Various constructs included in this application provide the transgenic plants with an improved ability to resist to abiotic stresses.

Figure 2:
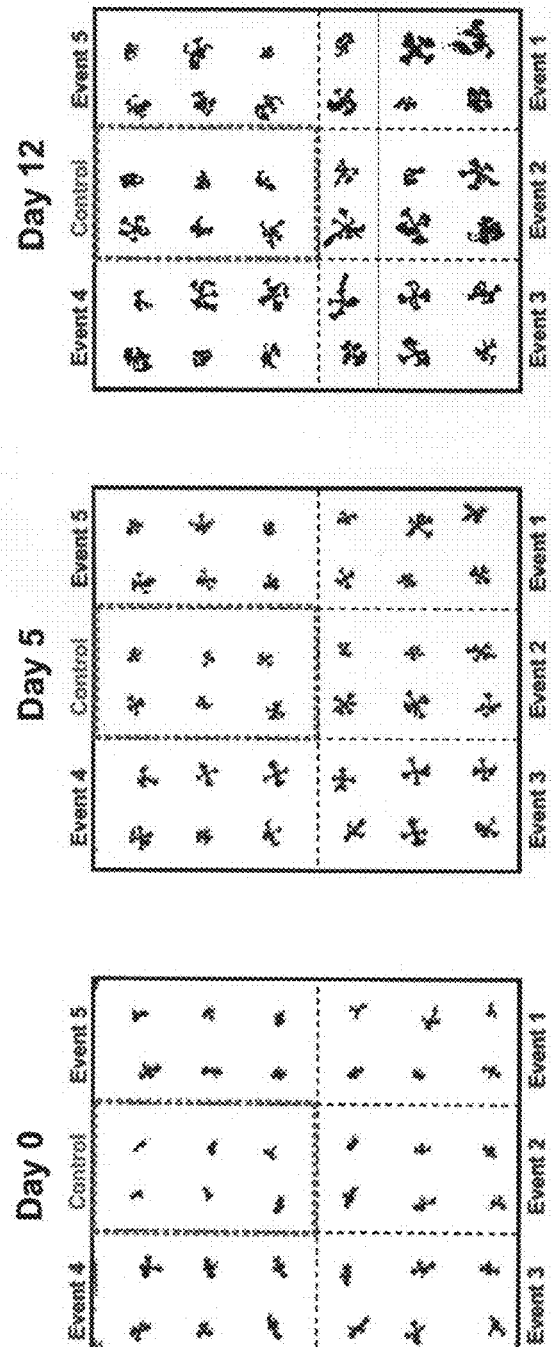
FIGS. 2A-B are representative results of a gene (SEQ ID 156) that confers abiotic stress tolerance uncovered according to the teachings of the present invention.
Figure 2:
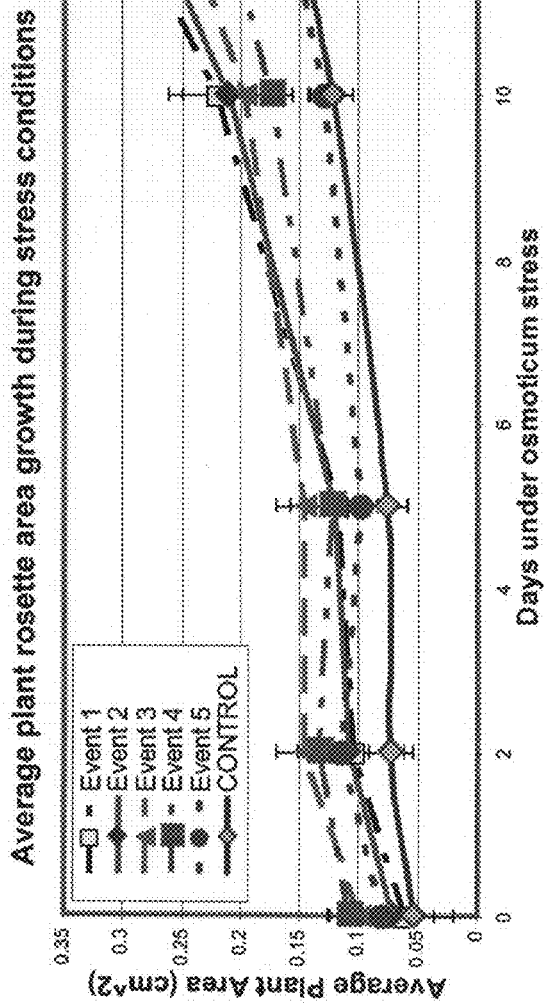

As shown, 4 out of 5 transformation events expressing SEQ ID 156 show significantly improved tolerance to osmoticum as judged by the ability of the transgenic plants to continue developing also at high osmoticum concentration (see Table 5, rows 1-5). The results obtained for SEQ ID 156 are also shown in FIG. 2. In panel A are shown processed images taken at day 0, 5 and 12 from the plate that contained the transgenic and control plants. Panel B shows the average plant area of the different events at the different time points. Events 1, 2, 3 and 4 are significantly more tolerant to osmoticum (p<0.05). Other constructs from this application also protect plants from the effects of high osmoticum. Again, four out of five independent transformation events expressing SEQ ID 159 showed significant increased capacity to grow under high osmoticum conditions (Table 5 below, rows 6-10). In addition, one of the events expressing SEQ ID 158 showed significantly high tolerance to high osmoticum than its corresponding control plants.

Independent experiments that assess the ability of the constructs to provide salinity and high osmoticum tolerance were carried out as part of this study. Genes were found to protect transgenic plants against the deleterious effects of both stresses. Taken as a whole the results clearly demonstrate the ability of the genes and constructs included in this application to provide abiotic stress tolerance.

TABLE 5

LS mean of $T_2$ transgenic *Arabidopsis* plants grown in the presence of 210 mM mannitol

| Row number | Transgene (SEQ ID NO) | Event No | Number of plants tested | Least Square Mean of areas measured ($cm^2$) | Std Error |
|---|---|---|---|---|---|
| 1 | 156 | Event 1 | n = 6 | 0.1635 | 0.0091 |
| 2 | 156 | Event 2 | n = 6 | 0.1566 | 0.0091 |
| 3 | 156 | Event 3 | n = 6 | 0.1547 | 0.0091 |
| 4 | 156 | Event 4 | n = 6 | 0.1480 | 0.0091 |
| 5 | CONTROL of events 1-4 SEQ ID 156, and event 1, SEQ ID 158 | — | n = 6 | 0.1150 | 0.0091 |
| 6 | 158 | Event 1 | n = 6 | 0.1141 | 0.0050 |
| 7 | 159 | Event 2 | n = 6 | 0.1104 | 0.0050 |
| 8 | 159 | Event 3 | n = 6 | 0.1020 | 0.0050 |
| 9 | 159 | Event 4 | n = 6 | 0.0824 | 0.0050 |
| 10 | CONTROL of Event 1-4 SEQ ID 159 | — | n = 6 | 0.0681 | 0.0050 |
| 11 | 158 | Event 1 | n = 6 | 0.1703 | 0.0090 |

The results of salinity tolerance tests are summarized in Table 6 below. As detailed in Table 6 (rows 1-4), three independent transgenic events with a construct containing SEQ ID 156 exhibited a significantly higher tolerance to salinity stress than the control plants in the experiment (p<0.05). Similar results were obtained with plants expressing SEQ ID 159. Also in this case, three different transgenic events showed significant increased tolerance to salinity stress compared to their matching control plants (see Table 6, rows 5-9).

Example 9

Evaluating Changes in Root Architecture Due to the Expression of Monocot ABST Genes Many key traits in modern agriculture can be explained by changes in the root architecture. Root size and depth correlates with drought tolerance and fertilizer use efficiency. Deeper root systems can access water in stored in deeper soil

TABLE 6

LS mean of $T_2$ transgenic *Arabidopsis* plants grown in the presence of 150 mM NaCl

| Row number | Transgene (SEQ ID NO) | Promoter | Number of plants tested | Least square Mean of areas measured ($cm^2$) | Std Error |
|---|---|---|---|---|---|
| 1 | 156 | Event 1 | n = 6 | 0.3146 | 0.0112 |
| 2 | 156 | Event 2 | n = 6 | 0.2459 | 0.0112 |
| 3 | 156 | Event 3 | n = 6 | 0.2445 | 0.0112 |
| 4 | CONTROL of all events SEQ ID 156 | — | n = 48 | 0.2165 | 0.003722 |
| 5 | 159 | Event 1 | n = 6 | 0.2541 | 0.0110 |
| 6 | CONTROL of Event 1 SEQ ID 159 | — | n = 6 | 0.2154 | 0.0110 |
| 7 | 159 | Event 2 | n = 6 | 0.2278 | 0.0122 |
| 8 | 159 | Event 3 | n = 6 | 0.2261 | 0.0122 |
| 9 | CONTROL of Event 2 and Event 3 SEQ ID 159 | — | n = 6 | 0.1906 | 0.0122 | layers. Similarly, a highly branched root system provides better coverage of the soil and therefore can effectively absorb all macro and micronutrients available resulting in enhanced fertilizer use efficiency. To test whether the transgenic plants produce a different root structure, plants are grown in agar plates placed vertically. Plates are photographed every few days and the size, length and area covered by the plant roots is assessed. From every construct created, several independent transformation events are checked. To assess significant differences between root features, it is possible to apply one and two-way ANOVA using Students t-test or Tukey HSD test to identify the events showing outstanding root features and to provide a statistical score to the findings (see Example 8 above).

Example 10

Increased Biomass of the Transgenic Plants of the Present Invention $T_1$ or $T_2$ transgenic plants generated as described above are individually transplanted into pots containing a growth mixture of peat and vermiculite (volume ratio 3:2, respectively). The pots are covered for 24 hr period for hardening, then placed in the greenhouse in complete random order and irrigated with tap water (provided from the pots' bottom every 3-5 days) for seven days. Thereafter, half of the plants are irrigated with a salt solution (100 mM NaCl and 5 mM $CaCl_2$) to induce salinity stress (stress conditions). The other half of the plants are continued to be irrigated with tap water (normal conditions). All plants are grown in the greenhouse at 100% RH for 28 days, then harvested (the above ground tissue) and weighted (immediately or following drying in oven at 50° C. for 24 hr).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent or patent application or sequence identified by their accession number was specifically and individually indicated to be incorporated herein by reference. In addition, citation or identification of any reference in this application shall not be construed as an admission that such reference is available as prior art to the present invention.

REFERENCES CITED

Additional References are Cited Hereinabove

1. World Wide Web (dot) fao (dot) org/agl/agll/spush/degrad (dot) htm.
2. World Wide Web (dot) fao (dot) org/ag/agl/aglw/water-management/introduc (dot) stm
3. McCue K F, Hanson A D (1990). Drought and salt tolerance: towards understanding and application. Trends Biotechnol 8: 358-362.
4. Flowers T J, Yeo A r (1995). Breeding for salinity resistance in crop plants: where next? Aust J Plant Physiol 22:875-884.
5. Nguyen B D, Brar D S, Bui B C, Nguyen T V, Pham L N, Nguyen H T (2003). Identification and mapping of the QTL for aluminum tolerance introgressed from the new source, ORYZA RUFIPOGON Griff., into indica rice (*Oryza sativa* L.). Theor Appl Genet. 106:583-93.
6. Sanchez A C, Subudhi P K, Rosenow D T, Nguyen H T (2002). Mapping QTLs associated with drought resistance in *sorghum* (*Sorghum bicolor* L. Moench). Plant Mol Biol. 48:713-26.
7. Quesada V, Garcia-Martinez S, Piqueras P, Ponce M R, Micol J L (2002). Genetic architecture of NaCl tolerance in *Arabidopsis*. Plant Physiol. 130:951-963.
8. Apse M P, Blumwald E (2002). Engineering salt tolerance in plants. Curr Opin Biotechnol. 13:146-150.
9. Rontein D, Basset G, Hanson A D (2002). Metabolic engineering of osmoprotectant accumulation in plants. Metab Eng 4:49-56
10. Clough S J, Bent A F (1998). Floral dip: a simplified method for *Agrobacterium*-mediated transformation of *Arabidopsis thaliana*. Plant J 16:735-43.
11. Desfeux C, Clough S J, Bent A F (2000). Female reproductive tissues are the primary target of *Agrobacterium*-mediated transformation by the *Arabidopsis* floral-dip method. Plant Physiol 123:895-904.

What is claimed is:

1. A method of increasing tolerance of a plant to an abiotic stress by at least 2% as compared to the tolerance of a non-transgenic plant to the abiotic stress, comprising transforming the plant with an exogenous polynucleotide encoding a polypeptide having the amino acid sequence set forth by SEQ ID NO: 12, expressing said polypeptide within the transformed plant, and thereby increasing the tolerance of the plant to the abiotic stress.

2. The method of claim 1, wherein said abiotic stress is selected from the group consisting of salinity, water deprivation, low temperature, high temperature, heavy metal toxicity, anaerobiosis, nutrient deficiency, nutrient excess, atmospheric pollution and UV irradiation.

3. The method of claim 1, wherein said plant is a dicotyledonous plant.

4. The method of claim 1, wherein said plant is a monocotyledonous plant.

5. The method of claim 1, wherein said polynucleotide comprises the nucleic acid sequence set forth by SEQ ID NO: 11.

6. A nucleic acid construct, comprising the nucleic acid sequence set forth by SEQ ID NO: 11, and a promoter capable of directing transcription of said nucleic acid sequence in a host cell.

7. The nucleic acid construct of claim 6, wherein said promoter is a constitutive promoter.

8. The nucleic acid construct of claim 6, wherein said promoter is an inducible promoter.

9. The nucleic acid construct of claim 6, wherein said host cell is a plant cell.

10. A plant cell transformed with an exogenous polynucleotide encoding a polypeptide having the amino acid sequence set forth by SEQ ID NO: 12.

11. A plant comprising the plant cell of claim 10.

12. The method of claim 1, further comprising growing the plant expressing said exogenous polynucleotide under the abiotic stress.

13. The plant cell of claim 10, wherein said exogenous polynucleotide comprising the nucleic acid sequence is set forth by SEQ ID NO: 11.

14. A nucleic acid construct comprising a nucleic acid sequence encoding a polypeptide having the amino acid sequence set forth by SEQ ID NO: 12, and a promoter capable of directing transcription of said nucleic acid sequence in a host cell.

* * * * *

SEQUENCE LISTING

```
<160> NUMBER OF SEQ ID NOS: 285

<210> SEQ ID NO 1
<211> LENGTH: 1037
<212> TYPE: DNA
<213> ORGANISM: Sorghum bicolor

<400> SEQUENCE: 1
acggtaacag agcaatttca gatcagtaga tgcgaacaaa aaccttgctc actcttctct      60
catttcatag cggaaagtaa ccaaagcgga cagtaacatc atcgaacacg ggggtaccaa     120
cacctaatcc aaaggttcaa cggacactaa cacatgggta actcagaatc caacggaacg     180
gtaacacgat actatagata gatagatagc taggataact tggccgaagc cagggtgggc     240
```

```
ccacacaatc agttctcgca ctcgcgcgcc tttcccattc gcgccgccgc cgccgccgct      300
gcaagcgcca gctcgccgtc gtccgagcca acaccccaa cgccgccatg gggcgtatgc       360
acagccgcgg gaagggtatc tcgtcgtcgg cgctgccgta caagaggacg ccgccgacct      420
ggctcaagac cgccgcctcc gacgtggagg agatgatcac taaggcggcg aagaagggtc      480
agatgccgtc gcagatcggc gtcctgctcc gtgaccagca cggtatcccc cttgtcaaga      540
gcgtcacggg cagcaagatc ctccgcatcc tcaaggccca tgggctggcg ccagaaatcc      600
cggaggacct ctacttcctc atcaagaagg cggtggcgat aaggaagcac cttgagagga      660
acaggaagga caaagactcc aaattcaggc tcattcttgt tgagagcagg atccaccgcc      720
ttgcccgcta ctacaagcgc acaaagaagc ttccacccac ctggaagtat gagtcaacca      780
ccgcaagcac tctggtggcc taagtgagga gctcaacatt aggtgcttga agctgggcta      840
ttcttggaat cattttatg taccgtttta tgagtttgga gtgaactaga gatcttgaat       900
gtcctgtgga ggatgccata aacccttttg gttacataga actgcctgtt gttaactttt      960
gctactcggc atccagattt tgtcagctat aatatgatca tttacattac atggtttgcc     1020
cctaccttcc tgcagtc                                                    1037

<210> SEQ ID NO 2
<211> LENGTH: 151
<212> TYPE: PRT
<213> ORGANISM: Sorghum bicolor

<400> SEQUENCE: 2

Met Gly Arg Met His Ser Arg Gly Lys Gly Ile Ser Ser Ser Ala Leu
1               5                   10                  15

Pro Tyr Lys Arg Thr Pro Thr Trp Leu Lys Thr Ala Ala Ser Asp
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 3
<211> LENGTH: 1346
<212> TYPE: DNA
<213> ORGANISM: Sorghum bicolor

<400> SEQUENCE: 3
aagagaagag cagcagcagc aacagccgcg ccatccgctt gcttccttcc ttcctcttct       60
ctccctccta ccccaccgcc ggcgtcgcct ttcgcgttg cgcgcccctcg cgtcgcaccc      120 gtgggtagca gccgcgtacc taccaacctg cgtgctgccg ggggagctct gcacgtctcc      180
```

-continued

```
tgtcgcctcg cctctcggca tggacgccgg gggagagaag ttcagcgacg cggcggcggc    240
ggagggcggt gagggcggcg gcgacctcta cgccgtcctc gggctcaaga aggagtgctc    300
cgacgccgac ctcaaggtcg cttaccggaa gctcgccaag aaatggcacc cggacaaatg    360
ctcctcctcc agcagcgtga acacatggag gaagccaag gagaagttcc aagagatcca    420
gggcgcctat tccgtactct ctgacgccaa taaacggctc ctctacgatg ttggagtata    480
cgacgatgag gacgacgagg atagcatgca ggggatgggt gacttcattg gtgagatggc    540
ccagatgatg agccaggtgc ggccgacgag gcaggaaagc tttgaggagc tgcagcagct    600
ttttgtggac atgttccagt ctgatattga ttcaggattc tgcaacgggt ctgctaagga    660
tcaagttcag gggcaagcca aaagtagaac atgctcgacc tcaccttcat catcaccgtc    720
cccacctcct cctcctacta tagtaaagga ggcagaggtg tcatcatgta atggcttcaa    780
taagcggggt tcatcagcaa tggactcagg gaagcctcca aggcctgttg aaggcggtgc    840
tggtcaggct ggattttgtt ttggggtgag cgatacgaag caaacgccga agccgagagg    900
tccgaacacc agccggagga ggaacggccg gaaacagaag ctgtcatcca gcacgatgt    960 ttcatctgaa gatgaaacgg ccggttccta gcaccagcag ctacggtagc agtttgacct   1020
gtggctttgg tgatatcatt cgttggtcct tggcggtgcc gagggcccta gtagccagca   1080
gcggcaggga ggcacagcat gtcgcttctg ctagctgctg tgatctgaag aggcgtttag   1140
ctcatcatat gccttacctt aggcctgtga gggacttcca ttgaaactcg tcgaggatac   1200 tgcattttc tttctccatc tgtgtcggtt gtgttgtaca atacattgag tgacttctaa    1260
tcgattcttt tttttacca ttaattaaca tctggtatat ccgattgatc gatccctagc    1320
cactgattac atgcatgagt tctttg                                         1346
```

<210> SEQ ID NO 4
<211> LENGTH: 258
<212> TYPE: PRT
<213> ORGANISM: Sorghum bicolor

<400> SEQUENCE: 4

```
Met Asp Ala Gly Gly Glu Lys Phe Ser Asp Ala Ala Ala Glu Gly
 1               5                  10                  15

Gly Glu Gly Gly Gly Asp Leu Tyr Ala Val Leu Gly Leu Lys Lys Glu
             20                  25                  30

Cys Ser Asp Ala Asp Leu Lys Val Ala Tyr Arg Lys Leu Ala Lys Lys
         35                  40                  45

Trp His Pro Asp Lys Cys Ser Ser Ser Ser Val Lys His Met Glu
     50                  55                  60

Glu Ala Lys Glu Lys Phe Gln Glu Ile Gln Gly Ala Tyr Ser Val Leu
 65                  70                  75                  80

Ser Asp Ala Asn Lys Arg Leu Leu Tyr Asp Val Gly Val Tyr Asp Asp
                 85                  90                  95

Glu Asp Asp Glu Asp Ser Met Gln Gly Met Gly Asp Phe Ile Gly Glu
             100                 105                 110

Met Ala Gln Met Met Ser Gln Val Arg Pro Thr Arg Gln Glu Ser Phe
         115                 120                 125

Glu Glu Leu Gln Gln Leu Phe Val Asp Met Phe Gln Ser Asp Ile Asp
     130                 135                 140

Ser Gly Phe Cys Asn Gly Ser Ala Lys Asp Gln Val Gln Gly Gln Ala
145                 150                 155                 160

Lys Ser Arg Thr Cys Ser Thr Ser Pro Ser Ser Ser Pro Ser Pro Pro
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Pro | Pro | Pro | Thr | Ile | Val | Lys | Glu | Ala | Glu | Val | Ser | Ser | Cys | Asn | Gly |
|     |     |     | 180 |     |     |     |     | 185 |     |     |     |     | 190 |     |     |

| Phe | Asn | Lys | Arg | Gly | Ser | Ser | Ala | Met | Asp | Ser | Gly | Lys | Pro | Pro | Arg |
| --- | --- | --- | --- | --- | --- | --- | --- | --- | --- | --- | --- | --- | --- | --- | --- |
|     |     |     | 195 |     |     |     |     | 200 |     |     |     |     | 205 |     |     |

| Pro | Val | Glu | Gly | Gly | Ala | Gly | Gln | Ala | Gly | Phe | Cys | Phe | Gly | Val | Ser |
| --- | --- | --- | --- | --- | --- | --- | --- | --- | --- | --- | --- | --- | --- | --- | --- |
|     |     |     | 210 |     |     |     |     | 215 |     |     |     |     | 220 |     |     |

| Asp | Thr | Lys | Gln | Thr | Pro | Lys | Pro | Arg | Gly | Pro | Asn | Thr | Ser | Arg | Arg |
| --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |

| Arg | Asn | Gly | Arg | Lys | Gln | Lys | Leu | Ser | Ser | Lys | His | Asp | Val | Ser | Ser |
| --- | --- | --- | --- | --- | --- | --- | --- | --- | --- | --- | --- | --- | --- | --- | --- |
|     |     |     |     | 245 |     |     |     |     | 250 |     |     |     |     | 255 |     |

Glu Asp

<210> SEQ ID NO 5
<211> LENGTH: 1092
<212> TYPE: DNA
<213> ORGANISM: Sorghum bicolor

<400> SEQUENCE: 5

```
atggaaggat acgatagaga gttctggcag ttctctgata ctcttaggct tcagaccgct      60
gctttctctg actttctct cggagattct atctggtctc cagctactgg aggagctgct     120
gctgctgata gaaggaacaa ctctaacgat ctcttcgctg cttctgcttc tccagctgat     180
acaaccgctg ctaagaacaa tggaggagtg ggacttaggc ttaaccttaa cgatggagga     240
ccaggactta ttggatctgg gaagttggct ttcggaggat ctaaggctga taggtacaac     300
aaccttccag ctactactga aaggctgct tcagcttaca ataacaacat caacgtgaac     360
gctggatacg ctaagaataa caataacaat gctctcgctt tcaacaagat gggaatctat     420
ggatacaaca ctaacaactc aaacatctct aacaactctt catctgggga ggtgaagtct     480
tacttcaata gagtgctgg aagggctgct tctaacaact ctcatggaca tggacatgct     540
ggaggaaaga agggaggaga gtacggaaat aagaagaagc acgggaagaa cgaaggaaat     600
aacgaggagg aggagctgg agctactgat aagaggttca agacccttcc agcttctgaa     660
gctcttccaa gaggacaagc tatcggaggt tacattttcg tgtgtaataa cgatacaatg     720
gatgagaact tgagaagaga gcttttcgga ctcccatcaa gataccgtga ttcagtgagg     780
gctattagac aggacttcc actcttcttg tacaattact ctacccatca gttgcatggg     840
attttcgagg ctgtttcttt cggaggaact aacatcgatc caaccgcttg gaagataag     900
aagtgtccag gggagtcaag attcccagct caagtgagag ttgctaccag aaagatctat     960
gatccactcg aggaggatgc tttcagacca atcctccatc attacgatgg accaaagttc    1020
aggcttgagc tttctgttac tgaggctctt gctcttctcg atatctttgc tgataaggat    1080
gatgcttgat ga                                                        1092
```

<210> SEQ ID NO 6
<211> LENGTH: 362
<212> TYPE: PRT
<213> ORGANISM: Sorghum bicolor

<400> SEQUENCE: 6

| Met | Glu | Gly | Tyr | Asp | Arg | Glu | Phe | Trp | Gln | Phe | Ser | Asp | Thr | Leu | Arg |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Leu | Gln | Thr | Ala | Ala | Phe | Ser | Gly | Leu | Ser | Leu | Gly | Asp | Ser | Ile | Trp |
| --- | --- | --- | --- | --- | --- | --- | --- | --- | --- | --- | --- | --- | --- | --- | --- |
|     |     |     | 20  |     |     |     |     | 25  |     |     |     |     | 30  |     |     |

Ser Pro Ala Thr Gly Gly Ala Ala Ala Ala Asp Arg Arg Asn Asn Ser

```
              35                  40                  45
Asn Asp Leu Phe Ala Ala Ser Ala Ser Pro Ala Asp Thr Thr Ala Ala
 50                  55                  60
Lys Asn Asn Gly Gly Val Gly Leu Arg Leu Asn Leu Asn Asp Gly Gly
 65                  70                  75                  80
Pro Gly Leu Ile Gly Ser Gly Lys Leu Ala Phe Gly Gly Ser Lys Ala
                 85                  90                  95
Asp Arg Tyr Asn Asn Leu Pro Ala Thr Thr Glu Lys Ala Ala Ser Ala
                100                 105                 110
Tyr Asn Asn Asn Ile Asn Val Asn Ala Gly Tyr Ala Lys Asn Asn
            115                 120                 125
Asn Asn Ala Leu Ala Phe Asn Lys Met Gly Ile Tyr Gly Tyr Asn Thr
130                 135                 140
Asn Asn Ser Asn Ile Ser Asn Asn Ser Ser Ser Gly Glu Val Lys Ser
145                 150                 155                 160
Tyr Phe Asn Lys Ser Ala Gly Arg Ala Ala Ser Asn Asn Ser His Gly
                165                 170                 175
His Gly His Ala Gly Gly Lys Lys Gly Gly Glu Tyr Gly Asn Lys Lys
                180                 185                 190
Lys His Gly Lys Asn Glu Gly Asn Asn Gly Gly Gly Ala Gly Ala
        195                 200                 205
Thr Asp Lys Arg Phe Lys Thr Leu Pro Ala Ser Glu Ala Leu Pro Arg
    210                 215                 220
Gly Gln Ala Ile Gly Gly Tyr Ile Phe Val Cys Asn Asn Asp Thr Met
225                 230                 235                 240
Asp Glu Asn Leu Arg Arg Glu Leu Phe Gly Leu Pro Ser Arg Tyr Arg
                245                 250                 255
Asp Ser Val Arg Ala Ile Arg Pro Gly Leu Pro Leu Phe Leu Tyr Asn
                260                 265                 270
Tyr Ser Thr His Gln Leu His Gly Ile Phe Glu Ala Val Ser Phe Gly
            275                 280                 285
Gly Thr Asn Ile Asp Pro Thr Ala Trp Glu Asp Lys Lys Cys Pro Gly
290                 295                 300
Glu Ser Arg Phe Pro Ala Gln Val Arg Val Ala Thr Arg Lys Ile Tyr
305                 310                 315                 320
Asp Pro Leu Glu Glu Asp Ala Phe Arg Pro Ile Leu His His Tyr Asp
                325                 330                 335
Gly Pro Lys Phe Arg Leu Glu Leu Ser Val Thr Glu Ala Leu Ala Leu
                340                 345                 350
Leu Asp Ile Phe Ala Asp Lys Asp Asp Ala
            355                 360

<210> SEQ ID NO 7
<211> LENGTH: 1726
<212> TYPE: DNA
<213> ORGANISM: Sorghum bicolor

<400> SEQUENCE: 7
aaaaattccc tgcactttat ttcatttaca tcggtggttg tatcttgcac acggttcatt     60
taccatacat acatccaaac tttcctcatc aattttcgt cgtcaggtac ttctaataaa    120
taccaaaaac ctcgggggca gctcctcttc actgccatga ttttggaagt cgccgcagta    180
gaaactcaaa gtattgtgca cctgttcaag ccaagagacg agaagatcct cctcgcagaa    240
ggccacaagc ggccaagaag cccaggcctc tcttcctcga aggcgtactc tggttctctg    300
```

```
gtcggactat ccattgtatt tgcacctcta tcagcacttg ttgcctcatc agagcccatg    360
tcccaccctc ctcctcctcc tgttgatcaa aatatctcgc tgcgcttttg cgagtccttt    420
tccctccaag gaacagaaac acccggcgct tttaccccac ccgcacccgc tttcccctcc    480
cggccaagaa caggagcaac aacaaggctc ctcctcgaga cattccattc atccatggcg    540
aagctcgtga acaagctggt cgattcgttc gaggagcaag acaccccgga cgtcggctgc    600
gtgcgcgccg tgctggccga gctcgtcctc accttcctct tcgtcttcac cggcgtctcc    660
gccgccatgg ccgccgggtc cggcgtgaag cccggcgagg ctatgccgat ggcgacgctg    720
gcggcggtgg caatcgcgca cgcgctggca gccggcgtac tggtgacggc cgggttccac    780
gtctccggcg gccacctcaa ccccgccgtg acggtggggc tcatggtgcg cggccacatc    840
accaagctcc gggcggtgct ctacgtcgcc gcgcaggtgc tggcgtcctc cctcgcctgc    900
atcctgctcc gctacctcag cggcggcatg gtgaccccgg tgcacgccct ggcgcgggc     960 atcagcccga tgcagggcct ggtgatggag gtgatcctca ccttctccct gctcttcgtc   1020
acctacgcca tgatcctgga cccacggagc caggtccgca ccatcggccc gctgctgacc   1080
ggcctcatcg ttggtgccaa cagcctcgcc ggtggcaact tcagcggcgc gtccatgaac   1140
ccggcacggt ccttcgggcc agccctggcc agcggggtct ggacaaacca ctggatctac   1200
tggatcggcc cgctgcttgg cgggcccctg gccgggttca tctacgagtc tttgttcatt   1260
gtgaacaaga cgcacgagcc gctgctcaat ggagacatct gacgaaccat cggcctgccc   1320
tgtggctgtg gcagggcag tcagcatggt tggttcatgc ttgtttctgt aaaatagttc    1380
attgtctaca agcatgatgg atacatatat tggtcaaggt aattagagag ggttgctgta   1440
aaatagttac cctggtatag gattgttgga tgtagaaatt gttgatgggc tttgtatttt   1500
tttccccctt ttcatgccaa ggaattcttt tttttttaga gggcggggtt ctgtcaagga   1560
tttgttaagg ctattagtag ttagccatgt agtagaaaac tagagaatgg tatacgtggg   1620
agtgggacct gaagtttttt caggtacact gtagtactat tgtaattttg tcttgaagat   1680
ggaattggat gtacagagta aaacttctc tttcaagcag taaaaa                   1726
```

<210> SEQ ID NO 8
<211> LENGTH: 381
<212> TYPE: PRT
<213> ORGANISM: Sorghum bicolor

<400> SEQUENCE: 8

```
Met Ile Leu Glu Val Ala Ala Val Glu Thr Gln Ser Ile Val His Leu
1               5                   10                  15

Phe Lys Pro Arg Asp Glu Lys Ile Leu Leu Ala Glu Gly His Lys Arg
            20                  25                  30

Pro Arg Ser Pro Gly Leu Ser Ser Ser Lys Ala Tyr Ser Gly Ser Leu
        35                  40                  45

Val Gly Leu Ser Ile Val Phe Ala Pro Leu Ser Ala Leu Val Ala Ser
    50                  55                  60

Ser Glu Pro Met Ser His Pro Pro Pro Val Asp Gln Asn Ile
65                  70                  75                  80

Ser Leu Arg Phe Cys Glu Ser Phe Ser Leu Gln Gly Thr Glu Thr Pro
                85                  90                  95

Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
        115                 120                 125
```

```
Lys Leu Val Asn Lys Leu Val Asp Ser Phe Glu Glu Gln Asp Thr Pro
            130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
            195                 200                 205

Val Ser Gly Gly His Leu Asn Pro Ala Val Thr Val Gly Leu Met Val
210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
                245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
            275                 280                 285

Thr Tyr Ala Met Ile Leu Asp Pro Arg Ser Gln Val Arg Thr Ile Gly
290                 295                 300

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
                325                 330                 335

Leu Ala Ser Gly Val Trp Thr Asn His Trp Ile Tyr Trp Ile Gly Pro
            340                 345                 350

Leu Leu Gly Gly Pro Leu Ala Gly Phe Ile Tyr Glu Ser Leu Phe Ile
            355                 360                 365

Val Asn Lys Thr His Glu Pro Leu Leu Asn Gly Asp Ile
            370                 375                 380

<210> SEQ ID NO 9
<211> LENGTH: 1097
<212> TYPE: DNA
<213> ORGANISM: Sorghum bicolor

<400> SEQUENCE: 9
gcatcagcct gataagctat agccagccat cttctctgaa ttccaactca gtccaagggc      60
tggaagcttg aagtaccgtc agagaaaaag aaaaaaagat ggtgaagctt gcatttggaa     120
gcttgggcga ctctttcagc gccgcgtccc tcaagtccta tgtggccgag ttcattgcca     180
cgctcctctt cgtgttcgcc ggcgtcgggt ccgccattgc ctactcgcaa ttgaccaagg     240
gtggcgctct ggaccccgcc ggctggtgg ccatgccat cgcccatgcg ttcgcgctct     300
tcgtcggcgt ctccatggcc gccaacgtct ccggcggcca cctgaacccc gccgtcacct     360
tcggcctcgc cgtcggcggc cacatcacca tcctcaccgg catcttctac tgggtcgccc     420
aggtgctcgg cgcgtccgtg gcgtgccttc tcctgaagta cgtcacccac ggacaggcta     480
tcccgacaca cggcgtgtcc gggatcagcg agatcgaggg cgtggtgatg agatcgtga     540 tcaccttcgc gctcgtgtac accgtgtacg ccaccgcggc cgaccccaag aagggtccc     600 tgggcaccat cgccgcccatc gccatcggct tcatcgtcgg cgccaacatc ctggcggccg     660 gaccctttcag cggcggctcc atgaacccgg cccgctcctt cggccccgcc gtggccgctg     720
```

| | | |
|---|---|---|
| gcaacttcgc cggcaactgg gtctactggg tcggcccct catcgcggc ggcctggccg | 780 | |
| ggctcgtcta cggcgacgtg ttcatcgcct cctaccagcc cgtcggccag caggatcagt | 840 | |
| acccatgaag aaagtcgatc cggacccaaa tgcaatgcaa cccgtcgtgt tgatttcacc | 900 | |
| gtcctcgtcg attcgccgtc gtgtcatcgc ttcgcgcttg tgattatgtt tggtcttgtt | 960 | |
| tgcattaccc cttctggttt aattttcacc aacggtgtca acatgctgta agcgagagaa | 1020 | |
| ccgttcgatc tataccgtgta taaatgtaat gtacggttca gtatttccaa gtacagtata | 1080 | |
| tgttccggac ggatttc | 1097 | |

<210> SEQ ID NO 10
<211> LENGTH: 249
<212> TYPE: PRT
<213> ORGANISM: Sorghum bicolor

<400> SEQUENCE: 10

Met Val Lys Leu Ala Phe Gly Ser Leu Gly Asp Ser Phe Ser Ala Ala
1               5                   10                  15

Ser Leu Lys Ser Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Val Ser Gly Gly
65                  70                  75                  80

His Leu Asn Pro Ala Val Thr Phe Gly Leu Ala Val Gly Gly His Ile
                85                  90                  95

Thr Ile Leu Thr Gly Ile Phe Tyr Trp Val Ala Gln Val Leu Gly Ala
            100                 105                 110

Ser Val Ala Cys Leu Leu Leu Lys Tyr Val Thr His Gly Gln Ala Ile
        115                 120                 125

Pro Thr His Gly Val Ser Gly Ile Ser Glu Ile Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asn Phe Ala Gly Asn Trp Val Tyr Trp Val Gly Pro Leu Ile Gly Gly
    210                 215                 220

Gly Leu Ala Gly Leu Val Tyr Gly Asp Val Phe Ile Ala Ser Tyr Gln
225                 230                 235                 240

Pro Val Gly Gln Gln Asp Gln Tyr Pro
                245

<210> SEQ ID NO 11
<211> LENGTH: 1160
<212> TYPE: DNA
<213> ORGANISM: Sorghum bicolor

<400> SEQUENCE: 11
gcacgaggcg gcgtcggagc ccacgaccgc ttccgcccca gtccccaccg ccctcgaccc      60

-continued

```
cgattccccc aatccctgcc gcgaccgctg aaccctagcc tactccggcc atctgccgct    120
ggccccggcg atccccgcc atggcctccc ccgagggaac cacgtgggtc ttcgactgtc     180
ccctcatgga cgacctcgcg gtggccgccg acttcgcggc agccccgcg ggggattttt     240 tctgggcagc gccgccgtcg ctacagccgc aggtggtgca ggcgccggtc cagtctgtcg    300
ttgccgcgtc ggctcccaac ccatgtgtgg aaatcagtag ctctgtggac tgtggtcagg    360
gaaaagaaca gccaacaaat aaacgtccta ggtcagaaag taccgcagaa ccaagcacaa    420
aagcatccag ggagaaaatt agaagggata agctgaacga gagattcctg gaattgggtg    480
ccattttgga gccagggaaa actcctaaaa tggacaagtc agctatatta aatgatgcta    540
ttcgtgtagt aggtgaattg cgtagcgaag caaagagct caaggattca aatgagagcc     600
tacaagagaa gattaaagag ctaaaggctg agaagaatga gctgcgagac gagaagcaaa    660
ggctgaaggc cgagaaggag agcctggagc agcagatcaa gttcctgaat gcccgcccaa    720
gtctggtacc acaccaccca gtgatctcag cctctgcctt cactgctccc caggggccgg    780
cagtcgccgg gcacaagctg atgatgcctg tgcttggcta ccctggattc ccgatgtggc    840
agttcatgcc gccttctgat gttgacacct ctgatgaccc caagtcttgc ccacctgtgg    900
cgtaagcaag tgaagaggcg atgctgccct ccattgattc aagtctagat cgtgatcagt    960
ctgcagtgtt gttggtgtag ttgactccac tctccagaat ggaagggaag gttatatgtg   1020
tcggatggtg acatggggtg atctgatgac ccctttgtat attatatggt aaatgaataa   1080
attccgtgac cagttgcaaa tgaggattag cagactagct catgtctatt cctgcctttt   1140
tgtcgtataa accacgttgt                                               1160
```

<210> SEQ ID NO 12
<211> LENGTH: 254
<212> TYPE: PRT
<213> ORGANISM: Sorghum bicolor

<400> SEQUENCE: 12

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Cys Val Glu
    50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
            100                 105                 110

Gly Ala Ile Leu Glu Pro Gly Lys Thr Pro Lys Met Asp Lys Ser Ala
        115                 120                 125

Ile Leu Asn Asp Ala Ile Arg Val Val Gly Glu Leu Arg Ser Glu Ala
    130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
```

```
                     180                 185                 190
Pro Ser Leu Val Pro His His Pro Val Ile Ser Ala Ser Ala Phe Thr
            195                 200                 205

Ala Pro Gln Gly Pro Ala Val Ala Gly His Lys Leu Met Met Pro Val
        210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250

<210> SEQ ID NO 13
<211> LENGTH: 151
<212> TYPE: PRT
<213> ORGANISM: Zea mays

<400> SEQUENCE: 13

Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Ser Asp
            20                  25                  30

Val Glu Glu Met Ile Thr Lys Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 14
<211> LENGTH: 171
<212> TYPE: PRT
<213> ORGANISM: Saccharum officinarum

<400> SEQUENCE: 14

Arg Arg Arg Arg Arg Lys Arg Gln Leu Ala Val Ala Arg Ala Lys
1               5                   10                  15

His Pro Asn Ala Ala Met Gly Arg Met His Ser Arg Gly Lys Gly Ile
            20                  25                  30

Ser Ser Ser Ala Leu Pro Tyr Lys Arg Thr Pro Pro Thr Trp Leu Lys
        35                  40                  45

Thr Ala Ala Ser Asp Val Glu Glu Met Ile Thr Lys Ala Lys Lys
    50                  55                  60

Gly Gln Met Pro Ser Gln Ile Gly Val Leu Leu Arg Asp Gln His Gly
65                  70                  75                  80

Ile Pro Leu Val Lys Ser Val Thr Gly Ser Lys Ile Leu Arg Ile Leu
                85                  90                  95

Lys Ala His Gly Leu Ala Pro Glu Ile Pro Glu Asp Leu Tyr Phe Leu
            100                 105                 110
```

```
Ile Lys Lys Ala Val Ala Ile Arg Lys His Leu Glu Arg Asn Arg Lys
        115                 120                 125

Asp Lys Asp Ser Lys Phe Arg Leu Ile Leu Val Glu Ser Arg Ile His
130                 135                 140

Arg Leu Ala Arg Tyr Tyr Lys Arg Thr Lys Lys Leu Pro Pro Thr Trp
145                 150                 155                 160

Lys Tyr Glu Ser Thr Thr Ala Ser Thr Leu Val
                165                 170

<210> SEQ ID NO 15
<211> LENGTH: 172
<212> TYPE: PRT
<213> ORGANISM: Sorghum bicolor

<400> SEQUENCE: 15

Arg Arg Arg Arg Arg Cys Lys Arg Gln Leu Ala Val Val Arg Ala
1               5                   10                  15

Lys His Pro Asn Ala Ala Met Gly Arg Met His Ser Arg Gly Lys Gly
                20                  25                  30

Ile Ser Ser Ser Ala Leu Pro Tyr Lys Arg Thr Pro Pro Thr Trp Leu
            35                  40                  45

Lys Thr Ala Ala Ser Asp Val Glu Glu Met Ile Thr Lys Ala Ala Lys
50                  55                  60

Lys Gly Gln Met Pro Ser Gln Ile Gly Val Leu Leu Arg Asp Gln His
65                  70                  75                  80

Gly Ile Pro Leu Val Lys Ser Val Thr Gly Ser Lys Ile Leu Arg Ile
                85                  90                  95

Leu Lys Ala His Gly Leu Ala Pro Glu Ile Pro Glu Asp Leu Tyr Phe
            100                 105                 110

Leu Ile Lys Lys Ala Val Ala Ile Arg Lys His Leu Glu Arg Asn Arg
        115                 120                 125

Lys Asp Lys Asp Ser Lys Phe Arg Leu Ile Leu Val Glu Ser Arg Ile
130                 135                 140

His Arg Leu Ala Arg Tyr Tyr Lys Arg Thr Lys Lys Leu Pro Pro Thr
145                 150                 155                 160

Trp Lys Tyr Glu Ser Thr Thr Ala Ser Thr Leu Val
                165                 170

<210> SEQ ID NO 16
<211> LENGTH: 151
<212> TYPE: PRT
<213> ORGANISM: Saccharum officinarum

<400> SEQUENCE: 16

Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Thr Glu
                20                  25                  30

Val Glu Glu Met Ile Thr Lys Ala Ala Lys Gly Gln Met Pro Ser
            35                  40                  45

Gln Ile Gly Val Leu Leu Arg Asp Gln His Gly Ile Pro Leu Val Lys
50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95
```

```
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 17
<211> LENGTH: 187
<212> TYPE: PRT
<213> ORGANISM: Sorghum bicolor

<400> SEQUENCE: 17

Met Pro His Ala Pro Pro Leu Ala Leu Ala Pro Pro Pro Pro Pro Gln
1               5                   10                  15

Leu Leu Gln Gln Gln Ala Pro Ala Arg Arg Arg Leu Gly Arg His
            20                  25                  30

Gln Ser Ala Ala Met Gly Arg Met His Ser Arg Gly Lys Gly Ile Ser
        35                  40                  45

Ser Ser Ala Leu Pro Tyr Lys Arg Thr Pro Pro Thr Trp Leu Lys Thr
    50                  55                  60

Ala Ala Thr Glu Val Glu Met Ile Thr Lys Ala Ala Lys Lys Gly
65                  70                  75                  80

Gln Met Pro Ser Gln Ile Gly Val Leu Leu Arg Asp Gln His Gly Ile
                85                  90                  95

Pro Leu Val Lys Ser Val Thr Gly Ser Lys Ile Leu Arg Ile Leu Lys
            100                 105                 110

Ala His Gly Leu Ala Pro Glu Ile Pro Glu Asp Leu Tyr Phe Leu Ile
        115                 120                 125

Lys Lys Ala Val Ala Ile Arg Lys His Leu Glu Arg Asn Arg Lys Asp
    130                 135                 140

Lys Asp Ser Lys Phe Arg Leu Ile Leu Val Glu Ser Arg Ile His Arg
145                 150                 155                 160

Leu Ala Arg Tyr Tyr Lys Arg Thr Lys Lys Leu Pro Pro Thr Trp Lys
                165                 170                 175

Tyr Glu Ser Thr Thr Ala Ser Thr Leu Val Ala
            180                 185

<210> SEQ ID NO 18
<211> LENGTH: 184
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 18

Xaa Xaa Glu Lys Thr Pro Ser Tyr Arg Arg Ser Arg Pro Ser Arg Pro
1               5                   10                  15

Arg Ala Pro Pro Pro Pro Ala Val Ala Gly Ala Lys Pro Leu Asp
            20                  25                  30

Ala Ala Met Gly Arg Met His Ser Arg Gly Lys Gly Ile Ser Ser Ser
        35                  40                  45

Ala Leu Pro Tyr Lys Arg Thr Pro Pro Ser Trp Leu Lys Thr Ala Ala
    50                  55                  60
```

```
Ser Asp Val Glu Glu Met Ile Met Lys Ala Ala Lys Lys Gly Gln Met
 65                  70                  75                  80

Pro Ser Gln Ile Gly Val Val Leu Arg Asp Gln His Gly Ile Pro Leu
                 85                  90                  95

Val Lys Ser Val Thr Gly Ser Lys Ile Leu Arg Ile Leu Lys Ala His
            100                 105                 110

Gly Leu Ala Pro Glu Ile Pro Glu Asp Leu Tyr Phe Leu Ile Lys Lys
        115                 120                 125

Ala Val Ala Ile Arg Lys His Leu Glu Arg Asn Arg Lys Asp Lys Asp
    130                 135                 140

Ser Lys Phe Arg Leu Ile Leu Val Glu Ser Arg Ile His Arg Leu Ala
145                 150                 155                 160

Arg Tyr Tyr Lys Arg Thr Lys Lys Leu Pro Pro Thr Trp Lys Tyr Glu
                165                 170                 175

Ser Thr Thr Ala Ser Thr Leu Val
            180

<210> SEQ ID NO 19
<211> LENGTH: 151
<212> TYPE: PRT
<213> ORGANISM: Zea mays

<400> SEQUENCE: 19

Met Gly Arg Met His Ser Arg Gly Lys Gly Ile Ser Ser Ser Ala Leu
 1               5                  10                  15

Pro Tyr Lys Arg Thr Pro Pro Ile Trp Leu Lys Thr Ala Thr Ala Glu
                20                  25                  30

Val Glu Glu Met Ile Thr Lys Ala Ala Lys Lys Gly Gln Met Pro Ser
            35                  40                  45

Gln Ile Gly Val Leu Leu Arg Asp Gln His Gly Ile Pro Leu Val Lys
        50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 20
<211> LENGTH: 183
<212> TYPE: PRT
<213> ORGANISM: Hordeum vulgare
<220> FEATURE:
<221> NAME/KEY: misc_feature
<222> LOCATION: (1)..(2)
<223> OTHER INFORMATION: Xaa can be any naturally occurring amino acid

<400> SEQUENCE: 20

Xaa Xaa Pro Leu Phe Tyr Pro Leu Thr Thr Arg Ala Ser Leu Ala Leu
 1               5                  10                  15

Pro Ala Ala Ala Ala Ala Ala Pro Leu Ala Ala Ala Ala Ala Ala Ala
                20                  25                  30
```

```
Ala Met Gly Arg Met His Ser Arg Gly Lys Gly Ile Ser Ser Ala
         35                  40                  45

Leu Pro Tyr Lys Arg Thr Pro Pro Ser Trp Val Lys Thr Ala Val Ala
 50                  55                  60

Asp Val Asp Glu Leu Ile Thr Lys Ala Ala Lys Lys Gly Gln Met Pro
 65                  70                  75                  80

Ser Gln Ile Gly Val Leu Leu Arg Asp Gln His Gly Ile Pro Leu Val
                 85                  90                  95

Lys Ser Val Thr Gly Ser Lys Ile Leu Arg Ile Leu Lys Ala His Gly
            100                 105                 110

Leu Ala Pro Glu Ile Pro Glu Asp Leu Tyr Phe Leu Ile Lys Lys Ala
        115                 120                 125

Val Ala Ile Arg Lys His Leu Glu Arg Asn Arg Lys Asp Lys Asp Ser
130                 135                 140

Lys Phe Arg Leu Ile Leu Val Glu Ser Arg Ile His Arg Leu Ala Arg
145                 150                 155                 160

Tyr Tyr Lys Arg Thr Lys Lys Leu Pro Pro Thr Trp Lys Tyr Glu Ser
                165                 170                 175

Thr Thr Ala Ser Thr Leu Val
            180

<210> SEQ ID NO 21
<211> LENGTH: 178
<212> TYPE: PRT
<213> ORGANISM: Oryza sativa

<400> SEQUENCE: 21

Ser Ser Arg Arg Arg Arg Leu Leu Arg Arg Ala Val Ala Asn Arg Arg
 1               5                  10                  15

Arg Arg Ser Pro Ser Pro Asn Ser Pro Leu Pro Pro Trp Gly Arg Met
             20                  25                  30

His Ser Arg Gly Lys Gly Ile Ser Ser Ala Ile Pro Tyr Lys Arg
         35                  40                  45

Thr Pro Pro Ser Trp Val Lys Thr Ala Ala Ala Asp Val Glu Glu Met
 50                  55                  60

Ile Met Lys Ala Ala Lys Lys Gly Gln Met Pro Ser Gln Ile Gly Val
 65                  70                  75                  80

Val Leu Arg Asp Gln His Gly Ile Pro Leu Val Lys Ser Val Thr Gly
                 85                  90                  95

Ser Lys Ile Leu Arg Ile Leu Lys Ala His Gly Leu Ala Pro Glu Ile
            100                 105                 110

Pro Glu Asp Leu Tyr Phe Leu Ile Lys Lys Ala Val Ala Ile Arg Lys
        115                 120                 125

His Leu Glu Arg Asn Arg Lys Asp Lys Asp Ser Lys Phe Arg Leu Ile
130                 135                 140

Leu Val Glu Ser Arg Ile His Arg Leu Ala Arg Tyr Tyr Lys Arg Thr
145                 150                 155                 160

Lys Lys Leu Pro Pro Thr Trp Lys Tyr Glu Ser Thr Thr Ala Ser Thr
                165                 170                 175

Leu Val

<210> SEQ ID NO 22
<211> LENGTH: 170
<212> TYPE: PRT
<213> ORGANISM: Triticum aestivum

<400> SEQUENCE: 22
```

```
Ala Leu Phe Tyr Pro Leu Thr Thr Arg Ala Ser Leu Ala Leu Pro Ala
1               5                   10                  15

Ala Ala Ala Ala Thr Pro Leu Ala Ala Ala Ala Ala Ala Ala Met Gly
            20                  25                  30

Arg Met His Ser Arg Gly Lys Gly Ile Ser Ser Ala Leu Pro Tyr
        35                  40                  45

Lys Arg Thr Pro Pro Ser Trp Val Lys Thr Ala Val Ala Asp Val Asp
50                  55                  60

Glu Leu Ile Thr Lys Ala Ala Lys Lys Gly Gln Met Pro Ser Gln Ile
65                  70                  75                  80

Gly Val Leu Leu Arg Asp Gln His Gly Ile Pro Leu Val Lys Ser Val
                85                  90                  95

Thr Gly Ser Lys Ile Leu Arg Ile Leu Lys Ala His Gly Leu Ala Pro
            100                 105                 110

Glu Ile Pro Glu Asp Leu Tyr Phe Leu Ile Lys Lys Ala Val Ala Ile
        115                 120                 125

Arg Lys His Leu Glu Arg Asn Arg Lys Asp Lys Asp Ser Lys Phe Arg
130                 135                 140

Leu Ile Leu Val Glu Ser Arg Ile His Arg Leu Ala Arg Tyr Tyr Lys
145                 150                 155                 160

Arg Thr Lys Lys Leu Pro Pro Thr Trp Lys
                165                 170
```

<210> SEQ ID NO 23
<211> LENGTH: 177
<212> TYPE: PRT
<213> ORGANISM: Triticum aestivum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 23

```
Xaa Xaa Ala Gly Asn Ser Ala Arg Gly Ser Ser Pro Ser Arg Pro Ser
1               5                   10                  15

Arg Arg Cys Cys Cys Arg Gln Pro Pro Pro Ser Pro Glu Leu Asn
            20                  25                  30

Pro Ser Pro Asp Ala Met Gly Arg Met His Ser Arg Gly Lys Gly Ile
        35                  40                  45

Ser Ser Ser Ala Leu Pro Tyr Lys Arg Thr Pro Pro Ser Trp Val Lys
50                  55                  60

Thr Ala Val Ala Asp Val Asp Glu Leu Ile Thr Lys Ala Ala Lys Lys
65                  70                  75                  80

Gly Gln Met Pro Ser Gln Ile Gly Val Leu Leu Arg Asp Gln His Gly
                85                  90                  95

Ile Pro Leu Val Lys Ser Val Thr Gly Ser Lys Ile Leu Arg Ile Leu
            100                 105                 110

Lys Ala His Gly Leu Ala Pro Glu Ile Pro Glu Asp Leu Tyr Phe Leu
        115                 120                 125

Ile Lys Lys Ala Val Ala Ile Arg Lys His Leu Glu Arg Asn Arg Lys
130                 135                 140

Asp Lys Asp Ser Lys Phe Arg Leu Ile Leu Val Glu Ser Arg Ile His
145                 150                 155                 160

Arg Leu Ala Arg Tyr Tyr Lys Arg Thr Lys Lys Leu Pro Pro Thr Trp
                165                 170                 175

Lys
```

```
<210> SEQ ID NO 24
<211> LENGTH: 171
<212> TYPE: PRT
<213> ORGANISM: Hordeum vulgare

<400> SEQUENCE: 24

Arg Arg Arg Ser Cys Pro Ser Ser Pro Ser Arg Arg Cys Cys Cys Arg
1               5                   10                  15

Gln Pro Pro Pro Ser Ser Pro Glu Leu Asn Pro Ser Pro Asp Ala Met
                20                  25                  30

Gly Arg Met His Ser Arg Gly Lys Gly Ile Ser Ser Ala Leu Pro
            35                  40                  45

Tyr Lys Arg Thr Pro Pro Ser Trp Val Lys Thr Ala Val Ala Asp Val
        50                  55                  60

Asp Glu Leu Ile Thr Lys Ala Ala Lys Lys Gly Gln Met Pro Ser Gln
65                  70                  75                  80

Ile Gly Val Leu Leu Arg Asp Gln His Gly Ile Pro Leu Val Lys Ser
                85                  90                  95

Val Thr Gly Ser Lys Ile Leu Arg Ile Leu Lys Ala His Gly Leu Ala
                100                 105                 110

Pro Glu Ile Pro Glu Asp Leu Tyr Phe Leu Ile Lys Lys Ala Val Ala
            115                 120                 125

Ile Arg Lys His Leu Glu Arg Asn Arg Lys Asp Lys Asp Ser Lys Phe
130                 135                 140

Arg Leu Ile Leu Val Glu Ser Arg Ile His Arg Leu Ala Arg Tyr Tyr
145                 150                 155                 160

Lys Arg Thr Lys Lys Leu Pro Pro Thr Trp Lys
                165                 170

<210> SEQ ID NO 25
<211> LENGTH: 116
<212> TYPE: PRT
<213> ORGANISM: Triticum aestivum

<400> SEQUENCE: 25

Met Ile Thr Lys Ala Ala Lys Lys Gly Gln Met Pro Ser Gln Ile Gly
1               5                   10                  15

Val Leu Leu Arg Asp Gln His Gly Ile Pro Leu Val Lys Ser Val Thr
                20                  25                  30

Gly Ser Lys Ile Leu Arg Ile Leu Lys Ala His Gly Leu Ala Pro Glu
            35                  40                  45

Ile Pro Glu Asp Leu Tyr Phe Leu Ile Lys Lys Ala Val Ala Ile Arg
        50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
                100                 105                 110

Thr Leu Val Ala
        115

<210> SEQ ID NO 26
<211> LENGTH: 116
<212> TYPE: PRT
<213> ORGANISM: Zea mays
```

-continued

<400> SEQUENCE: 26

Met Ile Thr Lys Ala Ala Lys Lys Gly Gln Met Pro Ser Gln Ile Gly
1               5                   10                  15

Val Leu Arg Asp Gln His Gly Ile Pro Leu Val Lys Ser Val Thr
            20                  25                  30

Gly Ser Lys Ile Leu Arg Ile Leu Lys Ala His Gly Leu Ala Pro Glu
        35                  40                  45

Ile Pro Glu Asp Leu Tyr Phe Leu Ile Lys Lys Ala Val Ala Ile Arg
    50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
            100                 105                 110

Thr Leu Val Ala
        115

<210> SEQ ID NO 27
<211> LENGTH: 122
<212> TYPE: PRT
<213> ORGANISM: Saccharum officinarum

<400> SEQUENCE: 27

Met Ile Thr Asn Ala Ala Lys Lys Gly Gln Met Pro Ser Gln Ile Gly
1               5                   10                  15

Val Leu Val Arg Asp Gln His Gly Ile Pro Leu Val Lys Ser Val Thr
            20                  25                  30

Gly Ser Met Ile Leu Arg Ile Leu Lys Ala His Gly Leu Ser Leu Glu
        35                  40                  45

Ile Pro Glu Asp Leu Tyr Phe Leu Ile Lys Lys Ala Val Trp Ile Arg
    50                  55                  60

Lys His Leu Glu Arg Asn Arg Lys Asp Lys Asp Phe Lys Phe Thr Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Cys Lys Tyr Glu Thr Thr Thr Gly Ser
            100                 105                 110

Thr Leu Val Ala Ile Val Val Ser Ser Thr
        115                 120

<210> SEQ ID NO 28
<211> LENGTH: 210
<212> TYPE: PRT
<213> ORGANISM: Triticum aestivum
<220> FEATURE:
<221> NAME/KEY: misc_feature
<222> LOCATION: (38)..(38)
<223> OTHER INFORMATION: Xaa can be any naturally occurring amino acid

<400> SEQUENCE: 28

Met Pro Ser Gln Ile Gly Val Leu Leu Arg Asp Gln His Gly Ile Pro
1               5                   10                  15

Leu Val Lys Ser Val Thr Gly Ser Lys Ile Leu Arg Ile Leu Lys Ala
            20                  25                  30

His Gly Leu Ala Pro Xaa Ile Pro Glu Asp Leu Tyr Phe Leu Ile Lys
        35                  40                  45

Lys Ala Val Ala Ile Arg Lys His Leu Glu Arg Asn Arg Arg Asp Lys

```
                50                  55                  60
Asp Ser Lys Phe Arg Leu Ile Leu Val Glu Ser Arg Ile His Arg Leu
 65                  70                  75                  80

Ala Arg Tyr Tyr Lys Arg Thr Lys Lys Leu Pro Pro Thr Trp Lys Trp
                 85                  90                  95

Glu Val Lys Ala Val Leu Asp Asp Tyr Pro Lys Leu Cys Leu Thr Lys
                100                 105                 110

Gly Arg Lys Val Leu Glu Ile Arg Pro Ser Ile Glu Trp Asn Lys Gly
                115                 120                 125

His Ala Leu Lys Phe Leu Leu Lys Ser Leu Gly Tyr Ala Gly Arg Ser
                130                 135                 140

Asp Val Phe Pro Ile Tyr Ile Gly Asp Asp Arg Thr Asp Glu Asp Ala
145                 150                 155                 160

Phe Lys Val Leu Gln Asn Met Gly Gln Gly Ile Gly Ile Leu Val Thr
                165                 170                 175

Lys Phe Pro Lys Asp Thr Ser Ala Ser Tyr Ser Leu Arg Glu Pro Ala
                180                 185                 190

Glu Val Lys Glu Phe Met Arg Lys Leu Val Lys Ser Asn Gly Ile Lys
                195                 200                 205

Lys Gly
    210

<210> SEQ ID NO 29
<211> LENGTH: 92
<212> TYPE: PRT
<213> ORGANISM: Zea mays

<400> SEQUENCE: 29

Met Pro Leu Val Lys Ser Val Thr Gly Ser Lys Ile Leu Arg Ile Leu
  1               5                  10                  15

Lys Ala His Gly Leu Ala Pro Glu Ile Pro Glu Asp Leu Tyr Phe Leu
                 20                  25                  30

Ile Lys Lys Ala Val Ala Ile Arg Lys His Leu Glu Arg Asn Arg Lys
                 35                  40                  45

Asp Lys Asp Ser Lys Phe Arg Leu Ile Leu Val Glu Ser Arg Ile His
             50                  55                  60

Arg Leu Ala Arg Tyr Tyr Lys Arg Thr Lys Lys Leu Pro Pro Thr Trp
 65                  70                  75                  80

Lys Tyr Glu Ser Thr Thr Ala Ser Thr Leu Val Ala
                 85                  90

<210> SEQ ID NO 30
<211> LENGTH: 96
<212> TYPE: PRT
<213> ORGANISM: Triticum aestivum
<220> FEATURE:
<221> NAME/KEY: misc_feature
<222> LOCATION: (86)..(86)
<223> OTHER INFORMATION: Xaa can be any naturally occurring amino acid

<400> SEQUENCE: 30

Met Gly Arg Met His Ser Arg Gly Lys Gly Ile Ser Ser Ser Ala Leu
  1               5                  10                  15

Pro Tyr Lys Arg Thr Pro Pro Trp Leu Lys Thr Ala Ala Ser Asp
                 20                  25                  30

Val Glu Glu Met Ile Thr Lys Ala Ala Lys Lys Gly Gln Met Pro Ser
                 35                  40                  45

Gln Ile Gly Val Leu Leu Arg Asp Gln His Gly Ile Pro Leu Val Lys
```

```
                50                  55                  60
Ser Val Thr Gly Ser Lys Ile Leu Arg Ile Leu Lys Ala His Gly Trp
 65                  70                  75                  80

His Gln Lys Ser Arg Xaa Leu Tyr Phe Ser Arg Arg Arg Trp Arg
                 85                  90                  95

<210> SEQ ID NO 31
<211> LENGTH: 327
<212> TYPE: PRT
<213> ORGANISM: Sorghum bicolor
<220> FEATURE:
<221> NAME/KEY: misc_feature
<222> LOCATION: (1)..(2)
<223> OTHER INFORMATION: Xaa can be any naturally occurring amino acid

<400> SEQUENCE: 31

Xaa Xaa Arg Glu Glu Gln Gln Gln Gln Pro Arg His Pro Leu Ala
 1               5                  10                  15

Ser Phe Leu Pro Leu Leu Ser Leu Leu Pro His Arg Arg Arg Leu
                20                  25                  30

Phe Ala Leu Arg Ala Leu Ala Ser His Pro Trp Val Ala Ala Tyr
                35                  40                  45

Leu Pro Thr Cys Val Leu Pro Gly Glu Leu Cys Thr Ser Pro Val Ala
 50                  55                  60

Ser Pro Leu Gly Met Asp Ala Gly Gly Lys Phe Ser Asp Ala Ala
 65                  70                  75                  80

Ala Ala Glu Gly Gly Glu Gly Gly Asp Leu Tyr Ala Val Leu Gly
                85                  90                  95

Leu Lys Lys Glu Cys Ser Asp Ala Asp Leu Lys Val Ala Tyr Arg Lys
                100                 105                 110

Leu Ala Lys Lys Trp His Pro Asp Lys Cys Ser Ser Ser Ser Val
                115                 120                 125

Lys His Met Glu Glu Ala Lys Glu Lys Phe Gln Glu Ile Gln Gly Ala
                130                 135                 140

Tyr Ser Val Leu Ser Asp Ala Asn Lys Arg Leu Leu Tyr Asp Val Gly
145                 150                 155                 160

Val Tyr Asp Asp Glu Asp Asp Glu Asp Ser Met Gln Gly Met Gly Asp
                165                 170                 175

Phe Ile Gly Glu Met Ala Gln Met Met Ser Gln Val Arg Pro Thr Arg
                180                 185                 190

Gln Glu Ser Phe Glu Glu Leu Gln Leu Phe Val Asp Met Phe Gln
                195                 200                 205

Ser Asp Ile Asp Ser Gly Phe Cys Asn Gly Ser Ala Lys Asp Gln Val
                210                 215                 220

Gln Gly Gln Ala Lys Ser Arg Thr Cys Ser Thr Ser Pro Ser Ser
225                 230                 235                 240

Pro Ser Pro Pro Pro Pro Thr Ile Val Lys Glu Ala Glu Val Ser
                245                 250                 255

Ser Cys Asn Gly Phe Asn Lys Arg Gly Ser Ser Ala Met Asp Ser Gly
                260                 265                 270

Lys Pro Pro Arg Pro Val Glu Gly Gly Ala Gly Gln Ala Gly Phe Cys
                275                 280                 285

Phe Gly Val Ser Asp Thr Lys Gln Thr Pro Lys Pro Arg Gly Pro Asn
                290                 295                 300

Thr Ser Arg Arg Arg Asn Gly Arg Lys Gln Lys Leu Ser Ser Lys His
305                 310                 315                 320
```

Asp Val Ser Ser Glu Asp Glu
            325

<210> SEQ ID NO 32
<211> LENGTH: 265
<212> TYPE: PRT
<213> ORGANISM: Saccharum officinarum

<400> SEQUENCE: 32

Met Asp Ala Gly Gly Glu Lys Cys Gly Asp Ala Ala Ala Glu Gly
1               5                   10                  15

Gly Glu Gly Gly Gly Asp Leu Tyr Ala Val Leu Gly Leu Lys Lys Glu
            20                  25                  30

Cys Ser Asp Ala Asp Leu Lys Val Ala Tyr Arg Lys Leu Ala Lys Lys
            35                  40                  45

Trp His Pro Asp Lys Cys Ser Ser Ser Ser Val Lys His Met Glu
    50                  55                  60

Glu Ala Lys Glu Lys Phe Gln Glu Ile Gln Gly Ala Tyr Ser Val Leu
65                  70                  75                  80

Ser Asp Ala Asn Lys Arg Leu Leu Tyr Asp Val Gly Val Tyr Asp Asp
                85                  90                  95

Glu Asp Asp Glu Asp Ser Met Gln Gly Met Gly Asp Phe Ile Gly Glu
            100                 105                 110

Met Ala Gln Met Met Ser Gln Val Arg Pro Thr Arg Gln Glu Ser Phe
            115                 120                 125

Glu Glu Leu Gln Gln Leu Phe Val Asp Met Phe Gln Ser Asp Ile Asp
            130                 135                 140

Ser Gly Phe Cys Asn Gly Thr Ala Lys Gly His Gln Val Gln Gly Gln
145                 150                 155                 160

Ala Lys Ser Arg Thr Cys Ser Thr Ser Pro Ser Ser Pro Ser Pro
                165                 170                 175

Pro Pro Pro Thr Ile Val Lys Glu Ala Glu Val Pro Ser Cys Asn Gly
            180                 185                 190

Phe Asn Lys Arg Gly Ser Ser Ala Met Asp Ser Gly Lys Pro Pro Arg
            195                 200                 205

Pro Val Glu Gly Gly Ala Gly Gln Arg Gln Ala Gly Phe Cys Phe Gly
    210                 215                 220

Val Ser Asp Thr Lys Gln Ala Ala Lys Pro Arg Gly Pro Asn Thr Ser
225                 230                 235                 240

Arg Arg Arg Asn Gly Arg Lys Leu Ser Ser Lys His Asp Val
                245                 250                 255

Ser Ser Glu Asp Glu Thr Ala Gly Ser
            260                 265

<210> SEQ ID NO 33
<211> LENGTH: 320
<212> TYPE: PRT
<213> ORGANISM: Sorghum bicolor

<400> SEQUENCE: 33

Met Asp Ser Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
            20                  25                  30

Ile Thr Arg Ser Lys Gly Glu Arg Met Asn Asp Leu Asp Tyr Ala Arg
            35                  40                  45

Met Asn Thr Val Pro Asp Ala Lys Gln Trp Asp Lys Thr Ser Phe Gln

```
                      50                  55                  60
His His Asp Gln Ser Arg Met Asp His Ile Asn Leu Gly Leu Met Asn
 65                  70                  75                  80

Leu Asp Leu Lys Met Asn Asp Leu Lys Met Asn Glu Ala Pro Thr Ala
                 85                  90                  95

Met Lys Leu Pro Phe His Asn Met Pro Tyr Asn Met Asn Pro Met Tyr
                100                 105                 110

Pro Lys Gly Ser Asn Ala Asn Val Asn Val Asn Ala Phe Lys Met Asn
                115                 120                 125

Val Gly Val Asn Lys Tyr Ser Asn Ser Pro Asn Gly Lys Asp Ala Asn
130                 135                 140

Gly Lys Asn Asn Gly Gly Ser Asn Asn Gly Gly Asn Ser Asn Gly
145                 150                 155                 160

Ser Ala Asn Gly Asn Ser Ala Val Asp Lys Arg Phe Lys Thr Leu Pro
                165                 170                 175

Thr Ser Glu Met Leu Pro Arg Asn Glu Val Leu Gly Gly Tyr Ile Phe
                180                 185                 190

Val Cys Asn Asn Asp Thr Met Gln Glu Asp Leu Lys Arg Gln Leu Phe
                195                 200                 205

Gly Leu Pro Ala Arg Tyr Arg Asp Ser Val Arg Ala Ile Thr Pro Gly
210                 215                 220

Leu Pro Leu Phe Leu Tyr Asn Tyr Thr Thr His Gln Leu His Gly Val
225                 230                 235                 240

Phe Glu Ala Ala Ser Phe Gly Gly Ser Asn Ile Asp Pro Thr Ala Trp
                245                 250                 255

Glu Asp Lys Lys Cys Lys Gly Glu Ser Arg Phe Pro Ala Gln Val Arg
                260                 265                 270

Ile Arg Ile Arg Lys Leu Cys Lys Pro Leu Glu Glu Asp Ser Phe Arg
                275                 280                 285

Pro Val Leu His His Tyr Asp Gly Pro Lys Phe Arg Leu Glu Leu Ser
                290                 295                 300

Ile Ala Glu Thr Leu Ser Leu Leu Asp Leu Cys Glu Lys Glu Gly Ile
305                 310                 315                 320

<210> SEQ ID NO 34
<211> LENGTH: 265
<212> TYPE: PRT
<213> ORGANISM: Saccharum officinarum

<400> SEQUENCE: 34

Met Asn Thr Asp Pro Asp Ala Lys Gln Trp Asp Lys Thr Ser Tyr Gln
 1               5                  10                  15

His His Asn Glu Ser Arg Met Asp His Ile Asn Leu Gly Leu Met Asn
                20                  25                  30

Leu Asp Leu Lys Met Asn Glu Ala Ala Thr Ala Met Lys Leu Pro Phe
                35                  40                  45

His Asn Met Pro Tyr Asn Met Asn Pro Met Tyr Pro Lys Gly Ser Asn
                50                  55                  60

Val Asn Val Asn Ala Phe Lys Met Asn Val Gly Val Asn Lys Tyr Ser
 65                  70                  75                  80

Asn Ser Pro Asn Gly Lys Asp Ala Asn Gly Lys Asn Asn Gly Gly Ser
                85                  90                  95

Asn Asn Asn Gly Gly Asn Ser Asn Gly Ser Ala Asn Ser Asn Ser Ala
                100                 105                 110

Val Asp Lys Arg Phe Lys Thr Leu Pro Thr Ser Glu Met Leu Pro Arg
```

```
                   115                 120                 125
Asn Glu Val Leu Gly Gly Tyr Ile Phe Val Cys Asn Asn Asp Thr Met
130                 135                 140

Gln Glu Asp Leu Lys Arg Gln Leu Phe Gly Leu Pro Ala Arg Tyr Arg
145                 150                 155                 160

Asp Ser Val Arg Ala Ile Thr Pro Gly Leu Pro Leu Phe Leu Tyr Asn
                    165                 170                 175

Tyr Thr Thr His Gln Leu His Gly Val Phe Glu Ala Ala Ser Phe Gly
                180                 185                 190

Gly Ser Asn Ile Asp Pro Thr Ala Trp Glu Asp Lys Lys Cys Lys Gly
            195                 200                 205

Glu Ser Arg Phe Pro Ala Gln Val Arg Ile Arg Ile Arg Lys Leu Cys
210                 215                 220

Lys Pro Leu Glu Glu Asp Ser Phe Arg Pro Val Leu His His Tyr Asp
225                 230                 235                 240

Gly Pro Lys Phe Arg Leu Glu Leu Ser Ile Ala Glu Thr Leu Ser Leu
                245                 250                 255

Leu Asp Leu Cys Glu Lys Glu Gly Ile
                260                 265

<210> SEQ ID NO 35
<211> LENGTH: 200
<212> TYPE: PRT
<213> ORGANISM: Saccharum officinarum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 35

Xaa Xaa Gln Pro Lys Val Val Glu Asp Arg Gln Trp Ser Leu Met Thr
1               5                   10                  15

Ser Lys Leu Ala Glu Ile Thr Arg Ser Lys Gly Glu Arg Met Asn Asp
                20                  25                  30

Leu Asp Tyr Ala Arg Met Asn Thr Val Pro Asp Ala Lys Gln Trp Asp
            35                  40                  45

Lys Thr Ser Tyr Gln His His Asp Glu Ser Arg Met Asp His Ile Asn
50                  55                  60

Leu Gly Leu Met Asn Leu Asp Leu Lys Met Asn Asp Leu Lys Met Asn
65                  70                  75                  80

Glu Ala Ala Thr Ala Met Lys Leu Pro Phe His Asn Met Pro Tyr Asn
                85                  90                  95

Met Asn Pro Met Tyr Pro Lys Gly Ser Asn Val Asn Val Asn Ala Phe
            100                 105                 110

Lys Met Asn Val Gly Val Asn Lys Tyr Ser Ser Ser Pro Asn Gly Lys
        115                 120                 125

Asp Ala Asn Gly Lys Asn Asn Gly Gly Ser Asn Asn Gly Gly Asn
    130                 135                 140

Ser Asn Gly Ser Ala Asn Ser Asn Ser Ala Val Asp Lys Arg Phe Lys
145                 150                 155                 160

Thr Leu Pro Thr Ser Glu Met Leu Pro Arg Asn Glu Val Leu Gly Gly
                165                 170                 175

Tyr Ile Phe Val Cys Asn Asn Asp Thr Met Gln Glu Asp Leu Lys Arg
            180                 185                 190

Gln Leu Phe Gly Leu Pro Ala Arg
        195                 200
```

<210> SEQ ID NO 36
<211> LENGTH: 381
<212> TYPE: PRT
<213> ORGANISM: Sorghum bicolor

<400> SEQUENCE: 36

```
Met Ile Leu Glu Val Ala Ala Val Glu Thr Gln Ser Ile Val His Leu
1               5                   10                  15

Phe Lys Pro Arg Asp Glu Lys Ile Leu Leu Ala Glu Gly His Lys Arg
            20                  25                  30

Pro Arg Ser Pro Gly Leu Ser Ser Lys Ala Tyr Ser Gly Ser Leu
        35                  40                  45

Val Gly Leu Ser Ile Val Phe Ala Pro Leu Ser Ala Leu Val Ala Ser
    50                  55                  60

Ser Glu Pro Met Ser His Pro Pro Pro Pro Val Asp Gln Asn Ile
65                  70                  75                  80

Ser Leu Arg Phe Cys Glu Ser Phe Ser Leu Gln Gly Thr Glu Thr Pro
                85                  90                  95

Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
        115                 120                 125

Lys Leu Val Asn Lys Leu Val Asp Ser Phe Glu Glu Gln Asp Thr Pro
130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
        195                 200                 205

Val Ser Gly Gly His Leu Asn Pro Ala Val Thr Val Gly Leu Met Val
    210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
                245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
        275                 280                 285

Thr Tyr Ala Met Ile Leu Asp Pro Arg Ser Gln Val Arg Thr Ile Gly
    290                 295                 300

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
                325                 330                 335

Leu Ala Ser Gly Val Trp Thr Asn His Trp Ile Tyr Trp Ile Gly Pro
            340                 345                 350

Leu Leu Gly Gly Pro Leu Ala Gly Phe Ile Tyr Glu Ser Leu Phe Ile
        355                 360                 365

Val Asn Lys Thr His Glu Pro Leu Leu Asn Gly Asp Ile
    370                 375                 380
```

-continued

```
<210> SEQ ID NO 37
<211> LENGTH: 308
<212> TYPE: PRT
<213> ORGANISM: Saccharum officinarum

<400> SEQUENCE: 37

Pro Thr Arg Pro Pro Pro Val Val Gln Asn Ile Ser Leu Arg Phe
1               5                   10                  15

Ser Glu Ser Phe Ser Leu Gln Gly Thr Gly Thr Thr Gly Ala Phe Thr
                20                  25                  30

Pro Pro Pro Ala Phe Pro Ser Pro Pro Gly Arg Leu Leu Leu Ala Ile
            35                  40                  45

Val His Ser Phe Met Ala Lys Leu Val Asn Lys Leu Val Asp Ser Phe
50                  55                  60

Asp His Asp Glu Thr Thr Pro Asp Val Gly Cys Val Arg Ala Val Leu
65                  70                  75                  80

Ala Glu Leu Val Leu Thr Phe Leu Phe Val Phe Thr Gly Val Ser Ala
                85                  90                  95

Ala Met Ala Ala Gly Ser Gly Gly Lys Pro Gly Glu Ala Met Pro Met
            100                 105                 110

Ala Thr Leu Ala Ala Val Ala Ile Ala His Ala Leu Ala Ala Gly Val
        115                 120                 125

Leu Val Thr Ala Gly Phe His Val Ser Gly Gly His Leu Asn Pro Ala
    130                 135                 140

Val Thr Val Gly Leu Met Val Cys Gly His Ile Thr Lys Leu Arg Ala
145                 150                 155                 160

Val Leu Tyr Ile Ala Ala Gln Leu Leu Ala Ser Ser Leu Ala Cys Ile
                165                 170                 175

Leu Leu Arg Tyr Leu Ser Gly Gly Met Val Thr Pro Val His Ala Leu
            180                 185                 190

Gly Ala Gly Ile Ser Pro Met Gln Gly Leu Val Met Glu Val Ile Leu
        195                 200                 205

Thr Phe Ser Leu Leu Phe Val Thr Tyr Ala Met Ile Leu Asp Pro Arg
    210                 215                 220

Ser Gln Val Arg Thr Ile Gly Pro Leu Leu Thr Gly Leu Ile Val Gly
225                 230                 235                 240

Ala Asn Ser Leu Ala Gly Gly Asn Phe Thr Gly Ala Ser Met Asn Pro
                245                 250                 255

Ala Arg Ser Phe Gly Pro Ala Leu Ala Thr Gly Val Trp Thr Asn His
            260                 265                 270

Trp Val Tyr Trp Ile Gly Pro Leu Leu Gly Gly Pro Leu Ala Gly Phe
        275                 280                 285

Val Tyr Glu Ser Leu Phe Ile Val Asn Lys Thr His Glu Pro Leu Leu
    290                 295                 300

Asn Gly Asp Ile
305

<210> SEQ ID NO 38
<211> LENGTH: 257
<212> TYPE: PRT
<213> ORGANISM: Zea mays

<400> SEQUENCE: 38

Met Ala Lys Leu Val Asn Lys Leu Val Asp Ser Phe Asp His His Glu
1               5                   10                  15

Ala Pro Ala Pro Asp Val Gly Cys Val Arg Ala Val Leu Ala Glu Leu
```

```
            20                  25                  30
Val Leu Thr Phe Leu Phe Val Phe Thr Gly Val Ser Ala Ser Met Ala
            35                  40                  45

Ala Gly Ala Gly Gly Lys Pro Gly Glu Ala Met Pro Met Ala Thr Leu
        50                  55                  60

Ala Ala Val Ala Ile Ala His Ala Leu Ala Ala Gly Val Leu Val Thr
 65                  70                  75                  80

Ala Gly Phe His Val Ser Gly Gly His Leu Asn Pro Ala Val Thr Val
                85                  90                  95

Gly Ile Leu Val Arg Gly His Ile Thr Lys Leu Arg Ala Leu Leu Tyr
            100                 105                 110

Val Ala Ala Gln Leu Leu Ala Ser Ser Leu Ala Cys Ile Leu Leu Arg
            115                 120                 125

Tyr Leu Ser Gly Gly Met Val Thr Pro Val His Ala Leu Gly Ala Gly
            130                 135                 140

Ile Ser Pro Met Gln Gly Leu Val Met Glu Val Ile Leu Thr Phe Ser
145                 150                 155                 160

Leu Leu Phe Val Thr Tyr Ala Met Ile Leu Asp Pro Arg Ser Gln Val
                165                 170                 175

Arg Thr Ile Gly Pro Leu Leu Thr Gly Leu Ile Val Gly Ala Asn Ser
            180                 185                 190

Leu Ala Gly Gly Asn Phe Thr Gly Ala Ser Met Asn Pro Ala Arg Ser
            195                 200                 205

Phe Gly Pro Ala Met Ala Thr Gly Val Trp Thr Asn His Trp Val Tyr
            210                 215                 220

Trp Ile Gly Pro Leu Leu Gly Gly Ser Leu Ala Gly Phe Val Tyr Glu
225                 230                 235                 240

Ser Leu Phe Met Val Tyr Lys Thr His Glu Pro Leu Leu Asn Gly Asp
                245                 250                 255

Ile

<210> SEQ ID NO 39
<211> LENGTH: 255
<212> TYPE: PRT
<213> ORGANISM: Zea mays

<400> SEQUENCE: 39

Met Ala Lys Leu Met Asn Lys Leu Val Asp Ser Phe Glu His Asp Glu
1               5                   10                  15

Ile Leu Asp Val Gly Cys Val Arg Ala Val Leu Ala Glu Leu Val Leu
            20                  25                  30

Thr Phe Leu Phe Val Phe Thr Gly Val Ser Ala Ala Met Ala Ala Gly
            35                  40                  45

Ser Asp Gly Lys Pro Gly Asp Ala Met Pro Met Ala Thr Leu Ala Ala
        50                  55                  60

Val Ala Ile Ala His Ala Leu Ala Ala Gly Val Leu Val Thr Ala Gly
 65                  70                  75                  80

Phe His Val Ser Gly Gly His Leu Asn Pro Ala Val Thr Val Gly Leu
                85                  90                  95

Met Val Arg Gly His Ile Thr Lys Leu Arg Ala Val Leu Tyr Val Ala
            100                 105                 110

Ala Gln Leu Leu Ala Ser Ser Ala Ala Cys Val Leu Leu Arg Phe Leu
            115                 120                 125

Ser Gly Gly Met Val Thr Pro Val His Ala Leu Gly Arg Gly Ile Ser
            130                 135                 140
```

```
Pro Met Gln Gly Leu Val Met Glu Val Ile Leu Thr Phe Ser Leu Leu
145                 150                 155                 160

Phe Val Thr Tyr Ala Met Ile Leu Asp Pro Arg Ser Gln Val Arg Ala
                165                 170                 175

Ile Gly Pro Leu Leu Thr Gly Leu Ile Val Gly Ala Asn Ser Leu Ala
            180                 185                 190

Gly Gly Asn Phe Thr Gly Ala Ser Met Asn Pro Ala Arg Ser Phe Gly
            195                 200                 205

Pro Ala Leu Ala Thr Gly Asp Trp Thr Asn His Trp Val Tyr Trp Ile
            210                 215                 220

Gly Pro Leu Leu Gly Gly Pro Leu Ala Gly Phe Val Tyr Glu Ser Leu
225                 230                 235                 240

Phe Leu Val Gln Lys Met His Glu Pro Leu Leu Asn Gly Glu Val
                245                 250                 255

<210> SEQ ID NO 40
<211> LENGTH: 254
<212> TYPE: PRT
<213> ORGANISM: Sorghum bicolor

<400> SEQUENCE: 40

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Pro Ala Gly Gly
            20                  25                  30

Phe Phe Trp Ala Ala Pro Pro Ser Leu Gln Pro Gln Val Val Gln Ala
            35                  40                  45

Pro Val Gln Ser Val Val Ala Ala Ser Ala Pro Asn Pro Cys Val Glu
        50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
                100                 105                 110

Gly Ala Ile Leu Glu Pro Gly Lys Thr Pro Lys Met Asp Lys Ser Ala
            115                 120                 125

Ile Leu Asn Asp Ala Ile Arg Val Val Gly Glu Leu Arg Ser Glu Ala
130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
                180                 185                 190

Pro Ser Leu Val Pro His His Pro Val Ile Ser Ala Ser Ala Phe Thr
            195                 200                 205

Ala Pro Gln Gly Pro Ala Val Ala Gly His Lys Leu Met Met Pro Val
            210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250

<210> SEQ ID NO 41
```

<211> LENGTH: 252
<212> TYPE: PRT
<213> ORGANISM: Zea mays

<400> SEQUENCE: 41

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Pro Ala Gly Gly
            20                  25                  30

Phe Phe Trp Ala Ala Pro Pro Ser Leu Gln Pro Gln Ala Pro Val Gln
        35                  40                  45

Ser Val Ala Ala Ser Ala Pro Asn Pro Cys Met Glu Ile Ser Ser
    50                  55                  60

Ser Val Asp Cys Gly Gln Glu Lys Glu Gln Pro Thr Asn Lys Arg Pro
65              70                  75                  80

Arg Ser Glu Ser Thr Thr Glu Ser Ser Thr Lys Ala Ser Arg Glu Lys
                85                  90                  95

Ile Arg Arg Asp Lys Leu Asn Glu Arg Phe Leu Glu Leu Gly Ala Ile
            100                 105                 110

Leu Glu Pro Gly Lys Thr Pro Lys Met Asp Lys Thr Ala Ile Leu Ser
        115                 120                 125

Asp Ala Ile Arg Val Val Gly Glu Leu Arg Ser Glu Ala Lys Lys Leu
    130                 135                 140

Lys Asp Ser Asn Glu Asn Leu Gln Glu Lys Ile Lys Glu Leu Lys Ala
145                 150                 155                 160

Glu Lys Asn Glu Leu Arg Asp Glu Lys Gln Arg Leu Lys Ala Glu Lys
                165                 170                 175

Glu Ser Leu Glu Gln Gln Ile Lys Phe Leu Asn Ala Arg Pro Ser Leu
            180                 185                 190

Val Pro His His Pro Val Ile Pro Ala Ser Ala Phe Pro Ala Pro Gln
        195                 200                 205

Gly Pro Ala Ala Ala Arg His Lys Leu Met Met Pro Val Ile Gly
    210                 215                 220

Tyr Pro Gly Phe Pro Met Trp Gln Phe Met Pro Pro Ser Asp Val Asp
225                 230                 235                 240

Thr Ser Asp Asp Pro Arg Ser Cys Pro Val Ala
                245                 250
```

<210> SEQ ID NO 42
<211> LENGTH: 159
<212> TYPE: PRT
<213> ORGANISM: Saccharum officinarum

<400> SEQUENCE: 42

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Pro Cys Val
    50                  55                  60

Glu Ile Ser Ser Ser Val Asp Cys Gly Gln Gly Lys Glu Gln Pro Thr
65              70                  75                  80

Asn Lys Arg Pro Arg Ser Glu Ser Thr Ala Glu Pro Ser Thr Lys Ala
                85                  90                  95
```

```
Ser Arg Glu Lys Ile Arg Arg Asp Lys Leu Asn Lys Arg Phe Leu Glu
            100                 105                 110

Trp Gly Ala Ile Val Glu Pro Gly Thr Pro Lys Met Asp Lys Ser
        115                 120                 125

Ala Ile Leu Asn Asp Ala Ile Arg Ala Val Ser Glu Leu Arg Ser Glu
        130                 135                 140

Thr Lys Lys Leu Lys Asp Ser Asn Glu Ser Leu Gln Gly Glu Asp
145                 150                 155

<210> SEQ ID NO 43
<211> LENGTH: 151
<212> TYPE: PRT
<213> ORGANISM: Brassica napus

<400> SEQUENCE: 43

Met Gly Arg Met His Ser Arg Gly Lys Gly Ile Ser Ala Ser Ala Leu
1               5                   10                  15

Pro Tyr Lys Arg Ser Pro Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 44
<211> LENGTH: 151
<212> TYPE: PRT
<213> ORGANISM: Brassica napus

<400> SEQUENCE: 44

Met Gly Arg Met His Ser Arg Gly Lys Gly Ile Ser Ala Ser Ala Leu
1               5                   10                  15

Pro Tyr Lys Arg Ser Pro Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
```

```
            115                 120                 125
Tyr Lys Lys Thr Lys Lys Leu Pro Pro Val Trp Lys Tyr Glu Ser Thr
        130                 135                 140

Thr Ala Ser Thr Leu Val Ala
145                 150

<210> SEQ ID NO 45
<211> LENGTH: 151
<212> TYPE: PRT
<213> ORGANISM: Solanum tuberosum

<400> SEQUENCE: 45

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Thr Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 46
<211> LENGTH: 151
<212> TYPE: PRT
<213> ORGANISM: Gossypium hirsutum

<400> SEQUENCE: 46

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140
```

```
Thr Ala Ser Thr Leu Val Ala
145                 150

<210> SEQ ID NO 47
<211> LENGTH: 151
<212> TYPE: PRT
<213> ORGANISM: Gossypium hirsutum

<400> SEQUENCE: 47

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
                20                  25                  30

Val Glu Glu Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 48
<211> LENGTH: 151
<212> TYPE: PRT
<213> ORGANISM: Lycopersicon esculentum

<400> SEQUENCE: 48

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
                20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150
```

<210> SEQ ID NO 49
<211> LENGTH: 151
<212> TYPE: PRT
<213> ORGANISM: Lycopersicon esculentum

<400> SEQUENCE: 49

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 50
<211> LENGTH: 151
<212> TYPE: PRT
<213> ORGANISM: Lycopersicon esculentum

<400> SEQUENCE: 50

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 51
<211> LENGTH: 151
<212> TYPE: PRT

```
<213> ORGANISM: Lycopersicon esculentum

<400> SEQUENCE: 51

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 52
<211> LENGTH: 151
<212> TYPE: PRT
<213> ORGANISM: Solanum tuberosum

<400> SEQUENCE: 52

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 53
<211> LENGTH: 151
<212> TYPE: PRT
<213> ORGANISM: Solanum tuberosum

<400> SEQUENCE: 53
```

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 54
<211> LENGTH: 151
<212> TYPE: PRT
<213> ORGANISM: Solanum tuberosum

<400> SEQUENCE: 54

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 55
<211> LENGTH: 151
<212> TYPE: PRT
<213> ORGANISM: Solanum tuberosum

<400> SEQUENCE: 55

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp

-continued

```
                    20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 56
<211> LENGTH: 151
<212> TYPE: PRT
<213> ORGANISM: Capsicum annuum

<400> SEQUENCE: 56

Met Gly Arg Met His Ser Arg Gly Lys Gly Ile Ser Ala Ser Ala Leu
1               5                   10                  15

Pro Tyr Lys Arg Thr Pro Ser Trp Leu Lys Ile Ser Ala Pro Asp
            20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 57
<211> LENGTH: 151
<212> TYPE: PRT
<213> ORGANISM: Arabidopsis thaliana

<400> SEQUENCE: 57

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Ser Gln Asp
            20                  25                  30

Val Asp Glu Ser Ile Cys Lys Phe Ala Lys Lys Gly Leu Thr Pro Ser
            35                  40                  45
```

```
Gln Ile Gly Val Ile Leu Arg Asp Ser His Gly Ile Pro Gln Val Lys
 50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
130                 135                 140

Thr Ala Ser Thr Leu Val Ala
145                 150

<210> SEQ ID NO 58
<211> LENGTH: 151
<212> TYPE: PRT
<213> ORGANISM: Brassica napus

<400> SEQUENCE: 58

Met Gly Arg Leu His Ser Lys Gly Lys Gly Ile Ser Ala Ser Ala Leu
 1               5                  10                  15

Pro Tyr Lys Arg Ser Pro Ser Trp Leu Lys Thr Thr Ser Gln Asp
            20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
 50                  55                  60

Ser Val Thr Gly Asn Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
130                 135                 140

Thr Ala Ser Thr Leu Val Ala
145                 150

<210> SEQ ID NO 59
<211> LENGTH: 151
<212> TYPE: PRT
<213> ORGANISM: Brassica napus

<400> SEQUENCE: 59

Met Gly Arg Leu His Ser Lys Gly Lys Gly Ile Ser Ala Ser Ala Leu
 1               5                  10                  15

Pro Tyr Lys Arg Ser Pro Ser Trp Leu Lys Thr Thr Ser Glu Asp
            20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
 50                  55                  60
```

```
Ser Val Thr Gly Asn Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150

<210> SEQ ID NO 60
<211> LENGTH: 151
<212> TYPE: PRT
<213> ORGANISM: Brassica napus

<400> SEQUENCE: 60

Met Gly Arg Leu His Ser Lys Gly Lys Gly Ile Ser Ala Ser Ala Leu
1               5                   10                  15

Pro Tyr Lys Arg Ser Pro Ser Trp Leu Lys Thr Thr Ser Gln Asp
                 20                  25                  30

Val Asp Glu Ser Ile Cys Lys Phe Ala Lys Lys Gly Leu Thr Pro Ser
             35                  40                  45

Gln Ile Gly Val Ile Leu Arg Asp Ser His Gly Ile Pro Gln Val Lys
        50                  55                  60

Ser Val Thr Gly Asn Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150

<210> SEQ ID NO 61
<211> LENGTH: 151
<212> TYPE: PRT
<213> ORGANISM: Gossypium hirsutum

<400> SEQUENCE: 61

Met Gly Arg Met His Ser Arg Gly Lys Gly Ile Ser Ala Ser Ala Leu
1               5                   10                  15

Pro Tyr Arg Arg Thr Pro Pro Ser Trp Leu Lys Ile Ser Ser Gln Asp
                 20                  25                  30

Val Glu Glu Asn Ile Cys Lys Phe Ala Lys Lys Gly Leu Thr Pro Ser
             35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
```

```
                    85                  90                  95
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 62
<211> LENGTH: 151
<212> TYPE: PRT
<213> ORGANISM: Gossypium hirsutum

<400> SEQUENCE: 62

Met Gly Arg Met His Ser Arg Gly Lys Gly Ile Ser Ala Ser Ala Leu
1               5                   10                  15

Pro Tyr Lys Arg Thr Pro Ser Trp Leu Lys Ile Ser Ser Gln Asp
            20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 63
<211> LENGTH: 151
<212> TYPE: PRT
<213> ORGANISM: Gossypium hirsutum

<400> SEQUENCE: 63

Met Gly Arg Met His Ser Arg Gly Lys Gly Ile Ser Ala Ser Ala Leu
1               5                   10                  15

Pro Tyr Lys Arg Thr Pro Ser Trp Leu Lys Ile Ser Ser Gln Asp
            20                  25                  30

Val Glu Glu Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Arg
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110
```

```
Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150

<210> SEQ ID NO 64
<211> LENGTH: 151
<212> TYPE: PRT
<213> ORGANISM: Arabidopsis thaliana

<400> SEQUENCE: 64

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Pro Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 65
<211> LENGTH: 151
<212> TYPE: PRT
<213> ORGANISM: Glycine max

<400> SEQUENCE: 65

Met Gly Arg Met His Ser Arg Gly Lys Gly Ile Ser Ser Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Asn
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125
```

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 66
<211> LENGTH: 215
<212> TYPE: PRT
<213> ORGANISM: Capsicum annuum
<220> FEATURE:
<221> NAME/KEY: misc_feature
<222> LOCATION: (1)..(3)
<223> OTHER INFORMATION: Xaa can be any naturally occurring amino acid

<400> SEQUENCE: 66

Xaa Xaa Xaa Glu Arg Glu Arg Glu Arg Glu Arg Glu Arg Glu Arg Glu
1               5                   10                  15

Arg Glu Arg Glu Arg Glu Arg Glu Arg Glu Arg Glu Arg Glu Arg Glu
            20                  25                  30

Arg Glu Arg Glu Arg Glu Arg Glu Arg Glu Arg Gly Gln Pro Asn Ser
        35                  40                  45

Ser Leu Ser Pro Pro Pro Ser Pro Leu Thr Thr Asn Thr Gln Pro Ala
50                  55                  60

Ile Met Gly Arg Met His Ser Arg Gly Lys Gly Ile Ser Ala Ser Ala
65                  70                  75                  80

Leu Pro Tyr Lys Arg Thr Pro Pro Ser Trp Leu Lys Ile Ser Ala Pro
                85                  90                  95

Asp Val Glu Asp Asn Ile Cys Lys Phe Ala Lys Lys Gly Leu Ala Pro
            100                 105                 110

Ser Gln Ile Gly Val Ile Leu Arg Asp Ser His Gly Ile Ala Gln Val
        115                 120                 125

Lys Ser Val Thr Gly Ser Lys Ile Leu Arg Ile Leu Lys Ala His Gly
130                 135                 140

Leu Ala Pro Glu Ile Pro Glu Asp Leu Tyr His Leu Ile Lys Lys Ala
145                 150                 155                 160

Val Ala Ile Arg Lys His Leu Glu Arg Asn Arg Lys Asp Lys Asp Ser
                165                 170                 175

Lys Phe Arg Leu Ile Leu Val Glu Ser Arg Ile His Arg Leu Ala Arg
            180                 185                 190

Tyr Tyr Lys Lys Thr Lys Lys Leu Pro Pro Val Trp Lys Tyr Glu Ser
        195                 200                 205

Thr Thr Ala Ser Thr Leu Val
    210                 215

<210> SEQ ID NO 67
<211> LENGTH: 151
<212> TYPE: PRT
<213> ORGANISM: Populus tremula x Populus tremuloides

<400> SEQUENCE: 67

Met Gly Arg Met His Ser His Gly Lys Gly Ile Ser Ala Ser Ala Leu
1               5                   10                  15

Pro Tyr Lys Arg Thr Pro Pro Ser Trp Leu Lys Ile Ser Ala Gln Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Arg
50                  55                  60

-continued

```
Ser Val Thr Gly Asn Gln Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Ser
    130                 135                 140

Thr Ala Ser Thr Leu Val Ala
145                 150

<210> SEQ ID NO 68
<211> LENGTH: 151
<212> TYPE: PRT
<213> ORGANISM: Medicago truncatula

<400> SEQUENCE: 68

Met Gly Arg Met His Ser Gly Gly Lys Gly Ile Ser Ser Ser Ala Leu
1               5                   10                  15

Pro Tyr Lys Arg Ser Ala Pro Gly Trp Leu Lys Thr Ser Thr Gln Asp
            20                  25                  30

Val Glu Glu Thr Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Phe Ile Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 69
<211> LENGTH: 151
<212> TYPE: PRT
<213> ORGANISM: Populus tremula x Populus tremuloides

<400> SEQUENCE: 69

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Gln Asp
            20                  25                  30

Val Asp Asp Ser Ile Cys Lys Phe Ala Lys Lys Gly Leu Thr Pro Ser
        35                  40                  45

Gln Ile Gly Val Ile Leu Arg Asp Ser His Gly Ile Ala Gln Val Arg
    50                  55                  60

Ser Val Thr Gly Asn Gln Ile Leu Arg Ile Leu Lys Ala His Gly Leu
 65                  70                  75                  80

Ala Pro Glu Ile Pro Glu Asp Leu Tyr His Leu Ile Lys Lys Ala Val
```

```
                85                  90                  95
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Ala Pro Val Trp Lys Tyr Glu Ser Ser
            130                 135                 140

Thr Ala Ser Thr Leu Val Ala
145                 150

<210> SEQ ID NO 70
<211> LENGTH: 151
<212> TYPE: PRT
<213> ORGANISM: Medicago truncatula

<400> SEQUENCE: 70

Met Gly Arg Met His Ser Gly Gly Lys Gly Ile Ser Ser Ser Ala Leu
1               5                   10                  15

Pro Tyr Lys Arg Thr Pro Ala Ser Trp Leu Lys Ile Ser Thr Gln Asp
            20                  25                  30

Val Asp Glu Thr Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ala Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 71
<211> LENGTH: 151
<212> TYPE: PRT
<213> ORGANISM: Populus tremula x Populus tremuloides

<400> SEQUENCE: 71

Met Gly Arg Met His Ser Lys Gly Lys Gly Ile Ser Ala Ser Ala Leu
1               5                   10                  15

Pro Tyr Lys Arg Thr Pro Pro Ser Trp Leu Lys Ile Ser Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ala Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110
```

```
Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Ser
130                 135                 140

Thr Ala Ser Thr Leu Val Ala
145                 150

<210> SEQ ID NO 72
<211> LENGTH: 148
<212> TYPE: PRT
<213> ORGANISM: Medicago truncatula

<400> SEQUENCE: 72

Met His Ser Lys Gly Lys Gly Ile Ser Ser Ala Leu Pro Tyr Lys
1               5                   10                  15

Arg Thr Ser Pro Ser Trp Leu Lys Ile Ser Ser Pro Glu Val Asp Glu
            20                  25                  30

Thr Ile Cys Lys Phe Ala Lys Lys Gly Leu Thr Pro Ser Gln Ile Gly
        35                  40                  45

Val Ile Leu Arg Asp Ser His Gly Ile Ala Gln Val Lys Ser Val Thr
50                  55                  60

Gly Ser Lys Ile Leu Arg Ile Leu Lys Ala His Gly Leu Ala Pro Glu
65                  70                  75                  80

Ile Pro Glu Asp Leu Tyr His Leu Ile Lys Lys Ala Val Ser Ile Arg
                85                  90                  95

Lys His Leu Glu Arg Asn Arg Lys Asp Lys Ser Lys Phe Arg Leu
            100                 105                 110

Ile Leu Val Glu Ser Arg Ile His Arg Leu Ala Arg Tyr Tyr Lys Lys
            115                 120                 125

Thr Lys Lys Leu Pro Pro Val Trp Lys Tyr Glu Ser Thr Ala Ser
            130                 135                 140

Thr Leu Val Ala
145

<210> SEQ ID NO 73
<211> LENGTH: 151
<212> TYPE: PRT
<213> ORGANISM: Oryza sativa

<400> SEQUENCE: 73

Met Gly Arg Leu His Ser Lys Gly Lys Gly Ile Ala Ser Ser Thr Leu
1               5                   10                  15

Pro Tyr Ser Arg Thr Pro Pro Ala Trp Leu Lys Thr Thr Pro Asp Gln
            20                  25                  30

Val Val Asp His Ile Cys Lys Leu Ala Lys Lys Gly Ala Thr Pro Ser
        35                  40                  45

Gln Ile Gly Val Val Leu Arg Asp Ser His Gly Val Ala Gln Val Lys
    50                  55                  60

Ile Val Thr Gly Asn Lys Ile Leu Arg Ile Leu Lys Ser Asn Gly Leu
65                  70                  75                  80

Ala Pro Glu Leu Pro Glu Asp Leu Tyr Phe Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ser Arg Tyr
            115                 120                 125
```

```
Tyr Lys Thr Val Gly Val Leu Pro Pro Thr Trp Arg Tyr Glu Ser Ala
        130                 135                 140

Thr Ala Ser Thr Leu Val Ala
145                 150

<210> SEQ ID NO 74
<211> LENGTH: 151
<212> TYPE: PRT
<213> ORGANISM: Oryza sativa

<400> SEQUENCE: 74

Met Gly Arg Met His Ser Ser Gly Lys Gly Met Ser Cys Ser Val Leu
1               5                   10                  15

Pro Tyr Arg Arg Ala Ala Pro Ala Trp Val Lys Thr Ser Ala Ser Glu
            20                  25                  30

Val Glu Glu Met Ile Val Arg Val Ala Lys Lys Gly Gln Leu Pro Ser
        35                  40                  45

Gln Ile Gly Ala Ile Leu Arg Asp Ala His Ala Val Pro Leu Ala Gln
    50                  55                  60

Gly Val Thr Gly Gly Lys Ile Leu Arg Val Leu Lys Ser Arg Gly Leu
65                  70                  75                  80

Ala Pro Glu Val Pro Glu Asp Leu Tyr Phe Leu Ile Lys Lys Ala Val
                85                  90                  95

Ala Met Arg Lys His Leu Glu Arg Asn Arg Lys Asp Lys Asp Thr Lys
            100                 105                 110

Phe Arg Leu Ile Leu Val Glu Ser Arg Val His Arg Leu Thr Arg Tyr
        115                 120                 125

Tyr Arg Leu Ala Lys Lys Ile Pro Ala Phe Phe Lys Tyr Asp Ser Thr
    130                 135                 140

Thr Ala Ser Thr Leu Val Ala
145                 150

<210> SEQ ID NO 75
<211> LENGTH: 151
<212> TYPE: PRT
<213> ORGANISM: Triticum aestivum

<400> SEQUENCE: 75

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
```

<210> SEQ ID NO 76
<211> LENGTH: 151
<212> TYPE: PRT
<213> ORGANISM: Hordeum vulgare

<400> SEQUENCE: 76

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150

<210> SEQ ID NO 77
<211> LENGTH: 151
<212> TYPE: PRT
<213> ORGANISM: Arabidopsis thaliana

<400> SEQUENCE: 77

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150

<210> SEQ ID NO 78

```
<211> LENGTH: 151
<212> TYPE: PRT
<213> ORGANISM: Hordeum vulgare

<400> SEQUENCE: 78

Met Gly Arg Met His Ser Gly Gly Lys Gly Ile Ala Lys Ser Ser Leu
1               5                   10                  15

Pro Tyr Arg Arg Ser Pro Pro Ser Trp Leu Lys Val Thr Ala Ser Gln
            20                  25                  30

Val Glu Asp His Val Asn Lys Leu Ala Lys Arg Gly Leu Thr Pro Ser
        35                  40                  45

Gln Ile Gly Val Ile Leu Arg Asp Ser Asn Gly Ile Ala Gln Val Lys
    50                  55                  60

Ser Val Thr Gly Asn Lys Ile Leu Arg Ile Leu Lys Lys Ser Gly Leu
65                  70                  75                  80

Ala Pro Ala Ile Pro Glu Asp Leu Tyr Met Leu Ile Lys Lys Ala Val
                85                  90                  95

Ala Val Arg Lys His Leu Glu Arg Asn Lys Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Arg Ala Ser Arg Lys Leu Asp Ala Asn Trp Lys Tyr Glu Ser Ala
    130                 135                 140

Thr Ala Ser Ala Leu Val Ala
145                 150

<210> SEQ ID NO 79
<211> LENGTH: 175
<212> TYPE: PRT
<213> ORGANISM: Saccharum officinarum

<400> SEQUENCE: 79

Leu Ala Thr Ala Ala Asn Leu Ser Leu Ala Leu Pro Pro Ala Arg Arg
1               5                   10                  15

Arg Pro Pro Leu Ala Ala Thr Ala Ala Met Gly Arg Met Tyr Gly Pro
            20                  25                  30

Gly Lys Gly Met Ser Ser Ser Val Leu Pro Tyr Ala Arg Val Ala Pro
        35                  40                  45

Gly Trp Val Arg Ser Thr Ala Gly Glu Val Glu Met Ile Val Arg
    50                  55                  60

Ala Ala Lys Lys Gly His Leu Pro Ser Gln Ile Gly Ala Leu Leu Arg
65                  70                  75                  80

Asp Thr His Gly Val Pro Leu Val His Gly Val Thr Gly Gly Lys Ile
                85                  90                  95

Leu Arg Met Leu Lys Ala Arg Gly Leu Ala Pro Glu Val Pro Glu Asp
            100                 105                 110

Leu Tyr Phe Leu Ile Lys Lys Ala Val Ala Ile Arg Lys His Leu Asp
        115                 120                 125

Arg Asn Arg Thr Asp Val Asp Ala Lys Phe Arg Leu Ile Leu Val Glu
    130                 135                 140

Ser Arg Val His Arg Leu Ile Arg Tyr Tyr Arg Arg Thr Lys Lys Ile
145                 150                 155                 160

Ala Pro Asn Leu Lys Tyr Glu Ser Thr Thr Ala Ser Ala Leu Val
                165                 170                 175

<210> SEQ ID NO 80
<211> LENGTH: 131
```

```
<212> TYPE: PRT
<213> ORGANISM: Hordeum vulgare

<400> SEQUENCE: 80

Ile Ser Ala Ser Ala Leu Pro Tyr Lys Arg Thr Pro Ser Trp Leu
1               5                   10                  15

Lys Ile Ser Ser Gln Asp Val Glu Asp Asn Ile Cys Lys Phe Ala Lys
                20                  25                  30

Lys Gly Leu Thr Pro Ser Gln Ile Gly Val Ile Leu Arg Asp Ser His
            35                  40                  45

Gly Ile Ala His Val Lys Ser Val Thr Gly Ser Lys Ile Leu Arg Ile
    50                  55                  60

Leu Lys Ala His Gly Leu Ala Pro Glu Ile Pro Glu Asp Leu Tyr His
65                  70                  75                  80

Leu Ile Lys Lys Ala Val Ala Ile Arg Lys His Leu Glu Arg Asn Arg
                85                  90                  95

Lys Asp Lys Asp Ser Lys Phe Arg Leu Ile Leu Val Glu Ser Arg Ile
                100                 105                 110

His Arg Leu Ala Arg Tyr Tyr Lys Lys Thr Lys Lys Leu Pro Pro Val
            115                 120                 125

Trp Lys Tyr
    130

<210> SEQ ID NO 81
<211> LENGTH: 151
<212> TYPE: PRT
<213> ORGANISM: Populus tremula x Populus tremuloides

<400> SEQUENCE: 81

Met Gly Arg Met His Asn Pro His Lys Gly Ile Ala Gly Ser Ala Leu
1               5                   10                  15

Pro Tyr Lys Arg Thr Pro Arg Trp Leu Lys Val Thr Pro Glu Glu
                20                  25                  30

Val Ser Glu Gln Ile Phe Lys Leu Ala Arg Lys Gly Met Thr Pro Ser
            35                  40                  45

Gln Ile Gly Val Val Leu Arg Asp Ser His Gly Ile Ala Gln Val Lys
    50                  55                  60

Ser Val Thr Gly Ala Lys Ile Leu Arg Ile Leu Lys Gly Asn Gly Leu
65                  70                  75                  80

Ala Pro Glu Leu Pro Glu Asp Leu Tyr His Leu Ile Lys Lys Ala Val
                85                  90                  95

Ser Val Arg Lys His Leu Glu Arg Asn Arg Lys Asp Lys Asp Ser Lys
                100                 105                 110

Phe Arg Leu Ile Leu Ile Glu Ser Arg Ile His Arg Leu Val Arg Tyr
            115                 120                 125

Tyr Lys Thr Lys Ser Gln Leu Ser Pro Ser Phe Lys Tyr Glu Ser Ala
    130                 135                 140

Thr Ala Ser Thr Ile Val Ser
145                 150

<210> SEQ ID NO 82
<211> LENGTH: 151
<212> TYPE: PRT
<213> ORGANISM: Hordeum vulgare

<400> SEQUENCE: 82

Met Gly Arg Met His Thr Pro Gly Lys Gly Ile Ser Lys Ser Ala Leu
1               5                   10                  15
```

```
Pro Tyr Arg Arg Ser Val Ala Thr Trp Leu Lys Ser Ser Glu Asp
         20                  25                  30

Val Lys Asp His Ile Phe Lys Leu Ala Lys Lys Gly Leu Thr Pro Ser
             35                  40                  45

Lys Ile Gly Val Ile Leu Arg Asp Ser His Gly Val Ala Gln Val Arg
 50                  55                  60

Phe Val Thr Gly Asn Lys Ile Leu Arg Ile Met Lys Ala Met Gly Leu
 65                  70                  75                  80

Ala Pro Gly Leu Pro Glu Asp Leu Tyr His Leu Ile Lys Lys Ala Val
                 85                  90                  95

Ala Ile Arg Lys His Leu Glu Arg Asn Arg Lys Asp Arg Asp Ser Lys
             100                 105                 110

Phe Arg Leu Ile Leu Val Glu Ser Arg Ile His Arg Leu Ala Arg Tyr
         115                 120                 125

Tyr Lys Arg Lys Ser Lys Ile Ala Pro Asn Trp Arg Tyr Glu Ser Ser
    130                 135                 140

Thr Ala Ser Ala Leu Val Ala
145                 150

<210> SEQ ID NO 83
<211> LENGTH: 164
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 83

Xaa Xaa Glu Lys Gly Ile Ser Ser Ser Ala Leu Pro Cys Lys Arg Ile
 1               5                  10                  15

Pro Pro Ser Leu Leu Lys Asn Ala Ala Ser Asn Val Glu Glu Met Ile
             20                  25                  30

Met Lys Ala Ala Lys Met Gly Gln Met Ser Ser Gln Ile Gly Val Val
         35                  40                  45

Leu Arg His Gln His Gly Ile Pro Leu Val Lys Ser Ile Ala Ser Ser
 50                  55                  60

Lys Ile Leu His Ile Leu Lys Ala His Gly Leu Ala Pro Lys Ile Leu
 65                  70                  75                  80

Glu Asp Leu Tyr Phe Leu Ile Lys Lys Ala Val Ala Ile Arg Lys His
                 85                  90                  95

Leu Glu Arg Asn Arg Lys Asp Lys Asp Ser Ser Phe Arg Leu Ile Leu
             100                 105                 110

Val Glu Ser Arg Ile His Arg Leu Val Arg Tyr Tyr Lys Arg Thr Lys
         115                 120                 125

Lys Leu Pro Pro Thr Leu Arg Phe Lys Trp Ile Leu Phe Lys Val Gly
    130                 135                 140

Leu Met Leu Ser Ser Leu Leu Leu Thr Cys Val Leu Ser Asn Leu Arg
145                 150                 155                 160

Asn Gly Leu Leu

<210> SEQ ID NO 84
<211> LENGTH: 118
<212> TYPE: PRT
<213> ORGANISM: Glycine max

<400> SEQUENCE: 84
```

```
Glu Glu Asn Ile Cys Lys Phe Ala Lys Lys Gly Leu Thr Pro Ser Gln
1               5                   10                  15

Ile Gly Val Ile Leu Arg Asp Ser His Gly Ile Ala Gln Val Asn Ser
            20                  25                  30

Val Thr Gly Ser Lys Ile Leu Arg Ile Leu Lys Ala His Gly Leu Ala
        35                  40                  45

Pro Glu Ile Pro Glu Asp Leu Tyr His Leu Ile Lys Lys Ala Val Ser
    50                  55                  60

Ile Arg Lys His Leu Glu Arg Asn Arg Lys Asp Lys Asp Ser Lys Phe
65                  70                  75                  80

Arg Leu Ile Leu Val Ser Arg Ile His Arg Leu Ala Arg Tyr Tyr
                85                  90                  95

Lys Lys Thr Lys Lys Leu Pro Pro Val Trp Lys Tyr Glu Ser Thr Thr
            100                 105                 110

Ala Ser Thr Leu Val Ala
            115
```

<210> SEQ ID NO 85
<211> LENGTH: 135
<212> TYPE: PRT
<213> ORGANISM: Populus tremula x Populus tremuloides

<400> SEQUENCE: 85

```
Ser Ala Leu Pro Tyr Lys Arg Thr Pro Pro Ser Trp Leu Lys Thr Ser
1               5                   10                  15

Ala Asn Glu Val Cys Asp His Val Cys Arg Leu Ala Lys Lys Gly Leu
            20                  25                  30

Thr Pro Ser Gln Ile Gly Val Val Leu Arg Asp Ser His Gly Ile Pro
        35                  40                  45

Gln Val Lys Ser Val Thr Asn Asn Lys Ile Leu Arg Ile Leu Lys Ala
    50                  55                  60

Asn Gly Phe Ala Pro Glu Leu Pro Glu Asp Leu Tyr His Leu Ile Lys
65                  70                  75                  80

Lys Ala Ala Ser Ile Arg Lys His Leu Lys Arg Ser Arg Gln Asp Lys
                85                  90                  95

Asp Ala Lys Phe His Leu Ile Leu Val Glu Ala Arg Ile His Arg Val
            100                 105                 110

Ser Arg Tyr Tyr Lys Glu Ser Lys His Leu Pro Ala Asn Trp Arg Tyr
        115                 120                 125

Glu Ser Pro Thr Ala Ala Thr
        130                 135
```

<210> SEQ ID NO 86
<211> LENGTH: 116
<212> TYPE: PRT
<213> ORGANISM: Nicotiana tabacum

<400> SEQUENCE: 86

```
Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
```

```
                65                  70                  75                  80
Ala Pro Glu Ile Pro Glu Asp Leu Tyr His Leu Ile Lys Lys Ala Val
                85                  90                  95

Ala Ile Arg Lys His Leu Glu Arg Asp Arg Lys Asp Lys Asp Ser Lys
            100                 105                 110

Phe Arg Leu Ile
        115

<210> SEQ ID NO 87
<211> LENGTH: 152
<212> TYPE: PRT
<213> ORGANISM: Triticum aestivum
<220> FEATURE:
<221> NAME/KEY: misc_feature
<222> LOCATION: (129)..(130)
<223> OTHER INFORMATION: Xaa can be any naturally occurring amino acid

<400> SEQUENCE: 87

Met Gly Gly Ile Asp Ser Arg Arg Glu Gly Tyr Met Val Val Gly Val
1               5                   10                  15

Ala Val Gln Glu Asp Ser Ser Glu Val Gly Ser Arg Pro Thr Val Ala
            20                  25                  30

Asp Val Asp Glu Leu Ile Thr Lys Ala Ala Lys Lys Gly Gln Met Pro
        35                  40                  45

Ser Gln Ile Gly Val Leu Leu Arg Asp Gln His Gly Ile Pro Leu Val
    50                  55                  60

Lys Ser Val Thr Gly Ser Lys Ile Leu Arg Ile Ile Lys Ala His Gly
65                  70                  75                  80

Leu Ala Pro Glu Ile Pro Glu Asp Leu Tyr Phe Leu Ile Lys Lys Ala
                85                  90                  95

Val Ala Ile Arg Lys His Leu Glu Arg Asn Arg Lys Asp Lys Asp Ser
            100                 105                 110

Lys Phe Arg Leu Ile Leu Val Glu Ser Arg Ile His Arg Pro Pro Arg
        115                 120                 125

Xaa Xaa Lys Gly Arg Lys Lys Phe Pro Asp Lys Trp Lys Pro Pro Pro
    130                 135                 140

Pro Pro Gly Ser Ile Leu Val Ala
145                 150

<210> SEQ ID NO 88
<211> LENGTH: 112
<212> TYPE: PRT
<213> ORGANISM: Brassica napus

<400> SEQUENCE: 88

Leu Gln Val Cys Glu Glu Gly Leu Thr Pro Ser Gln Ile Gly Val Ile
1               5                   10                  15

Leu Arg Asp Ser His Gly Ile Pro Gln Val Lys Ser Val Thr Gly Asn
            20                  25                  30

Lys Ile Leu Arg Ile Leu Lys Ala His Gly Leu Ala Pro Glu Ile Pro
        35                  40                  45

Asp Asp Leu Tyr His Leu Ile Lys Lys Ala Val Ala Ile Arg Lys His
    50                  55                  60

Leu Glu Arg Asn Arg Lys Asp Lys Asp Ser Lys Phe Arg Leu Ile Leu
65                  70                  75                  80

Ala Glu Ser Arg Ile His Arg Leu Ala Arg Tyr Tyr Lys Lys Thr Lys
                85                  90                  95

Lys Leu Pro Pro Val Trp Lys Tyr Glu Ser Thr Thr Ala Ser Thr Leu
```

```
                       100                 105                 110

<210> SEQ ID NO 89
<211> LENGTH: 121
<212> TYPE: PRT
<213> ORGANISM: Triticum aestivum
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 89

Ala Ala Met Gly Arg Met His Ser Arg Gly Lys Gly Ile Ser Ser Ser
1               5                   10                  15

Ala Leu Pro Tyr Lys Arg Thr Pro Thr Trp Leu Lys Thr Ala Ala
            20                  25                  30

Ser Asp Val Glu Glu Met Ile Thr Lys Ala Ala Lys Lys Gly Gln Met
        35                  40                  45

Pro Ser Gln Ile Gly Val Leu Leu Arg Asp Gln His Gly Ile Pro Leu
    50                  55                  60

Val Lys Ser Val Thr Gly Ser Lys Ile Leu Arg Ile Leu Lys Ala Met
65                  70                  75                  80

Gly Trp Asn Arg Asn Pro Gly Gly Leu Tyr Ser His Gln Glu Ala Val
                85                  90                  95

Ala Ile Arg Asn Thr Leu Glu Glu Gln Glu Gly Gln Arg Ser Lys Ser
            100                 105                 110

Xaa Ser Ser Xaa Gln Asn Arg Phe Asn
        115                 120

<210> SEQ ID NO 90
<211> LENGTH: 102
<212> TYPE: PRT
<213> ORGANISM: Populus tremula x Populus tremuloides

<400> SEQUENCE: 90

Met Gly Arg Met His Ser Lys Gly Lys Gly Ile Ser Ala Ser Ala Leu
1               5                   10                  15

Pro Tyr Lys Arg Thr Ser Pro Ser Trp Leu Lys Ile Ser Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Thr Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Cys Tyr Leu Gly Ser Ile
            100

<210> SEQ ID NO 91
<211> LENGTH: 142
<212> TYPE: PRT
<213> ORGANISM: Oryza sativa

<400> SEQUENCE: 91

Glu Asp Gly Ser Asp Val Val Ala Asp Trp Arg Cys Ala Pro Ser Gln
```

```
                1               5                  10                 15
His Gly Ile Pro Leu Val Lys Ser Ile Ala Ser Ser Lys Ile Leu His
                    20                  25                  30

Ile Leu Asn Ala His Gly Leu Ala Pro Lys Ile Leu Glu Asp Leu Tyr
                    35                  40                  45

Phe Leu Ile Lys Lys Ala Val Ala Ile Arg Lys His Leu Glu Arg Asn
 50                      55                  60

Arg Lys Asp Lys Asp Ser Ser Phe Arg Leu Ile Leu Val Glu Ser Arg
 65                      70                  75                  80

Ile His Arg Leu Val Arg Tyr Tyr Lys Arg Thr Lys Lys Leu Pro Pro
                    85                  90                  95

Thr Leu Arg Ser Trp Ile Ile Phe Leu Glu Phe Ser Thr Val Phe Ser
                    100                 105                 110

Cys Ser Arg Met Leu Gln Met Asp Thr Leu Gln Ser Arg Leu Asp Val
                    115                 120                 125

Glu Phe Leu Val Ala His Met Cys Ser Val Lys Phe Lys Glu
                    130                 135                 140

<210> SEQ ID NO 92
<211> LENGTH: 163
<212> TYPE: PRT
<213> ORGANISM: Triticum aestivum

<400> SEQUENCE: 92

Phe Pro Ser Pro Pro Gln Gln Leu Leu Pro Ile Ser Leu Leu Ala
 1               5                  10                  15

Ala Ala Leu Arg Ser Pro Leu Ala Ala Met Gly Arg Met His Ser Asn
                    20                  25                  30

Gly Lys Gly Met Ser Ser Ser Val Ile Pro Tyr Lys Arg Glu Ala Pro
                    35                  40                  45

Thr Trp Val Lys Thr Ser Ala Pro Asp Val Glu Glu Ile Ile Val Arg
 50                      55                  60

Ala Ala Lys Lys Gly Gln Leu Pro Ser Gln Ile Gly Ala Leu Leu Arg
 65                      70                  75                  80

Asp Gly Tyr Gly Ile Pro Leu Ser Lys Ala Val Thr Gly Ala Lys Ile
                    85                  90                  95

Val Arg Leu Leu Lys Ala Arg Gly Leu Ala Pro Glu Met Pro Arg Gly
                    100                 105                 110

Pro Leu Leu Pro His Gln Glu Gly Arg Cys Asp Ser Glu Ala Pro Gly
                    115                 120                 125

Arg Gly Thr Ser Arg Thr Trp Thr Pro Ser Ser Ala Ser Ser Ser Ser
                    130                 135                 140

Arg Thr Arg Ser Asn Ala Ser Thr Ala Thr Thr Ala Ser Thr Arg Arg
145                     150                 155                 160

Cys Arg Arg

<210> SEQ ID NO 93
<211> LENGTH: 333
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 93

Xaa Xaa Val Glu Thr Ser Asp Leu Arg Glu Arg Glu Arg Glu Gly Lys
 1               5                  10                  15
```

```
Gly Arg Arg Arg Arg Gly Thr Lys Arg Thr Arg Ala Arg Ala
            20                  25                  30

Ile Phe Ala Leu Leu Pro Leu Ser Ser Leu Ser Ser Pro Leu Leu Arg
            35                  40                  45

Ser Ser Ala Ser Pro Ala Gly Arg Arg Leu Pro Val Leu Glu Ala Ala
        50                  55                  60

Ala Ala Asp Thr Gly Gly Asp Asp Met Ala Asp Gly Gly Glu Lys Cys
65                  70                  75                  80

Arg Asp Ala Ala Gly Glu Gly Gly Gly Gly Asp Leu Tyr Ala Val
                85                  90                  95

Leu Gly Leu Lys Lys Glu Cys Ser Asp Ala Asp Leu Lys Leu Ala Tyr
            100                 105                 110

Arg Lys Leu Ala Met Arg Trp His Pro Asp Lys Cys Ser Ser Ser
            115                 120                 125

Ser Ala Lys His Met Glu Glu Ala Lys Glu Lys Phe Gln Glu Ile Gln
    130                 135                 140

Gly Ala Tyr Ser Val Leu Ser Asp Ser Asn Lys Arg Phe Leu Tyr Asp
145                 150                 155                 160

Val Gly Val Tyr Asp Asp Asp Asn Asp Asp Asn Leu Gln Gly
                165                 170                 175

Met Gly Asp Phe Ile Gly Glu Met Ala Gln Met Met Ser Gln Ala Arg
            180                 185                 190

Pro Thr Arg Gln Glu Ser Phe Lys Glu Leu Gln Gln Leu Phe Val Asp
            195                 200                 205

Met Phe Gln Ala Asp Leu Asp Ser Gly Phe Cys Asn Gly Pro Ser Lys
    210                 215                 220

Cys Tyr His Thr Gln Ala Gln Ser Gln Thr Arg Thr Ser Ser Thr Ser
225                 230                 235                 240

Pro Ser Met Ser Pro Ser Pro Pro Val Ala Thr Glu Ala Glu
                245                 250                 255

Ser Pro Ser Cys Asn Gly Ile Asn Lys Arg Gly Ser Ser Ala Met Asp
            260                 265                 270

Ser Gly Lys Pro Pro Arg Ala Ser Glu Val Ser Ala Gly Gln Ser Gln
        275                 280                 285

Ser Gly Phe Cys Phe Gly Lys Ser Asp Ala Lys Gln Ala Ala Lys Thr
    290                 295                 300

Arg Ser Gly Asn Thr Ala Ser Arg Arg Asn Gly Arg Lys Gln Lys
305                 310                 315                 320

Val Ser Ser Lys His Asp Val Ser Ser Glu Asp Met
            325                 330

<210> SEQ ID NO 94
<211> LENGTH: 294
<212> TYPE: PRT
<213> ORGANISM: Hordeum vulgare

<400> SEQUENCE: 94

Trp Arg Gly Ala Gln Thr Ala Glu Glu Arg Glu Arg Gly Lys Leu Gln
1               5                   10                  15

Glu Pro Pro Pro Pro Pro Ala His Pro Ala Gly Asp Ala Arg
            20                  25                  30

Gly Met Ala Thr Gly Gly Asp Gly Asp Pro Ala Ala Pro Gly Gly Gly
            35                  40                  45

Asp Leu Tyr Ala Val Leu Gly Leu Ser Lys Glu Cys Ser Asp Ala Asp
    50                  55                  60
```

Leu Lys Val Ala Tyr Arg Lys Leu Ala Met Arg Trp His Pro Asp Arg
65                  70                  75                  80

Cys Ser Ser Ser Gly Thr Lys His Met Glu Ala Lys Glu Lys
                85                  90                  95

Phe Gln Glu Ile Gln Gly Ala Tyr Ser Val Leu Ser Asp Ala Asn Lys
            100                 105                 110

Arg Phe Leu Tyr Asp Val Gly Val Tyr Gln Glu Glu Asp Ser Asp
            115                 120                 125

Asp Ser Met Gln Gly Met Gly Asp Phe Leu Gly Glu Met Ala His Met
130                 135                 140

Met Ser Gln Thr Arg Pro Ala Arg Gln Glu Ser Phe Glu Glu Leu Gln
145                 150                 155                 160

Gln Leu Phe Val Asp Met Phe Gln Ser Asp Ile Asp Ser Gly Phe Cys
                165                 170                 175

Asn Gly Pro Ala Lys Gly His His Asp Pro Phe Gln Arg Gln Thr Gln
            180                 185                 190

Thr Phe Ser Thr Ser Pro Ser Ser Pro Pro Ser Pro Pro Pro Pro Leu
            195                 200                 205

Ala Thr Glu Ala Glu Ala Ala Ser Cys Asn Gly Ile Asn Lys Arg Gly
    210                 215                 220

Ser Ser Ala Met Gly Ser Gly Lys Pro Pro Arg Ala Ala Glu Ala Gly
225                 230                 235                 240

Ala Gly Tyr Gly Gln Ser Glu Phe Cys Phe Gly Thr Ser Asp Ala Lys
                245                 250                 255

Gln Ala Pro Arg Ala Arg Gly Gly Asn Thr Ser Arg Arg Asn Gly
            260                 265                 270

Gln Lys Gln Lys Leu Ser Ser Lys His Asp Val Ser Glu Asp Glu
            275                 280                 285

Met Leu Ser Pro Gln Gln
    290

<210> SEQ ID NO 95
<211> LENGTH: 301
<212> TYPE: PRT
<213> ORGANISM: Triticum aestivum

<400> SEQUENCE: 95

Arg Glu Arg Glu Arg Glu Gly Arg Lys Arg Gln Glu Pro Pro Pro Pro
1               5                   10                  15

Ser Ser Pro Leu Ser Ser Ser Ser Pro Ala His Pro Arg Ala Pro
            20                  25                  30

Gln Ala Gly Gly Ala Gly Arg Gly Met Ala Thr Gly Gly Asp Gly Cys
            35                  40                  45

Gly Gly Gly Glu Pro Ala Ala Pro Gly Gly Gly Asp Leu Tyr Ala Val
        50                  55                  60

Leu Gly Leu Ser Lys Glu Cys Ser Asp Ala Asp Leu Lys Leu Ala Tyr
65                  70                  75                  80

Arg Lys Leu Ala Met Arg Trp His Pro Asp Arg Cys Ser Ser Ser
                85                  90                  95

Gly Thr Lys Arg Met Glu Glu Ala Lys Glu Lys Phe Gln Glu Ile Gln
            100                 105                 110

Gly Ala Tyr Ser Val Leu Ser Asp Ala Asn Lys Arg Phe Leu Tyr Asp
            115                 120                 125

Val Gly Val Tyr Gln Glu Glu Glu Asp Ser Asp Ser Met Gln Gly
130                 135                 140

-continued

Met Gly Asp Phe Leu Gly Glu Met Ala His Met Met Ser Gln Thr Arg
145                 150                 155                 160

Pro Ala Arg Gln Glu Ser Phe Glu Glu Leu Gln Gln Leu Phe Val Asp
            165                 170                 175

Met Phe Gln Ser Asp Ile Asp Ser Gly Phe Cys Asn Arg Pro Ala Lys
            180                 185                 190

Gly His His Asp Pro Phe Gln Thr Phe Ser Thr Ser Pro Ser Ser Ser
            195                 200                 205

Pro Ser Pro Pro Pro Val Ala Thr Glu Ala Glu Ala Ser Cys
            210                 215                 220

Asn Gly Ile Asn Lys Arg Gly Ser Ser Ala Met Gly Ser Gly Lys Pro
225                 230                 235                 240

Pro Arg Ala Gly Glu Ala Gly Ala Gly Tyr Gly Gln Pro Glu Phe Cys
            245                 250                 255

Phe Gly Thr Ser Asp Ala Lys Gln Ala Pro Lys Ala Arg Gly Arg Asn
            260                 265                 270

Thr Ser Arg Arg Arg Asn Gly Gln Lys Gln Lys Leu Ser Ser Lys His
            275                 280                 285

Asp Val Ser Ser Glu Asp Glu Met Leu Ser Pro Gln Gln
            290                 295                 300

<210> SEQ ID NO 96
<211> LENGTH: 203
<212> TYPE: PRT
<213> ORGANISM: Zea mays

<400> SEQUENCE: 96

Met Glu Glu Ala Lys Glu Lys Phe Gln Glu Ile Gln Gly Ala Tyr Ser
1               5                   10                  15

Val Leu Ser Asp Ala Asn Lys Arg Leu Leu Tyr Asp Val Gly Val Tyr
            20                  25                  30

Asp Asp Glu Asp Glu Glu Ser Met Gln Gly Met Gly Asp Phe Ile
            35                  40                  45

Gly Glu Met Ala Gln Met Met Ser Gln Ala Gln Pro Thr Arg Gln Glu
50                  55                  60

Ser Phe Glu Glu Leu Gln Gln Leu Phe Val Asp Met Phe Gln Ser Asp
65                  70                  75                  80

Ile Asp Ser Gly Phe Cys Asn Arg Thr Ala Lys Ala His Gln Phe Gln
            85                  90                  95

Gly Pro Ala Lys Ser Arg Thr Cys Ser Thr Ser Pro Ser Ser Ser Pro
            100                 105                 110

Ser Pro Pro Thr Thr Ala Lys Asp Ala Glu Val Pro Ser Cys Asn
            115                 120                 125

Gly Phe Asn Lys Arg Gly Ser Ser Ala Leu Asp Ser Gly Lys Pro Pro
            130                 135                 140

Lys Pro Val Glu Gly Gly Ala Gly Gln Asn Gln Ala Gly Phe Cys Phe
145                 150                 155                 160

Gly Val Ser Asp Thr Lys Glu Thr Pro Lys Leu Pro Gly Gln Asn Ala
            165                 170                 175

Ser Arg Arg Arg Asn Gly Arg Lys Gln Lys Leu Ser Ser Lys His Asp
            180                 185                 190

Val Ser Ser Glu Asp Glu Thr Ala Ala Gly Ser
            195                 200

<210> SEQ ID NO 97

```
<211> LENGTH: 164
<212> TYPE: PRT
<213> ORGANISM: Triticum aestivum

<400> SEQUENCE: 97

Met Gln Gly Met Gly Asp Phe Leu Gly Glu Met Ala His Met Met Ser
1               5                   10                  15

Gln Thr Arg Pro Ala Arg Gln Glu Ser Phe Glu Glu Leu Gln Gln Leu
            20                  25                  30

Phe Val Asp Met Phe Gln Ser Asp Ile Asp Ser Gly Phe Cys Asn Gly
        35                  40                  45

Pro Ala Lys Gly His His Asp Pro Phe Gln Thr Phe Ser Thr Phe Pro
    50                  55                  60

Ser Ser Ser Pro Ser Pro Pro Pro Leu Ala Thr Glu Ala Glu Ala
65                  70                  75                  80

Ala Ser Cys Asn Gly Ile Asn Lys Arg Gly Ser Ser Ala Met Gly Ser
                85                  90                  95

Gly Lys Pro Pro Arg Thr Gly Glu Ala Gly Ala Gly Tyr Gly Gln Pro
            100                 105                 110

Glu Phe Cys Phe Gly Arg Ser Asp Ala Lys Gln Ala Pro Lys Ala Arg
        115                 120                 125

Gly Gly Asn Thr Ser Arg Arg Arg Asn Gly Lys Gln Lys Pro Ser
    130                 135                 140

Ser Lys His Asp Val Ser Ser Glu Asp Glu Met Leu Ser Pro Gln Gln
145                 150                 155                 160

Pro Arg Val Val

<210> SEQ ID NO 98
<211> LENGTH: 134
<212> TYPE: PRT
<213> ORGANISM: Zea mays

<400> SEQUENCE: 98

Met Arg Gln Glu Ser Phe Glu Glu Leu Gln Gln Leu Phe Val Asp Met
1               5                   10                  15

Phe Gln Ser Asp Ile Asp Ser Gly Phe Cys Asn Gly Thr Ala Lys Gly
            20                  25                  30

His Gln Val Gln Gly Gln Ala Lys Ser Arg Thr Cys Ser Pro Arg Ser
        35                  40                  45

Pro Pro Thr Thr Ile Val Lys Glu Ala Glu Val Ser Ser Cys Asn Gly
    50                  55                  60

Phe Asn Lys Arg Gly Ser Ser Ala Met Asp Ser Gly Lys Pro Pro Arg
65                  70                  75                  80

Pro Val Glu Cys Gly Ala Gly Gln Ser Gln Ala Gly Phe Cys Phe Gly
                85                  90                  95

Val Ser Asp Thr Pro Lys Pro Arg Gly Pro Asn Ala Asn Arg Lys Arg
            100                 105                 110

Asn Gly Arg Lys Gln Lys Leu Phe Pro Lys His Tyr Val Thr Ser Glu
        115                 120                 125

Asp Asp Thr Ala Gly Ser
    130

<210> SEQ ID NO 99
<211> LENGTH: 143
<212> TYPE: PRT
<213> ORGANISM: Triticum aestivum
<220> FEATURE:
<221> NAME/KEY: misc_feature
```

<222> LOCATION: (132)..(132)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid

<400> SEQUENCE: 99

Gly Ala Leu Val Leu Pro Ser Arg Cys Cys Ser Cys Ala Val Leu Ser
1               5                   10                  15

Asp Ala Asn Lys Arg Phe Leu Tyr Asp Val Gly Val Tyr Gln Glu Glu
            20                  25                  30

Glu Asp Ser Asp Ser Met Gln Gly Met Gly Asp Phe Leu Gly Glu
        35                  40                  45

Met Ala His Met Met Ser Gln Ala Arg Pro Ala Arg Gln Glu Ser Phe
50                  55                  60

Glu Glu Leu Gln Gln Leu Phe Val Asp Met Phe Gln Ser Asp Ile Asp
65                  70                  75                  80

Ser Gly Phe Cys Asn Gly Pro Ala Lys Gly His His Asp Pro Phe Gln
                85                  90                  95

Thr Phe Ser Thr Ser Pro Ser Ser Pro Ser Pro Pro Pro Pro Leu
            100                 105                 110

Ala Thr Glu Ala Glu Ala Ala Ser Cys Asn Gly Ile Asn Lys Arg Gly
        115                 120                 125

Ser Ser Ala Xaa Gly Leu Trp Gly Lys Pro Pro Arg Xaa Xaa Gly
    130                 135                 140

<210> SEQ ID NO 100
<211> LENGTH: 322
<212> TYPE: PRT
<213> ORGANISM: Zea mays

<400> SEQUENCE: 100

Met Asp Gly Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
            20                  25                  30

Ile Thr Arg Ser Arg Gly Glu Arg Thr Asn Asp Leu Asp Tyr Ala Arg
        35                  40                  45

Met Asn Ala Ala Pro Asp Ala Lys Arg Trp Gly Lys Ala Ala Ser Tyr
50                  55                  60

Gln His His Asp Glu Gly Arg Met Asp His His Val Gly Leu Ser Leu
65                  70                  75                  80

Lys Met Asn Asp Leu Lys Met Asn Glu Ala Ala Ala Ala Val Met
                85                  90                  95

Lys Leu Pro Phe Arg Gly Val Pro Tyr Asn Val Asn Pro Met Tyr Pro
            100                 105                 110

Lys Gly Ser Asn Ala Asn Ala Asn Val Asn Ala Phe Lys Met Asn Val
        115                 120                 125

Gly Val Asn Lys Tyr Ser Ser Ser Ala Asn Gly Lys Asp Ser Gly Gly
    130                 135                 140

Lys Ser Ser Gly Gly Ser Asn Asn Ser Gly Gly Gly Asn Gly
145                 150                 155                 160

Asn Gly Thr Ala Asn Gly Ser Ser Ala Val Asp Lys Arg Phe Lys Thr
                165                 170                 175

Leu Pro Thr Ser Glu Met Leu Pro Lys Asn Glu Val Leu Gly Gly Tyr
            180                 185                 190

```
Ile Phe Val Cys Asn Asn Asp Thr Met Gln Glu Asp Leu Lys Arg Gln
            195                 200                 205

Leu Phe Gly Leu Pro Ala Arg Tyr Arg Asp Ser Val Arg Ala Ile Thr
    210                 215                 220

Pro Gly Leu Pro Leu Phe Leu Tyr Asn Tyr Thr Thr His Gln Leu His
225                 230                 235                 240

Gly Val Phe Glu Ala Ala Ser Phe Gly Gly Ser Asn Ile Asp Pro Thr
                245                 250                 255

Ala Trp Glu Asp Lys Lys Cys Lys Gly Glu Ser Arg Phe Pro Ala Gln
                260                 265                 270

Val Arg Ile Arg Val Arg Lys Leu Cys Lys Pro Leu Glu Glu Asp Ser
                275                 280                 285

Phe Arg Pro Val Leu His His Tyr Asp Gly Pro Lys Phe Arg Leu Glu
    290                 295                 300

Leu Ser Ile Ala Glu Thr Leu Ser Leu Leu Asp Leu Cys Glu Lys Glu
305                 310                 315                 320

Gly Ile

<210> SEQ ID NO 101
<211> LENGTH: 310
<212> TYPE: PRT
<213> ORGANISM: Triticum aestivum

<400> SEQUENCE: 101

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
                20                  25                  30

Ile Thr Lys Ser Lys Ala Glu Arg Met Asn Asp Phe Glu Tyr Ala Arg
            35                  40                  45

Met Asn Thr Val Pro Asp Val Lys Gln Trp Asp Lys Leu Ser Tyr His
        50                  55                  60

Gln Glu Asp Asn Lys Met Asp His Leu Asn Leu Gly Leu Met Asn Leu
65                  70                  75                  80

Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
        115                 120                 125

Tyr Pro Asn Asn Gln Asn Gly Lys Glu Ala Asn Gly Lys His Asn Gly
    130                 135                 140

Gly Asn Asn Asn Gly Gly Asn Ser Asn Asn Ser Val Asp Lys
145                 150                 155                 160

Arg Phe Lys Thr Leu Pro Thr Ser Glu Met Leu Pro Arg Asn Glu Val
                165                 170                 175

Leu Gly Gly Tyr Ile Phe Val Cys Asn Asn Asp Thr Met Gln Glu Asp
            180                 185                 190

Leu Lys Arg Gln Leu Phe Gly Leu Pro Ala Arg Tyr Arg Asp Ser Val
        195                 200                 205

Arg Ala Ile Thr Pro Gly Leu Pro Leu Phe Leu Tyr Asn Tyr Thr Thr
    210                 215                 220

His Gln Leu His Gly Val Phe Glu Ala Ala Ser Phe Gly Gly Ser Asn
225                 230                 235                 240

Ile Asp Pro Thr Ala Trp Glu Asp Lys Lys Cys Lys Gly Glu Ser Arg
```

```
                    245                 250                 255
Phe Pro Ala Gln Val Arg Ile Arg Ile Arg Arg Leu Cys Lys Ala Leu
                260                 265                 270

Glu Glu Asp Ala Phe Arg Pro Val Leu His His Tyr Asp Gly Pro Lys
            275                 280                 285

Phe Arg Leu Glu Leu Ser Ile Ala Glu Thr Leu Ser Leu Leu Asp Leu
        290                 295                 300

Cys Lys Thr Glu Asp Ala
305                 310

<210> SEQ ID NO 102
<211> LENGTH: 309
<212> TYPE: PRT
<213> ORGANISM: Hordeum vulgare

<400> SEQUENCE: 102

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Thr Lys Ser Lys Ala Glu Arg Met Asn Asp Phe Glu Tyr Ala Arg
        35                  40                  45

Met Asn Thr Val Pro Asp Val Lys Gln Trp Asp Lys Leu Ser Tyr His
    50                  55                  60

Gln Glu Asp Asn Lys Met Asp His Leu Asn Leu Gly Leu Met Asn Leu
65                  70                  75                  80

Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
        115                 120                 125

Tyr Pro Asn Asn Gln Asn Gly Lys Glu Ala Asn Gly Lys His Asn Gly
    130                 135                 140

Gly Asn Asn Asn Gly Gly Asn Ser Asn Asn Ser Val Asp Lys Arg
145                 150                 155                 160

Phe Lys Thr Leu Pro Thr Ser Glu Met Leu Pro Arg Asn Glu Val Leu
                165                 170                 175

Gly Gly Tyr Ile Phe Val Cys Asn Asn Asp Thr Met Gln Glu Asp Leu
            180                 185                 190

Lys Arg Gln Leu Phe Gly Leu Pro Ala Arg Tyr Arg Asp Ser Val Arg
        195                 200                 205

Ala Ile Thr Pro Gly Leu Pro Leu Phe Leu Tyr Asn Tyr Thr Thr His
    210                 215                 220

Gln Leu His Gly Val Phe Glu Ala Ala Ser Phe Gly Gly Ser Asn Ile
225                 230                 235                 240

Asp Pro Thr Ala Trp Glu Asp Lys Lys Cys Lys Gly Glu Ser Arg Phe
                245                 250                 255

Pro Ala Gln Val Arg Ile Arg Ile Arg Arg Leu Cys Lys Ala Leu Glu
            260                 265                 270

Glu Asp Ala Phe Arg Pro Val Leu His His Tyr Asp Gly Pro Lys Phe
        275                 280                 285

Arg Leu Glu Leu Ser Ile Ala Glu Thr Leu Ser Leu Leu Asp Leu Cys
    290                 295                 300

Lys Ser Glu Asp Ala
305
```

<210> SEQ ID NO 103
<211> LENGTH: 314
<212> TYPE: PRT
<213> ORGANISM: Oryza sativa

<400> SEQUENCE: 103

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
        35                  40                  45

Met Asn Thr Ile Pro Asp Val Lys Gln Trp Asp Lys Val Ser Tyr His
    50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
        115                 120                 125

Tyr Leu His Ser Pro Asn Gly Lys Asp Val Asn Gly Lys Asn Ser Gly
    130                 135                 140

Ala Asn Ser Asn Gly Ser Asn Ser Ser Gly Asn Asn Ser Ser Asn Ser
145                 150                 155                 160

Ala Val Asp Lys Arg Phe Lys Thr Leu Pro Thr Ser Glu Met Leu Pro
                165                 170                 175

Arg Asn Glu Val Leu Gly Gly Tyr Ile Phe Val Cys Asn Asn Asp Thr
            180                 185                 190

Met Gln Glu Asp Leu Lys Arg Gln Leu Phe Gly Leu Pro Ala Arg Tyr
        195                 200                 205

Arg Asp Ser Val Arg Ala Ile Ile Pro Gly Leu Pro Leu Phe Leu Tyr
    210                 215                 220

Asn Tyr Thr Thr His Gln Leu His Gly Val Phe Glu Ala Ser Ser Phe
225                 230                 235                 240

Gly Gly Ser Asn Ile Asp Pro Thr Ala Trp Glu Asp Lys Lys Cys Lys
                245                 250                 255

Gly Glu Ser Arg Phe Pro Ala Gln Val Arg Ile Arg Ile Arg Lys Leu
            260                 265                 270

Cys Lys Pro Leu Glu Glu Asp Ala Phe Arg Pro Val Leu His His Tyr
        275                 280                 285

Asp Gly Pro Lys Phe Arg Leu Glu Leu Ser Ile Ala Glu Thr Leu Ser
    290                 295                 300

Leu Leu Asp Leu Cys Glu Lys Glu Gly Val
305                 310

<210> SEQ ID NO 104
<211> LENGTH: 356
<212> TYPE: PRT
<213> ORGANISM: Zea mays
<220> FEATURE:
<221> NAME/KEY: misc_feature
<222> LOCATION: (1)..(2)
<223> OTHER INFORMATION: Xaa can be any naturally occurring amino acid

<400> SEQUENCE: 104

```
Xaa Xaa Ala Thr Cys Leu Leu Ser Phe Leu Pro Ser Ile Pro Pro Cys
1               5                   10                  15

Leu Arg Pro Leu Leu Thr Pro Val Gly Arg Gly Ala Ala Ala Asp Cys
            20                  25                  30

Trp Asp Cys Pro Thr Pro Ser Ala Gln Val Ile Phe Gly Pro Phe Ala
        35                  40                  45

Gly Asp Glu His His Gln Val Cys Gln Val Asp Arg Ala Met Asp Ser
    50                  55                  60

Leu Trp His Leu Gly Asp Glu Leu Arg Gly Gln Pro Lys Val Val Glu
65                  70                  75                  80

Asp Arg Gln Trp Ser Leu Met Thr Ser Lys Leu Ala Glu Ile Thr Arg
                85                  90                  95

Ser Lys Gly Glu Arg Met Asn Thr Val Pro Asp Ala Lys Gln Trp Asp
            100                 105                 110

Lys Thr Ser Tyr Gln Leu His Asp Asp Ser Arg Met Gly His Ile Asn
        115                 120                 125

Leu Gly Leu Met Asn Leu Asp Leu Lys Met Asn Glu Ala Ala Ala Met
130                 135                 140

Lys Leu Pro Phe Arg Gly Met Pro Tyr Asn Met Asn Gln Met Tyr Leu
145                 150                 155                 160

Lys Gly Ser Asn Ala Asn Ser Asn Val Asn Ala Phe Lys Met Asn Val
            165                 170                 175

Gly Val Asn Lys Tyr Ser Asn Ser Pro Asn Gly Lys Asp Ala Asn Gly
        180                 185                 190

Lys Asn Asn Gly Gly Ser Gly Gly Asn Asn Asn Gly Ser Ala Asn
195                 200                 205

Gly Thr Ser Val Ala Asp Lys Arg Phe Lys Thr Leu Pro Thr Ser Glu
210                 215                 220

Met Leu Pro Arg Asn Glu Val Leu Gly Gly Tyr Ile Phe Val Cys Asn
225                 230                 235                 240

Asn Asp Thr Met Gln Glu Asp Leu Lys Arg Gln Leu Phe Gly Leu Pro
            245                 250                 255

Ala Arg Tyr Arg Asp Ser Val Arg Ala Ile Thr Pro Gly Leu Pro Leu
        260                 265                 270

Phe Leu Tyr Asn Tyr Thr Thr His Gln Leu His Gly Val Phe Glu Ala
    275                 280                 285

Ala Ser Phe Gly Gly Ser Asn Ile Asp Pro Thr Ala Trp Glu Asp Lys
290                 295                 300

Lys Cys Lys Gly Glu Ser Arg Phe Pro Ala Gln Val Arg Ile Cys Ile
305                 310                 315                 320

Arg Lys Leu Cys Lys Pro Leu Glu Glu Asp Ser Phe Arg Pro Val Leu
            325                 330                 335

His His Tyr Asp Gly Pro Lys Phe Arg Leu Glu Leu Ser Ile Ala Glu
        340                 345                 350

Thr Leu Ser Leu
        355
```

<210> SEQ ID NO 105
<211> LENGTH: 340
<212> TYPE: PRT
<213> ORGANISM: Triticum aestivum
<220> FEATURE:
<221> NAME/KEY: misc_feature
<222> LOCATION: (338)..(340)
<223> OTHER INFORMATION: Xaa can be any naturally occurring amino acid

<400> SEQUENCE: 105

```
Val Gly Gly Ala Lys Trp Glu Pro Thr Pro Ser Gln Pro Ser Gly Leu
1               5                   10                  15

Leu Ser Ser Gln Gln Phe Ala Ile Arg Pro Gln Ile Gln Arg Pro
            20                  25                  30

Pro Arg Arg Asn Pro Ala Pro Asn Leu Ala Glu Ser Leu Asn Arg Ala
            35                  40                  45

Met Asp Asn Leu Trp His Leu Gly Asp Glu Phe Arg Gly Gln Ser Lys
        50                  55                  60

Val Val Glu Asp Arg Gln Trp Ser Leu Met Thr Ser Lys Leu Ala Glu
65                  70                  75                  80

Ile Thr Lys Ser Lys Ala Glu Arg Met Asn Asp Phe Glu Tyr Ala Arg
                85                  90                  95

Met Asn Thr Val Pro Asp Val Lys Gln Trp Asp Lys Leu Ser Tyr His
            100                 105                 110

Gln Glu Asp Asn Lys Met Asp His Leu Asn Leu Gly Leu Met Asn Leu
        115                 120                 125

Asp Leu Lys Met Asn Asp Leu Lys Met Asn Glu Ala Ala Met Lys Tyr
    130                 135                 140

Pro Phe Arg Asn Met Ala Tyr Asn Met Asn Pro Met Tyr Pro Lys Gly
145                 150                 155                 160

Asn Asn Gly Asn Val Asn Ser Phe Lys Met Asn Val Gly Val Asn Lys
                165                 170                 175

Tyr Pro Asn Asn Gln Asn Gly Lys Glu Ala Asn Gly Lys His Asn Gly
            180                 185                 190

Gly Asn Asn Asn Gly Gly Asn Ser Asn Asn Ser Val Asp Lys
        195                 200                 205

Arg Phe Lys Thr Leu Pro Thr Ser Glu Met Leu Pro Arg Asn Glu Val
    210                 215                 220

Leu Gly Gly Tyr Ile Phe Val Cys Asn Asn Asp Thr Met Gln Glu Asp
225                 230                 235                 240

Leu Lys Arg Gln Leu Phe Gly Leu Pro Ala Arg Tyr Arg Asp Ser Val
                245                 250                 255

Arg Ala Ile Thr Pro Gly Leu Pro Leu Phe Leu Tyr Asn Tyr Thr Thr
            260                 265                 270

His Gln Leu His Gly Val Phe Glu Ala Ala Ser Phe Gly Gly Ser Asn
        275                 280                 285

Ile Asp Pro Thr Ala Trp Glu Asp Lys Lys Cys Lys Gly Glu Ser Arg
    290                 295                 300

Phe Pro Ala Gln Val Arg Ile Arg Ile Arg Arg Leu Cys Lys Ala Leu
305                 310                 315                 320

Glu Glu Asp Ala Phe Arg Pro Val Leu His His Tyr Asp Gly Pro Lys
                325                 330                 335

Phe Xaa Xaa Xaa
            340

<210> SEQ ID NO 106
<211> LENGTH: 314
<212> TYPE: PRT
<213> ORGANISM: Oryza sativa

<400> SEQUENCE: 106

Met Asp Asn Leu Trp His Leu Gly Asp Glu Phe Arg Gly Gln Ser Lys
1               5                   10                  15
```

```
Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
        35                  40                  45

Met Asn Thr Ile Pro Asp Val Lys Gln Trp Asp Lys Val Ser Tyr His
 50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
        115                 120                 125

Tyr Leu His Ser Pro Asn Gly Lys Asp Val Asn Gly Lys Asn Ser Gly
    130                 135                 140

Ala Asn Ser Asn Gly Ser Asn Ser Ser Gly Asn Asn Ser Asn Ser Asn Ser
145                 150                 155                 160

Ala Val Asp Lys Arg Phe Lys Thr Leu Pro Thr Ser Glu Met Leu Pro
                165                 170                 175

Arg Asn Glu Val Leu Gly Gly Tyr Ile Phe Val Cys Asn Asn Asp Thr
            180                 185                 190

Met Gln Glu Asp Leu Lys Arg Gln Leu Phe Gly Leu Pro Ala Arg Tyr
        195                 200                 205

Arg Asp Ser Val Arg Ala Ile Ile Pro Gly Leu Pro Leu Phe Leu Tyr
    210                 215                 220

Asn Tyr Thr Thr His Gln Leu His Gly Val Ser Glu Ala Ser Ser Phe
225                 230                 235                 240

Gly Gly Ser Asn Leu Asp Pro Thr Glu Trp Asp Asp Thr Thr Cys Asn
                245                 250                 255

Gly Glu Ser Arg Phe Pro Ala Gln Val Thr Leu Arg Leu Pro Lys Leu
            260                 265                 270

Cys Lys Pro Leu Glu Asp Ala Ala Ser Thr Pro Val Leu His His Tyr
        275                 280                 285

Asp Gly Pro Gln Ser Arg Leu Asp Leu Ser Ile Ala Asp Asn Leu Ser
    290                 295                 300

Leu Leu His Leu Cys Ala Gln Gln Arg Val
305                 310

<210> SEQ ID NO 107
<211> LENGTH: 184
<212> TYPE: PRT
<213> ORGANISM: Oryza sativa

<400> SEQUENCE: 107

Met Asp Asn Leu Trp His Leu Gly Asp Glu Phe Arg Gly Gln Ser Lys
 1               5                  10                  15

Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
        35                  40                  45

Met Asn Thr Ile Pro Asp Val Lys Gln Trp Asp Lys Val Ser Tyr His
 50                  55                  60

Gln Asp Glu Ser Lys Met Asp His Leu Asn Leu Gly Leu Met Asn Leu
65                  70                  75                  80
```

Asp Leu Lys Met Asn Asp Ile Arg Met Asn Asp Ala Ala Met Lys Asn
             85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Val Gly Val Asn Lys
            115                 120                 125

Tyr Leu His Ser Pro Asn Gly Lys Asp Val Asn Gly Lys Arg Phe Lys
            130                 135                 140

Thr Leu Pro Thr Ser Glu Met Leu Pro Arg Asn Glu Val Leu Gly Gly
145                 150                 155                 160

Tyr Ile Phe Val Cys Asn Asn Asp Thr Met Gln Glu Asp Leu Lys Arg
                165                 170                 175

Gln Leu Phe Gly Leu Pro Ala Arg
            180

<210> SEQ ID NO 108
<211> LENGTH: 197
<212> TYPE: PRT
<213> ORGANISM: Gossypium hirsutum

<400> SEQUENCE: 108

Met Gly Thr Arg Ala Lys Glu Lys Asn Ile Met Glu Pro Arg Val Gly
1               5                   10                  15

Arg Arg Thr Ala Thr Arg Lys Asn Asn Asn Asn Asp Asn Asn
            20                  25                  30

Glu Asn Lys Asp Gly Lys Ser Ala Ala Asp Lys Arg Phe Lys Thr Leu
            35                  40                  45

Pro Pro Ser Glu Ser Leu Pro Arg Asn Glu Thr Val Gly Gly Tyr Ile
        50                  55                  60

Phe Val Cys Asn Asn Asp Thr Met Glu Glu Asn Leu Arg Arg Gln Leu
65                  70                  75                  80

Phe Gly Leu Pro Pro Arg Tyr Arg Asp Ser Val Arg Ala Ile Thr Pro
                85                  90                  95

Gly Leu Pro Leu Phe Leu Tyr Asn Tyr Ser Thr His Gln Leu His Gly
            100                 105                 110

Val Phe Glu Ala Ala Ser Phe Gly Gly Thr Asn Ile Asp Pro Thr Ala
            115                 120                 125

Trp Glu Asp Lys Lys Cys Pro Gly Glu Ser Arg Phe Pro Ala Gln Val
            130                 135                 140

Arg Val Ile Thr Arg Lys Ile Cys Glu Pro Leu Glu Glu Asp Ser Phe
145                 150                 155                 160

Arg Pro Ile Leu His His Tyr Asp Gly Pro Lys Phe Arg Leu Glu Leu
                165                 170                 175

Asn Ile Pro Glu Ala Leu Ser Leu Leu Asp Ile Phe Ala Asp Gln Gln
            180                 185                 190

Asp Thr Cys Ile Ser
            195

<210> SEQ ID NO 109
<211> LENGTH: 188
<212> TYPE: PRT
<213> ORGANISM: Solanum tuberosum

<400> SEQUENCE: 109

Lys Phe Gly Lys Gly Phe Phe Glu Asp Glu His Lys Ser Val Lys Lys
1               5                   10                  15

Asn Asn Lys Ser Val Lys Glu Ser Asn Lys Asp Val Asn Ser Glu Lys

```
                20                  25                  30
Gln Asn Gly Val Asp Lys Arg Phe Lys Thr Leu Pro Pro Ala Glu Ser
            35                  40                  45

Leu Pro Arg Asn Glu Thr Val Gly Gly Tyr Ile Phe Val Cys Asn Asn
 50                  55                  60

Asp Thr Met Ala Glu Asn Leu Lys Arg Glu Leu Phe Gly Leu Pro Pro
65                  70                  75                  80

Arg Tyr Arg Asp Ser Val Arg Gln Ile Thr Pro Gly Leu Pro Leu Phe
                85                  90                  95

Leu Tyr Asn Tyr Ser Thr His Gln Leu His Gly Val Phe Glu Ala Ala
            100                 105                 110

Ser Phe Gly Gly Ser Asn Ile Asp Pro Ser Ala Trp Glu Asp Lys Lys
        115                 120                 125

Asn Pro Gly Glu Ser Arg Phe Pro Ala Gln Val Leu Val Val Thr Arg
    130                 135                 140

Lys Val Cys Glu Pro Leu Glu Glu Asp Ser Phe Arg Pro Ile Leu His
145                 150                 155                 160

His Tyr Asp Gly Pro Lys Phe Arg Leu Glu Leu Asn Val Pro Glu Ala
                165                 170                 175

Ile Ser Leu Leu Asp Ile Phe Glu Glu Asn Lys Asn
            180                 185

<210> SEQ ID NO 110
<211> LENGTH: 255
<212> TYPE: PRT
<213> ORGANISM: Triticum aestivum

<400> SEQUENCE: 110

Met Asp Thr Lys His Ala Asp Ser Phe Asp Glu Arg Asp Val Val Val
1               5                   10                  15

Asp Ala Gly Cys Val Arg Ala Val Leu Gly Glu Leu Val Leu Thr Phe
            20                  25                  30

Leu Phe Val Phe Thr Gly Val Ala Ala Met Ala Ala Gly Val Pro
        35                  40                  45

Glu Leu Gln Gly Ala Ala Met Pro Met Ala Thr Leu Ala Gly Val Ala
 50                  55                  60

Leu Ala Gln Ala Leu Ala Ala Gly Val Leu Val Thr Ala Gly Phe His
65                  70                  75                  80

Val Ser Gly Gly His Leu Asn Pro Ala Val Thr Val Ala Leu Leu Ala
                85                  90                  95

Arg Gly His Ile Thr Ala Phe Arg Ala Val Leu Tyr Val Ala Ala Gln
            100                 105                 110

Leu Leu Ala Ser Ser Leu Ala Cys Ile Leu Leu Arg Tyr Leu Ser Gly
        115                 120                 125

Gly Gln Ala Thr Pro Val Pro Val His Thr Leu Gly Ala Gly Ile Gly
    130                 135                 140

Pro Met Gln Gly Leu Val Met Glu Val Ile Leu Thr Phe Ser Leu Leu
145                 150                 155                 160

Phe Val Val Tyr Ala Thr Ile Ile Asp Pro Arg Thr Thr Val Pro Gly
                165                 170                 175

Tyr Gly Pro Met Leu Thr Gly Leu Ile Val Gly Ala Asn Thr Ile Ala
            180                 185                 190

Gly Gly Asn Phe Ser Gly Ala Ser Met Asn Pro Ala Arg Ser Phe Gly
        195                 200                 205

Pro Ala Leu Ala Thr Gly Val Trp Thr Asn His Trp Val Tyr Trp Val
```

```
                    210                 215                 220

Gly Pro Leu Val Gly Gly Pro Leu Ala Gly Phe Val Tyr Glu Thr Val
225                 230                 235                 240

Phe Met Val Thr Lys Thr His Glu Pro Leu Leu Gly Trp Asp Phe
                245                 250                 255

<210> SEQ ID NO 111
<211> LENGTH: 256
<212> TYPE: PRT
<213> ORGANISM: Triticum aestivum

<400> SEQUENCE: 111

Met Asp Thr Lys His Ala Asp Ser Leu Asp Glu Arg Asp Val Val
1               5                   10                  15

Val Asp Ala Gly Cys Val Arg Ala Val Leu Gly Glu Leu Val Leu Thr
                20                  25                  30

Phe Leu Phe Val Phe Thr Gly Val Ala Ala Met Ala Ala Gly Val
                35                  40                  45

Pro Glu Leu Gln Gly Ala Ala Met Pro Met Ala Thr Leu Ala Gly Val
    50                  55                  60

Ala Leu Ala Gln Ala Leu Ala Gly Val Leu Val Thr Ala Gly Phe
65                  70                  75                  80

His Val Ser Gly Gly His Leu Asn Pro Ala Val Thr Val Ala Leu Leu
                85                  90                  95

Ala Arg Gly His Ile Thr Ala Phe Arg Ala Val Leu Tyr Val Ala Ala
                100                 105                 110

Gln Leu Leu Ala Ser Ser Leu Ala Cys Ile Leu Leu Arg Tyr Leu Ser
                115                 120                 125

Gly Gly Gln Ala Thr Pro Val Pro Val His Thr Leu Gly Thr Gly Ile
                130                 135                 140

Gly Pro Met Gln Gly Leu Val Met Glu Ile Ile Leu Thr Phe Ser Leu
145                 150                 155                 160

Leu Phe Val Val Tyr Ala Thr Ile Leu Asp Pro Arg Thr Thr Val Pro
                165                 170                 175

Gly Tyr Gly Pro Met Leu Thr Gly Leu Ile Val Gly Ala Asn Thr Ile
                180                 185                 190

Ala Gly Gly Asn Phe Ser Gly Ala Ser Met Asn Pro Ala Arg Ser Phe
                195                 200                 205

Gly Pro Ala Leu Ala Thr Gly Val Trp Thr Asn His Trp Val Tyr Trp
                210                 215                 220

Val Gly Pro Leu Val Gly Gly Pro Leu Ala Gly Phe Val Tyr Glu Thr
225                 230                 235                 240

Val Phe Met Val Thr Lys Thr His Glu Pro Leu Leu Gly Trp Asp Phe
                245                 250                 255

<210> SEQ ID NO 112
<211> LENGTH: 257
<212> TYPE: PRT
<213> ORGANISM: Hordeum vulgare

<400> SEQUENCE: 112

Met Ala Ala Thr Lys His Ala Asp Ser Phe Asp Glu Arg Glu Val Ala
1               5                   10                  15

Val Val Asp Thr Gly Cys Val Arg Ala Val Leu Gly Glu Leu Val Leu
                20                  25                  30

Thr Phe Leu Phe Val Phe Thr Gly Val Ala Ala Ala Met Ala Ala Gly
                35                  40                  45
```

```
Val Pro Glu Leu Pro Gly Ala Ala Met Pro Met Ala Thr Leu Ala Gly
 50                  55                  60

Val Ala Leu Ala Gln Ala Leu Ala Ala Gly Val Leu Val Thr Ala Gly
 65                  70                  75                  80

Phe His Val Ser Gly Gly His Leu Asn Pro Ala Val Thr Val Ala Leu
                 85                  90                  95

Leu Ala Arg Gly His Ile Thr Ala Phe Arg Ala Val Leu Tyr Val Val
            100                 105                 110

Ala Gln Leu Leu Ala Ser Ser Leu Ala Cys Ile Leu Leu Arg Cys Leu
        115                 120                 125

Thr Gly Gly Gln Pro Thr Pro Val Pro Val His Thr Leu Gly Ala Gly
130                 135                 140

Ile Gly Pro Met Gln Gly Leu Val Met Glu Ile Ile Leu Thr Phe Ser
145                 150                 155                 160

Leu Leu Phe Val Val Tyr Ala Thr Ile Leu Asp Pro Arg Thr Thr Val
                165                 170                 175

Pro Gly Tyr Gly Pro Met Leu Thr Gly Leu Ile Val Gly Ala Asn Thr
            180                 185                 190

Ile Ala Gly Gly Asn Phe Ser Gly Ala Ser Met Asn Pro Ala Arg Ser
        195                 200                 205

Phe Gly Pro Ala Leu Ala Thr Gly Val Trp Thr Asn His Trp Ile Tyr
210                 215                 220

Trp Val Gly Pro Leu Val Gly Gly Pro Leu Ala Gly Phe Val Tyr Glu
225                 230                 235                 240

Met Val Phe Met Val Lys Lys Thr His Glu Pro Leu Leu Gly Trp Asp
                245                 250                 255

Phe
```

<210> SEQ ID NO 113
<211> LENGTH: 336
<212> TYPE: PRT
<213> ORGANISM: Triticum aestivum

<400> SEQUENCE: 113

```
Met Gly Pro Val Phe Leu Leu Gly Leu Ser Gln His Gly Ser Ala Pro
 1               5                  10                  15

Gly Leu Phe Arg Ala Leu Phe Leu Pro Arg Ser His Thr Asp Tyr Ser
                 20                  25                  30

His His Ile Pro Arg Ser Arg Ala Thr Ser Leu Val Ser Met Asp Thr
             35                  40                  45

Lys His Ala Asp Ser Phe Glu Glu Arg Asp Val Val Val Asp Ala Gly
 50                  55                  60

Cys Val Arg Ala Val Leu Gly Glu Leu Val Leu Thr Phe Leu Phe Val
 65                  70                  75                  80

Phe Thr Gly Val Ala Ala Ala Met Ala Ala Gly Val Pro Glu Leu Pro
                 85                  90                  95

Gly Ala Ala Met Pro Met Ala Thr Leu Ala Gly Val Ala Leu Ala Gln
            100                 105                 110

Ala Leu Ala Ala Gly Val Leu Val Thr Ala Gly Phe His Val Ser Gly
        115                 120                 125

Gly His Leu Asn Pro Ala Val Thr Val Ala Leu Leu Ala Arg Gly His
130                 135                 140

Ile Thr Ala Phe Arg Ala Val Leu Tyr Val Ala Ala Gln Leu Leu Ala
145                 150                 155                 160
```

```
Ser Ser Leu Ala Cys Ile Leu Arg Tyr Leu Ser Gly Gly Gln Ala
                165                 170                 175

Thr Pro Val Pro Val His Thr Leu Gly Ala Gly Ile Gly Pro Met Gln
            180                 185                 190

Gly Leu Val Met Glu Val Ile Leu Thr Phe Ser Leu Leu Phe Val Val
        195                 200                 205

Tyr Ala Thr Ile Ile Asp Pro Arg Thr Thr Val Pro Gly Tyr Gly Pro
    210                 215                 220

Met Leu Thr Gly Leu Ile Val Gly Ala Asn Thr Ile Ala Gly Gly Asn
225                 230                 235                 240

Phe Ser Gly Ala Ser Met Asn Pro Ala Arg Ser Phe Gly Pro Ala Leu
                245                 250                 255

Ala Met Gly Val Trp Thr Asn His Trp Val Tyr Trp Val Gly Pro Leu
            260                 265                 270

Val Gly Gly Pro Leu Ala Gly Phe Val Tyr Glu Met Val Phe Met Val
        275                 280                 285

Lys Lys Asp Ala Arg Ala Ser Ala Trp Leu Gly Leu Leu Glu Asn Arg
    290                 295                 300

Leu Leu Pro Tyr Leu His Leu His Phe Ala Met Tyr Thr Ser Val Tyr
305                 310                 315                 320

Lys Ala Ile Asp Val Ala Gly Arg Phe Phe Arg Pro Ser Asp Ser Ser
                325                 330                 335

<210> SEQ ID NO 114
<211> LENGTH: 315
<212> TYPE: PRT
<213> ORGANISM: Oryza sativa

<400> SEQUENCE: 114

Ile Lys Ser Arg Gly Lys Gln Arg Arg Gln Ala Glu Gln Arg Arg Glu
1               5                   10                  15

Pro His Leu Gly Lys Lys Arg Lys Ile Ile Ser Ser His Phe Leu
            20                  25                  30

Leu Pro Phe Ser Ser Pro Arg Ile Phe Thr Lys Gln Ile Ser Leu Gln
        35                  40                  45

Phe Phe Ser Phe Phe Leu Ile Leu Arg Ile Phe Ser Ile Glu Glu
    50                  55                  60

Arg Arg Glu Leu Trp Asp Arg Phe Arg Ala Met Ala Lys Glu Val Asp
65                  70                  75                  80

Pro Cys Asp His Gly Glu Val Val Asp Ala Gly Cys Val Arg Ala Val
                85                  90                  95

Leu Ala Glu Leu Val Leu Thr Phe Val Phe Val Phe Thr Gly Val Ala
            100                 105                 110

Ala Thr Met Ala Ala Gly Val Pro Glu Val Ala Gly Ala Ala Met Pro
        115                 120                 125

Met Ala Ala Leu Ala Gly Val Ala Ile Ala Thr Ala Leu Ala Ala Gly
    130                 135                 140

Val Leu Val Thr Ala Gly Phe His Val Ser Gly Gly His Leu Asn Pro
145                 150                 155                 160

Ala Val Thr Val Ala Leu Leu Arg Gly His Ile Thr Ala Phe Arg
                165                 170                 175

Ser Ala Leu Tyr Val Ala Ala Gln Leu Leu Ala Ser Ser Leu Ala Cys
            180                 185                 190

Ile Leu Leu Arg Tyr Leu Thr Gly Gly Met Ala Thr Pro Val His Thr
        195                 200                 205
```

```
Leu Gly Ser Gly Ile Gly Pro Met Gln Gly Leu Val Met Glu Ile Ile
    210                 215                 220

Leu Thr Phe Ser Leu Leu Phe Val Val Tyr Ala Thr Ile Leu Asp Pro
225                 230                 235                 240

Arg Ser Ser Val Pro Gly Phe Gly Pro Leu Leu Thr Gly Leu Ile Val
                245                 250                 255

Gly Ala Asn Thr Ile Ala Gly Gly Asn Phe Ser Gly Ala Ser Met Asn
                260                 265                 270

Pro Ala Arg Ser Phe Gly Pro Ala Leu Ala Thr Gly Val Trp Thr His
            275                 280                 285

His Trp Ile Tyr Trp Leu Gly Pro Leu Ile Gly Gly Pro Leu Ala Gly
    290                 295                 300

Leu Val Tyr Glu Ser Leu Phe Leu Val Lys Arg
305                 310                 315

<210> SEQ ID NO 115
<211> LENGTH: 202
<212> TYPE: PRT
<213> ORGANISM: Saccharum officinarum
<220> FEATURE:
<221> NAME/KEY: misc_feature
<222> LOCATION: (198)..(198)
<223> OTHER INFORMATION: Xaa can be any naturally occurring amino acid

<400> SEQUENCE: 115

Pro Pro Pro Pro Pro Pro Val Val Gln Asn Ile Ser Leu Arg
1               5                   10                  15

Phe Ser Glu Ser Phe Ser Leu Gln Gly Thr Gly Thr Thr Gly Ala Phe
                20                  25                  30

Thr Pro Pro Pro Ala Phe Pro Ser Pro Pro Gly Thr Gly Ala Thr Arg
            35                  40                  45

Leu Leu Leu Ala Ile Val His Ser Phe Met Ala Lys Leu Val Asn Lys
50                  55                  60

Leu Leu Asp Ser Phe Asp His Asp Thr Thr Pro Asp Val Gly Cys
65                  70                  75                  80

Val Arg Ala Val Leu Ala Glu Leu Val Leu Thr Phe Leu Phe Val Phe
                85                  90                  95

Thr Gly Val Ser Ala Ala Met Ala Ala Gly Ser Gly Gly Lys Pro Gly
            100                 105                 110

Glu Ala Met Pro Met Ala Thr Leu Ala Ala Val Ala Ile Ala Asn Ala
        115                 120                 125

Leu Ala Ala Gly Val Leu Val Thr Ala Gly Phe His Val Ser Gly Gly
130                 135                 140

His Leu Asn Pro Ala Val Thr Val Gly Leu Met Val Cys Arg His Ile
145                 150                 155                 160

Thr Lys Leu Arg Ala Val Leu Tyr Ile Ala Ala Gln Leu Leu Ala Ser
                165                 170                 175

Ser Leu Ala Cys Ile Leu Leu Arg Tyr Leu Ser Gly Gly Met Val Thr
            180                 185                 190

Pro Val His Ala Leu Xaa Ala Gly Ile Lys
        195                 200

<210> SEQ ID NO 116
<211> LENGTH: 256
<212> TYPE: PRT
<213> ORGANISM: Oryza sativa

<400> SEQUENCE: 116
```

```
Met Ala Ser Pro Glu Gly Ser Thr Trp Val Phe Asp Cys Pro Leu Met
1               5                   10                  15

Asp Asp Leu Ala Ala Ala Gly Phe Asp Ala Ala Pro Ala Gly Gly
            20                  25                  30

Phe Tyr Trp Thr Thr Pro Ala Pro Gln Ala Ala Leu Gln Pro Pro
        35                  40                  45

Pro Pro Gln Gln Gln Pro Val Ala Pro Thr Ala Ala Pro Asn Ala
    50                  55                  60

Cys Ala Glu Ile Asn Gly Ser Val Asp Cys Glu His Gly Lys Glu Gln
65                  70                  75                  80

Pro Thr Asn Lys Arg Pro Arg Ser Glu Ser Gly Thr Arg Pro Ser Ser
                85                  90                  95

Lys Ala Cys Arg Glu Lys Val Arg Arg Asp Lys Leu Asn Glu Arg Phe
            100                 105                 110

Leu Glu Leu Gly Ala Val Leu Glu Pro Gly Lys Thr Pro Lys Met Asp
            115                 120                 125

Lys Ser Ser Ile Leu Asn Asp Ala Ile Arg Val Met Ala Glu Leu Arg
130                 135                 140

Ser Glu Ala Gln Lys Leu Lys Glu Ser Asn Glu Ser Leu Gln Glu Lys
145                 150                 155                 160

Ile Lys Glu Leu Lys Ala Glu Lys Asn Glu Leu Arg Asp Glu Lys Gln
                165                 170                 175

Lys Leu Lys Ala Glu Lys Glu Ser Leu Glu Gln Ile Lys Phe Leu
            180                 185                 190

Asn Ala Arg Pro Ser Phe Val Pro His Pro Val Ile Pro Ala Ser
            195                 200                 205

Ala Phe Thr Ala Pro Gln Gly Gln Ala Ala Gly Gln Lys Leu Met Met
            210                 215                 220

Pro Val Ile Gly Tyr Pro Gly Phe Pro Met Trp Gln Phe Met Pro Pro
225                 230                 235                 240

Ser Asp Val Asp Thr Thr Asp Asp Thr Lys Ser Cys Pro Pro Val Ala
                245                 250                 255

<210> SEQ ID NO 117
<211> LENGTH: 251
<212> TYPE: PRT
<213> ORGANISM: Triticum aestivum

<400> SEQUENCE: 117

Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Ser Ala Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
            115                 120                 125
```

Asn Asp Ala Ile Arg Ala Val Thr Glu Leu Arg Ser Glu Ala Glu Lys
        130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Ser
                180                 185                 190

Leu Val Pro His Pro Ser Val Ile Pro Ala Ala Ala Phe Ala Ala Ala
            195                 200                 205

Gln Gly Gln Ala Ala Gly His Lys Leu Met Met Pro Val Met Ser Tyr
        210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250

<210> SEQ ID NO 118
<211> LENGTH: 251
<212> TYPE: PRT
<213> ORGANISM: Hordeum vulgare

<400> SEQUENCE: 118

Met Ala Ser Pro Glu Gly Ser Asn Trp Val Phe Asp Cys Pro Leu Met
1               5                   10                  15

Asp Asp Leu Ala Ala Ala Asp Phe Ala Ala Val Pro Ala Gly Gly Phe
                20                  25                  30

Tyr Trp Asn Pro Pro Met Pro Pro Gln Met His Thr Leu Ala Gln Ala
            35                  40                  45

Val Ser Ala Thr Pro Ala Pro Asn Pro Cys Ala Glu Ile Asn Ser Ser
50                  55                  60

Val Ser Val Asp Trp Asp His Ala Lys Gly Gln Pro Leu Asn Lys Arg
65                  70                  75                  80

Pro Arg Ser Glu Thr Gly Ala Gln Pro Ser Lys Ala Cys Arg Glu
                85                  90                  95

Lys Val Arg Arg Asp Lys Leu Asn Glu Arg Phe Leu Glu Leu Gly Ala
                100                 105                 110

Val Leu Asp Pro Gly Lys Thr Pro Lys Ile Asp Lys Cys Ala Ile Leu
            115                 120                 125

Asn Asp Ala Ile Arg Ala Val Thr Glu Leu Arg Ser Glu Ala Glu Lys
        130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Arg
                180                 185                 190

Leu Val Pro His Pro Ser Val Ile Pro Ala Thr Ala Phe Ala Ala Ala
            195                 200                 205

Gln Gly Gln Ala Ala Gly His Lys Leu Met Met Pro Val Met Ser Tyr
        210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250

<210> SEQ ID NO 119
<211> LENGTH: 214
<212> TYPE: PRT
<213> ORGANISM: Oryza sativa

<400> SEQUENCE: 119

Met Tyr Leu Leu Tyr Ile Ile Val Thr Tyr Gly Ile Leu Lys Tyr
1               5                   10                  15
Lys Phe Ile Phe Phe Thr Ser Ala Glu Ile Asn Gly Ser Val Asp Cys
            20                  25                  30
Glu His Gly Lys Glu Gln Pro Thr Asn Lys Arg Pro Arg Ser Glu Ser
        35                  40                  45
Gly Thr Arg Pro Ser Ser Lys Ala Cys Arg Glu Lys Val Arg Arg Asp
    50                  55                  60
Lys Leu Asn Glu Arg Phe Leu Glu Leu Gly Ala Val Leu Glu Pro Gly
65                  70                  75                  80
Lys Thr Pro Lys Met Asp Lys Ser Ser Ile Leu Asn Asp Ala Ile Arg
                85                  90                  95
Val Met Ala Glu Leu Arg Ser Glu Ala Gln Lys Leu Lys Glu Ser Asn
            100                 105                 110
Glu Ser Leu Gln Glu Lys Ile Lys Glu Leu Lys Ala Glu Lys Asn Glu
        115                 120                 125
Leu Arg Asp Glu Lys Gln Lys Leu Lys Ala Glu Lys Glu Ser Leu Glu
    130                 135                 140
Gln Gln Ile Lys Phe Leu Asn Ala Arg Pro Ser Phe Val Pro His Pro
145                 150                 155                 160
Pro Val Ile Pro Ala Ser Ala Phe Thr Ala Pro Gln Gly Ala Ala
                165                 170                 175
Gly Gln Lys Leu Met Met Pro Val Ile Gly Tyr Pro Gly Phe Pro Met
            180                 185                 190
Trp Gln Phe Met Pro Pro Ser Asp Val Asp Thr Thr Asp Asp Thr Lys
        195                 200                 205
Ser Cys Pro Pro Val Ala
    210

<210> SEQ ID NO 120
<211> LENGTH: 877
<212> TYPE: DNA
<213> ORGANISM: Cauliflower mosaic virus

<400> SEQUENCE: 120
aagcttgcat gcctgcaggt ccccagatta gccttttcaa tttcagaaag aatgctaacc    60
cacagatggt tagagaggct tacgcagcag gtctcatcaa gacgatctac ccgagcaata   120
atctccagga aatcaaatac cttcccaaga aggttaaaga tgcagtcaaa agattcagga   180
ctaactgcat caagaacaca gagaaagata tatttctcaa gatcagaagt actattccag   240
tatggacgat tcaaggcttg cttcacaaac caaggcaagt aatagagatt ggagtctcta   300
aaaaggtagt tcccactgaa tcaaaggcca tggagtcaaa gattcaaata gaggacctaa   360
cagaactcgc cgtaaagact ggcgaacagt tcatacagag tctcttacga ctcaatgaca   420
agaagaaaat cttcgtcaac atggtggagc acgacacact tgtctactcc aaaaatatca   480
aagatacagt ctcagaagac caaagggcaa ttgagacttt tcaacaaagg gtaatatccg   540
gaaacctcct cggattccat tgcccagcta tctgtcactt tattgtgaag atagtggaaa   600
aggaaggtgg ctcctacaaa tgccatcatt gcgataaagg aaaggccatc gttgaagatg   660

| | |
|---|---:|
| cctctgccga cagtggtccc aaagatggac ccccacccac gaggagcatc gtggaaaaag | 720 |
| aagacgttcc aaccacgtct tcaaagcaag tggattgatg tgatatctcc actgacgtaa | 780 |
| gggatgacgc acaatcccac tatccttcgc aagacccttc ctctatataa ggaagttcat | 840 |
| ttcatttgga gagaacacgg gggactctag aggatcc | 877 |

<210> SEQ ID NO 121
<211> LENGTH: 2322
<212> TYPE: DNA
<213> ORGANISM: Arabidopsis thaliana

<400> SEQUENCE: 121

| | |
|---|---:|
| aagctttaag ctccaagccc acatctatgc acttcaacat atcttttcct agatgagttg | 60 |
| gtaaaagtag aaaaagatat gatgatttta aatttgtttc tatttatatg tgttcatcga | 120 |
| aacttcattt ttttagttt taatagagag tttatatgac ttttaaaaat tgatttaaaa | 180 |
| ctgtgtcaaa aattaaaagg acaataaaaa atttgcatac aaccgaaaat acttatattt | 240 |
| agacaagaaa aataatact tgtgatgctg attttatttt attatatatc atgaatcatg | 300 |
| atcatccaat tttccggata agccaaagtc aaaatgatgg gttcccccta atcttttatg | 360 |
| ctgagaaata gatgtatatt cttagatagt aatataaaat tgggttaaag aatgatgatt | 420 |
| cgattatagc ctcaactaga agatacgtgt agtgcaggtg tgtagttaac tggtggtagt | 480 |
| ggcagacaac cagattagga gttaaataaa gcctttagat ttgagagatt gaaatattcg | 540 |
| attggaacct ttctagattt ttacagccat ctaaaattag atgcagatca cctactacca | 600 |
| ttcaaaaatg aacaaaataa tttcatttac attttcctag cataagatat aataataaaa | 660 |
| tagtgctcat tttaattact ttttctaaat attttcgtta tttttaaattt tgcttgtcta | 720 |
| tactctacag ctcatttaat aacgaaaaca aaaataattg cagggatacg gatgggtagc | 780 |
| tttcaaaact tacatcatct tctgtttctt gagatcaact atttttggag ctttgtctca | 840 |
| atcgtaccaa aggataatgg tcctacctcc ttttgcattc ttaactttat cttctctact | 900 |
| tatttctttt ttgggatttt tgggggtatt attttatctt ttgtagatat acacattgat | 960 |
| ttactacaaa cgtatactac tatccatctt caactcttcg gaatatgatt tcgaaaaaac | 1020 |
| tatgaagatt aacgggtatc ttaaacatgt taagatacac cggacaattt tcatttagaa | 1080 |
| gaattgatat gcaattaaca ataaatagtt gatgatcttt tagttttgaa gatgtgcgtt | 1140 |
| aagacttaag cgtgtggtaa caaggtggga ctcgggcaac gcaaagcctt gtagagtcca | 1200 |
| cttgctcaac ttgtctttct tttatctctt ttccaagtct caagattcaa tgaactccgt | 1260 |
| gtaacacaaa cacgcccata gatgagctca ttttggtat ttccaatatt gccactccat | 1320 |
| gataatatca tctagggatg gggttcattt attttgaaat ctcaacaaat ctcgtcgatt | 1380 |
| ctaacacaca tgattgattt gtttacttac ttgaaagttg gcaactatct gggattaaaa | 1440 |
| tttatctttt tctactgcta gctagaagca tctatatatg ttagcctaat acgtggaaga | 1500 |
| tgtcattgct aataatggct aaagatgtgt attaattttt cttctttttt ccttgaattt | 1560 |
| ttgttctttg acataaacta tgctgtcaaa atgtgtagaa tcttttttaca taaatcattc | 1620 |
| cctgttacac actaaaaggt tcacaacgga cgattgtatt ggacttccag atcataaacc | 1680 |
| atgcaaaact gaaaaccaca agaataatta gttctaactt tagaacgttc gtacgtgttt | 1740 |
| catgttcaaa aagcgtcaat tataaaagtt gggaaattac ttttgagttt tgacatttct | 1800 |
| aaggacagtc aaatatgaca acattgggat gcaacttacc ttgtattaac ttattttgtt | 1860 |
| ataaaaccat atattacata ttttaaaggg ttgataaata atcaaatata ccaaaacata | 1920 |

```
gcttttcaat atatttgtaa aacacgtttg gtctactagc taattatgag aacatttgtt    1980
caatgcatga ttatctagta tctactagtg gattatgaaa attagatatt ttcattgcat    2040
gattatcttc catatatagt gataacatca aaagaatcta caccaattat tgcattttt     2100 cattatataa taagcactaa actgtaaaat tatattcagc cacccaaacc atgacaaatc    2160
accttaaagg cttaaacaca taacagccat tacgagtcac aggtaagggt ataatagtaa    2220
agaatcaatc tatataatat acgacccacc ctttctcatt ctttctggag agtaacatcg    2280
agacaaagaa gaaaaactaa aaaagagaac cccaaaggat cc                      2322

<210> SEQ ID NO 122
<211> LENGTH: 456
<212> TYPE: DNA
<213> ORGANISM: Lycopersicon esculentum

<400> SEQUENCE: 122
atgggtcgta tgcacagtcg tggtaagggt atttcagctt ctgctctccc ttacaagaga      60
actcctccta gttggctcaa gatctctgct ccagatgttg aggacaacat ctgcaagttc     120
gctaagaaag gattgacccc ttcacagatt ggtgtgattc ttcgtgattc tcatggaatt     180
gcacaagtga agagtgttac tggtagcaag atcttgcgta tcctcaaggc acatgggctt     240
gcacctgaga ttccagagga tttgtaccac ctgattaaga aggctgttgc cattaggaag     300
catttggaga ggaacaggaa ggataaggat tctaagttcc gtttgatttt ggtggagagc     360
aggattcatc gccttgctcg ttattacaag aaaacaaaaa agctcccacc tgtctggaaa     420
tacgaatcta ccactgctag cacacttgtg gcatag                              456

<210> SEQ ID NO 123
<211> LENGTH: 657
<212> TYPE: DNA
<213> ORGANISM: Lycopersicon esculentum

<400> SEQUENCE: 123
atggaagaca aaagcaatga ttattatgca gttttggggt tgaagaagga atgcactgac      60
acagaactta ggaatgccta taagaagctt gcactgaaat ggcacccaga tcgctgttca     120
gcatcgggga atttgaagtt tgtagatgaa gcaaagaagc aatttcaggc aattcaagaa     180
gcatattctg tgttatcgga tgcaaacaaa agttttttgt acgatgtagg agtttatgac     240
tctggtgatg atgacgacga aaatggcatg ggtgatttcc tgaatgaaat ggcagctatg     300
atgagccaaa ataagtccaa tgaaaatcag ggagaagaaa cctttgagga attgcaggat     360
atgtttaatg aaatgttcaa cagtgataat ggaacgtttt cttcttcttc ttcttcttct     420
tcttcttgga ctggaactcc ttcaatgtgc tctactacat catctacatc ttcaagtgag     480 actttttaa cctttcccaa caagagaagt tcaggtgaaa tgaagtcggg tagtagtgta     540
agaggcgatt cttgccaatt ccaaggattt tgtgtagggg caggtggaac ttctggaaaa     600
tgcaatgaaa gagaacgaag ttggaggaaa aattccaaga gtggacggaa gcattag       657

<210> SEQ ID NO 124
<211> LENGTH: 897
<212> TYPE: DNA
<213> ORGANISM: Lycopersicon esculentum

<400> SEQUENCE: 124
atggagaata tgcagagcta ttggcaattt ggcgacgagc ttcgaggaca atcaaaagcc      60
tcagaggatc ataaatggtc aacagctgct ataaaattat ctgaacagat gaagtacaaa     120
```

-continued

```
ggtgaacgta ggaataacct tgaccttcca aagagctctg ctgaaattag gcccaggggt      180
aatcatatgt ttcaggaaga taacaagtgg gaaagcctta acttcaatat gttaaatttg      240
gaaagcaaga tgactgaaaa tatgagcaag aatcgcatta tggatagcat tttcaatgca      300
aatccagttt atcttaagcc caattttaac agcttgggaa attcatcttt aagcaagttc      360
aatgctagca actataccaa ggaacctagc aagaataaca ataacaacgt tgagagcaca      420
aatgaaaata actccgttga caaaaggttt aagactctgc ctgctgctga aacactgccg      480
aagaatgagg ttcttggtgg atatatattt gtttgtaaca atgacacaat gcaggaagac      540
ctaaagcgcc tgctctttgg ccttcctcct agatacagag attccgtgag gcaataaca      600 ccagggttgc ccttgttcct atataattac actactcacc agttgcatgg tatctttgag      660
gcatcgagtt ttggaggttc caacattgat ccaactgcct gggaggataa aaagtgtaaa      720
ggagagtcaa ggttccctgc tcaggtgagg atccgtgtcc ggaaagtctg taatcctttg      780
gaggaagatg ctttcagacc agttttacat cattatgatg gccccaagtt ccgtctggag      840
ctctccattc ctgagacttt ggacttacta gatctctgtg aaaaagccgg tgtgtag        897
```

<210> SEQ ID NO 125
<211> LENGTH: 750
<212> TYPE: DNA
<213> ORGANISM: Lycopersicon esculentum

<400> SEQUENCE: 125

```
atggctggcg gcgtagctat tggaagtttt agtgattcat tcagcgttgt ctctcttaag       60
tcctatcttg ccgaattcat ctccacactc atctttgtct tcgccggagt tggttccgcc      120
attgcttacg gcaagttgac aacaaatgct gcacttgatc cggctgggct tgtagctatt      180
gcagtttgcc atggatttgc tctattcgta gccgtttcga tttccgctaa catctccggt      240
ggtcatgtta accctgcggt cacctgtgga ttaaccttcg gcggacatat tacctttatc      300
actggctcct tctacatgct tgctcaactt accggcgccg ctgtagcttg cttcctcctc      360
aaattcgtca ccggaggatg tgctattcca acccatggag tgggagctgg tgtgagcata      420
ctagaaggac tcgtgatgga aataataatc acatttggtt tagtttatac tgtgttcgca      480
accgccgctg acccgaagaa gggttcattg gcacaattg caccgattgc aattggtctc       540
attgttggag ctaatatttt ggctgccgga ccattctccg tggatcaat gaacccagct       600 cgttcatttg gacctgcaat ggttagtggt aactttgagg gtttctggat ctactggatt      660
ggtccattag ttggtggtag tttggctggt cttattttaca caaatgtgtt catgacacaa      720
gaacatgctc ctttatccaa tgagttctaa                                       750
```

<210> SEQ ID NO 126
<211> LENGTH: 735
<212> TYPE: DNA
<213> ORGANISM: Lycopersicon esculentum

<400> SEQUENCE: 126

```
atggaggtcg attctagtgg gaatcctaat tggttatttg attatgagtt gatgacggat       60
attacttctg ctgcatctgt taccgtcgct gagtttcagt ctccggctac tattgatttc      120
agctggcctc ctcaaacgat ctatgcttct tctaatctca ttactgaaac agattacaca      180
tttgcggatt cagaagttag caaggaggca agctcacgaa agcggttaaa aagtgaatgt      240
tgcagctctc cgagatctaa ggcatgcaga gagaaattgc ggagggacag actgaatgag      300
aggttcctcg cattgagctc tgtccttgat cctggaaggc caccaaaaac tgagaaagtt      360
```

```
gcaattctaa gtgatgctca aaggatgctg attgagctgc gaactgaaac ccagaagctg      420
aaggagtcaa atgaggagct gcaagagaag ataaaagaac ttaaggcaga gaagaatgag      480
ctccgagatg aaaagcaaag gctaaaggaa gaaaaggata atttggagca gcaggttaaa      540
agcttagctt ctaaagcagg atttctctcc catccttctg ccatgggagc tgcatttact      600
gcacaaggac aagttgctgc aggcaacaaa ttgatgcctt tcattggtta tcccagygty      660
gcgatgtggc rattcatgca acctgctgtt gttgacacat ctcaagatca tgtgctccgt      720
cctccagttg cttaa                                                      735
```

<210> SEQ ID NO 127
<211> LENGTH: 151
<212> TYPE: PRT
<213> ORGANISM: Lycopersicon esculentum

<400> SEQUENCE: 127

```
Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
                20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150
```

<210> SEQ ID NO 128
<211> LENGTH: 219
<212> TYPE: PRT
<213> ORGANISM: Lycopersicon esculentum

<400> SEQUENCE: 128

```
Met Glu Asp Lys Ser Asn Asp Tyr Tyr Ala Val Leu Gly Leu Lys Lys
1               5                   10                  15

Glu Cys Thr Asp Thr Glu Leu Arg Asn Ala Tyr Lys Lys Leu Ala Leu
                20                  25                  30

Lys Trp His Pro Asp Arg Cys Ser Ala Ser Gly Asn Leu Lys Phe Val
            35                  40                  45

Asp Glu Ala Lys Lys Gln Phe Gln Ala Ile Gln Glu Ala Tyr Ser Val
        50                  55                  60

Leu Ser Asp Ala Asn Lys Lys Phe Leu Tyr Asp Val Gly Val Tyr Asp
65                  70                  75                  80

Ser Gly Asp Asp Asp Glu Asn Gly Met Gly Asp Phe Leu Asn Glu
                85                  90                  95

Met Ala Ala Met Met Ser Gln Asn Lys Ser Asn Glu Asn Gln Gly Glu
            100                 105                 110
```

Glu Thr Phe Glu Glu Leu Gln Asp Met Phe Asn Glu Met Phe Asn Ser
            115                 120                 125

Asp Asn Gly Thr Phe Ser Ser Ser Ser Ser Ser Ser Ser Trp
    130                 135                 140

Thr Gly Thr Pro Ser Met Cys Ser Thr Thr Ser Ser Thr Ser Ser Ser
145                 150                 155                 160

Glu Thr Phe Leu Thr Phe Pro Asn Lys Arg Ser Ser Gly Glu Met Lys
                165                 170                 175

Ser Gly Ser Ser Val Arg Gly Asp Ser Cys Gln Phe Gln Gly Phe Cys
                180                 185                 190

Val Gly Ala Gly Gly Thr Ser Gly Lys Cys Asn Glu Arg Glu Arg Ser
            195                 200                 205

Trp Arg Lys Asn Ser Lys Ser Gly Arg Lys His
    210                 215

<210> SEQ ID NO 129
<211> LENGTH: 298
<212> TYPE: PRT
<213> ORGANISM: Lycopersicon esculentum

<400> SEQUENCE: 129

Met Glu Asn Met Gln Ser Tyr Trp Gln Phe Gly Asp Glu Leu Arg Gly
1               5                   10                  15

Gln Ser Lys Ala Ser Glu Asp His Lys Trp Ser Thr Ala Ala Ile Lys
            20                  25                  30

Leu Ser Glu Gln Met Lys Tyr Lys Gly Glu Arg Arg Asn Asn Leu Asp
        35                  40                  45

Leu Ser Lys Ser Ser Ala Glu Ile Arg Pro Arg Gly Asn His Met Phe
    50                  55                  60

Gln Glu Asp Asn Lys Trp Glu Ser Leu Asn Phe Asn Met Leu Asn Leu
65                  70                  75                  80

Glu Ser Lys Met Thr Glu Asn Met Ser Lys Asn Arg Ile Met Asp Ser
                85                  90                  95

Ile Phe Asn Ala Asn Pro Val Tyr Leu Lys Pro Asn Phe Asn Ser Leu
            100                 105                 110

Gly Asn Ser Ser Leu Ser Lys Phe Asn Ala Ser Asn Tyr Thr Lys Glu
        115                 120                 125

Pro Ser Lys Asn Asn Asn Asn Val Glu Ser Thr Asn Gly Asn Asn
    130                 135                 140

Ser Val Asp Lys Arg Phe Lys Thr Leu Pro Ala Glu Thr Leu Pro
145                 150                 155                 160

Lys Asn Glu Val Leu Gly Gly Tyr Ile Phe Val Cys Asn Asn Asp Thr
                165                 170                 175

Met Gln Glu Asp Leu Lys Arg Leu Leu Phe Gly Leu Pro Pro Arg Tyr
            180                 185                 190

Arg Asp Ser Val Arg Ala Ile Thr Pro Gly Leu Pro Leu Phe Leu Tyr
        195                 200                 205

Asn Tyr Thr Thr His Gln Leu His Gly Ile Phe Glu Ala Ser Ser Phe
    210                 215                 220

Gly Gly Ser Asn Ile Asp Pro Thr Ala Trp Glu Asp Lys Lys Cys Lys
225                 230                 235                 240

Gly Glu Ser Arg Phe Pro Ala Gln Val Arg Ile Arg Val Arg Lys Val
                245                 250                 255

Cys Asn Pro Leu Glu Glu Asp Ala Phe Arg Pro Val Leu His His Tyr
            260                 265                 270

```
Asp Gly Pro Lys Phe Arg Leu Glu Leu Ser Ile Pro Glu Thr Leu Asp
        275                 280                 285

Leu Leu Asp Leu Cys Glu Lys Ala Gly Val
    290                 295

<210> SEQ ID NO 130
<211> LENGTH: 249
<212> TYPE: PRT
<213> ORGANISM: Lycopersicon esculentum

<400> SEQUENCE: 130

Met Ala Gly Gly Val Ala Ile Gly Ser Phe Ser Asp Ser Phe Ser Val
1               5                   10                  15

Val Ser Leu Lys Ser Tyr Leu Ala Glu Phe Ile Ser Thr Leu Ile Phe
            20                  25                  30

Val Phe Ala Gly Val Gly Ser Ala Ile Ala Tyr Gly Lys Leu Thr Thr
        35                  40                  45

Asn Ala Ala Leu Asp Pro Ala Gly Leu Val Ala Ile Ala Val Cys His
    50                  55                  60

Gly Phe Ala Leu Phe Val Ala Val Ser Ile Ser Ala Asn Ile Ser Gly
65                  70                  75                  80

Gly His Val Asn Pro Ala Val Thr Cys Gly Leu Thr Phe Gly Gly His
                85                  90                  95

Ile Thr Phe Ile Thr Gly Ser Phe Tyr Met Leu Ala Gln Leu Thr Gly
            100                 105                 110

Ala Ala Val Ala Cys Phe Leu Leu Lys Phe Val Thr Gly Gly Cys Ala
        115                 120                 125

Ile Pro Thr His Gly Val Gly Ala Gly Val Ser Ile Leu Glu Gly Leu
    130                 135                 140

Val Met Glu Ile Ile Ile Thr Phe Gly Leu Val Tyr Thr Val Phe Ala
145                 150                 155                 160

Thr Ala Ala Asp Pro Lys Lys Gly Ser Leu Gly Thr Ile Ala Pro Ile
                165                 170                 175

Ala Ile Gly Leu Ile Val Gly Ala Asn Ile Leu Ala Ala Gly Pro Phe
            180                 185                 190

Ser Gly Gly Ser Met Asn Pro Ala Arg Ser Phe Gly Pro Ala Met Val
        195                 200                 205

Ser Gly Asn Phe Glu Gly Phe Trp Ile Tyr Trp Ile Gly Pro Leu Val
    210                 215                 220

Gly Gly Ser Leu Ala Gly Leu Ile Tyr Thr Asn Val Phe Met Thr Gln
225                 230                 235                 240

Glu His Ala Pro Leu Ser Asn Glu Phe
                245

<210> SEQ ID NO 131
<211> LENGTH: 244
<212> TYPE: PRT
<213> ORGANISM: Lycopersicon esculentum

<400> SEQUENCE: 131

Met Glu Val Asp Ser Ser Gly Asn Pro Asn Trp Leu Phe Asp Tyr Glu
1               5                   10                  15

Leu Met Thr Asp Ile Thr Ser Ala Ala Ser Val Thr Val Ala Glu Phe
            20                  25                  30

Gln Ser Pro Ala Thr Ile Asp Phe Ser Trp Pro Ala Gln Thr Ile Tyr
        35                  40                  45
```

-continued

Ala Ser Ser Asn Leu Ile Thr Glu Thr Asp Tyr Thr Phe Ala Asp Ser
            50                  55                  60

Glu Val Ser Lys Glu Ala Ser Ser Arg Lys Arg Leu Lys Ser Glu Cys
 65                  70                  75                  80

Cys Ser Ser Pro Arg Ser Lys Ala Cys Arg Glu Lys Leu Arg Arg Asp
                 85                  90                  95

Arg Leu Asn Glu Arg Phe Leu Ala Leu Ser Ser Val Leu Asp Pro Gly
            100                 105                 110

Arg Pro Pro Lys Thr Glu Lys Val Ala Ile Leu Ser Asp Ala Gln Arg
            115                 120                 125

Met Leu Ile Glu Leu Arg Thr Glu Thr Gln Lys Leu Lys Glu Ser Asn
130                 135                 140

Glu Glu Leu Gln Glu Lys Ile Lys Glu Leu Lys Ala Glu Lys Asn Glu
145                 150                 155                 160

Leu Arg Asp Glu Lys Gln Arg Leu Lys Glu Glu Lys Asp Asn Leu Glu
                165                 170                 175

Gln Gln Val Lys Ser Leu Ala Ser Lys Ala Gly Phe Leu Ser His Pro
            180                 185                 190

Ser Ala Met Gly Ala Ala Phe Thr Ala Gln Gly Gln Val Ala Ala Ser
            195                 200                 205

Asn Lys Leu Met Pro Phe Ile Gly Tyr Pro Ser Val Ala Met Trp Arg
210                 215                 220

Phe Met Gln Pro Ala Val Val Asp Thr Ser Gln Asp His Val Leu Arg
225                 230                 235                 240

Pro Pro Val Ala

<210> SEQ ID NO 132
<211> LENGTH: 20
<212> TYPE: DNA
<213> ORGANISM: Artificial sequence
<220> FEATURE:
<223> OTHER INFORMATION: Single strand DNA oligonulcotide

<400> SEQUENCE: 132
aggcgattaa gttgggtaac                                              20

<210> SEQ ID NO 133
<211> LENGTH: 23
<212> TYPE: DNA
<213> ORGANISM: Artificial sequence
<220> FEATURE:
<223> OTHER INFORMATION: Single strand DNA oligonulcotide

<400> SEQUENCE: 133
gcgggactct aatcataaaa acc                                          23

<210> SEQ ID NO 134
<211> LENGTH: 22
<212> TYPE: DNA
<213> ORGANISM: Artificial sequence
<220> FEATURE:
<223> OTHER INFORMATION: Single strand DNA oligonulcotide

<400> SEQUENCE: 134
tagtttggtc agatgggaaa cg                                           22

<210> SEQ ID NO 135
<211> LENGTH: 25
<212> TYPE: DNA
<213> ORGANISM: Artificial sequence
<220> FEATURE:

<223> OTHER INFORMATION: Single strand DNA oligonulcotide

<400> SEQUENCE: 135
aaatattgga tcctttgggg ttctc        25

<210> SEQ ID NO 136
<211> LENGTH: 3207
<212> TYPE: DNA
<213> ORGANISM: Artificial sequence
<220> FEATURE:
<223> OTHER INFORMATION: Plasmid vector

<400> SEQUENCE: 136

| | | | | | |
|---|---|---|---|---|---|
| taaattatcg | cgcgcggtgt | catctatgtt | actagatcgg | gaattcaatg | cggccgccac | 60 |
| cgcggtggcc | agcttttgtt | ccctttagtg | agggttaatt | gcgcgcttgg | cgtaatcatg | 120 |
| gtcatagctg | tttcctgtgt | gaaattgtta | tccgctcaca | attccacaca | acatacgagc | 180 |
| cggaagcata | aagtgtaaag | cctggggtgc | ctaatgagtg | agctaactca | cattaattgc | 240 |
| gttgcgctca | ctgcccgctt | tccagtcggg | aaacctgtcg | tgccagctgc | attaatgaat | 300 |
| cggccaacgc | gcggggagag | gcggtttgcg | tattgggcgc | tcttccgctt | cctcgctcac | 360 |
| tgactcgctg | cgctcggtcg | ttcggctgcg | gcgagcggta | tcagctcact | caaaggcggt | 420 |
| aatacggtta | tccacagaat | caggggataa | cgcaggaaag | aacatgtgag | caaaaggcca | 480 |
| gcaaaaggcc | aggaaccgta | aaaaggccgc | gttgctggcg | tttttccata | ggctccgccc | 540 |
| ccctgacgag | catcacaaaa | atcgacgctc | aagtcagagg | tggcgaaacc | cgacaggact | 600 |
| ataaagatac | caggcgtttc | cccctggaag | ctccctcgtg | cgctctcctg | ttccgaccct | 660 |
| gccgcttacc | ggatacctgt | ccgcctttct | cccttcggga | agcgtggcgc | tttctcatag | 720 |
| ctcacgctgt | aggtatctca | gttcggtgta | ggtcgttcgc | tccaagctgg | gctgtgtgca | 780 |
| cgaacccccc | gttcagcccg | accgctgcgc | cttatccggt | aactatcgtc | ttgagtccaa | 840 |
| cccggtaaga | cacgacttat | cgccactggc | agcagccact | ggtaacagga | ttagcagagc | 900 |
| gaggtatgta | ggcggtgcta | cagagttctt | gaagtggtgg | cctaactacg | gctacactag | 960 |
| aaggacagta | tttggtatct | gcgctctgct | gaagccagtt | accttcggaa | aaagagttgg | 1020 |
| tagctcttga | tccggcaaac | aaaccaccgc | tggtagcggt | ggtttttttg | tttgcaagca | 1080 |
| gcagattacg | cgcagaaaaa | aaggatctca | agaagatcct | ttgatctttt | ctacggggtc | 1140 |
| tgacgctcag | tggaacgaaa | actcacgtta | agggattttg | gtcatgagat | tatcaaaaag | 1200 |
| gatcttcacc | tagatccttt | taaattaaaa | atgaagtttt | aaatcaatct | aaagtatata | 1260 |
| tgagtaaact | tggtctgaca | gttaccaatg | cttaatcagt | gaggcaccta | tctcagcgat | 1320 |
| ctgtctattt | cgttcatcca | tagttgcctg | actccccgtc | gtgtagataa | ctacgatacg | 1380 |
| ggagggctta | ccatctggcc | ccagtgctgc | aatgataccg | cgagacccac | gctcaccggc | 1440 |
| tccagattta | tcagcaataa | accagccagc | cggaagggcc | gagcgcagaa | gtggtcctgc | 1500 |
| aactttatcc | gcctccatcc | agtctattaa | ttgttgccgg | gaagctagag | taagtagttc | 1560 |
| gccagttaat | agtttgcgca | acgttgttgc | cattgctaca | ggcatcgtgg | tgtcacgctc | 1620 |
| gtcgtttggt | atggcttcat | tcagctccgg | ttcccaacga | tcaaggcgag | ttacatgatc | 1680 |
| ccccatgttg | tgcaaaaaag | cggttagctc | cttcggtcct | ccgatcgttg | tcagaagtaa | 1740 |
| gttggccgca | gtgttatcac | tcatggttat | ggcagcactg | cataattctc | ttactgtcat | 1800 |
| gccatccgta | agatgctttt | ctgtgactgg | tgagtactca | accaagtcat | tctgagaata | 1860 |
| gtgtatgcgg | cgaccgagtt | gctcttgccc | ggcgtcaata | cgggataata | ccgcgccaca | 1920 |

| | |
|---|---:|
| tagcagaact ttaaaagtgc tcatcattgg aaaacgttct tcggggcgaa aactctcaag | 1980 |
| gatcttaccg ctgttgagat ccagttcgat gtaacccact cgtgcaccca actgatcttc | 2040 |
| agcatctttt actttcacca gcgtttctgg gtgagcaaaa acaggaaggc aaaatgccgc | 2100 |
| aaaaaaggga ataagggcga cacgaaaatg ttgaatactc atactcttcc tttttcaata | 2160 |
| ttattgaagc atttatcagg gttattgtct catgagcgga tacatatttg aatgtattta | 2220 |
| gaaaaataaa caatagggg ttccgcgcac atttccccga aaagtgccac ctaaattgta | 2280 |
| agcgttaata ttttgttaaa attcgcgtta aattttgtt aaatcagctc attttttaac | 2340 |
| caataggccg aaatcggcaa aatcccttat aaatcaaaag aatagaccga gatagggttg | 2400 |
| agtgttgttc cagtttggaa caagagtcca ctattaaaga acgtggactc caacgtcaaa | 2460 |
| gggcgaaaaa ccgtctatca gggcgatggc ccactacgtg aaccatcacc ctaatcaagt | 2520 |
| tttttggggt cgaggtgccg taaagcacta atcggaacc ctaaagggag cccccgattt | 2580 |
| agagcttgac ggggaaagcc ggcgaacgtg cgagaaagg aagggaagaa agcgaaagga | 2640 |
| gcgggcgcta gggcgctggc aagtgtagcg gtcacgctgc gcgtaaccac cacacccgcc | 2700 |
| gcgcttaatg cgccgctaca gggcgcgtcc cattcgccat tcaggctgcg caactgttgg | 2760 |
| gaagggcgat cggtgcgggc ctcttcgcta ttacgccagc tggcgaaagg gggatgtgct | 2820 |
| gcaaggcgat taagttgggt aacgccaggg ttttcccagt cacgacgttg taaaacgacg | 2880 |
| gccagtgagc gcgcgtaata cgactcacta tagggcgaat tgggtaccgc ggccgctatt | 2940 |
| gataagctta atatgtcgac gatttctcta gaatacgagc tcgaatttcc ccgatcgttc | 3000 |
| aaacatttgg caataaagtt tcttaagatt gaatcctgtt gccggtcttg cgatgattat | 3060 |
| catataattt ctgttgaatt acgttaagca tgtaataatt aacatgtaat gcatgacgtt | 3120 |
| atttatgaga tgggttttta tgattagagt cccgcaatta cattttaat acgcgataga | 3180 |
| aaacaaaata tagcgcgcaa actagga | 3207 |

<210> SEQ ID NO 137
<211> LENGTH: 3868
<212> TYPE: DNA
<213> ORGANISM: Artificial sequence
<220> FEATURE:
<223> OTHER INFORMATION: Plasmid vector

<400> SEQUENCE: 137

| | |
|---|---:|
| gtaggtatct cagttcggtg taggtcgttc gctccaagct gggctgtgtg cacgaacccc | 60 |
| ccgttcagcc cgaccgctgc gccttatccg gtaactatcg tcttgagtcc aacccggtaa | 120 |
| gacacgactt atcgccactg gcagcagcca ctggtaacag gattagcaga gcgaggtatg | 180 |
| taggcggtgc tacagagttc ttgaagtggt ggcctaacta cggctacact agaaggacag | 240 |
| tatttggtat ctgcgctctg ctgaagccag ttaccttcgg aaaaagagtt ggtagctctt | 300 |
| gatccggcaa acaaaccacc gctggtagcg gtggtttttt tgtttgcaag cagcagatta | 360 |
| cgcgcagaaa aaaaggatct caagaagatc ctttgatctt ttctacgggg tctgacgctc | 420 |
| agtggaacga aaactcacgt taagggattt tggtcatgag attatcaaaa aggatcttca | 480 |
| cctagatcct tttaaattaa aaatgaagtt ttaaatcaat ctaaagtata tatgagtaaa | 540 |
| cttggtctga cagttaccaa tgcttaatca gtgaggcacc tatctcagcg atctgtctat | 600 |
| ttcgttcatc catagttgcc tgactcccg tcgtgtagat aactacgata cgggagggct | 660 |
| taccatctgg ccccagtgct gcaatgatac cgcgagaccc acgctcaccg gctccagatt | 720 |
| tatcagcaat aaaccagcca gccggaaggg ccgagcgcag aagtggtcct gcaactttat | 780 |

```
ccgcctccat ccagtctatt aattgttgcc gggaagctag agtaagtagt tcgccagtta      840
atagtttgcg caacgttgtt gccattgcta caggcatcgt ggtgtcacgc tcgtcgtttg      900
gtatggcttc attcagctcc ggttcccaac gatcaaggcg agttacatga tcccccatgt      960
tgtgcaaaaa agcggttagc tccttcggtc ctccgatcgt tgtcagaagt aagttggccg     1020
cagtgttatc actcatggtt atggcagcac tgcataattc tcttactgtc atgccatccg     1080
taagatgctt ttctgtgact ggtgagtact caaccaagtc attctgagaa tagtgtatgc     1140
ggcgaccgag ttgctcttgc ccggcgtcaa tacgggataa taccgcgcca catagcagaa     1200
ctttaaaagt gctcatcatt ggaaaacgtt cttcggggcg aaaactctca aggatcttac     1260
cgctgttgag atccagttcg atgtaaccca ctcgtgcacc caactgatct tcagcatctt     1320
ttactttcac cagcgtttct gggtgagcaa aaacaggaag gcaaaatgcc gcaaaaaagg     1380
gaataagggc gacacggaaa tgttgaatac tcatactctt cctttttcaa tattattgaa     1440
gcatttatca gggttattgt ctcatgagcg gatacatatt tgaatgtatt tagaaaaata     1500
aacaaatagg ggttccgcgc acatttcccc gaaaagtgcc acctaaattg taagcgttaa     1560
tattttgtta aaattcgcgt taaattttg ttaaatcagc tcatttttta accaataggc     1620
cgaaatcggc aaaatccctt ataaatcaaa agaatagacc gagatagggt tgagtgttgt     1680
tccagtttgg aacaagagtc cactattaaa gaacgtggac tccaacgtca aagggcgaaa     1740
aaccgtctat cagggcgatg gcccactacg tgaaccatca ccctaatcaa gttttttggg     1800
gtcgaggtgc cgtaaagcac taaatcggaa ccctaaaggg agcccccgat ttagagcttg     1860
acggggaaag ccggcgaacg tggcgagaaa ggaagggaag aaagcgaaag gagcgggcgc     1920
tagggcgctg gcaagtgtag cggtcacgct gcgcgtaacc accacacccg ccgcgcttaa     1980
tgcgccgcta caggcgcgt cccattcgcc attcaggctg cgcaactgtt gggaagggcg     2040
atcggtgcgg gcctcttcgc tattacgcca gctggcgaaa gggggatgtg ctgcaaggcg     2100
attaagttgg gtaacgccag ggttttccca gtcacgacgt tgtaaaacga cggccagtga     2160
gcgcgcgtaa tacgactcac tatagggcga attgggtacc gcggccgcta ttgataagct     2220
tgcatgcctg caggtcaatt ctcatgtttg acagcttatc atcggtgcga tgccccccat     2280
cgtaggtgaa ggtggaaatt aatgatccat cttgagacca caggcccaca acagctacca     2340
gtttcctcaa gggtccacca aaaacgtaag cgcttacgta catggtcgat aagaaaaggc     2400
aatttgtaga tgttaacatc caacgtcgct ttcagggatc cccctcaga agaccagagg     2460 gctattgaga ctttcaaca aagggtaata tcgggaaacc tcctcggatt ccattgccca     2520
gctatctgtc acttcatcga aggacagta gaaaggaag gtggctccta caaatgccat     2580
cattgcgata aggaaaggc tatcgttcaa gatgcctcta ccgacagtgg tcccaaagat     2640
ggacccccac ccacgaggaa catcgtggaa aaagaagacg ttccaaccac gtcttcaaag     2700
caagtggatt gatgtgatat ctccactgac gtaagggatg acgcacaatc ccactatcct     2760
tcgcaagacc cttcctctat ataaggaagt tcatttcatt tggagaggac aggcttcttg     2820
agatccttca acaattacca acaacaacaa acaacaaaca acattacaat tactatttac     2880
aattacagtc gacgatttct ctagaatacg agctcgaatt tccccgatcg ttcaaacatt     2940
tggcaataaa gttccttaag attgaatcct gttgccggtc ttgcgatgat tatcatataa     3000
tttctgttga attacgttaa gcatgtaata attaacatgt aatgcatgac gttatttatg     3060
agatgggttt ttatgattag agtcccgcaa ttatacattt aatacgcgat agaaaacaaa     3120
atatagcgcg caaactagga taattatcg cgcgcggtgt catctatgtt actagatcgg     3180
```

-continued

```
gaattcaatg cggccgccac cgcggtggcc agcttttgtt cccctttagtg agggttaatt    3240
gcgcgcttgg cgtaatcatg gtcatagctg tttcctgtgt gaaattgtta tccgctcaca    3300
attccacaca acatacgagc cggaagcata aagtgtaaag cctggggtgc ctaatgagtg    3360
agctaactca cattaattgc gttgcgctca ctgcccgctt tccagtcggg aaacctgtcg    3420
tgccagctgc attaatgaat cggccaacgc gcggggagag gcggtttgcg tattgggcgc    3480
tcttccgctt cctcgctcac tgactcgctg cgctcggtcg ttcggctgcg gcgagcggta    3540
tcagctcact caaaggcggt aatacggtta tccacagaat caggggataa cgcaggaaag    3600
aacatgtgag caaaaggcca gcaaaaggcc aggaaccgta aaaaggccgc gttgctggcg    3660
ttttttccata ggctccgccc ccctgacgag catcacaaaa atcgacgctc aagtcagagg    3720
tggcgaaacc cgacaggact ataaagatac caggcgtttc ccctggaag ctccctcgtg     3780
cgctctcctg ttccgaccct gccgcttacc ggatacctgt ccgcctttct cccttcggga    3840
agcgtggcgc tttctcatag ctcacgct                                       3868
```

<210> SEQ ID NO 138
<211> LENGTH: 20
<212> TYPE: DNA
<213> ORGANISM: Artificial sequence
<220> FEATURE:
<223> OTHER INFORMATION: Single strand DNA oligonulcotide

<400> SEQUENCE: 138

```
tcagccaccc aaaccatgac                                                 20
```

<210> SEQ ID NO 139
<211> LENGTH: 882
<212> TYPE: PRT
<213> ORGANISM: Oryza sativa

<400> SEQUENCE: 139

```
Met Val Lys Leu Ala Phe Gly Ser Cys Gly Asp Ser Phe Ser Ala Ser
1               5                   10                  15

Ser Ile Lys Ala Tyr Val Ala Glu Phe Ile Ala Thr Leu Leu Phe Val
                20                  25                  30

Phe Ala Gly Val Gly Ser Ala Ile Ala Tyr Gly Gln Leu Thr Lys Gly
            35                  40                  45

Gly Ala Leu Asp Pro Ala Gly Leu Val Ala Ile Ala Ile Ala His Ala
        50                  55                  60

Phe Ala Leu Phe Val Gly Val Ser Met Ala Ala Asn Ile Ser Gly Gly
65                  70                  75                  80

His Leu Asn Pro Val Val Thr Phe Gly Leu Ala Val Gly Gly His Ile
                85                  90                  95

Thr Ile Leu Thr Gly Ile Phe Tyr Trp Val Ala Gln Leu Leu Gly Ala
                100                 105                 110

Ser Val Ala Cys Leu Leu Cys Ser Ser Pro Thr Asp Arg Leu Ala
            115                 120                 125

Ile Pro Thr His Ala Ile Ala Gly Ile Ser Glu Ile Glu Gly Met Val
        130                 135                 140

Met Glu Ile Val Ile Thr Phe Ala Leu Val Tyr Thr Gly Tyr Ala Thr
145                 150                 155                 160

Ala Ala Asp Pro Lys Lys Gly Ser Leu Gly Thr Val Ala Pro Met Asp
                165                 170                 175

Ile Gly Phe Ile Val Gly Ala Asn Ile Leu Ala Ala Gly Pro Phe Ser
            180                 185                 190
```

```
Gly Ser Ser Met Asn Pro Ala Arg Ser Phe Gly Pro Ala Val Ala Ala
            195                 200                 205
Gly Asn Phe Ala Gly Asn Trp Val Tyr Trp Val Gly Pro Leu Ile Gly
        210                 215                 220
Gly Gly Leu Ala Gly Leu Val Tyr Asp Asp Val Phe Ile Ala Ser Tyr
225                 230                 235                 240
Gln Pro Val Met Ile Gly Phe Thr Val Ile Leu Cys Asp Arg Ser Asp
                245                 250                 255
Gln Ala Val Tyr Ala Gly Gln Thr Ser Gly Asp Arg Ala Val Thr Pro
            260                 265                 270
Cys Leu Gly Arg Val Phe Ala Val Met Asp Arg Glu Ser Ala Trp Cys
        275                 280                 285
Arg Met Gln Ser Tyr Ile Met Ala Glu Asn Tyr Asp Ile Trp Arg Lys
        290                 295                 300
Val Ser His Pro Tyr Val Ile Pro Glu Ala Ile Asn Thr Ala Ala Glu
305                 310                 315                 320
Lys Thr Ala Phe Glu Gln Asn Cys Lys Ala Arg Asn Ile Leu Leu Ser
                325                 330                 335
Gly Ile Ser Arg Ser Asp Tyr Asp Arg Val Ala His Leu Gln Thr Ala
            340                 345                 350
His Glu Ile Trp Ile Ala Leu Ser Asn Phe His Gln Gly Thr Asn Asn
        355                 360                 365
Ile Lys Glu Leu Arg Arg Asp Leu Phe Lys Lys Glu Tyr Ile Lys Phe
370                 375                 380
Glu Met Lys Pro Gly Ala Leu Asp Asp Tyr Leu Ser Arg Phe Asn
385                 390                 395                 400
Lys Ile Leu Ser Asp Leu Arg Ser Val Asp Ser Ser Tyr Asp Ala Asn
                405                 410                 415
Tyr Pro Gln Ser Glu Ile Ser Arg His Phe Leu Asn Gly Leu Asp Met
            420                 425                 430
Ser Ile Trp Glu Met Lys Val Thr Ser Ile Gln Glu Ser Val Asn Met
        435                 440                 445
Ser Thr Leu Thr Leu Asp Ser Leu Tyr Thr Lys Leu Lys Thr His Glu
        450                 455                 460
Met Asn Ile Leu Ala Arg Lys Val Asp Ser Lys Ser Ser Ala Leu Val
465                 470                 475                 480
Ser Ser Ser Thr Ser Leu Asp Val Gly Ala Ser Ser Ser Lys Ser Ser
                485                 490                 495
Val Leu Ala Leu Phe Asn Ala Met Ser Asp Asp Gln Leu Glu Gln Phe
            500                 505                 510
Glu Glu Glu Asp Leu Val Leu Leu Ser Asn Lys Phe Ser Arg Ala Met
        515                 520                 525
Lys Asn Val Arg Asn Arg Lys Arg Gly Glu Pro Asn Arg Cys Phe Glu
        530                 535                 540
Cys Gly Ala Leu Asp His Leu Arg Ser His Cys Pro Lys Leu Gly Arg
545                 550                 555                 560
Gly Lys Lys Glu Asp Asp Gly Arg Val Lys Glu Asp Val Asn Lys
                565                 570                 575
Lys Lys Asn Met Lys Glu Lys Glu Lys Lys Lys His Cys Met Gln Trp
            580                 585                 590
Leu Ile Gln Glu Leu Ile Lys Val Phe Asp Glu Ser Glu Asp Glu Asp
        595                 600                 605
Glu Gly Lys Gly Lys Gln Val Val Asp Leu Ala Phe Ile Ala Arg Asn
        610                 615                 620
```

```
Ala Ser Ser Asp Val Asp Glu Ser Asp Asp Asn Glu Glu Lys Leu
625                 630                 635                 640

Ser Tyr Asp Gln Leu Glu Tyr Ala Ala Tyr Lys Phe Ala Lys Lys Leu
            645                 650                 655

Gln Thr Cys Ser Ile Val Leu Asp Glu Lys Asp His Thr Ile Glu Ile
                660                 665                 670

Leu Asn Ala Glu Ile Ala Arg Leu Lys Ser Leu Ile Pro Asn Asp Asp
                675                 680                 685

Asn Cys Gln Ser Cys Glu Val Leu Phe Ser Glu Ile Asn Ala Leu Arg
        690                 695                 700

Asp Val Asn Ser Val Asn Cys Lys Lys Leu Glu Phe Glu Ile Glu Lys
705                 710                 715                 720

Ser Lys Lys Leu Glu Ser Ser Phe Ala Leu Gly Phe Ala Leu His Ala
                725                 730                 735

Arg Val Val Asp Glu Leu Ile Leu Thr Lys Asn Val Leu Lys Lys Ile
                740                 745                 750

Gln Ser Cys Phe Leu Cys Lys Phe Phe Gly Gln Cys Phe Met Cys Asn
        755                 760                 765

Lys Ala Lys Gln Asn Asn Gly Val Leu Ile Ser Gln Asp Cys Ser Lys
770                 775                 780

Cys Val Leu Asn Glu Leu Lys Leu Lys Asp Ala Leu Glu Arg Val Lys
785                 790                 795                 800

His Met Glu Glu Ile Ile Lys Gln Asp Glu Val Phe Ser Cys Ser Thr
                805                 810                 815

Cys Arg Lys Gln Lys Gly Leu Leu Asp Ala Cys Lys Asn Cys Ala Ile
                820                 825                 830

Leu Thr Gln Glu Val Ser Tyr Leu Lys Ser Ser Leu Gln Arg Phe Ser
                835                 840                 845

Asp Gly Lys Lys Asn Leu Asn Met Ile Leu Asp Gln Ser Asn Val Ser
        850                 855                 860

Thr His Asn Arg Gly Leu Gly Phe Asp Ser Tyr Ser Lys Asp Leu Asp
865                 870                 875                 880

Val Ala

<210> SEQ ID NO 140
<211> LENGTH: 249
<212> TYPE: PRT
<213> ORGANISM: Glycine max

<400> SEQUENCE: 140

Met Val Lys Ile Ala Leu Gly Thr Leu Asp Asp Ser Phe Ser Ala Ala
1               5                   10                  15

Ser Leu Lys Ala Tyr Phe Ala Glu Phe His Ala Thr Leu Ile Phe Val
                20                  25                  30

Phe Ala Gly Val Gly Ser Ala Ile Ala Tyr Asn Glu Leu Thr Lys Asp
            35                  40                  45

Ala Ala Leu Asp Pro Thr Gly Leu Val Ala Val Ala His Ala
        50                  55                  60

Phe Ala Leu Phe Val Gly Val Ser Val Ala Asn Ile Ser Gly Gly
65                  70                  75                  80

His Leu Asn Pro Ala Val Thr Phe Gly Leu Ala Ile Gly Gly Asn Ile
                85                  90                  95

Thr Leu Ile Thr Gly Phe Leu Tyr Trp Ile Ala Gln Leu Leu Gly Ser
                100                 105                 110
```

```
Ile Val Ala Cys Leu Leu Asn Leu Ile Thr Ala Lys Ser Ile Pro
        115                 120                 125

Ser His Ser Pro Ala Asn Gly Val Asn Asp Leu Gln Ala Val Val Phe
130                 135                 140

Glu Ile Val Ile Thr Phe Gly Leu Val Tyr Thr Val Tyr Ala Thr Ala
145                 150                 155                 160

Val Asp Pro Lys Lys Gly Ser Leu Gly Ile Ile Ala Pro Ile Ala Ile
                165                 170                 175

Gly Phe Val Val Gly Ala Asn Ile Leu Ala Ala Gly Pro Phe Ser Gly
            180                 185                 190

Gly Ser Met Asn Pro Ala Arg Ser Phe Gly Pro Ala Val Val Ser Gly
        195                 200                 205

Asp Leu Ala Ala Asn Trp Ile Tyr Trp Val Gly Pro Leu Ile Gly Gly
    210                 215                 220

Gly Leu Ala Gly Leu Ile Tyr Gly Asp Val Phe Ile Gly Ser Tyr Ala
225                 230                 235                 240

Pro Val Pro Ala Ser Glu Thr Tyr Pro
                245

<210> SEQ ID NO 141
<211> LENGTH: 248
<212> TYPE: PRT
<213> ORGANISM: Triticum aestivum

<400> SEQUENCE: 141

Met Pro Ala Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
                20                  25                  30

Val Phe Ala Gly Val Gly Ser Ala Ile Ala Tyr Ser Lys Val Ser Gly
            35                  40                  45

Gly Ala Pro Leu Asp Pro Ser Gly Leu Ile Ala Val Ala Ile Cys His
        50                  55                  60

Gly Phe Gly Leu Phe Val Ala Val Ala Val Gly Ala Asn Ile Ser Gly
65                  70                  75                  80

Gly His Val Asn Pro Ala Val Thr Phe Gly Leu Ala Leu Gly Gly Gln
                85                  90                  95

Ile Thr Ile Leu Thr Gly Ile Phe Tyr Trp Val Ala Gln Leu Leu Gly
                100                 105                 110

Ala Ile Val Gly Ala Phe Leu Val Gln Phe Cys Thr Gly Val Ala Thr
        115                 120                 125

Pro Thr His Gly Leu Ser Gly Val Gly Ala Phe Glu Gly Val Val Met
130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
    210                 215                 220

Gly Leu Ala Gly Val Val Tyr Arg Tyr Leu Tyr Met Cys Asp Asp His
225                 230                 235                 240
```

```
Thr Ala Val Ala Gly Asn Asp Tyr
                245

<210> SEQ ID NO 142
<211> LENGTH: 248
<212> TYPE: PRT
<213> ORGANISM: Triticum aestivum

<400> SEQUENCE: 142

Met Pro Gly Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
                20                  25                  30

Val Phe Ala Gly Val Gly Ser Ala Ile Ala Tyr Thr Lys Val Ser Gly
            35                  40                  45

Gly Ala Pro Leu Asp Pro Ser Gly Leu Ile Ala Val Ala Ile Cys His
        50                  55                  60

Gly Phe Gly Leu Phe Val Ala Val Ala Ile Gly Ala Asn Ile Ser Gly
65                  70                  75                  80

Gly His Val Asn Pro Ala Val Thr Phe Gly Leu Ala Leu Gly Gly Gln
                85                  90                  95

Ile Thr Ile Leu Thr Gly Ile Phe Tyr Trp Val Ala Gln Leu Leu Gly
                100                 105                 110

Ala Ile Val Gly Ala Phe Leu Val Gln Phe Cys Thr Gly Val Ala Thr
            115                 120                 125

Pro Thr His Gly Leu Ser Gly Val Gly Ala Phe Glu Gly Val Val Met
        130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
    210                 215                 220

Gly Leu Ala Gly Val Val Tyr Arg Tyr Val Tyr Met Cys Asp Asp His
225                 230                 235                 240

Ser Ser Val Ala Gly Asn Asp Tyr
                245

<210> SEQ ID NO 143
<211> LENGTH: 207
<212> TYPE: PRT
<213> ORGANISM: Solanum tuberosum

<400> SEQUENCE: 143

Met Val Lys Ile Ala Phe Gly Ser Ile Gly Asp Ser Leu Ser Val Gly
1               5                   10                  15

Ser Leu Lys Ala Tyr Leu Ala Glu Phe Ile Ala Thr Leu Leu Phe Val
                20                  25                  30

Phe Ala Gly Val Gly Ser Ala Ile Ala Tyr Asn Lys Leu Thr Ser Asp
            35                  40                  45

Ala Ala Leu Asp Pro Ala Gly Leu Val Ala Ile Ala Val Ala His Ala
        50                  55                  60

Phe Ala Leu Phe Val Gly Val Ser Met Ala Ala Asn Ile Ser Gly Gly
```

```
                65                  70                  75                  80
His Leu Asn Pro Ala Val Thr Leu Gly Leu Ala Val Gly Gly Asn Ile
                85                  90                  95

Thr Ile Leu Thr Gly Leu Phe Tyr Trp Val Ala Gln Leu Leu Gly Ser
                100                 105                 110

Thr Val Ala Cys Leu Leu Lys Tyr Val Thr Asn Gly Leu Ala Val
                115                 120                 125

Pro Thr His Gly Val Ala Ala Gly Met Asn Gly Ala Glu Gly Val Val
                130                 135                 140

Met Glu Ile Val Ile Thr Phe Ala Leu Val Tyr Thr Val Tyr Ala Thr
145                 150                 155                 160

Ala Ala Val Val Ala Gly Asp Phe Ser Gln Asn Trp Ile Tyr Trp Val
                165                 170                 175

Gly Pro Leu Ile Gly Gly Leu Ala Gly Phe Ile Tyr Gly Asp Val
                180                 185                 190

Phe Ile Gly Ser His Thr Pro Leu Pro Thr Ser Glu Asp Tyr Ala
                195                 200                 205

<210> SEQ ID NO 144
<211> LENGTH: 224
<212> TYPE: PRT
<213> ORGANISM: Saccharum officinarum
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid

<400> SEQUENCE: 144

Phe Gln Pro Arg Arg Ala Lys Arg Glu Ser Lys Met Val Lys Leu Ala
1               5                   10                  15

Phe Gly Ser Val Gly Asp Ser Phe Ser Ala Thr Ser Ile Lys Ala Tyr
                20                  25                  30

Val Ser Glu Phe Ile Ala Thr Leu Leu Phe Val Phe Ala Gly Val Gly
                35                  40                  45

Ser Ala Ile Ala Tyr Gly Gln Leu Thr Asn Asp Gly Ala Leu Asp Pro
50                  55                  60

Ala Gly Leu Val Ala Ile Ala Ile Ala His Ala Leu Ala Leu Phe Val
65                  70                  75                  80

Gly Val Ser Ile Ala Ala Asn Ile Ser Gly Gly His Leu Asn Pro Ala
                85                  90                  95

Val Thr Phe Gly Leu Ala Val Gly Gly His Ile Thr Ile Leu Thr Gly
                100                 105                 110

Leu Phe Tyr Trp Val Ala Gln Leu Leu Gly Ala Ser Val Ala Cys Leu
                115                 120                 125

Leu Leu Lys Phe Val Thr His Gly Lys Ala Ile Pro Thr His Gly Val
                130                 135                 140

Ser Gly Ile Ser Glu Leu Glu Gly Val Val Phe Glu Ile Val Ile Thr
145                 150                 155                 160

Phe Ala Leu Val Tyr Thr Val Tyr Ala Thr Ala Xaa Arg Pro Gln Glu
                165                 170                 175

Gly Leu Pro Arg His His Arg Ala His Arg Leu His Arg Arg
                180                 185                 190

Arg Gln His Pro Arg Arg Gly Ala Leu Gln Pro Arg Leu His Glu Pro
                195                 200                 205
```

-continued

Gly Pro Ser Phe Gly Pro Xaa Val Ala Arg Gly Asn Phe Ala Gly Asn
    210                 215                 220

<210> SEQ ID NO 145
<211> LENGTH: 128
<212> TYPE: PRT
<213> ORGANISM: Populus tremula x Populus tremuloides

<400> SEQUENCE: 145

Met Ile Thr Trp Phe Gln Gln Ala Val Pro Ile His Ser Val Ala Ala
1               5                   10                  15

Gly Val Gly Ala Ile Glu Gly Val Met Glu Ile Ile Ile Thr Phe
            20                  25                  30

Ala Leu Val Tyr Thr Val Tyr Ala Thr Ala Ala Asp Pro Lys Lys Gly
        35                  40                  45

Ser Leu Gly Thr Ile Ala Pro Ile Ala Ile Gly Phe Ile Val Gly Ala
    50                  55                  60

Asn Ile Leu Ala Ala Gly Pro Phe Ser Gly Gly Ser Met Asn Pro Ala
65                  70                  75                  80

Arg Ser Phe Gly Pro Ala Val Ala Ser Gly Asp Phe His Asp Asn Trp
                85                  90                  95

Ile Tyr Trp Ala Gly Pro Leu Val Gly Gly Ile Ala Gly Leu Ile
            100                 105                 110

Tyr Gly Asn Val Phe Ile Thr Asp His Thr Pro Leu Ser Gly Asp Phe
        115                 120                 125

<210> SEQ ID NO 146
<211> LENGTH: 114
<212> TYPE: PRT
<213> ORGANISM: Solanum tuberosum

<400> SEQUENCE: 146

Met Ser Gly Ala Glu Gly Val Val Met Glu Ile Val Ile Thr Phe Ala
1               5                   10                  15

Leu Val Tyr Thr Val Tyr Ala Thr Ala Ala Asp Pro Lys Lys Gly Ser
            20                  25                  30

Leu Gly Thr Ile Ala Pro Met Ala Ile Gly Phe Ile Val Gly Ala Asn
        35                  40                  45

Ile Leu Ala Ala Gly Pro Phe Ser Gly Gly Ser Met Asn Pro Ala Arg
    50                  55                  60

Ser Phe Gly Pro Ala Val Val Ala Gly Asp Phe Phe Gln Asn Trp Ile
65                  70                  75                  80

Tyr Trp Val Gly Pro Leu Ile Gly Gly Leu Ala Gly Phe Ile Tyr
                85                  90                  95

Gly Asp Val Phe Ile Gly Ser Pro Pro Leu Pro Thr Ser Glu Asp
            100                 105                 110

Tyr Ala

<210> SEQ ID NO 147
<211> LENGTH: 128
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid

<400> SEQUENCE: 147

Met Ser Gln Glu Ala Phe Gln Leu Gln Ser Thr Val Xaa Xaa Xaa Gly

```
                1               5                  10                 15
Val Gly Ala Val Glu Gly Val Thr Glu Ile Ile Thr Phe Gly
                      20                 25                 30

Leu Val Tyr Thr Val Tyr Ala Thr Ala Ala Asp Pro Lys Lys Gly Ser
                      35                 40                 45

Leu Gly Thr Ile Ala Pro Ile Ala Ile Gly Phe Ile Val Gly Ala Asn
 50                       55                 60

Ile Leu Ala Ala Gly Pro Phe Ser Gly Gly Ser Met Asn Pro Ala Arg
 65                       70                 75                 80

Ser Phe Gly Pro Ala Val Val Ser Gly Asp Phe His Asp Asn Trp Ile
                      85                 90                 95

Tyr Trp Val Gly Pro Leu Ile Gly Gly Leu Ala Gly Leu Ile Tyr
                     100                105                110

Gly Asn Val Phe Ile Arg Ser Asp His Ala Pro Leu Ser Glu Phe
                     115                120                125

<210> SEQ ID NO 148
<211> LENGTH: 104
<212> TYPE: PRT
<213> ORGANISM: Solanum tuberosum

<400> SEQUENCE: 148

Met Glu Ile Ile Ile Thr Phe Gly Leu Val Tyr Thr Val Phe Ala Thr
 1               5                  10                 15

Ala Ala Asp Pro Lys Lys Gly Ser Leu Gly Thr Ile Ala Pro Ile Ala
                      20                 25                 30

Ile Gly Phe Ile Val Gly Ala Asn Ile Leu Ala Ala Gly Pro Phe Ser
                      35                 40                 45

Gly Gly Ser Met Asn Pro Ala Arg Ser Phe Gly Pro Ala Met Ala Thr
 50                       55                 60

Gly Asn Phe Glu Gly Phe Trp Ile Tyr Trp Ile Gly Pro Leu Val Gly
 65                       70                 75                 80

Gly Ser Leu Ala Gly Leu Ile Tyr Thr Asn Val Phe Met Gln Gln Glu
                      85                 90                 95

His Ala Pro Leu Ser Asn Glu Phe
                     100

<210> SEQ ID NO 149
<211> LENGTH: 149
<212> TYPE: PRT
<213> ORGANISM: Zea mays

<400> SEQUENCE: 149

Met Val Lys Leu Ala Phe Gly Ser Phe Arg Asp Ser Leu Ser Ala Ala
 1               5                  10                 15

Ser Leu Lys Ala Tyr Val Ala Glu Phe Ile Ala Thr Leu Leu Phe Val
                      20                 25                 30

Phe Ala Gly Val Gly Ser Ala Ile Ala Tyr Ser Gln Leu Thr Lys Gly
                      35                 40                 45

Gly Ala Leu Asp Pro Ala Gly Leu Val Ala Ile Ala Ile Ala His Ala
 50                       55                 60

Phe Ala Leu Phe Val Gly Val Ser Met Ala Ala Asn Ile Ser Gly Gly
 65                       70                 75                 80

His Leu Asn Pro Ala Val Thr Phe Gly Pro Phe Asp Gly Ala Ser Met
                      85                 90                 95

Asn Pro Ala Arg Ser Phe Gly Pro Ala Val Ala Ala Gly Asn Phe Ala
                     100                105                110
```

```
Gly Asn Trp Val Tyr Trp Val Gly Pro Leu Val Gly Gly Leu Ala
        115                 120                 125

Gly Leu Val Tyr Gly Asp Val Phe Ile Ala Ser Tyr Gln Pro Val Gly
        130                 135                 140

Gln Gln Glu Tyr Pro
145

<210> SEQ ID NO 150
<211> LENGTH: 149
<212> TYPE: PRT
<213> ORGANISM: Zea mays

<400> SEQUENCE: 150

Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Pro Phe Asp Gly Ala Ser Met
                85                  90                  95

Asn Pro Ala Arg Ser Phe Gly Pro Ala Val Ala Ala Gly Asn Phe Ala
            100                 105                 110

Gly Asn Trp Val Tyr Trp Val Gly Pro Leu Val Gly Gly Leu Ala
        115                 120                 125

Gly Leu Val Tyr Gly Asp Val Phe Ile Ala Ser Tyr Gln Pro Val Gly
        130                 135                 140

Gln Gln Glu Tyr Pro
145

<210> SEQ ID NO 151
<211> LENGTH: 105
<212> TYPE: PRT
<213> ORGANISM: Oryza sativa

<400> SEQUENCE: 151

Met Glu Ile Ile Val Thr Phe Gly Leu Val Tyr Thr Val Tyr Ala Thr
1               5                   10                  15

Ala Ala Asp Pro Lys Lys Gly Ser Leu Gly Thr Ile Ala Pro Ile Ala
            20                  25                  30

Ile Gly Phe Ile Val Gly Ala Asn Ile Leu Val Ala Gly Pro Phe Ser
        35                  40                  45

Gly Gly Ser Met Asn Pro Ala Arg Ser Phe Gly Pro Ala Val Ala Ser
    50                  55                  60

Gly Asp Tyr Thr Asn Ile Trp Ile Tyr Trp Val Gly Pro Leu Val Gly
65                  70                  75                  80

Gly Gly Leu Ala Gly Leu Val Tyr Arg Tyr Val Tyr Met Cys Gly Asp
                85                  90                  95

His Ala Pro Val Ala Ser Ser Glu Phe
            100                 105

<210> SEQ ID NO 152
<211> LENGTH: 104
```

```
<212> TYPE: PRT
<213> ORGANISM: Lycopersicon esculentum

<400> SEQUENCE: 152

Met Glu Ile Ile Ile Thr Phe Gly Leu Val Tyr Thr Val Phe Ala Thr
1               5                   10                  15

Ala Ala Asp Pro Lys Lys Gly Ser Leu Gly Thr Ile Ala Pro Ile Ala
            20                  25                  30

Ile Gly Leu Ile Val Gly Ala Asn Ile Leu Ala Ala Gly Pro Phe Ser
        35                  40                  45

Gly Gly Ser Met Asn Pro Ala Arg Ser Phe Gly Pro Ala Met Val Ser
50                  55                  60

Gly Asn Phe Glu Gly Phe Trp Ile Tyr Trp Ile Gly Pro Leu Val Gly
65                  70                  75                  80

Gly Ser Leu Ala Gly Leu Ile Tyr Thr Asn Val Phe Met Thr Gln Glu
                85                  90                  95

His Ala Pro Leu Ser Asn Glu Phe
            100

<210> SEQ ID NO 153
<211> LENGTH: 140
<212> TYPE: PRT
<213> ORGANISM: Capsicum annuum

<400> SEQUENCE: 153

Met Ala Gly Ile Ala Phe Gly Arg Val Asp Asp Ser Phe Ser Ala Gly
1               5                   10                  15

Ser Leu Lys Ala Tyr Leu Ala Glu Phe Ile Ser Thr Leu Leu Phe Val
            20                  25                  30

Phe Ala Gly Val Gly Ser Ala Ile Ala Tyr Asn Lys Leu Thr Val Asn
        35                  40                  45

Ala Ala Leu Asp Pro Ala Gly Leu Val Ala Ile Ala Val Cys His Gly
50                  55                  60

Phe Gly Leu Phe Val Ala Val Ser Ile Ala Ala Asn Ile Ser Gly Gly
65                  70                  75                  80

His Val Asn Pro Ala Val Thr Phe Gly Leu Ala Leu Gly Gly Gln Ile
                85                  90                  95

Thr Leu Leu Thr Gly Leu Phe Leu His His Cys Ser Thr Phe Gly Leu
            100                 105                 110

His Cys Ser Leu His Pro Pro Gln Ile Arg His Arg Arg Ile Gly Tyr
        115                 120                 125

Ser Asn Ser Trp Ser Gly Ser Trp Cys Gly Cys His
    130                 135                 140

<210> SEQ ID NO 154
<211> LENGTH: 101
<212> TYPE: PRT
<213> ORGANISM: Hordeum vulgare

<400> SEQUENCE: 154

Met Thr Phe Gly Leu Val Tyr Thr Val Tyr Ala Thr Ala Val Asp Pro
1               5                   10                  15

Lys Lys Gly Ser Leu Gly Thr Ile Ala Pro Ile Ala Ile Gly Phe Ile
            20                  25                  30

Val Gly Ala Asn Ile Leu Val Gly Gly Ala Phe Ser Gly Ala Ser Met
        35                  40                  45

Asn Pro Ala Val Ser Phe Gly Pro Ala Leu Val Ser Trp Glu Trp Gly
50                  55                  60
```

Tyr Gln Trp Val Tyr Trp Val Gly Pro Leu Ile Gly Gly Leu Ala
65                  70                  75                  80

Gly Val Ile Tyr Glu Leu Leu Phe Ile Ser Arg Thr His Glu Gln Leu
            85                  90                  95

Pro Thr Thr Asp Tyr
            100

<210> SEQ ID NO 155
<211> LENGTH: 154
<212> TYPE: PRT
<213> ORGANISM: Gossypium hirsutum

<400> SEQUENCE: 155

Met Val Met Pro Phe Gly Leu Val Tyr Pro Val Tyr Ala Pro Ala Val
1               5                   10                  15

Asp Pro Lys Lys Gly Ser Leu Gly Thr Ile Ala Pro Leu Ala Ile Gly
            20                  25                  30

Phe Ile Val Gly Ala Asn Ile Leu Ala Gly Gly Ala Phe Asp Gly Ala
            35                  40                  45

Ser Met Asn Pro Ala Val Ser Phe Gly Pro Pro Leu Val Ser Trp Thr
50                  55                  60

Trp Asp Asn Pro Trp Ile Tyr Trp Val Gly Pro Leu Ile Gly Gly Gly
65                  70                  75                  80

Leu Ala Gly Phe Phe Arg Ser Ser Phe Ser Ser Ala Thr Pro Arg Ser
            85                  90                  95

Ser Ser Gln Pro Pro Ile Ile Lys Pro Asn Gln Gly Leu Ile Asp Leu
            100                 105                 110

Phe Val Pro Leu Lys Pro Asp Phe Phe Arg Phe His Leu Ser Phe Leu
            115                 120                 125

Phe Leu Ser Leu Phe Val Phe Asn Leu Gly Pro Val Asp Phe Val
            130                 135                 140

Tyr Phe Phe Phe Ile Pro His Pro Phe Ser
145                 150

<210> SEQ ID NO 156
<211> LENGTH: 488
<212> TYPE: DNA
<213> ORGANISM: Artificial sequence
<220> FEATURE:
<223> OTHER INFORMATION: Artificially optimized ABSTgene

<400> SEQUENCE: 156
gtcgactcta gaggatcccc gggatgggaa gaatgcattc taggggaag ggaatctctt      60 cttctgcttt gccatacaag agaactccac caacttggct taagaccgca gcttctgatg    120
ttgaggaaat gattaccaag gctgctaaaa agggtcaaat gccatctcag attggagtgc    180
ttcttaggga tcagcatgga atcccacttg tgaagtctgt gaccggatct aaaatcctca    240
ggatcttgaa ggctcatgga cttgctccag agattccaga ggatctctac ttcttgatta    300
agaaggctgt tgctatcaga aagcacctcg agagaaatag aaaggataag gattcaaagt    360
tcaggcttat cctcgttgag tctaggattc ataggctcgc taggtactat aagaggacca    420
agaagttgcc accaacttgg aagtacgaga gtactactgc ttctactctc gtggcttgat    480
gagagctc                                                             488

<210> SEQ ID NO 157
<211> LENGTH: 830
<212> TYPE: DNA

```
<213> ORGANISM: Artificial sequence
<220> FEATURE:
<223> OTHER INFORMATION: Artificially optimized ABSTgene

<400> SEQUENCE: 157
ggtaccgtcg actctagagg atccccggga tggatgctgg aggagagaag ttctctgatg      60
ctgctgctgc tgaaggagga gagggaggag gagatcttta cgctgtgctc ggacttaaga     120
aagaatgctc tgatgctgat ctcaaggtgg cataccgtaa gttggctaag aagtggcatc     180
cagataagtg ctcttcatct tcttcagtta agcacatgga agaggctaag gaaaagtttc     240
aggagattca gggagcttac tctgtgcttt ctgatgctaa caagaggctc ttgtacgatg     300
ttggggtgta cgatgatgag gatgatgaag attctatgca aggaatggga gatttcattg     360
gggaaatggc tcaaatgatg tctcaagtga ggccaactag acaagagtct ttcgaggagc     420
ttcaacagct cttcgttgat atgttccagt ctgatattga tagtggtttc tgcaacggat     480
ctgctaagga tcaagttcag gggcaagcta agtctaggac ttgctctacc tctccatctt     540
cttctccatc tccaccacca ccaccaacta tcgttaagga ggctgaggtt tcatcttgca     600
acgggttcaa caagcgtgga tcttctgcta tggattctgg aaagccacca agaccagttg     660
aaggaggagc tggacaagct ggtttctgct tcggagtgtc tgatacaaag cagactccaa     720
agccaagagg accaaacact tctaggagaa ggaacggaag gaagcaaaag ctctctagta     780
agcacgatgt gtctagtgag gatgagactg ctgggtcttg atgagagctc               830

<210> SEQ ID NO 158
<211> LENGTH: 1127
<212> TYPE: DNA
<213> ORGANISM: Artificial sequence
<220> FEATURE:
<223> OTHER INFORMATION: Artificially optimized ABSTgene

<400> SEQUENCE: 158
ggtaccgtcg actctagagg atccccggga tggaaggata cgatagagag ttctggcagt      60
tctctgatac tcttaggctt cagaccgctg ctttctctgg actttctctc ggagattcta     120
tctggtctcc agctactgga ggagctgctg ctgctgatag aaggaacaac tctaacgatc     180
tcttcgctgc ttctgcttct ccagctgata caaccgctgc taagaacaat ggaggagtgg     240
gacttaggct taaccttaac gatggaggac caggacttat tggatctggg aagttggctt     300
tcggaggatc taaggctgat aggtacaaca accttccagc tactactgag aaggctgctt     360
cagcttacaa taacaacatc aacgtgaacg ctggatacgc taagaataac aataacaatg     420
ctctcgcttt caacaagatg ggaatctatg gatacaacac taacaactca aacatctcta     480
acaactcttc atctggggag gtgaagtctt acttcaataa gagtgctgga agggctgctt     540
ctaacaactc tcatggacat ggacatgctg gaggaaagaa gggaggagag tacggaaata     600
agaagaagca cgggaagaac gaaggaaata acggaggagg aggagctgga gctactgata     660
agaggttcaa gaccctttcca gcttctgaag ctcttccaag aggacaagct atcggaggtt     720
acattttcgt gtgtaataac gatacaatgg atgagaactt gagaagagag cttttcggac     780
tcccatcaag ataccgtgat tcagtgaggg ctattagacc aggacttcca ctcttcttgt     840
acaattactc tacccatcag ttgcatggga ttttcgaggc tgtttctttc ggaggaacta     900
acatcgatcc aaccgcttgg gaagataaga agtgtccagg ggagtcaaga ttcccagctc     960
aagtgagagt tgctaccaga aagatctatg atccactcga ggaggatgct ttcagaccaa    1020
tcctccatca ttacgatgga ccaaagttca ggcttgagct ttctgttact gaggctcttg    1080
```

-continued ctcttctcga tatctttgct gataaggatg atgcttgatg agagctc    1127

<210> SEQ ID NO 159
<211> LENGTH: 803
<212> TYPE: DNA
<213> ORGANISM: Artificial sequence
<220> FEATURE:
<223> OTHER INFORMATION: Artificially optimized ABSTgene

<400> SEQUENCE: 159
ggtaccgtcg actctagagg atccccggga tggcttctcc agaaggaact acctgggttt    60
tcgattgccc actcatggat gatcttgctg tggctgctga ttttgctgct gctccagctg    120
gaggattctt ttgggctgct ccaccatctc ttcagccaca agttgttcaa gctccagttc    180
agtcagttgt tgctgcttct gctccaaatc catgcgtgga gatctcttca tctgttgatt    240
gcggacaagg aaaggagcag ccaactaaca agagaccaag gagtgagtct actgctgagc    300
catctactaa ggcttctagg gagaagatca ggagggataa gctcaacgaa agatttctcg    360
agcttggagc tattcttgag cctggaaaga ccccaaagat ggataagtct gctatcctca    420
acgatgctat cagagttgtt ggggagctta gatctgaggc taaggagctt aaggattcta    480
acgagtcact ccaggagaag atcaaggaac tcaaggctga aaagaacgag cttagggatg    540
agaagcagag actcaaggca gaaaaggagt ctcttgagca acagattaag tttctcaacg    600
ctaggccatc tcttgttcca catcaccctg tgatttctgc ttcagctttc actgctccac    660
aaggaccagc tgttgctgga cataagctca tgatgccagt tcttggatac ccagggtttc    720
caatgtggca attcatgcca ccatctgatg tggataccag tgatgatcca aagtcttgcc    780
caccagttgc ttgatgagag ctc    803

<210> SEQ ID NO 160
<211> LENGTH: 775
<212> TYPE: DNA
<213> ORGANISM: Zea mays

<400> SEQUENCE: 160
gacgcgcttc ctctcgccct cgctcctccg ccgccgccgc cgccgcatca agccccgcc    60
ccgccgtcgc ctgaggtaga caccaatccg ccgccatggg gcgtatgcac agccgcggga    120
agggtatctc atcgtcggcg cttccctaca agaggacgcc tcctacctgg ctcaagaccg    180
ctgcctccga cgtggaggag atgatcacaa aggcagcgaa gaagggacag atgccgtcgc    240
agatcggcgt cctgctccgt gaccagcacg gtatcccccct tgtcaagagc gtcaccggca    300
gcaagatcct ccgcatcctc aaggcccatg gctggcacc agaaatcccc gaggacctgt    360
acttcctcat caagaaggcg gtggcgtaa ggaagcacct tgagaggaac aggaaggaca    420
aagactctaa attcaggctc attcttgtgg agagcaggat ccaccgcctt gcccgctact    480
acaagcgcac aaagaagctt ccacccacct ggaagtatga gtcaaccaca gcgagcactc    540
tggtggccta agtgtggtat cctccgacag cttgttctag atatgaattt gtgtaatgct    600
tcttatgtct cgatccggtt aaatggacaa cggacctcat ctttttttat gtttaccttg    660
agaatcccgt aaaccatttt ggggttttga attgtctgtt aaacgtaaca tgcatatgtt    720
ttgaagccta gggtgagctt ttacttcacc atcacttatt attgttggct tgttc    775

<210> SEQ ID NO 161
<211> LENGTH: 877
<212> TYPE: DNA
<213> ORGANISM: Saccharum officinarum

<400> SEQUENCE: 161

```
agatagcgga cgccgctgca gcagtttcgt ccgctatcca cgcgcagcgg acgcggatag        60
cggacgcggt gcggacagtc taatccgtcc ccctcttctc gcactcgcgc ctctttccca       120
ttcgcgccgc cgccgccgcc gcaagcgcca gctcgccgtc gcccgagcca aacaccccaa       180
cgccgccatg gggcgtatgc acagccgcgg aagggtatc tcgtcgtcgg cgctgccgta        240
caagaggacg ccgccgacct ggctcaagac cgccgcctcc gacgtggagg agatgatcac       300
taaggcggcg aagaagggtc agatgccgtc gcagatcggc gtcctgctcc gtgaccagca       360
cggtatcccc cttgtcaaga gcgtcaccgg cagcaagatc ctccgcatcc tcaaggcaca       420
tgggctggca ccagaaatcc cagaggacct gtacttcctc atcaagaagg cggtggcgat       480
aaggaagcac cttgagagga acaggaagga caaagactcc aaattcaggc tcattcttgt       540
tgagagcagg atccaccgcc ttgcccgcta ctacaagcgc acaaagaagc ttccacccac       600
ctggaagtat gagtcaacca ccgcaagcac tctggtggcc taagtgggga gctcaacatg       660
aggtgcttga agctggggct attcttggaa tcaattttat gtaccgtttt atgagtttgg       720
agtgaactag agatcgtgaa tgtcctgtgg aggatgccat aaaccctttt ggttacatag       780
aactgtctgt tgttaacttt tgctactcgg catccagatt ttgtcagtta taatgatcat       840
ttatattaca tggttttgtcc attcctgcct gcggtcc                              877
```

<210> SEQ ID NO 162
<211> LENGTH: 1037
<212> TYPE: DNA
<213> ORGANISM: Sorghum bicolor

<400> SEQUENCE: 162

```
acggtaacag agcaatttca gatcagtaga tgcgaacaaa aaccttgctc actcttctct       60
catttcatag cggaaagtaa ccaaagcgga cagtaacatc atcgaacacg ggggtaccaa      120
cacctaatcc aaaggttcaa cggacactaa cacatgggta actcagaatc caacggaacg      180
gtaacacgat actatagata gatagatagc taggataact tggccgaagc cagggtgggc      240
ccacacaatc agttctcgca ctcgcgcgcc tttcccattc gcgccgccgc cgccgccgct      300
gcaagcgcca gctcgccgtc gtccgagcca aacaccccaa cgccgccatg gggcgtatgc      360
acagccgcgg aagggtatc tcgtcgtcgg cgctgccgta caagaggacg ccgccgacct       420
ggctcaagac cgccgcctcc gacgtggagg agatgatcac taaggcggcg aagaagggtc      480
agatgccgtc gcagatcggc gtcctgctcc gtgaccagca cggtatcccc cttgtcaaga      540
gcgtcacggg cagcaagatc ctccgcatcc tcaaggccca tgggctggcg ccagaaatcc      600
cggaggacct ctacttcctc atcaagaagg cggtggcgat aaggaagcac cttgagagga      660
acaggaagga caaagactcc aaattcaggc tcattcttgt tgagagcagg atccaccgcc      720
ttgcccgcta ctacaagcgc acaaagaagc ttccacccac ctggaagtat gagtcaacca      780
ccgcaagcac tctggtggcc taagtgagga gctcaacatt aggtgcttga agctgggcta      840
ttcttggaat catttttatg taccgtttta tgagttgga gtgaactaga gatcttgaat       900
gtcctgtgga ggatgccata aacccttttg gttacataga actgcctgtt gttaactttt      960
gctactcggc atccagattt tgtcagctat aatatgatca tttacattac atggtttgcc     1020
cctaccttcc tgcagtc                                                    1037
```

<210> SEQ ID NO 163
<211> LENGTH: 947
<212> TYPE: DNA

```
<213> ORGANISM: Saccharum officinarum
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t

<400> SEQUENCE: 163
cggacgcgtg gcggacgcg tgggcgcgcc gcagccgccg ccgccgccgc tgcagcagca        60
agcccccgcc ccgccgtcgc ctgaggtaga caccaatccg ccgccatggg gcgtatgcac       120
agccgcggga agggtatctc gtcgtcggcg ctgccgtaca agaggactcc tccgacctgg       180
ctcaagacgg ccgccaccga ggtggaggag atgattacca aggctgcgaa gaagggccag       240
atgccgtcgc agattggcgt cctgctccgt gaccagcacg gtatcccgct cgtcaagagc       300
gtcactggta gcaagatcct ccgcatcctt aaggcccatg gctggcgcc ggagatccct        360
gaggatctct acttcctgat taagaaggct gtggcgatta ggaagcatct ggagaggaac       420
aggaaggaca aggactccaa attcaggctt attcttgttg agagcaggat ccaccgcctt       480
gcccgctact acaagcgcac caagaagctc ccgcccacct ggaagtatga atcaaccacg       540
gccagcactc tggtggccta agtgatatcc tccgatggcg tggtctgtag cacctttgag       600
cttgttctag atatggattt atgtaatggt tattatgtct ggagcgggtt agatggacaa       660
ggaacctcaa ccgttttatg tttacttgtt tactgagaat cccataaacc atttttggtt       720
ttgcaattct gtctgttaaa acgtaacatg catccatgtt ttgtcgccta cagtgagcgt       780
tcactgagcc atcatttang atcggtgctt ggcccctgt atcccggttt ctatgactat        840
taatattaaa aattggccac ttaaaccctc atantnaaaa accaacctca actaccctac       900
aatccgagct ctctttttt tatatttctt ccccacttct attcact                     947

<210> SEQ ID NO 164
<211> LENGTH: 889
<212> TYPE: DNA
<213> ORGANISM: Sorghum bicolor

<400> SEQUENCE: 164
ctactggctc tcctatgccg cacgcgcctc ctctcgccct cgcgccgccg ccgccgccgc        60
agctgctgca gcagcaagct cccgcccgcc gtcgtcgcct gaggtagaca ccaatccgcc       120
gccatggggc gtatgcacag ccgcgggaag ggtatctcgt cgtcggccct gccgtacaag       180
aggactcctc cgacctggct caagacggcc gccaccgagg tggaggagat gattaccaag       240
gctgcgaaga gggtcagat gccgtcgcag attggcgtcc tgctccgtga ccagcacggc        300
atccctctcg tcaagagcgt tactggtagc aagatcctcc gcatccttaa ggcccatggg       360
ctggcgccgg atcccggga ggacctgtac ttcctgatta agaaggctgt ggcaattagg        420
aagcatttgg agaggaacag gaaggataag gactccaaat tcaggctcat tcttgttgag       480
agcaggatcc accgccttgc ccgctactac aagcgcacca agaagctccc gcccacctgg       540
aagtatgaat caaccacggc cagcactctg gtggcctaag tgatatcctc cgatggcgtg       600
gtcttgagca ccttttgaact tgttctagat atgaatttat gtaatgctta atatgtctgg      660
agcgggttag atggacaagg aacctcaact tttttatgtt attacttgga gaatctataa       720
```

| | |
|---|---:|
| accattttttg gttttgcaat tctgtctgtt aaacgtaaca tggatccatg ttttgtcgcc | 780 |
| ttcagtgagc gtttactgtg ccaccatttta gattgttgct tgccccctg tagcccggtt | 840 |
| ttctatttgg ttatatgact attaattaat atgaaaattg tccacttat | 889 |

<210> SEQ ID NO 165
<211> LENGTH: 940
<212> TYPE: DNA
<213> ORGANISM: Oryza sativa

<400> SEQUENCE: 165

| | |
|---|---:|
| aagaaaaaac tccatcctac cgccgctcgc gcccctctcg ccctcgcgcg ccgccgccgc | 60 |
| cgcccgccgt cgccggagct aaaccccctcg acgccgccat ggggcgcatg cacagccgcg | 120 |
| ggaagggtat ctcgtcgtcg gcgctgccgt acaagaggac tcccccgagc tggctcaaga | 180 |
| ccgccgcctc cgatgtggag gagatgatca tgaaggccgc gaagaagggt cagatgccgt | 240 |
| cgcagatcgg cgtggtgctc cgtgaccagc acggaatccc cctcgtcaag agcgtcaccg | 300 |
| gcagcaagat cctccgcatc ctcaaggccc acgggcttgc cccggagatc ccggaggacc | 360 |
| tctacttctt gatcaagaag gctgttgcta ttaggaagca cttggagagg acaggaagg | 420 |
| acaaggactc caagttcagg cttattcttg ttgagagcag gatccaccgc ctcgcccgct | 480 |
| actataagcg cacaaagaag ctcccaccca cctggaagta tgagtcaacc acggccagca | 540 |
| ctctggtggc ctaagagaac actggcgtgc tcttagatgc ttcgatatgg acctggttct | 600 |
| agaaatcaat ttatgtactg ctttgagttt ggagcgagtt agacgtggac aagaaactgc | 660 |
| aagtttttct atgtttactc gggggatcct ataaaccatt tttggtttca caattctgtc | 720 |
| tgttaaacat gcatcggtat tttgttattt acaattagct gttaccttac cataatgttc | 780 |
| ggcatcgttt gcatccagct ctatcccgta ctttggtatt gtgtttgaac tcatcgtacg | 840 |
| atgttagttc ataattctgg ttgatcgagg ctaatttgct cacaagcgct tctcatagaa | 900 |
| cttttcacaa tatttgtgag agaaatccgg tgctatgaat | 940 |

<210> SEQ ID NO 166
<211> LENGTH: 810
<212> TYPE: DNA
<213> ORGANISM: Zea mays

<400> SEQUENCE: 166

| | |
|---|---:|
| cgccgctcgc gcatcctatt gccctcgcgc caccgtcgcc gccgccgctg cagcgagcca | 60 |
| ccgccctgcc gtcgcctgag gtagacacca atccaccgcc atggggcgta tgcacagccg | 120 |
| cgggaagggt atctcttcat cggcgctgcc gtacaagagg actcctccga tctggctcaa | 180 |
| gacagctacc gccgaggtgg aggagatgat taccaaggct gcgaagaagg gccagatgcc | 240 |
| gtcgcagatt ggtgttctgc tccgtgacca gcacggcatc ccgcttgtca agagcgtgac | 300 |
| tggtagcaag atcctccgca tcctcaaggc ccatggggttg gcgccggaga tcccggagga | 360 |
| tctctacttc ctcattaaga aggccgtggc gattaggaag catttggaga ggaacaggaa | 420 |
| ggacaaggac tccaaattca gactcattct tgttgagagc aggatccacc gccttgcccg | 480 |
| ctactacaag cgtaccaaga agctcccacc cacctggaag tacgagtcaa ccacggcgag | 540 |
| cactctggtg gcctaagtga tatcctctga tggcttggtc tttagcacct atgagcttgt | 600 |
| tctagatatg aatttatgta attcttgtta tgtctggagc tggttagatg gacaaggaac | 660 |
| ctcaactttt tctatgttta cttggagaat cccataaacc attttttggtt tcgcaattct | 720 |
| gtctgttaaa cgtaacatgc atccatgttt tgtcgagcgt ttcctccacc atcataaatt | 780 |

```
cctgtagatt atatttttct tctagttatc                               810
```

<210> SEQ ID NO 167
<211> LENGTH: 820
<212> TYPE: DNA
<213> ORGANISM: Hordeum vulgare

<400> SEQUENCE: 167

```
cctctttcct atcctctcac cactcgcgcc tctctcgccc ttcccgccgc cgccgccgcc    60
gccgctcccc tcgccgcagc agcagccgca gccatggggc gcatgcacag tcgcgggaag   120
ggcatctcgt cgtcggcgct gccgtacaag aggactccac cgagctgggt caagaccgcc   180
gtcgccgatg tggacgagtt aatcaccaag gccgcgaaga agggccagat gccgtcgcag   240
atcggcgtcc tgctccgtga ccagcacggc atcccctcg tcaagagcgt caccgggagc    300
aagatcctcc gcatcctcaa ggcccatggg ctggcaccag agatcccgga ggacctctac   360
tttctgatca agaaggcggt ggcgataagg aagcacctgg agaggaacag gaaggacaag   420
gactctaagt tcagactcat ccttgtggag agcaggatcc accgcctcgc tcgctactac   480
aagcgcacca gaagctccc acccacctgg aagtacgagt ctaccaccgc cagcactctg    540
gtggcctaag ggagatatgc atctggtgtg ctcttagctg attaaagctt gattgttcca   600
gaaaccattc ttatgtaacg ctttatgaga gtttggagcc aagtcgatgc tgcaaatttt   660
ctatgtttga ctggaggatg ctgtaaaacc tttgttgttt cactgttctg tctgttaaac   720
gactgttata atgtacccag attttgtcag ttacagttag cagttacctt atgtgttttc   780
agatagctca tgttgctctt tggctaaaga tcatatagtt                          820
```

<210> SEQ ID NO 168
<211> LENGTH: 867
<212> TYPE: DNA
<213> ORGANISM: Oryza sativa

<400> SEQUENCE: 168

```
ctcactactc gctcttcccg ccgccgccgc ctcctccgcc gcgcagtcgc caaccgccgt    60
cgccggtcgc cgtcgccaaa ttccccactg ccaccatggg ggcgtatgca cagccgcggg   120
aagggcatct cgtcgtcggc gattccgtac aagaggactc ccccaagctg ggtcaagacc   180
gccgccgccg atgtggagga gatgatcatg aaggccgcga agaagggcca gatgccgtcg   240
cagatcggcg tggtgctccg tgaccagcac ggaatccccc tcgtcaagag cgtcaccggc   300
agcaagatcc tccgcatcct caaggcccat ggtcttgcgc ggagatccc ggaggacctg    360
tacttcctga tcaagaaggc tgttgctatt aggaagcatt tggagaggaa caggaaggac   420
aaggactcca agtttaggct catccttgtt gagagcagga tccaccgcct cgctcgctac   480
tacaagcgca ccaagaagct cccgcccacc tggaagtatg agtcgaccac agccagcact   540
ctggtggcct agagagagag ctctgcttct gctgtgctcc ttgctgcttc aagcttagct   600
tgttctagga atggatttta tttatgtagc gcattatgag tcttgagaca agcaggagct   660
gctaattttc ctttgtctgg agaatgccat aaaacccttta tgcattcaat attctgaacg   720
ttaaacttct agtaatgtgc atcgagacta tgtaaatcaa taacaatctg gagcaaaaac   780
aatcaatcac atgcagaaaa aattttttgac aggcttgaca agttacactt gaacaaggaa   840
ggtataataa tgggcaaaat caacttg                                        867
```

<210> SEQ ID NO 169
<211> LENGTH: 817
<212> TYPE: DNA

<213> ORGANISM: Triticum aestivum

<400> SEQUENCE: 169

```
ccaggctctt ttctatcctc tcaccactcg cgcctctctc gcccttcccg ccgccgccgc      60
cgccactccc ctcgccgccg cagcagccgc agccatgggg cgcatgcaca gccgcgggaa     120
gggcatctcg tcgtcggcgc tgccgtacaa gaggactcca ccgagctggg tcaagaccgc     180
cgtcgccgat gtggacgagt taatcaccaa ggccgcgaag aagggccaga tgccgtcgca     240
gatcggcgtc ctgctccgtg accagcacgg catcccccctc gtcaagagcg tcaccgggag    300
caagatcctc cgcatcctca aggcccatgg gctggcacca gagatcccgg aggacctcta    360
ctttctgatc aagaaggcgg tggcgataag gaagcacctg gagaggaaca ggaaggacaa    420
ggactctaag ttcaggctca tccttgtgga gagcaggatc caccgcctcg ctcgctacta    480
caagcgcacc aagaagctcc cgcccacctg gaagtacgag tctaccaccg ccagcactct    540
ggtggcttaa gggagatcca gatctggtgt gctcttagct gattaaagct tgattgttct    600
ggaaaccatt cttatgtaat gctttatgag agtttggagc caagcagatg ctgcaaattt    660
tctatgtttg cctggaggat gctgtaaaac ctttatggtt tcactgttct gtctgttaaa    720
cgactgttat aatgtaccca gattttgtca gttacagtta gcagttaccg tatgttttt     780
ccaatagtac atgttgctct tcggctgaag atcgtat                             817
```

<210> SEQ ID NO 170
<211> LENGTH: 912
<212> TYPE: DNA
<213> ORGANISM: Triticum aestivum
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t

<400> SEQUENCE: 170

```
tgcaggnaat tcggcacgag gctcgagccc ctctcgccct tcgcgccgct gctgctgcag      60
gcaaccgccg ccgccgtcgc cggagctaaa ccccctcgcct gacgccatgg ggcgtatgca   120
cagccgcggg aagggtatct cgtcgtcggc gctgccgtac aagaggactc ccccgagctg    180
ggtcaagacc gccgtcgctg atgtcgacga gttgatcacg aaggctgcga agaagggtca    240
gatgccctcg cagatcggtg ttctgctccg tgaccagcac ggtatccccc tcgtcaagag    300
cgttaccgga agcaagatcc tccgcatcct caaggctcat ggcctggcgc cggaaatccc    360
agaggatctg tactttttga ttaagaaggc tgtggccatt aggaagcatc ttgagaggaa    420
caggaaggac aaggactcca aattcaggct cattcttgtt gagagcagga tccaccgtct    480
tgcccgttac tacaagcgca ccaagaagct cccgcccacc tggaagtacg agtctaccac    540
tgccagcact ctggtggctt aggagggctc ttcatctggt gtgctcttac cggcttcagg    600
atggtcttgt tctacatatt atcaatttca tgtaacgctt ttgagtttgg agcgatttag    660
atgaacaaga gaccaaattt tctatgttta cttggagaat cccataaacc attttttggtt   720
ttgcaattct gtctggttct gtttagcgtc tatctacaat tcatcagtta aaattagaca    780
ttgtgatatt cgtgttgtct gatctgagtg agtgtaatcg ctgctttcag tgcactcaag    840
cttggacagt ttgactatat ggttatcctg aaatctaaaa agtggccgca cactttttgg    900
tcaanaaaaa aa                                                        912
```

<210> SEQ ID NO 171
<211> LENGTH: 863
<212> TYPE: DNA
<213> ORGANISM: Hordeum vulgare

<400> SEQUENCE: 171

```
cacgaggcaa tcgcgccgcc gctcgtgccc ctctagccct tcgcgccgct gctgctgcag      60
gcaaccgccg ccgtcgtcgc cggagctaaa cccctcgcct gacgccatgg ggcgcatgca     120
cagccgcggg aagggtatct cgtcgtcggc gctgccgtac aagaggactc ccccgagctg     180
ggtcaagacc gccgtcgctg atgtggatga gttgatcacg aaggctgcga agaagggtca     240
gatgccctcg cagatcggtg ttctgctccg cgaccagcac ggtatccccc tcgtgaagag     300
tgttaccgga agcaagatcc tccgcatcct caaggctcat ggcctggcgc cggaaatccc     360
cgaggatctg tacttttgta ttaagaaggc cgtggccatt aggaagcatc ttgagaggaa     420
caggaaggac aaggactcca aattcaggct cattcttgtt gagagcagga tccaccgtct     480
tgcccgttac tacaagcgca ccaagaagct cccgcccacc tggaagtacg agtctaccac     540
agccagcact ctggtggctt aggagggctc ttcatctggt gtgctcttac cagcctcagg     600
atggtcttgt tctacatatc atcaatttta tgtaacgctt ttgagtttgg agcgatttag     660
atgaacaaga gaccaaattt tctatgttta ctcggagaat cccataaacc atttttggtt     720
ttgcagttct gtctggttac ttttggcatg catccacatt tcattcagtt aaactttga      780
cgtcatgata tttgtgttgt gattgtagcg agtgcctcgc tagtttcagt gcatcttctc     840
gtgcccgaat ggtttgactg act                                             863
```

<210> SEQ ID NO 172
<211> LENGTH: 568
<212> TYPE: DNA
<213> ORGANISM: Triticum aestivum

<400> SEQUENCE: 172

```
gcaaaaccaa aaatggttta tagattctcc aagtaataac ataaaaaagt tgaggttcct      60
tgtccatcta acccgctcca gacatattaa gcattacata aattcatatc tagaacaagt     120
tcaaaggtgc tcaagaccac gccatcggag gatatcactt aggccaccag agtgctggcc     180
gtggttgatt catacttcca ggtgggcggg agcttcttgg tgcgcttgta gtagcgggca     240
aggcggtgga tcctgctctc aacaagaatg agcctgaatt tggagtcctt atccttcctg     300
ttcctctcca aatgcttcct aattgccaca gccttcttaa tcaggaagta caggtcctcc     360
gggatctccg gcgccagccc atgggcctta aggatgcgga ggatcttgct accagtaacg     420
ctcttgacga gagggatgcc gtgctggtca cggagcagga cgccaatctg cgacggcatc     480
tgacccttct tcgcagcctt ggtaatcatc tcctccacct cggtggcggc cgtcttgagc     540
caggtcggag gagtcctctt gtacggcc                                        568
```

<210> SEQ ID NO 173
<211> LENGTH: 778
<212> TYPE: DNA
<213> ORGANISM: Zea mays

<400> SEQUENCE: 173

```
actcgcgtct ctttccctat ttcgcgccgc cgccgctgct gcaagcgcca gctcgccgtc      60
gtccgaatag tacactctaa cgccgccatg gggcgtatgc acagccgcgg gaagggtatc     120
tcgtcgggtc ggcgctgccg tacaagagga cgcctcctac ctggctgaag accgccgcct     180
```

```
ccgacgtgga ggagatgatc acaaaggcag cgaagaaggg acagatgccg tcgcagatcg      240
gcgtcctgct ccgtgaccag cacggtatcc cccttgtcaa gagtgtcacc ggcagcaaaa      300
tcctccgcat cctcaaggcc catgggctgg cacccgaaat cccggaggac ctgtacttcc      360
tcatcaagaa ggcggtggcg ataaggaagc accttgagag gaacaggaag gacaaagact      420
ctaaattcag gctcattctt gtcgagagca ggatccaccg ccttgcccgc tactacaagc      480
gcacaaagaa gcttccaccc acgtggaagt acgagtcaac cactgcaagc actctggtgg      540
cctaagcgag gagctcagcg tacggcgctt gaagccgagg gcattgttgg aaatcatttt      600
tatgtaccgt tttaagagtt tggagtgaac tagagatggt gaatgtccct cctctggagg      660
atgccatgga cccttttgt ttacatagaa ctgccctgct gttaaacttt tgctacttgg       720
cgaaggcagt tgattgcttg cctccattaa cacctgctat gcgagaagct tttagcct         778

<210> SEQ ID NO 174
<211> LENGTH: 697
<212> TYPE: DNA
<213> ORGANISM: Saccharum officinarum

<400> SEQUENCE: 174
ctcaagcgcc agctcgccgt gtgccgagcc aaacacccga acgccggcat ggggcgtatg        60
cacagctcgc gggaagggta tctcgacgtc ggagctgccg tacaaggaga cgccggcgac       120
ctggctcaag accgccgtct tcgacgtgga ggagatgatc actaacgcgg cgaagaaggg       180
tcagatgccg tcgcagatcg gcgtcctggt tcgtgaccag cacggtatcc cccttgtcaa       240
gagcgtaacc ggcagcatga tcctccgcat cctcaaggca catgggctgt cactagaaat       300
cccagaggac ctgtacttcc tcataaagaa agcggtgtgg ataaggaagc accttgagag       360
gaacaggaag gacaaagact tcaaattcac gctcattctt gttgagagca ggatccaccg       420
tcttgcccgt tactacaagc gcacaaagaa gcttccaccc acctgcaaat atgagacaac       480
caccggaagc actctggtgg ccatagtggt gagctcaaca tgacgggctt tgatgctggc       540
gctattcttg gaatcaattt tatgtaccgg ttaatgagtt tggagtgaac taaagatcgt       600
gaatggcctg tggaggatgc cataaaccct tttggctaca tagaactggc tgtggtaact       660
tgtgctactc gccatcagat tttgtcagta taatgat                                697

<210> SEQ ID NO 175
<211> LENGTH: 1050
<212> TYPE: DNA
<213> ORGANISM: Triticum aestivum
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 175
gggnagagga ctccaccaag cgtgggtcaa gaccgccgtc gccgatgtgg acgagttaat        60
caccaaggcc gcgaagaagg gccagatgcc gtcgcagatc ggcgtcctgc tccgtgacca       120
gcacggcatc cccctcgtca agagcgtcac cgggagcaag atcctccgca tcctcaaggc       180
ccatgggctg gcgccagana tcccggagga tctctacttt ctgatcaaga aggcggtggc       240
gataaggaag cacctggaga ggaacaggag ggacaaggac tctaagttca ggctcatcct       300
tgtggagagc aggatccacc gcctcgctcg ctactacaag cgcaccaaga agctcccgcc       360
```

```
cacctggaag tgggaggtga aggcagttct ggacgactac ccgaaactct gcctcaccaa        420
ggggagaaag gtcctcgaga tccggccctc catcgagtgg aacaagggac acgctctcaa        480
gttcttgctc aagtctctcg gctatgcggg gcgcagcgac gttttcccga tatacatcgg        540
ggatgaccgt acagacgagg atgcattcaa ggtgctgcag aacatgggac aaggcatcgg        600
gatccttgtg accaagtttc caaaggacac cagcgcatcc tactctctgc gtgagcctgc        660
tgaggtaaag gagttcatgc gcaagctagt gaagagcaac gggataaaga agggttaatt        720
catcaatcaa cagccttcta gctctaactc gcatgaagat cgagcaggct atatagctag        780
tacatcaagt ctagcttgtt tcctttttgg acttggtgtt gtctctcctt tcatctagta        840
gaacaatgca tgcatgcgtg tcagggtcga tatagaagat ccagatcgat cagtgaccca        900
tgccaggcct tggctctgaa ggtttctatt actgtatcct tctctcaagg tcttgtaatt        960
agccttccct tagctatgac agaaatggta ttgacaaagt agccctcctt tttctcgccc       1020
tgcactataa aattgttcta ttgcttgctt                                         1050

<210> SEQ ID NO 176
<211> LENGTH: 375
<212> TYPE: DNA
<213> ORGANISM: Zea mays

<400> SEQUENCE: 176
acataaaaat gatttccaac aatgccctcg gcttcaagcg ccgtacgctg agctcctcgc         60
ttaggccacc agagtgcttg cagtggttga ctcgtacttc cacgtgggtg gaagcttctt        120
tgtgcgcttg tagtagcggg caaggcggtg gatcctgctc tcaacaagaa tgagtctgaa        180
tttggagtcc ttgtccttcc tgttcctctc caaatgcttc ctaatcgcca ccgccttctt        240
aatgaggaag tagagatcct ccgggatctc cggcgccaac ccatgggcct tgaggatgcg        300
gaggatcttg ctaccagtca cgctcttgac aagcggcatg ccgtgctggt cacggagcag        360
aacaccaatc tgcga                                                         375

<210> SEQ ID NO 177
<211> LENGTH: 528
<212> TYPE: DNA
<213> ORGANISM: Triticum aestivum
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
```

```
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t

<400> SEQUENCE: 177
atcaagcccc cgccccgccg tcgcctgagg tagacaccaa tccgccgcca tggggcgtat      60
gcacagccgc gggaagggta tctcatcgtc ggcgcttccc tacaagagga cgcctcctac     120
ctggctcaag accgctgcct ccgacgtgga ggagatgatc acaaaggcag cgaagaaggg     180
acagatgccg tcgcagatcg gcgtcctgct ccgtgaccag cacggtatcc cccttgtcaa     240
gagcgtcacc ggcagcaaga tcctccgcat tctcaaggcc catggctggc accagaaatc     300
ccgangactg tacttctcat caagaaggcg gtggcgataa ggaagcactt gagangaaca     360
ggaangacaa agactctaaa ttcangntca ttcttgtnga aacaggatt caccgcttgc      420 ccgctactac aagcgcacaa gaagtttcan ccacttgaag tatgagtaan cacagcgagn    480
atctggtggc taagtttgta tcttcganag ttgttctaga tatgatt                   528

<210> SEQ ID NO 178
<211> LENGTH: 1346
<212> TYPE: DNA
<213> ORGANISM: Sorghum bicolor

<400> SEQUENCE: 178
aagagaagag cagcagcagc aacagccgcg ccatccgctt gcttccttcc ttcctcttct      60
ctccctccta ccccaccgcc ggcgtcgcct cttcgcgttg cgcgccctcg cgtcgcaccc     120
gtgggtagca gccgcgtacc taccaacctg cgtgctgccg gggagctct gcacgtctcc      180 tgtcgcctcg cctctcggca tggacgccgg gggagagaag ttcagcgacg cggcggcggc     240
ggagggcggt gagggcggcg cgacctcta cgccgtcctc gggctcaaga aggagtgctc      300
cgacgccgac ctcaaggtcg cttaccggaa gctcgccaag aaatggcacc cggacaaatg     360
ctcctcctcc agcagcgtga aacacatgga ggaagccaag gagaagttcc aagagatcca     420
gggcgcctat tccgtactct ctgacgccaa taaacggctc ctctacgatg ttggagtata     480
cgacgatgag gacgacgagg atagcatgca ggggatgggt gacttcattg gtgagatggc     540
ccagatgatg agccaggtgc ggccgacgag gcaggaaagc tttgaggagc tgcagcagct     600
ttttgtggac atgttccagt ctgatattga ttcaggattc tgcaacgggt ctgctaagga     660
tcaagttcag gggcaagcca aaagtagaac atgctcgacc tcaccttcat catcaccgtc     720
cccacctcct cctcctacta tagtaaagga ggcagaggtg tcatcatgta atggcttcaa     780 taagcgggt tcatcagcaa tggactcagg gaagcctcca aggcctgttg aaggcggtgc     840
tggtcaggct ggattttgtt ttggggtgag cgatacgaag caaacgccga agccgagagg     900
tccgaacacc agccggagga ggaacggccg gaaacagaag ctgtcatcca gcacgatgt     960 ttcatctgaa gatgaaacgg ccggttccta gcaccagcag ctacggtagc agtttgacct    1020
gtggctttgg tgatatcatt cgttggtcct ggcggtgcc gagggcccta gtagccagca    1080
gcggcaggga ggcacagcat gtcgcttctg ctagctgctg tgatctgaag aggcgtttag    1140
ctcatcatat gccttacctt aggcctgtga gggacttcca ttgaaactcg tcgaggatac    1200
```

```
tgcattttc tttctccatc tgtgtcggtt gtgttgtaca atacattgag tgacttctaa    1260
tcgattcttt ttttttacca ttaattaaca tctggtatat ccgattgatc gatccctagc    1320
cactgattac atgcatgagt tctttg                                         1346
```

<210> SEQ ID NO 179
<211> LENGTH: 1209
<212> TYPE: DNA
<213> ORGANISM: Saccharum officinarum

<400> SEQUENCE: 179

```
cgtaccatgg acgccggggg agagaagtgt ggcgacgcgg cggcggcgga gggcggtgag      60
ggcggcggcg acctctacgc cgtcctcggg ctcaagaagg agtgctccga cgccgacctc     120
aaggtcgctt accggaagct cgccaagaaa tggcacccgg acaaatgctc ctcctccagc     180
agcgtgaagc acatggagga agcgaaggag aagttccaag agatccaggg cgcctattct     240
gtactctctg acgccaataa acggctcctc tacgacgtgg gagtatatga tgatgaggac     300
gacgaggata gtatgcaggg gatggggggac ttcattggtg agatggccca gatgatgagc     360
caggtgcggc cgacgaggca ggaaagcttt gaggagctgc agcagctttt tgtggacatg     420
ttccagtctg atattgattc aggattctgc aatgggactg ctaagggcca tcaagttcag     480
gggcaagcca aaagtagaac atgctcgacc tcaccttcat catcaccgtc ccctcctcct     540
cctactatag taaaggaggc agaggtgcca tcatgtaatg gcttcaacaa gcggggttca     600
tcagcaatgg actcagggaa gcctccaagg cctgttgaag gtggtgcggg tcagaggcag     660
gctggatttt gttttggggt gagcgacacg aaacaagcgg caaagccgcg aggtccaaac     720
accagccgga ggaggaacgg ccggaaacag aagctgtcat ccaagcacga tgtttcatct     780
gaagatgaaa ctgccggttc ctagcaccag cagctatggt agcagtttga cccttggctt     840
tggtgatatc attcgttggc ccttggatgt gccgaaggcc ctagtagcca gcagcagcag     900
ggagggcaca gcatgtcgcc tctgctagct gctgtgatct gaagaggcgt ttagctcatc     960
atatgcctta cctttaggcc cgtgagggac ttacattgaa actcgtcgat gatactgcat    1020
ttttctttct ccatctgtgt cagttgtgtt gtaccaatac attgagtgac ttctaatcga    1080 ttagccttttt atcattaatt aacttctggt atatatacgt tgctgcctgt tgttgacagg    1140
ctacggtagc ctgttggtaa gatcttaatc tcgaagggag aaaaataaat aacattgtgg    1200
acgtagctc                                                            1209
```

<210> SEQ ID NO 180
<211> LENGTH: 1623
<212> TYPE: DNA
<213> ORGANISM: Sorghum bicolor

<400> SEQUENCE: 180

```
gcacgaggcc ctcttccgcc tcctctctct ctctctctct ctctcggctc tcgctctcag      60
acgactgctg ggcagccgcc gccctaggcc aggtgctgag gctttccctg gtctcttcgc     120
cgtcgacgag cacccaccag taggtacttg attggacgag ccatggacag cctgtggcat     180
ctgggggacg agctccgtgg gcaaccgaag gtggtggagg accgccagtg gtcgctcatg     240
acgtccaagc tggcggagat caccaggtcc aagggcgaga ggatgaacga cctcgactac     300
gccaggatga acaccgtccc tgacgccaag cagtgggaca agacgtcctt ccagcatcat     360
gaccagagca ggatggacca catcaatctc ggcctcatga acctggatct caagatgaac     420
gatctcaaga tgaacgaggc ccccaccgcc atgaagctcc ccttccacaa catgccctat     480
```

```
aacatgaacc caatgtaccc caaggggagc aatgccaatg tcaatgtcaa tgcgttcaag      540
atgaatgttg gggtgaacaa gtactccaat agtcctaacg ggaaagacgc caatgggaaa      600
aacaatggcg gcagcaacaa caatggagga aacagcaatg ggagcgcaaa cggcaattct      660
gcagttgaca agcgcttcaa gacattgcca acaagtgaga tgctaccgag gaatgaagtc      720
cttggtggat acatctttgt ctgcaacaac gataccatgc aggaggatct caagaggcag      780 cttttttggat tgccagcaag atatcgtgat tcagtccgag caattactcc tggcctgcct      840
cttttcctct ataactacac aacccaccag cttcatgggg tatttgaggc tgccagcttt      900
ggtgggtcta atatcgatcc cactgcatgg gaggataaga agtgtaaagg tgaatctaga      960
ttcccagctc aggtgaggat ccgcattagg aagctttgca agccgttgga agaggattcc     1020
ttcaggccag ttttgcacca ttatgatggc ccaaagtttc gccttgagct ctctatcgcg     1080
gagaccttgt cgctgctaga cctatgtgag aaggaaggta tctgagctgt ggggaggtg      1140 gttgccttgt gagcttctag taaatatcaa tcatccttgt atgttttgtg atggtggtt      1200 ggttggcaat gttgtttatt ttagcgaaag ctgctgctgg ttttgttttc cctaccctgg     1260
atgaaagcaa ggacctggta cttggaaggc cccctcaaac aagctgtgag cctgtcagtg     1320
tactgcgttg tgtctgtcgt cgtcaagaac caaaccaatc ttggaccgac tgagagttgg     1380
agtgtgtatg ttttgctgtc tatctacatg tgttagtaga gtgggtatac ctgggcagaa     1440
tgggtcctca aaagatgggg ggcctatctg tatactatgt gtaatggtta agatgcatgc     1500
ggccctaagt aagggctggt gatgtcgatg ctggtgctcc tggtgtgtat tttgtactct     1560
gttgtacctt gaacctcctt tgcatttgcc ttaatgctgc tgcttttttgc actgtcaaaa     1620 aaa                                                                   1623

<210> SEQ ID NO 181
<211> LENGTH: 1336
<212> TYPE: DNA
<213> ORGANISM: Saccharum officinarum

<400> SEQUENCE: 181
agatcaccag gtccaaaggc gagaggataa acgatctcga ctacgcaacg atgaacaccg       60
accctgacgc caagcagtgg gacaagacgt cctaccagca tcacaacgag agcaggatgg      120
accacatcaa cctcggcctc atgaacctgg atctcaagat gaacgaggcc gccaccgcca      180
tgaagctccc cttccacaac atgccctata acatgaaccc aatgtacccc aaggggagca      240
atgtcaatgt caatgcgttc aagatgaatg ttggggtgaa caagtactcc aatagtccta      300
acgggaaaga cgccaatggg aaaaacaatg gtggcagcaa caacaatgga ggaaacagca      360
atgggagcgc caacagcaat tctgcagttg acaagcgctt caagacattg ccaacgagtg      420
agatgctacc gaggaatgaa gtccttggtg gatacatctt tgtctgcaac aatgatacca      480
tgcaggagga tctcaaaagg cagcttttttg gattgccagc aagatatcgt gattcagtcc      540
gagcaattac tcctggcctg ccacttttcc tctataacta cacgactcac cagcttcatg      600
gggtatttga ggctgccagt tcggtgggt ctaatatcga tcccactgca tgggaggata      660
agaagtgtaa aggtgaatct agattcccag cgcaggtgag gatccgcatt aggaagcttt      720
gcaagccgtt ggaagaggat ccttcaggcc agttttgca ccattatgat ggcccaaagt      780
ttcgccttga gctctccatt gcggagacct tgtcgctgct agacctatgc gagaaggaag      840
gcatctgagc tgttggggag gtggttgcct tgtgagcttc tagtaaatat caatcatcct      900
tgtatgtttt gtggatggtg gttggcaatg ttgtttattt aagcgcaagc tgctactggt      960
```

```
tccgttttcc ctaccctgga tggaaggaat gacctggtac ttggaaggcc ccctcaaaca   1020
agctgtgagc ctgtcagtgt actgcgttgt gtctgtcgtc gtcaagaacc aaaccaatct   1080
tggaccgact gagagttgga gtgtgtatgt tttgctatct atctacatgt cttagtagag   1140
tgggtatacc ttggcagaat gggtccccaa aagatgggg cctgtctgta tactatgtgt    1200
aatggttaag atgcatgtag ggccggtgat gtcgatgccg gtgctccggg tgtttatttt   1260
gtcctctgtt gtaccttgaa cctcctttgc atttgcctta atgctgctgc tttgcactgt   1320
aacggagtgt tggctt                                                   1336

<210> SEQ ID NO 182
<211> LENGTH: 674
<212> TYPE: DNA
<213> ORGANISM: Saccharum officinarum

<400> SEQUENCE: 182
ggcagccgaa ggtggtggag gaccgccagt ggtctctcat gacgtccaag ctggcggaga     60
tcaccaggtc caagggcgag aggatgaacg acctcgacta cgcgaggatg aacaccgtcc    120
ctgacgccaa gcagtgggac aagacgtcct accagcatca cgacgagagc aggatggacc    180
acatcaacct cggcctcatg aacctggatc tcaagatgaa cgatctcaag atgaacgagg    240
ccgccaccgc catgaagctc cccttccaca acatgcccta aacatgaacc caatgtacc     300 ccaaggggag caatgtcaat gtcaatgcgt tcaagatgaa tgttggggtg aacaagtact    360
ccagtagtcc taacgggaaa gacgccaatg ggaaaaacaa tggtggcagc aacaacaatg    420
gaggaaacag caatgggagc gccaacagca attctgcagt tgacaagcgc ttcaagacat    480
tgccaacgag tgagatgcta ccgaggaatg aagtccttgg tggatacatc tttgtctgca    540
acaatgatac catgcaggag gatctcaaaa ggcagctttt tggattgcca gcaagatatc    600
gtgattcagt ccgagcaatt actcctggcc tgcctctttt cctctataac tacacgactc    660
accagcttca tggg                                                     674

<210> SEQ ID NO 183
<211> LENGTH: 1726
<212> TYPE: DNA
<213> ORGANISM: Sorghum bicolor

<400> SEQUENCE: 183
aaaaattccc tgcactttat ttcatttaca tcggtggttg tatcttgcac acggttcatt     60
taccatacat acatccaaac tttcctcatc aattttttcgt cgtcaggtac ttctaataaa   120
taccaaaaac ctcgggggca gctcctcttc actgccatga ttttggaagt cgccgcagta   180
gaaactcaaa gtattgtgca cctgttcaag ccaagagacg agaagatcct cctcgcagaa   240
ggccacaagc ggccaagaag cccaggcctc tcttcctcga aggcgtactc tggttctctg    300
gtcggactat ccattgtatt tgcacctcta tcagcacttg ttgcctcatc agagcccatg    360
tcccaccctc ctcctcctcc tgttgatcaa atatctcgc tgcgcttttg cgagtccttt     420
tccctccaag gaacagaaac acccggcgct tttaccccac ccgcaccgc tttccctcc     480 cggccaagaa caggagcaac aacaaggctc ctcctcgaga cattccattc atccatggcg    540
aagctcgtga acaagctggt cgattcgttc gaggagcaag acaccccgga cgtcggctgc    600
gtgcgcgccg tgctggccga gctcgtcctc accttcctct tcgtcttcac cggcgtctcc    660
gccgccatgg ccgccgggtc cggcgtgaag cccggcgagg ctatgccgat ggcgacgctg    720
gcggcggtgg caatcgcgca cgcgctggca gccggcgtac tggtgacggc cgggttccac    780
```

```
gtctccggcg gccacctcaa ccccgccgtg acggtggggc tcatggtgcg cggccacatc      840
accaagctcc gggcggtgct ctacgtcgcc gcgcaggtgc tggcgtcctc cctcgcctgc      900
atcctgctcc gctacctcag cggcggcatg gtgaccccgg tgcacgccct ggcgcgggc       960 atcagcccga tgcagggcct ggtgatggag gtgatcctca ccttctccct gctcttcgtc     1020
acctacgcca tgatcctgga cccacggagc caggtccgca ccatcggccc gctgctgacc     1080
ggcctcatcg ttggtgccaa cagcctcgcc ggtggcaact tcagcggcgc gtccatgaac     1140
ccggcacggt ccttcgggcc agccctggcc agcggggtct ggacaaacca ctggatctac     1200
tggatcggcc cgctgcttgg cgggcccctg gccgggttca tctacgagtc tttgttcatt     1260
gtgaacaaga cgcacgagcc gctgctcaat ggagacatct gacgaaccat cggcctgccc     1320
tgtggctgtg ggcagggcag tcagcatggt tggttcatgc ttgtttctgt aaaatagttc     1380
attgtctaca agcatgatgg atacatatat tggtcaaggt aattagagag ggttgctgta     1440
aaatagttac cctggtatag gattgttgga tgtagaaatt gttgatgggc tttgtatttt     1500
tttccccctt ttcatgccaa ggaattcttt ttttttttaga gggcggggtt ctgtcaagga    1560
tttgttaagg ctattagtag ttagccatgt agtagaaaac tagagaatgg tatacgtggg     1620
agtgggacct gaagttttt caggtacact gtagtactat tgtaatttg tcttgaagat       1680 ggaattggat gtacagagta aaacttctc tttcaagcag taaaaa                     1726

<210> SEQ ID NO 184
<211> LENGTH: 1290
<212> TYPE: DNA
<213> ORGANISM: Saccharum officinarum
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t

<400> SEQUENCE: 184
nacctcccgg nncgacccac gcgtccgcct cctcctgtcg ttcaaaatat ctcgctgcgc       60
ttttccgagt ccttttccct ccaaggaaca ggaacaaccg gcgcttttac cccaccaccc      120
gctttcccct ccccgccagg aaggctcctc ctcgcaatag ttcattcatt catggcgaag      180
ctcgtgaaca agctggtcga ttcgttcgac cacgacgaga ctacgccgga cgtcggctgc      240
gtgcgcgccc tgctggccga gctcgtcctc accttcctct tcgtcttcac cggcgtctcc      300
gccgccatgg ccgccgggtc cggcgggaag cccggcgagg ctatgccgat ggcgacgctg      360
gcggcggtgg caatcgcgca cgccctggcc gccggcgtcc tggtgacggc cgggttccac      420
gtctccggcg gccacctcaa ccccgccgtg acggtggggc tcatggtgtg cggccacatc      480
accaagctcc gggcggtgct ctacatcgcc gcgcagctgc tggcctcctc cctcgcctgc      540
atcctcctcc gctacctcag cggcggcatg gtgaccccgg tgcacgccct gggcgctggc      600
atcagcccga tgcagggcct ggtgatggag gtgatcctca ccttctccct gctgttcgtc      660
acctacgcca tgatcctgga cccgcggagc caggtccgca ccatcggccc gctgctcacg      720
ggcctcatcg tgggcgccaa cagcctcgcc ggcggcaact tcaccggcgc gtccatgaac      780
ccggcgcggt cctttgggcc ggccctggcc accggggtct ggacaaacca ctgggtctac      840
tggatcggcc cactgctcgg cgggcccctg gctggcttcg tgtacgagtc gctgttcatt      900
gtgaacaaga cgcacgagcc gctgctcaat ggagacatct gacgaactat cggcctgccc      960
```

| | |
|---|---:|
| tgtgggcagt cagcatggtc catgcatgct tgtttctgta aaatagttca ttgtctacaa | 1020 |
| gcatgataca tacatatatt ggccaaggta attagagagg gttgctgtaa aatagctacc | 1080 |
| ctggtaggat tgttggctgt agaaattgtg gatgggcctt gtgttttttt ttccttttcc | 1140 |
| tgccatggaa ttcttttttt agagggctgg gttttgtcaa ggatttgtta aggtactttg | 1200 |
| tagaactatg ttattttgc cttccagatg aaattggatg tacagaattg cagtattttt | 1260 |
| ggcttccaga tgaaattcga tgtgcagagt | 1290 |

<210> SEQ ID NO 185
<211> LENGTH: 1243
<212> TYPE: DNA
<213> ORGANISM: Zea mays

<400> SEQUENCE: 185

| | |
|---|---:|
| caaaatatct ccctgcgctt ttccgagtcc ttttccctcc aaggaacaga acaaccgga | 60 |
| gcttttaccc cacccgcttt ccctccccg ccaggaacaa cagggctcct cgcaataatt | 120 |
| cgtccatcca tggcgaagct cgtcaacaag ctggtcgatt cgttcgacca ccacgaggcg | 180 |
| ccggcgccgg acgtcggctg cgtgcgcgcc gtgctggccg agctcgtcct caccttcctc | 240 |
| ttcgtcttca ccggcgtctc cgcctccatg gccgccgggg ccggcgggaa gcccggggag | 300 |
| gctatgccga tggcgacgct ggcggcggtg gctatcgcgc acgcgctggc cgctggcgtc | 360 |
| ctggtgacgg ccggcttcca cgtctccggc ggccacctca ccccgcggt gacggtgggg | 420 |
| atcttggttc gcggccacat caccaagctc cgggcgctgc tgtacgtcgc cgcccagctg | 480 |
| ctggcgtcct ccctcgcctg catcctcctc cgctacctca gcggcggcat ggtgaccccg | 540 |
| gtgcacgccc tgggcgctgg catcagcccg atgcagggcc tggtgatgga ggtgatcctc | 600 |
| accttctcgc tgctcttcgt cacctacgcc atgatcctgg accgcggag ccaggtccgc | 660 |
| accatcggcc cgctgctgac ggggctcata gtcggcgcca acagcctcgc cggcggcaac | 720 |
| ttcaccggcg cgtccatgaa cccggcgcgg tccttcggtc cgccatggc caccggggtc | 780 |
| tggaccaacc actgggtcta ctggatcggc ccgctgctcg gcgggtccct ggccggcttc | 840 |
| gtgtacgagt cgctgttcat ggtgtacaag acgcacgagc cgctgctcaa tggagacatc | 900 |
| tgacgaccgt cgggcccca gggcagtgag cacggttcat gcttgttttc tgtaaaatag | 960 |
| ttcgttacct acaagcatga tgcatatatt gaccaaggta attaatagga gagggttgct | 1020 |
| gttataccct ggtgggattg tgggatgtag aaattgttgc tgggctttgc tttttttttt | 1080 |
| acttttcctc ccaaggaatt ttttaagagg gctgggttct gtaaaggatt tgtttaggct | 1140 |
| attagttagc tatgtagtag aaaactagag aatgctatac gttggacgtg attttttttc | 1200 |
| acgtatattg ttgtacgata tggtattttt tatcttccgg atg | 1243 |

<210> SEQ ID NO 186
<211> LENGTH: 1274
<212> TYPE: DNA
<213> ORGANISM: Zea mays

<400> SEQUENCE: 186

| | |
|---|---:|
| aatatctccc tgcgcttttc ctagcccttt gtcatccaag gatacaataa acaaccggcg | 60 |
| cttttacacc cccgccaaga acaggagcaa caacaataag gctcctcgca acaatccatt | 120 |
| ctcatccatg gcgaagctca tgaacaagtt ggtcgattcg tttgagcacg acgagatact | 180 |
| ggacgtcggc tgcgtgcgcg ccgtgctggc cgagctcgtc ctcaccttcc tcttcgtctt | 240 |
| caccggcgtc tccgccgcca tggccgccgg atccgacggg aagcccggcg acgctatgcc | 300 |

-continued

```
gatggcgacg ctggcggcgg tggcaatcgc gcacgcgctg gccgctggcg tcctggtgac      360
ggccgggttc cacgtctccg gcggccacct gaacccgcg gtgacggtgg ggctcatggt       420
gcgcggccac atcaccaagc tccgggcggt gctgtacgtc gccgcccagc tgctggcctc      480
ctccgccgcc tgcgtcctcc tccgcttcct cagcggcggc atggtgaccc cggtgcacgc      540
cctgggcagg ggcatcagcc cgatgcaggg cctggtgatg gaggtcatcc tcaccttctc      600
cctgctcttc gtcacctacg ccatgatcct ggacccgcgg agccaggtcc gcgccatcgg      660
cccgctgctg acgggcctca tcgtcggcgc caacagcctc gccggcggca acttcaccgg      720
cgcgtccatg aacccggcac gctccttcgg cccggccctg gccaccgggg actggacaaa      780
ccactgggtc tactggatcg gcccgctgct cggcgggccc ctggcaggct tcgtgtacga      840
gtcgctgttc ctggtgcaga agatgcacga gccgctgctc aatggggaag tctgacgacc      900
atcagcccct gtgttgtggc gcatgcttca tgcttgtttc tgtaaaacag gtcattctct      960
gcaagcatgg tacatacatt ggccaaggta attagagagg cttgctgtaa agcagtagga     1020
ttgctggctg tagaaattgt tgatgggctt ttttttgggg tttcctgcca aggaattctt     1080
tcttttatat aatctcaaaa aagttttttt tttttggta tgggctgggt tctatcaagg      1140
gtttgttaag gctattagtt taccatgtag cagaaaaact agtgggacgt gaagtttttt      1200
cacgtacatt gtaatacttt ggtattttg tctaccagat gaaactggaa gtacagagca      1260
aaaacttctc tatc                                                        1274
```

<210> SEQ ID NO 187
<211> LENGTH: 1160
<212> TYPE: DNA
<213> ORGANISM: Sorghum bicolor

<400> SEQUENCE: 187

```
gcacgaggcg gcgtcggagc ccacgaccgc ttccgcccca gtccccaccg ccctcgaccc       60
cgattccccc aatccctgcc gcgaccgctg aaccctagcc tactccggcc atctgccgct      120
ggccccggcg atccccgcc atggcctccc ccgagggaac cacgtgggtc ttcgactgtc       180
ccctcatgga cgacctcgcg gtggccgccg acttcgcggc agccccgcg gggggatttt       240 tctgggcagc gccgccgtcg ctacagccgc aggtggtgca ggcgccggtc cagtctgtcg      300
ttgccgcgtc ggctcccaac ccatgtgtgg aaatcagtag ctctgtggac tgtggtcagg      360
gaaaagaaca gccaacaaat aaacgtccta ggtcagaaag taccgcagaa ccaagcacaa      420
aagcatccag ggagaaaatt agaagggata agctgaacga gagattcctg gaattgggtg      480
ccatttggga gccagggaaa actcctaaaa tggacaagtc agctatatta aatgatgcta      540
ttcgtgtagt aggtgaattg cgtagcgaag caaagagct caaggattca aatgagagcc       600
tacaagagaa gattaaagag ctaaaggctg agaagaatga gctgcgagac gagaagcaaa      660
ggctgaaggc cgagaaggag agcctggagc agcagatcaa gttcctgaat gcccgcccaa      720
gtctggtacc acaccaccca gtgatctcag cctctgcctt cactgctccc cagggccgg       780 cagtcgccgg gcacaagctg atgatgcctg tgcttggcta ccctggattc ccgatgtggc      840
agttcatgcc gccttctgat gttgacacct ctgatgaccc caagtcttgc ccacctgtgg      900
cgtaagcaag tgaagaggcg atgctgccct ccattgattc aagtctagat cgtgatcagt      960
ctgcagtgtt gttggtgtag ttgactccac tctccagaat ggaagggaag gttatatgtg     1020
tcggatggtg acatggggtg atctgatgac ccctttgtat attatatggt aaatgaataa     1080
attccgtgac cagttgcaaa tgaggattag cagactagct catgtctatt cctgcctttt    1140
```

```
tgtcgtataa accacgttgt                                                 1160
```

<210> SEQ ID NO 188
<211> LENGTH: 1242
<212> TYPE: DNA
<213> ORGANISM: Zea mays

<400> SEQUENCE: 188

```
ccacgcgtcc gggctacacg gcctatattc cgtactcgtg aacctcgtgc tgacgtgctc     60
acacagtcac tccgtttagc tcaaatcctt atcggcgact cggcgtcgga gctcacgacc    120
acgaccgctt ccacgccctc gaccccgaac ccccaatccc ggacgcgacc gctgaaccct    180
agcatactcc ggccatctgc tgccggcccc ggcgatcccc cgccatggcc tccccgagg     240
gcacaacgtg ggtcttcgac tgtcccctta tggacgacct cgcggtcgcc gccgacttcg    300
cggcagcccc cgcggggagga ttttctggg cagcgccgcc gtcgctgcag ccgcaggcgc    360
cagtgcagtc tgtcgttgcc gcgtcggctc ccaacccatg tatggaaatc agtagctctg    420
tggactgtgg tcaggaaaaa gaacagccaa caaataaacg tccaaggtca gaaagtacta    480
cagaatcaag cacaaaagca tccagggaga aaattagaag ggacaagctg aacgagagat    540
tcttggaatt gggtgccatt ttggagccag ggaaaactcc taaaatggac aaaacagcta    600
tattgagtga tgctattcgt gtagtaggtg aattgcgtag tgaagcaaaa aagctcaagg    660
attcaaatga gaatctccaa gagaagatta agagctgaa ggccgagaag aatgagctgc     720
gagacgagaa gcaaaggctg aaggccgaga aggagagcct ggagcagcag atcaagttcc    780
tgaatgcccg gccaagcctc gtaccacacc acccagtgat cccagcctct gcgttccctg    840
ctccccaggg gccagcagcc gccgccaggc acaagctgat gatgcctgtg attggctacc    900
ctggattccc gatgtggcag ttcatgccgc cttcagatgt tgacacctct gatgacccta    960
ggtcttgtcc tcctgtggcg tagaagccgt gcgaaatcct gttggaaaga ggcgatgctg   1020
ccttccattg attcaaatct tgatcggtcc gcagtgttgt tggtgtagtt gattccagaa   1080
ctgaagggga tgttacatgt gtcggacggt gacatggggt gatctgatga cccctttgta   1140
tattatatat ggtatggtat aaataaattc cgcgaccaga agctaatgtg gatcggtgga   1200
ttaacttatg ttctattctt gcctgtttgt cctataaccc ac                      1242
```

<210> SEQ ID NO 189
<211> LENGTH: 706
<212> TYPE: DNA
<213> ORGANISM: Saccharum officinarum

<400> SEQUENCE: 189

```
cgtagtgacc gggtcgaccc acgcgtccgc cgccctcgac cccgaatccc ccaatccctg     60
acgcgaccgc tgaaccctag cctactccgg ccatctgccg ctggccccgg cgatcccccg    120
ccatggcctc ccccgaggga accacgtggg tcttcgactg tccccttatg gacgacctcg    180
cggtggccgc cgacttcgcg gcagcccccg cgggggattt tttctgggcg cgccgccgt    240
cgctgcagcc gcaggtggtg caggcgccgg tgcagtctgt cgttgccgcg tcggctccta    300
accccccatg tgtggaaatt agtagctctg tggattgtgg tcaggaaaaa gaacaaccaa    360
caaataaacg tccaaggtca gaaagtactg cagaaccaag cacaaaagca tccagggaga    420
aaattagaag ggacaagctg aacaagagat tcctggaatg gggtgccatt gtggagccag    480
gggaaactcc taaaatggac aaatcagcta tattgaatga tgctattcgt gcagtaagtg    540
aattgcgtag cgaaacaaaa aagctgaagg actcaaatga gagtttgcag ggagaagatt    600
```

```
aaagagctga aggctgagaa gaatgagtcg cgagacgaga agcaaaggct gaaagccgag    660
aacgagagcc tggagcagca gatcaagttc ctgaatgccc gcccaa                    706
```

<210> SEQ ID NO 190
<211> LENGTH: 658
<212> TYPE: DNA
<213> ORGANISM: Brassica napus

<400> SEQUENCE: 190

```
gaactcatct catcgagaca gggaaacaaa ccctagttcg tcaagatggg gcgtatgcat     60
tcgagaggaa agggtatctc cgcatctgcg ttgccgtaca agcgctcacc tccgacatgg    120
ctcaagacca cggcccttga tgttgatgag tcgatctgca agtttgcgaa gaagggtttg    180
acaccatctc agattggtgt gattcttcgt gactctcacg gtatccctca ggtgaagagt    240
gtcaccggaa acaagatctt gcgtattctc aaagctcacg gtcttgcacc tgagattcct    300
gaggatctgt accatttgat caagaaggca gttgctatcc gcaagcactt ggagaggaac    360
aggaaggaca aggattccaa gtttaggttg attcttgttg agagcaggat ccaccgtctt    420
gcccgttact acaagaagac caagaagctt cctcctgtct ggaagtacga gtctactact    480
gcttctaccc ttgtggctta gatcatggtc aagagcacta ctgtttcttt tggctgtctt    540
attatgaact tagtttctat gcttctcagt acttggtttg gtcaagtgac aatgacgttt    600
ggatgatttc aaggaaccaa tgtgtttcaa tctatggtca gaattgctta tgccgggt     658
```

<210> SEQ ID NO 191
<211> LENGTH: 671
<212> TYPE: DNA
<213> ORGANISM: Brassica napus

<400> SEQUENCE: 191

```
gctcttcacg cgcagctgct acgagctcat cgagacagtg aagaaactct tagttgttca     60
agatggggcg tatgcactca gaggaaaggg gaatctccgc atctgctttg ccgtacaaac    120
gttcacctcc gacatggctc aagaccaccg cactcgatgt tgatgagtcg atttgcaagt    180
ttgcaaagaa gggtttgaca ccatctcaga ttggtgtcat tctccgggac tctcacggta    240
tccctcaggt caagagcgtt accggaaaca agatcttgcg tattctcaaa gcacacggtc    300
ttgctcctga gattcctgag gatctgtacc atttgatcaa gaaagcagtt gctatccgca    360
agcacttgga gaggacagg aaagacaagg attccaagtt caggttgatt cttgtcgaga    420
gcaggatcca ccgccttgct cgctattaca gaagaccaa gaagcttcct ccagtctgga    480
agtacgagtc tactactgcc tccacgcttg ttgcttagag agcatgaagt gcatggattg    540
aagtggagtt gttggtcgtt tctattcgta tcaactagag ttgttttttt ttctcatttt    600
cgttttattg tttgtttttt caagttacaa ttgtggtttt gatgatttca aggaaaaaaa    660
ctttttaact t                                                          671
```

<210> SEQ ID NO 192
<211> LENGTH: 713
<212> TYPE: DNA
<213> ORGANISM: Solanum tuberosum
<220> FEATURE:
<221> NAME/KEY: misc_feature
<222> LOCATION: (13)..(13)
<223> OTHER INFORMATION: n is a, c, g, or t

<400> SEQUENCE: 192

```
gttgctgtac cgncgcacat cggagcacgc cgtcagccac catgggtcgt atgcacagtc     60
```

| | |
|---|---|
| gaggtaaggg tatttcagct tcagcacttc cgtataagag gactccaccg agttggttga | 120 |
| aaacatctgc tcccgatgtt gaggataata tatgcaagtt tgccaagaag ggtttgacac | 180 |
| cttctcaaat tggtgttata cttcgtgatt ctcatgggat tgctcaggtg aagagtgtaa | 240 |
| ctggtagcaa gattctcaga attttgaagg ctcacggact tgctcctgag attccggagg | 300 |
| atctctatca ccttatcaag aaggccgttg caatccggaa gcatcttgag agaaacagga | 360 |
| aagacaaaga ttccaagttt aggttgattc ttgttgagag caggattcac cgacttgctc | 420 |
| gttactataa gaaaaccaag aagcttcccc cagtctggaa gtatgaatct accaccgcca | 480 |
| gtactctcgt ggcatagaga agactctgct tttgcggtca aattttgcct ccaaagttca | 540 |
| atattaagtc ggaactgcca ggatgcttaa ttgagaaata aaactgttaa gatattggtg | 600 |
| atgatttagt tgtttttga gttggtattt aattcccttt tctttcttta gatgttgtga | 660 |
| tatattcaaa tcttggctgc ttatgtttaa tagttgatct taccaaaaaa aag | 713 |

<210> SEQ ID NO 193
<211> LENGTH: 694
<212> TYPE: DNA
<213> ORGANISM: Gossypium hirsutum

<400> SEQUENCE: 193

| | |
|---|---|
| aagcaagaaa ggagcagagg ttaattaaac cgagagagaa gcagccgtaa agctcgaaac | 60 |
| tctgtcgcca tgggtcgtat gcatagccga ggtaagggta tttccgcatc tgctcttccg | 120 |
| tacaaaagaa ctccacctag ttggctcaag atctcctctc aagatgtgga ggagaacatt | 180 |
| tgcaagtttg cgaagaaggg tttgacccca tctcaaattg gtgtcattct ccgtgattca | 240 |
| catgggattg ctcaggtgaa gagtgttacg ggcagcaaga ttttgcggat actgaaagcc | 300 |
| catggtctcg ctcctgaaat tcccgaagat ttgtaccacc tgattaagaa agctgttgcc | 360 |
| atcagaaagc atcttgagag gaaccgcaaa gacaaggatt ccaagttccg gttgatcctg | 420 |
| gttgagagca gaatccatcg ccttgcccgc tattataaga agacaaagaa gcttccaccc | 480 |
| gtctggaaat acgagtcgac tactgccagc acacttgtgg cctaagggaa gacactgctg | 540 |
| gaaccagctt cttgggcttt gattgatgga cgcctggata tgggttggag tagtaaagtt | 600 |
| ttaattacat gctatattta tgcttttaaa gaaccagttc acattatggt tggaaattga | 660 |
| tatacttagg agggataata ttatgtttag tgat | 694 |

<210> SEQ ID NO 194
<211> LENGTH: 757
<212> TYPE: DNA
<213> ORGANISM: Gossypium hirsutum

<400> SEQUENCE: 194

| | |
|---|---|
| tgagccagcc agccagccag ccaagcaatc gagctcggaa ctccgcaacc atgggtcgta | 60 |
| tgcacagccg aggtaagggt atttccgcat ctgctctgcc ctacaagagg actccaccaa | 120 |
| gttggttgaa gatctcttct caagatgtgg aggagaacat ttgtaagttt gcaaagaaag | 180 |
| gtttgacccc atcacaaatt ggtgtcattc tccgtgattc tcacgggatt gctcaggtga | 240 |
| agagtgttac aggcagcaag attttgcgga tactgaaagc ccacggactt gctcctgaaa | 300 |
| tccccgagga tctgtaccac ttgatcaaga agccgttgc catcagaaag catcttgaga | 360 |
| ggaacaggaa agacaaggat tccaaattca ggttgatctt ggtcgagagc agaatccatc | 420 |
| gtcttgcccg ctattacaag aaaacaaaga agctcccacc cgtgtggaaa tatgagtcaa | 480 |
| ccaccgccag tactcttgtg gcttagggca gccacatttt tgaaccagtt tcctggtgct | 540 |

-continued

```
tcaatagcga ttcgcctttg acttttagct aatggtggtt tgaaattgag aggggaaata    600
ttatgtttag tgtattagaa taattgatat ttttttcgtt tgaaatgttt ttgaatctta    660
atggttacat ggaattgttt tcttaatatt tttggcttac aaattttaat gtagtatgaa    720
attaaattaa ataattcga aggagaatat taatact                              757

<210> SEQ ID NO 195
<211> LENGTH: 767
<212> TYPE: DNA
<213> ORGANISM: Lycopersicon esculentum

<400> SEQUENCE: 195
aaaccctaga agaagaaaga gccttttaag gtttgtcaac ttccatcaac caaacgaagc     60
tacaatttga gcaacacagt tcagtgagct cactctaatc ttcgccatgg gtcgtatgca    120
cagtcgcggt aagggtatct cagcgtcggc tcttccttac aagagaactc ctccaagttg    180
gcttaagatc tctgctccag atgtggagga caatatctgc aagtttgcga aaaaggact    240
gacaccttca caaattggtg tgattcttcg tgattctcat ggaattgctc aagtcaagag    300
tgtcaccggg agcaagattt tgcgtatcct caaagctcac ggacttgctc ctgagattcc    360
ggaggatcta taccacctta ttaagaaggc agttgccatc aggaagcatt tggagaggaa    420
cagaaaggac aaggattcca agttccgctt gattttggtg gagagtagga ttcaccgcct    480
tgctcgttat tacaagaaaa ctaagaagct accacctgtc tggaaatatg agtctaccac    540
agcaagtaca ctagtagctt aaactgagac atggatggat tattagcttt gagaagaaag    600
attgatcagc tgaagtcttt tcttctctat gtattcgaat agttctcagg tccatttttt    660
tgaattctga tacttataga tgctttaatt tgggtattga tgtcaatttc tttcgactac    720
ctcgatgaat atcaagcctc tactcagcct ttttcttgtt caccctc                  767

<210> SEQ ID NO 196
<211> LENGTH: 717
<212> TYPE: DNA
<213> ORGANISM: Lycopersicon esculentum

<400> SEQUENCE: 196
cggccggggg tcattttaga gatttcgctg ctacttatag ccaatcggag cgcggcagcc     60
accgtcacac caccaaccag ccaccatggg tcgtatgcac agtcgaggta agggtatttc    120
agcttcagct cttccataca agaggactcc accaagttgg ctgaaaatct ctgctcctga    180
tgttgaggat aacatatgca agttcgccaa aaaaggtttg acaccttctc aaattggtgt    240
tattcttcgt gattctcatg ggattgctca ggtgaagagt gttactggta gcaagattct    300
cagaattttg aaggctcatg gacttgctcc cgagattccc gaggatctct accaccttat    360
caagaaagca gtggcaatca ggaagcatct tgagaggaac agaaaagaca aggactccaa    420
gtttagattg attcttgttg agagcaggat tcatcgactt gctcgctact ataagaaaac    480
aaagaagctt ccaccagtct ggaagtacga gtctaccacc gcgagtactc ttgtggctta    540
gagaaggtca tggattggga ttacaagttt gttggtcaag tcccatcttc ataattacag    600
acttaagttg ttttttgtatg agagaccagg ttgtttgaaa ctttgaatgg aacaaatttt    660
gttttatgag agatgataag gggaacgttt cctactttaa atttgcatcc aattctt       717

<210> SEQ ID NO 197
<211> LENGTH: 767
<212> TYPE: DNA
<213> ORGANISM: Lycopersicon esculentum
```

```
<400> SEQUENCE: 197
gtccattcta gggtttcctt cttcagagct aaccggacag cagccccaga aacacaccgg    60
cagcgaagat gggtcgtatg cacagtcgag gtaagggtat ttctgcttca gcactcccat   120
acaagaggac tccaccaagt tggctcaaaa tatctgcacc agatgttgaa gataacatct   180
gcaagtttgc caaaaaaggt ttaacaccct ctcaaattgg tgttattctt cgtgattccc   240
atggcattgc tcaggtgaag agtgtaactg gtagcaagat tctcagaatt ttgaaggctc   300
atggacttgc tcctgagatt cccgaggatc tctaccacct tatcaaaaaa gcagttgcaa   360
tccggaagca tcttgagaga aacaggaaag acaaggattc caagtttagg ttgattcttg   420
ttgagagcag gattcaccga cttgctcgct actacaagaa aacaaaaaag cttccaccag   480
tctggaagta tgaatctacc actgccagta ctcttgtggc ataagagatg acaaaaggag   540
cattcagagt gctactttct ttgccaagtc atatcttaga aattctacat taagctgttt   600
tggcatggcc aggatacttg atttggtgaa caaattatgt actcgaggag atgatagggg   660
gcttcacgta atttcttgtt tgagattttg acattgagac ttgttatctg tggtatactt   720
attttagttt agctatgttt taattatcat cttgtgaaaa tctcgat                  767

<210> SEQ ID NO 198
<211> LENGTH: 820
<212> TYPE: DNA
<213> ORGANISM: Lycopersicon esculentum

<400> SEQUENCE: 198
aaatccttcc gcacaaccaa aggtaagcct ccattgcaga ccaccagtag cctccgccat    60
catgggtcgt atgcacagtc gtggtaaggg tatttcagct tctgctctcc cttacaagag   120
aactcctcct agttggctca agatctctgc tccagatgtt gaggacaaca tctgcaagtt   180
cgctaagaaa ggattgaccc cttcacagat tggtgtgatt cttcgtgatt ctcatggaat   240
tgcacaagtg aagagtgtta ctggtagcaa gatcttgcgt atcctcaagg cacatgggct   300
tgcacctgag attccagagg atttgtacca cctgattaag aaggctgttg ccattaggaa   360
gcatttggag aggaacagga aggataagga ttctaagttc cgtttgattt tggtggagag   420
caggattcat cgccttgctc gttattacaa gaaaacaaaa aagctcccac ctgtctggaa   480
atacgaatct accactgcta gcacacttgt ggcataggct gagacgtgag ctggagtagc   540
tttggctgat cgcaatatgt agttttcttg tgtcatgaac tgtttgctat atccaatttt   600
gtttgattta atcatgctac tcaatggaaa atagttttct ggatagtatt tgctcctatt   660
tttaccaagt gttaagcata gatgctttta tttagatatt caaatgaatg acttgtttct   720
caagctcatg gtggtaatct gtaatttgga ttgctgaaaa ttgtggttta atgcctcatc   780
attctatgtt catggcagtg aagtaccact tttaaagcag                          820

<210> SEQ ID NO 199
<211> LENGTH: 834
<212> TYPE: DNA
<213> ORGANISM: Solanum tuberosum

<400> SEQUENCE: 199
ccgaccgaag ctacgctttg agcaacacag ttcagtgagc tcactctaat cttcgccatg    60
ggtcgtatgc acagtcgcgg taaaggtatc tcagcgtcgg ctcttcctta caagagaact   120
cctcccagtt ggcttaagat ctccgctcca gatgttgagg acaatatctg caagtttgcg   180
aaaaaaggat tgacaccttc acaaattggt gtgattcttc gtgattctca tggaattgct   240
```

```
caagttaaga gtgtcactgg gagcaagatt ttgcgtatcc tcaaagctca cggacttgct      300
cctgagatcc cggaggatct ataccacctt attaagaagg cagttgccat caggaagcat      360
ttggagagga acagaaagga caaggattcc aagttccgct tgattttggt ggagagtagg      420
attcaccgcc ttgctcgtta ttacaagaaa actaagaagc ttccacctgt ctggaaatat      480
gagtctacca cagcaagtac acttgtagct taaactgaga catggatgga ttattagctt      540
tgagaagatt gatcagctga agtcttcttc tctatgtatt cgaatagttc tcaggtccat      600 tttttttgaat tttgatactt aatggtgata gtttctggat actttctcca acttttacta     660
aatgttatgc atagatgctt taatttgggt attgatgtca atttctttcg actactcgat      720
aaatatccag ctctactcaa ccttttctgg ttcaccccaa caaaaaaaaa aaaaaaaatg      780
cccaacttta cccgtggcaa tgcccgcgca gacttaaaca agatgaagtg ttta           834

<210> SEQ ID NO 200
<211> LENGTH: 815
<212> TYPE: DNA
<213> ORGANISM: Solanum tuberosum
<220> FEATURE:
<221> NAME/KEY: misc_feature
<222> LOCATION: (28)..(28)
<223> OTHER INFORMATION: n is a, c, g, or t

<400> SEQUENCE: 200
attcttcata gcgaaccggg acagcagncc caggaaacac acctgcagcc aagatgggtc       60
gtatgcacag tcgaggtaag ggtatttctg cttcagcact cccatacaag aggactccac      120
caagttggct caaaatatct gcaccagatg ttgaagataa catctgcaag tttgccaaaa      180
aaggtttaac accctctcaa attggtgtta ttcttcgtga ttcccatggc attgctcagg      240
tgaagagtgt aactggtagc aagattctca gaattttgaa ggctcatgga cttgctcccg      300
agattcccga ggatctctac cacccttatca aaaaagcagt tgcaattcgg aagcatcttg      360
agagaaacag gaaagacaag gattccaagt ttaggttgat tcttgttgag agcaggattc      420
accgacttgc tcgctactac aagaaaacaa aaaagcttcc accagtctgg aagtatgaat      480
ctaccactgc cagtactctt gtggcatgag agaagacaac gggagcattc agattgctac      540
tttcttcgcc aagtcatatc ttagatattc tatattaagc tgttttggca tgtccaggat      600
acttgaaatc gtaaacaaaa ttatgtactc gaggagatga tagggcctcc ttttagtttc      660
ttgtttgaga ttttgacatt gagactttgt tatctgtggt atacttcttt tggtttagct      720
atgttttaat tatcatgttg cgaaattctc ggtaaagcta gaaatgctgg gatatggtta      780
tactcgccgc tctggtctgt ggacctgtgc ccagc                                 815

<210> SEQ ID NO 201
<211> LENGTH: 959
<212> TYPE: DNA
<213> ORGANISM: Solanum tuberosum

<400> SEQUENCE: 201
ctttcaagaa aaatccttcc gcacaaccca aggtaagcct ccattgcaga ccaccagtcg       60
ccaaccctaa ctccgccatc atgggtcgca tgcacagtcg tggtaagggt atttcagctt      120
ctgctctccc ttacaagaga actcctccta gttggctcaa gatctccgct ccagatgttg      180
aggacaacat ttgcaagttc gctaagaaag gattgacccc ttcacagatt ggtgtgattc      240
ttcgtgattc tcatggaatt gcacaagtga agagtgttac tggtagcaag atcttgcgta      300
tcctcaaggc acacgggctt gcacctgaga ttccagagga tttgtaccac ctgattaaga      360
```

```
aggctgttgc catcaggaag catttggaga ggaacaggaa ggataaggat tccaagttcc    420
gtttgatttt ggtggagagc aggatccatc gccttgctcg ctattacaag aaaacaaaaa    480
agctcccacc tgtctggaaa tacgaatcta ccactgccag cacacttgtg cataggtg     540 agacttgagc tggagtagct ttggctgatc gcaatatgta gttttcttgt gtcatgaatt    600
gtttgctaaa tccaattttg tttgatttaa tcatgctact caatggaaga tagttttctg    660
gatagtattt gctcctattt ttaccaagtg ttaagcatag atgcttttat ttagatattc    720
gaatgaatga cttgtttctc aagctcatag tggtaacatg aaagccaata tccaactggt    780
ctggctgctc tgtaatttgg attgctgaaa attatggttt aatgctcttc actttatgtg    840
catggcagtg aagtaccatt tttaagccta aggggtcgt tattctgtga ttatattctt     900
gggattgtaa tccttcgact aagcttgagt tatttcatga ttaagcttgg attaaattt     959

<210> SEQ ID NO 202
<211> LENGTH: 940
<212> TYPE: DNA
<213> ORGANISM: Solanum tuberosum

<400> SEQUENCE: 202
agccaaccgg agcgcggcag ccaccgtcac accgccaaac agccaccatg ggtcgtatgc     60
acagtcgagg taagggtatt tcagcttcag ctcttccata caagaggact ccaccaagtt    120
ggctgaaaat ctctgctcct gatgttgagg ataacatctg caagtttgcc aaaaaaggtt    180
tgacaccttc tcaaattggt gttattcttc gtgattctca tgggattgct caggtgaaga    240
gtgtcactgg tagcaagatt ctcagaattt tgaaggctca tggacttgct cccgagattc    300
ccgaggatct ctaccacctt atcaagaaag cagtggcaat caggaagcat cttgagagga    360
acaggaaaga caaggactcc aagtttagat tgattcttgt tgagagcagg attcatcgac    420
ttgctcgcta ctataagaaa acaaagaagc ttccaccagt ctggaagtac gagtctacca    480
ccgcgagtac tcttgtggct tagagaagat catggattgg gattacaagt ttcttggtca    540
agtcccatct tcaaaattac agacttgagt tgttttgta tggccgggt gtttgaaact     600 atgaatggaa caaattttgt tttatgagag atgataaggg ttacatttcc taaaaaaaaa    660
aacctcgtgc cgaattcggc acgaggatga aaactgccac tcaactcgat cctctcaaag    720
ttgaatttat caatgatgta cattaacaaa atccaatatc aaagtatgta ttcctaaatt    780
attgtaatgc tttcataata cttaattcac tttcttttcc aaaatattcg ggtccaatat    840
ttttgcagtg attgtggcat gtacacatgt atattcgatg aatgtatacg caatgacgtt    900
ttttatatgg gtcacattga cattgatgtc aaatatcctc                         940

<210> SEQ ID NO 203
<211> LENGTH: 765
<212> TYPE: DNA
<213> ORGANISM: Capsicum annum

<400> SEQUENCE: 203
gctttgagaa aaaatccttt gcgaacaacc aaaggtaagg cagaccaccc caaagtaagg     60
catcatgggt cgcatgcaca gtcgtggtaa gggtatttca gcttcggctc tcccttacaa    120
gagaactcct cctagttggc tcaagatctc cgctcctgat gttgaggaca catttgcaa    180 gttcgctaag aaaggattga caccttcaca gattggtgtg attcttcgtg attcacacgg    240
aattgctcaa gttaagagtg tcactggtag caagatcttg cgtatcctca aggcccacgg    300
gctcgcacct gagattccag aggatctgta ccacctgatt aagaaagctg ttgccattag    360
```

```
gaagcatttg gagaggaaca ggaaggacaa ggattccaag ttccgattga ttttggtcga    420
gagcaggatc catcgccttg ctcgctatta caagaaaact aaaaaactcc cacctgtctg    480
gaaatacgaa tctaccactg ccagcacact ggtggcatag ggtgaaacgc gagctggagt    540
agctttggct gatggcgata tgtagttttc tcgtgtcatt gcttacttgc taaatccaat    600
tttgtttgat tcgatcgtgc tactcaatgg aagagagtct tgctgtgttt acccaagtat    660
tgaggataga tgctttcatt cacatattca tatgaatgac tttgtttctc aagctcaaaa    720
aaccaatgtc catctggtat ggctgctccc taatttggcc tgcag                    765
```

<210> SEQ ID NO 204
<211> LENGTH: 723
<212> TYPE: DNA
<213> ORGANISM: Arabidopsis thaliana

<400> SEQUENCE: 204

```
gagccagaat tagggtttct ctttgtcttc agcagtcagt gcgcatccgt aggagaaaag     60
tgtgagaatc tgccaccatg gtcgtatgc acagtcgagg aaagggtatt tcagcctctg    120
cgttgcctta caagagatcg tctccgagct ggctcaagac cacctctcag gatgttgatg    180
aatcaatctg caaatttgcc aaaaagggat tgacccctt ccagattggt gtgattctcc    240
gtgactctca cggtatccct caggtcaaga gtgttactgg aagcaagatc ttgaggatac    300
tcaaagctca tggccttgct cctgagatcc ctgaggatct gtaccatcta attaagaagg    360
ctgttgccat ccgtaaacat ctcgagagga acaggaagga caaggattcc aagttcaggc    420
tcatcttggt tgagagcagg attcaccgcc tcgctcgcta ttacaagaag accaagaagc    480
tccctcccgt ctggaagtac gaatccacta ccgcgagcac ccttgtggct aagctggag    540 tctggaggag gattctacta gtctgttgct tcccttttgt tttgatgaat ctcaactttt    600
agtcttaatg tgtcagcagg attttttgtgt ttgcctctct ttttttttccg gaatcttatg    660 ctcccttgtt aagagaatc gtatgatctt gaatttacta ttgaatatgc ttttgcatca    720
aaa                                                                  723
```

<210> SEQ ID NO 205
<211> LENGTH: 669
<212> TYPE: DNA
<213> ORGANISM: Brassica napus

<400> SEQUENCE: 205

```
gacacagtcg ccgccggaaa aaaccgagg aagaaccatc ttcagagaaa gtacactccg     60
tccaccgccg tcgtcatggg ccgactccac tctaaaggta agggaatctc agcttctgct    120
ttgccgtaca agcgatcacc tccaagttgg ctcaagacaa cctctcagga tgttgatgag    180
tcaatctgca gtttgcgaa gaagggtttg actccatctc agattggtgt cattcttcgt    240
gactctcacg gtatcccaca agtgaagagt gtaaccggaa caagattttt gagaatcttg    300
aaagctcatg gtcttgctcc tgagatccca gaggatttgt atcacctgat caagaaagca    360
gttgctatcc gcaagcacct tgagaggaac aggaaagaca aggattccaa gttcaggttg    420
attctcgtgg agagcagaat ccaccgtctt gctcgttact acaagaagac caagaagctc    480
ccacctgtct ggaagtatga gtccaccacg gcaagcactc ttgtggctta aggaaaagca    540
tagagtaggt caaagtcatt catgagcgac tatgtcatta caagggactt ggtatctcat    600
ttctctagtt ttgatgtgtt acaacttaca aggcgatttg gaatttaatg aaaactcttt    660
gttcttgtc                                                            669
```

```
<210> SEQ ID NO 206
<211> LENGTH: 675
<212> TYPE: DNA
<213> ORGANISM: Brassica napus

<400> SEQUENCE: 206
gaagcgcagt cgcagccgga cgaagaacag acagcaacaa acgtcggcat ggggcgactc      60
cactccaaag gtaagggaat ctcagcatct gctttgccgt acaagcgttc accccgagc     120 tggctcaaga caacctccga ggatgttgat gaatccattt gcaagtttgc gaagaagggt    180
ttgactccgt ctcagattgg tgtgattctt cgtgactctc acggtatccc tcaggtgaag    240
agtgttaccg ggaacaagat tctgagaatc ttgaaagctc atggtcttgc tcctgagatc    300
cctgaggatc tgtaccacct gatcaagaaa gcagttgcta ccgcaagca cttgagagg     360 aacaggaagg acaaggactc caagttcagg ttgattcttg ttgagagcag aatccaccgt    420
cttgctcgtt actacaagaa gaccaagaag ctccctcccg tctggaagta cgagtcaact    480
accgcaagca ctcttgtggc ttgagtaatc atagagcttg tcaaagtcct tcatgaacta    540
caatttgatt gctgcatttg caactctatt tctatgacga tggattttgt atctgttttt    600
tttatggttt ttgtggggtt tacaacttaa caatgcgaat tttgaattga atgaatactt    660
ttgataaaaa aaaat                                                     675

<210> SEQ ID NO 207
<211> LENGTH: 713
<212> TYPE: DNA
<213> ORGANISM: Brassica napus
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t

<400> SEQUENCE: 207
ctctttagcg cagtcgcagc ccgaccaaac cgaagaagaa ccttctcaga gtaaagcaat      60
ctccgttaac ttacgtcagc atggggaggc tccactctaa aggtaaggga atctcagcat    120
ctgctttgcc gtacaagcgc tcaccccga gctggctcaa gacaacctcc caggatgttg    180
atgagtccat ttgcaagttt gcgaagaagg gtttgacacc atctcagatt ggtgtcattc    240
ttcgtgactc tcacggtatc cctcaggtga agagtgttac cggaaacaag attttgagaa    300
tcttgaaagc tcatggtctt gctcctgaga tccctgagga tctctaccac ctgattaaga    360
aagcagtggc tatccgcaag caccttgaga ggaacaggaa agacaaggac tccaagttca    420
ggttgattct tgtcgagagc agaatccacc gtcttgctcg ttactacaag aagaccaaga    480
agctccctcc cgtttggaaa tacgagtcta ccacagcaag cactcttgtg cttaaggaa    540 tcatagagct ggtcaaagtc tttcatgaac atccatttca tttccattgc aactcaaaag    600
ttctatgaca atagactttg tatctgtttt tgatagtttt gattattttg aatttaatga    660
aaactctcgt tgatgttttg tttcatttat cttaacgagn ctacaattgn gcc            713

<210> SEQ ID NO 208
<211> LENGTH: 618
<212> TYPE: DNA
<213> ORGANISM: Gossypium hirsutum

<400> SEQUENCE: 208
```

-continued

| | |
|---|---|
| aatcagccga gctcgaaact ctgccaccat gggtcgtatg cacagccgag gtaagggtat | 60 |
| ttccgcatcc gctttgcctt acaggagaac tcctcctagt tggttgaaga tctcttctca | 120 |
| agatgttgag gagaacattt gcaagtttgc aaagaagggt ttgactccat ctcaaattgg | 180 |
| tgtcattctc cgtgattctc atggcattgc tcaggtgaag agtgttactg gcagcaagat | 240 |
| tttgcgaata ttgaaagccc atggtcttgc tccagaaatc cctgaggatc tgtaccacct | 300 |
| gattaagaaa gcggtagcca tcagaaagca cctcgagcgg aacaggaaag acaaggattc | 360 |
| caagtttagg ttaatcttgg ttgagagcag aattcaccgt cttgcccgtt attacaaaaa | 420 |
| gacaaagaag ctaccaccag tgtggaaata tgaatctacc actgccagca ctcttgtggc | 480 |
| ttagaggtgg cacagtttga accatcttcc aagcgctgca gttgacattc tccttgatgc | 540 |
| agggctaaac ttttggtatt tatgctttta aaatttaaag aactagttca tttgtggttt | 600 |
| gaaaatgaga tacttggg | 618 |

<210> SEQ ID NO 209
<211> LENGTH: 727
<212> TYPE: DNA
<213> ORGANISM: Gossypium hirsutum

<400> SEQUENCE: 209

| | |
|---|---|
| gtttcttttc tcttagcaat tagcaggcaa tacagaatca gagtgaagca gctaagcttg | 60 |
| gaattcttcc atcatgggtc gtatgcacag ccgaggtaag gggatttctg catctgccct | 120 |
| gccttacaag aggactccac ctagttggtt gaagatctcc tctcaagatg ttgaggataa | 180 |
| catttgcaag tttgctaaga agggtttgac cccatctcaa attggtgtca ttctccgaga | 240 |
| ttctcatggg attgctcagg tgaagagtgt tactggcagc aagattctgc gcatactgaa | 300 |
| agcccatggt cttgctcctg aaatacccga ggatctgtac cacctgatta agaaagccgt | 360 |
| tgccatcaga aagcatcttg agaggaaccg aaaagacaag gattccaagt ttaggttgat | 420 |
| cttggttgag agcaggatcc accgactcgc ccgctattat aagaagacaa agaagctgcc | 480 |
| accagtgtgg aaatatgagt ctactactgc cagcactctt gtggcctaga taatcaaat | 540 |
| tttgaactgt cttcctgtgc ttcgattgat attcttctgg atcggctagg aggagttgga | 600 |
| cttttgtat tacgttctat taatgccgta aaagaactag tccacttaat ttgaagttga | 660 |
| gatacttaat gtgttaaatc ttatgtttag tatattggaa taattcatct ttcatttcat | 720 |
| ttttcat | 727 |

<210> SEQ ID NO 210
<211> LENGTH: 1125
<212> TYPE: DNA
<213> ORGANISM: Gossypium hirsutum
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (63)..(63)

<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 210

| | | | | | |
|---|---|---|---|---|---|
| atcacacatt | ctatatatcg | aatgttcaaa | ctattaattc | nntnnnttna | aaatagaaca | 60 |
| ntngtangaa | acaattggag | ctcccgcgca | cggctgtcca | cactagtgca | tccaaataat | 120 |
| tcggcccgag | gtacttcgtc | acaatctcgg | gaaagagaga | agcctcacca | ccgctgccgc | 180 |
| agccaccatg | ggtcgtatgc | acagtcgcgg | taagggtatt | tcagcctcag | ctctgcctta | 240 |
| caagaggacc | ccgccaagct | ggctcaagat | ctcttctcaa | gatgttgagg | aaaacatttg | 300 |
| caagttcgca | agaaaggct | tgaccccatc | tcagattggt | gtcattctcc | gtgattctca | 360 |
| tggtattgct | caagttagga | gcgttactgg | cagcaagatc | ttgcgtatcc | tcaaggctca | 420 |
| tggtctggcc | cctgaaattc | ctgaggattt | gtatcacctt | atcaagaagg | cagttgccat | 480 |
| ccgcaagcat | ttggagagaa | acaggaagga | caaggattcc | aagttcaggt | tgatccttgt | 540 |
| tgagagccgg | attcacaggc | ttgctcgcta | ctacaagaaa | acaaagaagc | ttccccggt | 600 |
| ctggaaatac | gaatctacaa | cagccagcac | tctcgttgct | taagttaggc | atgtggggtg | 660 |
| gtgcaatttt | gtgggaatcc | gggtttgatg | ttgatgctac | ggtggaagct | agattgtgtt | 720 |
| ttgttgttct | agtgagatgt | cctgatataa | gactttaatt | atagctgtta | aaatttttgt | 780 |
| tatgcttgga | aaagaaagtc | gaaaacttgt | tttacttatg | agattgtact | tgttttcttt | 840 |
| tcgtccattt | gaaattttaa | gcaagaaatc | tttgaatttt | gaaaccctag | tacacccttt | 900 |
| tcctataagg | gttctcgaaa | tggaaagggt | tggtgtttga | agaggcattt | ttgtgttcaa | 960 |
| catcggtttt | gttcaaaacc | ttcacatgga | ctttggtttt | aaaacaattt | ctccttcatc | 1020 |
| tccttcaagg | tgctgacatg | ctatgttgaa | cgtataaatt | atttgttgta | aactagcgta | 1080 |
| gtttgtacaa | tttatggtat | taatttatta | acataatttt | agtgt | | 1125 |

<210> SEQ ID NO 211
<211> LENGTH: 784
<212> TYPE: DNA
<213> ORGANISM: Arabidopsis thaliana

<400> SEQUENCE: 211

| | | | | | |
|---|---|---|---|---|---|
| gcacgagatt | ctctgaagcg | cagcagcagc | cgtaagaaag | aaaccgagga | agaacgatct | 60 |
| cagtgagagg | acgatcactt | cgccgtcgca | gtcatgggtc | gaatgcatag | tagaggtaag | 120 |
| ggtatctcgg | catctgcttt | gccgtacaag | cgttcatctc | cgagctggct | caagacaacc | 180 |
| cctcaagatg | ttgatgagtc | catctgcaaa | tttgcgaaga | agggtttgac | cccatcgcag | 240 |
| attggtgtca | ttcttcgtga | ctctcacgga | attccacagg | tgaaaagtgt | tactggaagc | 300 |
| aagattctca | gaattttgaa | agctcatggt | cttgcacctg | agatccctga | ggatctgtat | 360 |
| cacttgatca | agaaagctgt | tgctatccgc | aagcatcttg | agaggaacag | gaaagataag | 420 |
| gattccaaat | tcaggctgat | tcttgtagag | agcagaatcc | atcgtcttgc | tcgttactac | 480 |
| aagaagacca | agaagctccc | acccgtctgg | aagtacgagt | ctacaactgc | aagcactctt | 540 |
| gtggcttgag | aagaatagag | ttgatcatgt | ccttcaagaa | ggaccatttc | attgtctgca | 600 |
| ttgcaactca | aagctcttct | tcttttgaac | ctatgtatct | gttttcgcta | gttttgatgg | 660 |
| gttacaactt | gctatgagat | tttgattta | gggaacgaat | ttgtttatgc | gaatctttcc | 720 |
| attatcgtta | cagcttatct | ttcaattaac | gttaattatc | gttctcagag | aatttttaca | 780 | gact                                                              784

<210> SEQ ID NO 212
<211> LENGTH: 1016
<212> TYPE: DNA
<213> ORGANISM: Glycine max
<220> FEATURE:
<221> NAME/KEY: misc_feature
<222> LOCATION: (6)..(6)
<223> OTHER INFORMATION: n is a, c, g, or t

<400> SEQUENCE: 212
ccgggnaatt cggccttacg gccggggggtt tcagagtggt ggagtgtgca gaagagcgtc    60
gcagtcgcaa ccctaatcag aagaagcgca gcttcaagcg agtgacagcc accagccatg   120
ggtcgtatgc acagccgcgg taagggtata tcctcttctg cttttgccta caaaaggaca   180
cctcctagct ggctcaagat ctcttcgcaa gatgtcgaag aaaatatctg caagtttgcg   240
aagaaaggtt tgaccccgtc tcagattggt gtcattctca gagattctca cggtattgct   300
caggtcaata gcgtcactgg cagcaaaatc cttcgcatcc tcaaagctca cggacttgcg   360
cctgaaattc cagaggacct gtaccatttg attaagaagg cagtttcaat taggaagcat   420
cttgagagga acaggaagga caaggactcc aagttcaggt tgattcttgt tgagagcaga   480
atccaccgac ttgctcgcta ttacaagaag actaagaagc tcccaccagt ctggaagtac   540
gaatcaacaa ctgctagcac tctggttgct tagagaatgt atcaactttc atgggttttg   600
ctaccgtgca gtcgccgttg agctagcaat ttgcgatatc attttgatgt ttatttgaag   660
gctggatagg ttatgtggct taattttgtt aagaacctat ggtttgactg ggaaagataa   720
tttaactagt taagtcaatt tatcaatgtg gtgttctttt tcttttagcc gttggaggtt   780
gtcttttaaa gagatgacta tggttttttgg ctttatttc aagtaatata tatgcttaga   840
agatttgaag gatcgtattc tttattgctt atgcattcaa ttggtttcca aaggaaaact   900
attacttgta actgaacttg agttcataaa gtcaagttca atcaaattcc acttcttaaa   960
atgtaatcca tacagacact aaggttttca cgtcatttcc ttatttaagc gtttct       1016

<210> SEQ ID NO 213
<211> LENGTH: 760
<212> TYPE: DNA
<213> ORGANISM: Capsicum annum

<400> SEQUENCE: 213
gagagagaga gagagagaga gagagagaga gagagagaga gagagagaga gagagagaga    60
gagagagaga gagagagaga gagagagaga gagagagaga gagagagaga gagagagaga   120
gaggccaacc gaacagcagc ctctcccccc ctccttcccc actcaccaca aacacacagc   180
cagccatcat gggtcgtatg cacagtcgag gtaagggtat ttctgcttca gcactgccat   240
acaagagaac tccaccaagt tggctgaaaa tatctgcacc agatgtcgaa gataacatct   300
gcaagtttgc caaaaaaggt ttagcacctt ctcaaattgg tgttattctt cgtgattcac   360
atggtattgc tcaggtgaag agtgtaactg gtagcaagat tctcagaatt ttgaaggctc   420
atggacttgc tcctgagatt cctgaggatc tctaccacct tatcaaaaaa gcagttgcaa   480
ttcggaagca tcttgagaga acaggaagg acaaggattc caagtttagg ttgattcttg   540
tcgagagcag gattcaccga cttgctcgct actacaagaa aacgaaaaag cttccaccag   600
tctggaagta tgaatctacc actgccagta ctctcgtggc atagagagga tggaggcatt   660
tggggtgcta cttttctttgt cgagtcatct ttgaaattct atattaagct gttttggcat   720

| | |
|---|---|
| gcccaggata gtttggaatc gtatcaaatt atgtactcga | 760 |

<210> SEQ ID NO 214
<211> LENGTH: 955
<212> TYPE: DNA
<213> ORGANISM: Populus tremula x Populus tremuloides

<400> SEQUENCE: 214

| | |
|---|---|
| cataaaaaag caattattgt tatcacttat gtataaagtg caaaccctag aaatggcgat | 60 |
| aataagtaag ctctagggtt gcggctagtc gcagaggaag cgaatcacaa acacacacac | 120 |
| agagcgccgg cttcatcacc gtcaccatgg gtcgtatgca cagtcacggt aagggtattt | 180 |
| cagcttcagc tttgccttac aagagaaccc caccaagctg gcttaagatt tctgctcaag | 240 |
| atgttgagga taacatctgc aaatttgcaa agaagggttt gacccatct cagattggtg | 300 |
| tcattcttcg tgactcgcac ggtattgctc aggtcaggag tgttactgga aaccagatct | 360 |
| tgcgtatcct taaggctcat ggtcttgccc ctgaaattcc tgaggatctg taccacctca | 420 |
| tcaagaaagc tgttgccatc agaaagcatt tggaaaggaa caggaaggat aaggattcca | 480 |
| agttcaggtt gatccttgtc gagagcagaa ttcacaggct tgctcgctac tacaagaaga | 540 |
| caaagaagct tcctcctgtc tggaaatacg agtcatccac tgccagcacg ctggtggctt | 600 |
| agacatagtt atgtatgtgg cacggtttgg tacatcctgc atggatgatg gtcttcgcgt | 660 |
| gtgggactcc gtcatagttc ataagcatta ttatgatatc atgttagctg gacaaaaga | 720 |
| tggagtggat cctagaacat aaattttgct ttaaatgttt gttttggcgt ttgagattct | 780 |
| gtactccgtg tatcctttaa gtatattttg tgttttgagc tattaaatta tcttttaaac | 840 |
| ataattgatt tgcctcaaac tgcctattcg ggagacggtg gttgtctccc aagtctcatc | 900 |
| tcgttgaaac ctgttaccaa ttttataaga taatgtacat cagtacatgg cccgc | 955 |

<210> SEQ ID NO 215
<211> LENGTH: 825
<212> TYPE: DNA
<213> ORGANISM: Medicago truncatula

<400> SEQUENCE: 215

| | |
|---|---|
| ggcacgaggc aaaaatcgtc atttcggcag agcaaaaccc taatcacaaa gctcgcagct | 60 |
| caaagcttca gcaatcatgg ggcgtatgca cagtggcggt aagggtattt catcttctgc | 120 |
| tttaccatac aagaggtctg caccaggatg gctcaagacc tctacacaag atgtggaaga | 180 |
| gactatttgc aagtttgcaa agaagggttt gactccatct cagatcggtg ttattcttag | 240 |
| ggattctcat ggaattgccc aggttaagtt tatcactggc agcaaaatcc ttaggatcct | 300 |
| caaggctcat ggacttgcac ctgaaattcc tgaggatctg taccatttga tcaagaaggc | 360 |
| agtttcaatt aggaagcatt tggagaggaa cagaaaggat aaggactcca agttcaggtt | 420 |
| gattcttgtg gagagcagaa tccaccgtct tgctcgctat tacaagaaga ccaagaagct | 480 |
| cccaccagtc tggaagtatg aatcaacaac tgccagcact ttggttgctt agagaagtcc | 540 |
| ttgattttga cttgttattc tgttctgcag tcgcatttgg actagaaatt tgctcgtatt | 600 |
| tagtttttt tggtgtcatg atcagtcctg gaagacttga actagttaat ttacttatca | 660 |
| atgtcttatt cctctttttt tatcagttgt agaactagct gttgtcattc gaagatgtga | 720 |
| gctgacttca gtttttggtt ttaattttaa gttatataca tgctagaaat cttggaaaaa | 780 |
| cccatttttac tgcatttgaa tgatacattg tttggttctt gaagg | 825 |

<210> SEQ ID NO 216

<211> LENGTH: 794
<212> TYPE: DNA
<213> ORGANISM: Populus tremula x Populus tremuloides

<400> SEQUENCE: 216

```
ggcccccct gagaggtcga ccccacgggt cccggcaagt tgcagaggaa gctagacaca      60
aacacacaca gagagctcca ccttcatcac cgtcaccatg ggtcgtatgc acagtcgagg    120
taagggtatt tcagcttcag ccctgcctta aagagaacc ccaccaagct ggctgaaaat    180
ttctgcacaa gatgttgatg atagcatttg caagtttgcg aagaagggtt tgactccatc   240
tcagattggt gtcattcttc gtgattctca tggtattgct caggtcagga gtgttactgg    300
aaaccagatc ttgcgtatcc ttaaggctca tggtcttgcc cctgaaattc ctgaggattt    360
gtaccacctc atcaagaagg ctgttgccat caggaaacat ttggaaagga acaggaagga    420
caaggattcc aagttcaggt tgatccttgt tgagagcagg attcacaggc ttgctcgcta    480
ctacaagaag acaagaaagc ttgctcctgt ctggaaatac gaatcaagca ctgccagcac    540
tctggtggct taggctagtt atgttatgcg gcacagtttt gggacatcct gcatagttgt    600
tcttcacgtg tggaactctg gcatggtttc ataagcatta ggagatcatg ttaactggga    660
aaaaggatgt agtggatcct agatttcaat ttttctttta aattttttgtt ttggccttga    720
gcttttgtac tccattctaa cttttttttct atactgtttg ttttgagcta taaaatttgc   780
aactttagac ctct                                                      794
```

<210> SEQ ID NO 217
<211> LENGTH: 744
<212> TYPE: DNA
<213> ORGANISM: Medicago truncatula

<400> SEQUENCE: 217

```
attatggccg gggggcacaa gctcaagcag cagcgaagcg tagtagttag agcctttgtt     60
cttcttcctc atctcaatca ttcaccatgg gtcgtatgca cagtggcgga aagggtattt    120
caagttcagc tcttccttac aagagaacac cagcaagctg gctcaagatc tctacccagg    180
atgttgacga gaccatctgc aagtttgcca agaaaggtct aactccatct caaattggtg    240
ttattcttcg tgactcccat ggaattgctc aggttaaggc tgtaaccgga aacaagattt    300
tgcgcatatt gaaggcgcat ggacttgctc ctgaaattcc tgaagatctg tatcacctga    360
tcaagaaggc tgtctctatt aggaagcatt ggagaggaa caggaaggac aaggattcca    420
agttcaggct aatttttggtc gagagcagga tccatcgcct tgctcgttac ataagaaga    480
caaagaagct tccaccagta tggaaatacg aatcaacaac tgccagcact cttgttgctt    540
gaagagatga tcggcgatat tattgtagtt gtgctttctg tgtactttat ttttgtatgc    600
aaatgaattg ctttcatgtg atttgaaat tttggaacat ttgaaattca tgtttagact    660
cgtttgatgt tagttttgat gatggacctt gttcctttaa ttgatatact ctctttcaat    720
cgcattagtt ttaaatttgc tatt                                            744
```

<210> SEQ ID NO 218
<211> LENGTH: 799
<212> TYPE: DNA
<213> ORGANISM: Populus tremula x Populus tremuloides

<400> SEQUENCE: 218

```
cgcccaacgc gtccggagcc accaaaggag ctgcgctaaa gtgactgcaa tagaagcagc     60
aaatctccaa agtccgtcac catgggtcgt atgcacagta aaggtaaggg tatttcagcg    120
```

```
tctgctttgc catacaagag aacccccacct agttggctca agatttctcc tcaagatgtt        180
gacgacaaca tctgtaagtt tgccaagaaa ggtttgacac catctcaaat tggtgttatt        240
cttcgtgatt ctcacggtat tgctcaggtg aaagctgtca ctggcaacca gattttgagg        300
atattgaagg cacatggcct tgcccctgaa attcctgagg atttgtacca cctcatcaag        360
aaagcagttg ctattaggaa gcatctagag aggaacagga aggataaaga ttccaagttt        420
aggttgattt tggttgagag caggattcac cgccttgctc gctattacaa gaagaccaag        480
aagcttccac ctgtctggaa atatgaatcc tccaccgcca gcactcttgt ggcttaggca        540
agatatgttt ggttttagtt gtcggaactt ccttgaactt aatcttggat gaactgatct        600 cagcttttg atatttgtta ttctcatttt ttcagaactt attcatgaat attaccttt         660 attttcgta atctcagctt ctggtttgat gtttttgatg ctacaagtaa tgtcgggatt         720
ctgaatttga atagatgctg aattaagttg atccttgtca acatttgcag aatttgaaac        780
ctggttgtta atgcctagc                                                     799

<210> SEQ ID NO 219
<211> LENGTH: 681
<212> TYPE: DNA
<213> ORGANISM: Medicago truncatula

<400> SEQUENCE: 219
agacaccatg gggccgtatg catagtaaag gcaagggtat ttcttcctct gctttaccct         60
acaaaagaac ttctcctagc tggcttaaga tctcctcacc agaggttgat gagactattt        120
gcaagtttgc taagaagggt ttgactcctt ctcagatcgg tgttattctt cgtgattctc        180
acggcattgc tcaggtcaag agcgttaccg gcagcaaaat ccttcgtatc ctcaaagctc        240
acggacttgc acctgagatt cctgaggatc tgtaccattt gataaagaag gcggtttcaa        300
tccgcaagca tttggagagg aacagaaagg acaaggactc caagttcaga ctcatccttg        360
ttgagagcag aatccaccgt cttgctcgtt attacaagaa aaccaagaag cttcctcctg        420
tgtggaaata cgaatcaaca actgccagca ctttggttgc ttagagattg tatgggctca        480
ttcttcatgc tttccgtttc cggtaacaga ggttgctgc actggcaatc tgcgaggtca        540
ttttgaggtt tatctagaga cttgatgggc catgcaattt cttatttgt taagaacctt         600 tgataaagta gaaagatatt aattatttta cgttgactgc attgtattct ttttaagtaa        660
actgttcgaa agttgtttca a                                                  681

<210> SEQ ID NO 220
<211> LENGTH: 775
<212> TYPE: DNA
<213> ORGANISM: Hordeum vulgare

<400> SEQUENCE: 220
aggtttccct ctccgccgcc acagccgctt ctccccccac ctccctcctc gccgccatgg         60
gacgcatgca cagcaacggg aaggggatgt cgtcctcggt gatcccctac aagcgggagg        120 cccccggcctg gtcaagaca gccgcgccgg acgtggagga gatgatcgtg cgcgccgcca        180
agaagggcca gctgccgtct cagatcggcg ccctgctccg cgacggccac ggcatcccgc        240
tgtccaaggc cgtcaccggc gccaagatcg tgcgcctgct caaggcgcgc gggctcgcgc        300
cggagatgcc cgaggacctc tacttcctca tcaagaaggc cgttgcgatc aggaagcacc        360
tggagaggaa caggtcggac gtcgacgcca gttccgcct catcctcgtc gagagcaggg        420
tccaccgcct cacccgctac taccgcctca ccaagaagat gcccgccgcc tggaagtacg        480
```

```
agtccaccac cgcgagcacc ctcgtcgcct gattcggtta atcttcggtt cttcgacgta    540
attctctgca gttttggact tcggttttgt gttaagtact gtagtaagca atgcttttgg    600
caatgtaagc ttttaaacct atcgattacc tctcgtgtgc ctggatagga gtatttcgag    660
agttcagtgg gagtggatta gattttgatc cttggaagtt gagactattt acaatgtgtt    720
gctttggtaa gaggtctttt aatgttagcc gagtggtaaa tcagttgttc atagc         775
```

<210> SEQ ID NO 221
<211> LENGTH: 889
<212> TYPE: DNA
<213> ORGANISM: Triticum aestivum

<400> SEQUENCE: 221

```
ggcacgagca tttttgctag gtttccctct ccgccgccac agcagcttct ccccatctcc     60
ctcctcgccg ccgccctccg ctcgccgctc gccgccatgg gacgcatgca cagcaacggg    120
aagggcatgt cgtcctcggt gatccctac aagcgggagg ccccggcctg ggtcaagacg    180
tccgcgccgg acgtggagga gatcatcgtc cgcgccgcca gaagggcca gctgccgtcg    240 cagatcggcg ccctgctccg cgacggctac ggcatcccgc tgtccaaggc cgtcaccggc    300
gccaagatcg tgcgcctgct caaggcgcgc gggctggcgc cggagatgcc cgaggacctc    360
tacttcctca tcaagaaggc cgttgcgatc cggaagcacc tggagaggaa caggtcggac    420
gtggacgcca agttccgcct catcctcgtc gagagcaggg tccaccgcct cacccgctac    480
taccgcctca ccaagaagat gcccgccgcc tggaagtacg agtccaccac cgcgagcact    540
ctcgtcgcct gattcggtta agcttcggtt ctttgacgta attctctgca gcttggactt    600 cggtttttg ttaagtactc cagtaagcaa tgcttttggg atgtaagct gttaaaccta     660 tcagctaccg ctcgtgtgcc tgcacagaag tatttcgaga gtttagtggg actggatcag    720
gttttgatcc ttggaagttg agactattta caatgtgttg gttcctaac ttcgagtagg     780 ctggtaatgc tcttcgtagg tgtattgctg tcgcaaatcc tgcagtggag tatgaaactt    840
gctaatgcac tcttcatgtt ttatcctgtt ttattgttgt tgcgaactc               889
```

<210> SEQ ID NO 222
<211> LENGTH: 626
<212> TYPE: DNA
<213> ORGANISM: Oryza sativa

<400> SEQUENCE: 222

```
atccaccaca tcgacaacct cacgccgtcg acaactttcc agccaaaatg ggtcgtcttc     60
actccaaggg caagggcatt gcctcctcca ccctcccta ctcccgcact cctcctgcgt    120
ggctcaagac caccccgac caggttgtcg accacatctg caagctggcc aagaaggtg     180 ccactccttc ccagatcggt gttgttctcc gtgactccca cggtgttgcc caggtcaaga    240
tcgtgaccgg taacaagatc ctccgtatcc tcaagtccaa cggcctcgcc ccgagcttc     300 ccgaggacct ttacttcctg atcaagaagg ccgtcgctgt ccgcaagcac cttgagcgta    360
accgcaagga caaggactcc aagttccgcc tcattctgat cgagtcccgt atccaccgtc    420
tgtcccgcta ctacaagacc gtcggtgtcc ttccccccac ctggcgctac gagtccgcca    480
ctgcctccac cctggtcgca taagcgaagg cgttggttgt ctgtggtcat ggagatagg     540 gcatgattga tattctgggc ttctgttcgg agtatctttc atgtgtgtta gatacgacca    600
ttaaaaaaga acttatgagt tatacc                                         626
```

<210> SEQ ID NO 223

<211> LENGTH: 757
<212> TYPE: DNA
<213> ORGANISM: Oryza sativa

<400> SEQUENCE: 223

```
atgggccgca tgcacagcag cgggaagggg atgtcctgct cggtgctccc ctacaggcgc    60
gccgctcccg cctgggtcaa gacgtccgcg tcggaggtgg aggagatgat cgtgcgcgtc   120
gccaagaagg gccagctgcc gtcgcagatc ggggcgatcc tccgcgacgc ccacgccgtc   180
ccgctcgccc agggcgtcac cggcggcaag atcctccgcg tgctcaagtc ccgcggcctc   240
gcgcccgagg tgcccgagga cctctacttc ctcatcaaga aggccgtcgc gatgaggaag   300
cacctcgaga ggaacaggaa ggacaaggac accaagttcc gcctcatcct cgtcgagagc   360
agggtgcacc gcctcacccg ctactaccgc ctcgccaaga agatccccgc cttcttcaag   420
tacgactcca ccaccgcgag cactctcgtg gcctgaagtg gaactgaagg tttcgttcgt   480
tttcagcttc ttttttgggc gacttgaatt ctccttgacag ccatggagtt ttgtttaatc   540
ttaagtaagt aggaatgctt tgttggtgt aatgtgttaa atctacctcc tgcacctgaa    600
gagaagttgc ttactgagac tcgatctagg aatgctttg ttggtgtaat gtgttaaatc    660
tacctcctgc acctgaagag aagttgctta ctgagactcg gatcagattt tattttcctg   720
aaagaaaggt tattcgcaat gatatgaagt tcaattt                            757
```

<210> SEQ ID NO 224
<211> LENGTH: 671
<212> TYPE: DNA
<213> ORGANISM: Triticum aestivum

<400> SEQUENCE: 224

```
cggcacgagg tccagtatca ccacgccaaa ccgacaagat gggccgtctt cacagcaagg    60
gaaagggcat ttctgcctcc gctctcccct actctcgatc ttcccctgcg tggttgaaga   120
ccaccccccga gcaggttgtc gagcagatct ccaagctcgc ccgtaagggt gccaccccctt   180
ctcagatcgg tgtcattctc cgtgactctc acggtattgc ccaggtcaag cacgtcactg   240
gtaaccgaat tctccgaatt ctcaagtcca gcggcctcgc ccccgagctc cccgaggatc   300
tgtacatgct tatcaagaag gctgttgccg tccgaaagca ccttgagcgc aaccgcaagg   360
acaaggactc caagttccgt ctcattctca ttgagtcccg aattcaccgt ctggcccgtt   420
actacaagac cgtcggtgtc cttccccccca cctggaagta cgagtccgct actgccagca   480
ccatcgtcgc ttaagcgaac ataaaaacga cggctggcca agttcggatg gaagtgatgg   540
tttcccggat cacggagtta gggacaaatt atggaaaaag cttgcattta gagccatgat   600
gcttatgcgc cctatctggg aggactgaca gcgaaatcga cggctcaaat agaaagcttt   660
tcgaccgctg c                                                        671
```

<210> SEQ ID NO 225
<211> LENGTH: 634
<212> TYPE: DNA
<213> ORGANISM: Hordeum vulgare

<400> SEQUENCE: 225

```
agtatcacca cgccaaaccg acaagatggg ccgtcttcac agcaagggaa agggcatttc    60
tgcctccgct ctcccctact ctcgatcttc ccctgcgtgg ttgaagacca ccccgagca   120
ggttgtcgag cagatctcca gctcgcccg taagggtgcc accccttctc agatcggtgt   180
cattctccgt gactctcacg gtattgccca ggtcaagcac gtcactggta accgaattct   240
```

```
ccgaattctc aagtccagcg gcctcgcccc cgagctcccc gaggatctgt acatgcttat    300
caagaaggct gttgccgtcc gaaagcacct tgagcgcaac cgcaaggaca aggactccaa    360
gttccgtctc attctcattg agtcccgaat tcaccgtctg gcccgttact acaagaccgt    420
cggtgtcctt cccccacct ggaagtacga gtccgctact gccagcacca tcgtcgctta    480
agcgaacata aaaacgacgg ctggccaagt tcggatggaa gtgatggttt cccggatcac    540
ggagttaggg acaaattatg gaaaaagctt gcatttagag ccatgatgct tatgcgccct    600
atctgggagg actgacagcg aaatcgacgg ctca                                634

<210> SEQ ID NO 226
<211> LENGTH: 623
<212> TYPE: DNA
<213> ORGANISM: Arabidopsis thaliana

<400> SEQUENCE: 226
gatccttatc cagtatcacc acgccaaacc gacaagatgg gccgtcttca cagcaaggga     60
aagggcattt ctgcctccgc tctcccctac tctcgatctt ccctgcgtg gttgaagacc    120 accccgagc aggttgtcga gcagatctcc aagctcgccc gtaagggtgc caccccttct    180
cagatcggtg tcattctccg tgactctcac ggtattgccc aggtcaagca cgtcactggt    240
aaccgaattc tccgaattct caagtccagc ggcctcgccc cgagctccc cgaggatctg    300 tacatgctta tcaagaaggc tgttgccgtc cgaaagcacc ttgagcgcaa ccgcaaggac    360
aaggactcca agttccgtct cattctcatt gagtcccgaa ttcaccgtct ggcccgttac    420
tacaagaccg tcggtgtcct tcccccacc tggaagtacg agtccgctac tgccagcacc    480
atcgtcgctt aagcgaacat aaaaacgacg gctggccaag ttcggatgga agtgatggtt    540
tcccggatca cggagttagg gacaaattat ggaaaaagct tgcatttaga gccatgatgc    600
ttatgcgccc tatctgagag gac                                           623

<210> SEQ ID NO 227
<211> LENGTH: 533
<212> TYPE: DNA
<213> ORGANISM: Hordeum vulgare
<220> FEATURE:
<221> NAME/KEY: misc_feature
<222> LOCATION: (528)..(528)
<223> OTHER INFORMATION: n is a, c, g, or t

<400> SEQUENCE: 227
ctattcaaga tgggacgcat gcacagtggt ggaaaaggta ttgcaaagtc ttctttgcct     60
tacagacgct ctcctccttc atggttgaaa gtgactgcta gtcaagttga ggaccatgtc    120
aataagcttg ccaaaagagg tttgactcct tcacagattg gtgtgattct tcgtgattcc    180
aatggaattg cgcaagtcaa gagtgtcaca ggaaataaaa ttcttcgtat cctgaagaaa    240
tcaggacttg cacctgccat ccctgaggat ttgtacatgt taattaaaaa ggccgtggct    300
gttagaaagc acttggaacg caacaagaaa gataaggact ccaaatttag attgatcttg    360
attgagagcc gcattcacag actggcgaga tactaccgcg cctcaagaaa gctggatgca    420
aactggaagt acgaatctgc caccgcttct gcccttgtgg cttaattgtc acggcaatac    480 catcctttg tcgatacttt tgtaactgct gctaaaacac cacaaatntt tta            533

<210> SEQ ID NO 228
<211> LENGTH: 1167
<212> TYPE: DNA
<213> ORGANISM: Saccharum officinarum
```

<400> SEQUENCE: 228

```
tcggtctcgc caccgccgcc aacttgtcac tcgctctccc tcctgctcgc cgccgccac      60
cgctcgccgc aaccgccgcc atgggtcgca tgtacggccc cgggaagggc atgtcctcgt    120
cggtgctgcc ctacgctcgc gtcgcccctg gctgggtgag gtcgaccgct ggggaggtgg    180
aggagatgat cgtgcgcgcc gccaagaagg ccacctgcc gtcgcagatc ggtgcgctgc     240
tccgcgacac gcacgcgtc ccgctggtcc acggcgtcac gggcggcaag atcctgcgca    300
tgctcaaggc ccgcgggctc gcgccggagg tgcccgagga cctctacttc ctcatcaaga    360
aggccgtcgc gatcaggaag cacctggaca ggaaccggac ggacgtggac gccaagttcc    420
gcctcatcct cgtcgagagc agggtccacc gcctgatccg ctactaccgc cgcaccaaga    480
agatcgcccc caacttgaag tacgaatcca ccaccgcgag cgctctggtg gcgtgatggc    540
tgtgaattga ttctctagag cttttggagct tgtcttaatc ctaaggaagt tatgtgatag    600
tagtagtact ttatgatatg ttactatgtg aggtctttaa atttatctac ccgatgcacc    660
taggaagagg tatgtatctt gagatttgac agttatgaga ctggatcggg ttttttgacct   720
ttgaaggtgc ataactcaaa atggtttgga gttgggctta accttgatta ggttggatgg    780
tgctctcatc aaaagttaag aatgaagcaa gagacttggt atttagtttc acttttttcc    840
gccctttcga tcttggtttc accaattggg tcatgttaaa gttttggtat agcttagcta    900
gtgagctact ctacattgtt tgagatttga ggagcctcca agaacacaat ggtacttatg    960
gatgtgggtt tccttatccc atagctcaaa tgatctgtgc gaagtgttat gtttggttgc   1020
ctatatcaag tttttggttt agttctagaa tcattcaggg cgcttcttag aaattttggg   1080
atgtaattcc aatttgaact aaatattaag gatttggatc ctgctgccca acaagtgtct   1140
ttgggtggta aggagcattc ctatgtc                                        1167
```

<210> SEQ ID NO 229
<211> LENGTH: 1812
<212> TYPE: DNA
<213> ORGANISM: Hordeum vulgare

<400> SEQUENCE: 229

```
ggcacgagcc gaggtaaggg gatttctgca tctgccctgc cttacaagag gactccacct     60
agttggttga agatctcctc tcaagatgtt gaggataaca tttgcaagtt tgctaagaag    120
ggtttgaccc catctcaaat tggtgtcatt ctacgagatt ctcatgggat tgctcacgtg    180
aagagtgtta ctggcagcaa gattctgcgc atactgaaag cccatggtct tgctcctgaa    240
atacccgagg atctgtacca cctgattaag aaagccgttg ccatcagaaa gcatcttgag    300
aggaaccgaa aagacaagga ttccaagttt aggttgatct tggttgagag caggatccac    360
cgactcgccc gctattataa gaagacaaag aagctgccac cagtgtggaa atatgagtct    420
actactgcca gcactcttgt ggcctagata aatcaaattt tgaactgtct tcctgtgctt    480
cgattgatat tcttctggat cggctaagag gagttggact ttttgtatta cgttctatta    540
atgccgtaaa agaactagtc cacttaattt gaagtggaga tacttaatgt gttaaatctt    600
atgtttagta tattggaata attcatctct catttcaaag aaaaatcggt ctcgccaccg    660
ccgccaactt gtcactcgct ctccctcctg ctcgccgccg cccaccgctc gccgcaaccg    720
ccgccatggg tcgcatgtac ggccccggga agggcatgtc ctcgtcggtg ctgccctacg    780
ctcgcgtcgc ccctggctgg gtgaggtcga ccgctgggga ggtggaggag atgatcgtgc    840
gcgccgccaa gaagggccac ctgccgtcgc agatcggtgc gctgctccgc gacacgcacg    900
```

```
gcgtcccgct ggtccacggc gtcacgggcg gcaagatcct gcgcatgctc aaggcccgcg    960
ggctcgcgcc ggaggtgccc gaggacctct acttcctcat caagaaggcc gtcgcgatca   1020
ggaagcacct ggacaggaac cggacggacg tggacgccaa gttccgcctc atcctcgtcg   1080
agagcagggt ccaccgcctg atccgctact accgccgcac caagaagatc gcccccaact   1140
tgaagtacga atccaccacc gcgagcgctc tggtggcgtg atggctgtga attgattctc   1200
tagagctttg gagcttgtct taatcctaag gaagttatgt gatagtagta gtactttatg   1260
atatgttact atgtgaggtc tttaaattta tctacccgat gcacctagga agaggtatgt   1320
atcttgagat ttgacagtta tgagactgga tcgggttttt gacctttgaa ggtgcataac   1380
tcaaaatggt ttggagttgg cttaacctt gattaggttg gatggtgctc tcatcaaaag   1440
ttaagaatga agcaagagac ttggtattta gtttcacttt tttccgccct ttcgatcttg   1500
gtttcaccaa ttgggtcatg ttaaagtttt ggtatagctt agctagtgag ctactctaca   1560
ttgtttgaga tttgaggagc ctccaagaac acaatggtac ttatggatgt gggtttcctt   1620
atcccatagc tcaaatgatc tgtgcgaagt gttatgtttg gttgcctata tcaagttttt   1680
ggtttagttc tagaatcatt cagggcgctt cttagaaatt tgggatgta attccaattt   1740 gaactaaata ttaaggattt ggatcctgct gcccaacaag tgtctttggg tggtaaggag   1800
cattcctatg tc                                                       1812

<210> SEQ ID NO 230
<211> LENGTH: 769
<212> TYPE: DNA
<213> ORGANISM: Populus tremula x Populus tremuloides

<400> SEQUENCE: 230
caccaatcga acgagcgcgc tcctcagcag actttgggtc gtcttctatc tgaaccggcc     60
attcttcaac aaggaagaag tacctcaagc ctcacatcat gggtcgtatg cacaatcccc    120
acaagggtat cgccggttcg gcacttccct acaagcgaac tcctccaaga tggttgaagg    180
tcaccccgga ggaagtctct gagcagatct tcaagcttgc ccgtaagggt atgaccccct    240
ctcaaattgg tgttgtcctc cgagacagcc acggtattgc ccaagtcaag agtgtcaccg    300
gtgccaaaat tcttcgtatc ctcaagggta acggtcttgc ccctgagctc cccgaagatc    360
tttaccactt gatcaagaag gctgtttctg tccgaaagca tcttgaacga aaccgaaagg    420
acaaggactc caaattccgt ttgattctca ttgaatctcg aatccaccgt cttgtccgtt    480
actacaagac aaaatctcaa ctctcgcctt ccttcaaata cgagagtgca accgcctcca    540
ccattgtctc atgaagactc tatccatctg accatctcct tgtggtctt ctctcatcgt    600 tcatgatcgt tatgggtttg ctaaatgcac caaccaatct tgttacatcc atgtgttctc    660
actatgcttc cctgatctcc atgtcccatg tccccgttca ttggaaatat caaactcctc    720
cagttggtcg tcatcaccga cttgcaagat aatctaaaca tgcacttta                769

<210> SEQ ID NO 231
<211> LENGTH: 559
<212> TYPE: DNA
<213> ORGANISM: Hordeum vulgare

<400> SEQUENCE: 231
ttaaattgta aattgtattt tttaaatgtc cgtacaaata acagtttact taagcaacca     60
aagcggaagc tgtactggac tcgtatctcc agtgggagc gatctttgat ttgcgtttgt    120
agtaccttgc caaacgatga atacgtgatt caaccaaaat caaacggaat ttggaatctc    180
```

```
tgtctttcct gttcctttcc aaatgttttc tgattgctac ggctttcttg atcaaatggt      240
acaaatcttc agggagacct ggagccaaac ccatagcttt catgatccta agaatttgt       300 ttccagtcac aaatcttact tgagcaacac catgggaatc tcgtaaaata acaccaattt      360
tagatggtgt caaacccttc ttggccaatt tgaaaatgtg gtccttgaca tcctcggacg      420
acgatttcag ccaggtggct acgctgcggc ggtatggaag agccgacttg gaaatacctt     480
ttccgggtgt gtgcatccga cccatgttga cgttttttgtt ttacactttta agaacgataa    540 aaaaattatt ccacaatgc                                                  559
```

```
<210> SEQ ID NO 232
<211> LENGTH: 779
<212> TYPE: DNA
<213> ORGANISM: Oryza sativa

<400> SEQUENCE: 232
aaccttccca atgtacatac tttacatatt agattgcaag gcatattaca aaaagtgctt      60
acagaaaggg gaagaatgcc cacttcaatc tgcttacaga aaggggaagg atgcacactc     120
caatctgttt caacaaacta atggtacaac aatatggcga gtagctgatt ctctggaaaa     180
aaactgccat agcctccaag atgttgctct aaggggaaaa tccccaaaaa atgctattta     240
cattgtattc ctgcgcctct ccatctcagc gcgtctcaat aaagttgcta gcacaacaat     300
ccattcctta aatttgacag aacacatgtg agcaacaagg aactcaacat caagccgact     360
ttgaagagta tccatttgaa gcgcaaagta ggtgggagct tctttgtgcg cttgtagtag     420
cggacgaggc ggtggatcct gctctcaaca agaataagcc tgaaacttga gtccttgtcc     480
ttcctgttcc tctccaaatg cttcctaata gcaacagcct tcttgatcag gaagtacagg     540
tcttccagga tcttcggtgc aagaccgtgg gccttgagga tgtgaagaat cttgctactg     600
gcgatgctct tgacgagggg gattccgtgc tggtgacgga gcacaacgcc aatctgcgac     660
gacatctgac ccatcttcgc ggccttcatg atcatctcct ccacattgga ggcggcgttc     720
ttgagcaagc tcgggggaat cctcttgcac ggcagcgccg acgacgagat acccttctc     779
```

```
<210> SEQ ID NO 233
<211> LENGTH: 674
<212> TYPE: DNA
<213> ORGANISM: Glycine max
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t

<400> SEQUENCE: 233
accaggaact agtctcgagt ttttatcctt aatttttgt tctaggtcga agaaaatatc        60
tgcaagtttg cgaagaaagg tttgaccccg tctcagattg gtgtcattct cagagattct     120
cacggtattg ctcaggtcaa tagcgtcact ggcagcaaaa tccttcgcat cctcaaagct     180
cacggacttg cgcctgaaat tccagaggat ctgtaccatt tgattaagaa ggcagtttca     240
attaggaagc atcttgagag gaacaggaag gacaaggact ccaagttcag gttgattctt     300
gttgagagca gaatccaccg acttgctcgc tattacaaga agactaagaa gctcccacca     360
gtctggaagt acgaatcaac aactgctagc actctggttg cttagagaat gtatcaactt     420
tcatgggttt tgctacccttg cagtcgccgt tgagctagca atttgccata tcattttgat    480
```

```
gtgtatttga aggctggata agttatgtgg tcttaattt tttaagaacc tataatttag      540
ctagttaagt caatttatca ttgtggtgtt cttttctt  tagccgttgg aggttgttct      600
ttaaagagat gactatggtt tttggtttta ttttcaagta atatatatgc tgagaagatt      660
tgaggatcan aana                                                        674

<210> SEQ ID NO 234
<211> LENGTH: 458
<212> TYPE: DNA
<213> ORGANISM: Populus tremula x Populus tremuloides

<400> SEQUENCE: 234
cacacttaca ataatgggtc gaatgcacag taatggtaaa ggtatgtcga agtcagcact       60
tccatacaag agaacaccac caagttggtt aaaaacaagc gcaaatgaag tttgtgacca      120
tgtttgtcga ttgcaaaga  aaggtttaac accatcacaa attggtgttg ttcttcgaga      180
ttcacatgga attccacaag ttaaatcagt cacaaataac aaaattcttc gtattttgaa      240
ggcaaacgga tttgcacctg aattgcctga agatttatac catttgatca agaaagctgc      300
ttcaattcgt aaacatttaa aaagatctcg tcaagataaa gatgcaaagt tccatcttat      360
tcttgttgaa gccagaattc accgtgtttc acgatactac aaggaaagca aacacttacc      420
agcaaactgg agatacgaat caccaactgc tgcaactt                              458

<210> SEQ ID NO 235
<211> LENGTH: 481
<212> TYPE: DNA
<213> ORGANISM: Nicotiana tabacum

<400> SEQUENCE: 235
acgccggtag ccaatcctca ctcgccatca tgggtcgcat gcacagtcgc ggtaagggta       60
tttcagcttc ggctcttcct tacaaaagaa ctcctcctag ttggctcaag atctccgctc      120
ctgatgttga ggacaacatt tgcaagtttg cgaagaaagg attgactcct tcacagattg      180
gtgtgattct tcgtgactca cacggaattg cacaagtcaa gagtgtcact ggcagcaaga      240
tcttgcgtat cctcaaggct cacgggcttg ctcctgagat accagaggat ctgtaccacc      300
tgattaagaa ggcagttgct attaggaagc atttggaaag ggacagaaag gataaggatt      360
ccaagttccg cttgatttag gtggagagca ggatccatcg tcttgctcgc tattacaaga      420
aaacaaagaa gctcccacct gtctggaaat acgaatcaac caatgctagc acgcttgtgg      480
c                                                                      481

<210> SEQ ID NO 236
<211> LENGTH: 717
<212> TYPE: DNA
<213> ORGANISM: Triticum aestivum
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t

<400> SEQUENCE: 236
atcacaatgt ctaattttcc ctcgataaat tggggatana ccctagggag gggggggatg       60
```

-continued

| | |
|---|---|
| aattccaaaa ccaaaaatgg tgggggggat tctccaagta aacataaaaa atttggtctc | 120 |
| ttgttcatct aaatcgctcc aaactcaaaa gcgttacatg aaattgataa tatgtagaac | 180 |
| aagaccatcc tgaagccggt aagagcacac cagatgaaga gccctcctaa gccaccaaaa | 240 |
| tgctcccggg ggggggggggg ggcttccatt tatccgggaa cttcttcctc cccttntant | 300 |
| aacgggggggg acgtggatc ctgctctcaa caagaatgag cctgaatttg gagtctttgt | 360 |
| ccttcctgtt cctctcaaga tgcttcctaa tggcgcacagc cttcttaatc aaaaagtaca | 420 |
| gatcctctgg gatttccgga gccaggccat gagccttgat gatgcggagg atcttgcttc | 480 |
| ccgtaacgct cttcacgagg gggataccgt gctggtcacg gaggagaacg ccgatctgcg | 540 |
| agggcatctg accttcttc gcagccttcg tgatcaactc gtcgacatca gcgacggtgg | 600 |
| gtcttgaccc cacctcggag gagtcctctt gtacggcaac cccgacaacc atataccctt | 660 |
| cccgccggct gtcaatgccc cccattgcgt caggcgacgg gtttaacttc cgcccac | 717 |

<210> SEQ ID NO 237
<211> LENGTH: 685
<212> TYPE: DNA
<213> ORGANISM: Brassica napus
<220> FEATURE:
<221> NAME/KEY: misc_feature
<222> LOCATION: (663)..(663)
<223> OTHER INFORMATION: n is a, c, g, or t

<400> SEQUENCE: 237

| | |
|---|---|
| ggcagcagga actcatctca tcgagacagt gaaaggaaac cctaactttt caagatgggg | 60 |
| cgtatgcatt cgagaggaaa gggtatctct gcatctgcgt tgccgtacaa gcgttcacct | 120 |
| ccgacatggc tcaagaccac ggccctcgat gttgatgagt caatctgcaa gtttgcgaag | 180 |
| aagggttgac accatctcag attggtgtga ttcttcgtga ctctcacggt atccctcagg | 240 |
| tgaagagtgt taccggaaac aagatcttgc gtattctcaa agctcacggt cttgcacctg | 300 |
| agattcctga tgatctgtac catttgatca agaaggcagt tgctatccgc aagcatttgg | 360 |
| agaggaacag gaaggacaag gattccaagt ttaggctgat tcttgcggag agcaggatcc | 420 |
| accgtcttgc tcgttactac aagaagacca agaagcttcc tccagtctgg aagtacgagt | 480 |
| ctactactgc ttctactctt gtagcttaga gcacggtctt ctcttaaaag gcttcaagag | 540 |
| ccactactgt tttttttttt tgatgtctta tctctgaact tgaacttagt ttctatgttt | 600 |
| cgcagtactt tgttttgtc aaggtacaat gatgttttga tgatttcatg gaaccaatgc | 660 |
| gtntaatcta ttgtcagaat tgcaa | 685 |

<210> SEQ ID NO 238
<211> LENGTH: 447
<212> TYPE: DNA
<213> ORGANISM: Triticum aestivum
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:

```
<221> NAME/KEY: misc_feature
<222> LOCATION: (423)..(424)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t

<400> SEQUENCE: 238
aagcgccagc tcgccgtcgt ccgaatagta cactctaacg ccgccatggg gcgtatgcac      60
agccgcggga agggtatctc gtcgtcggcg ctgccgtaca agaggacgcc tcctacctgg     120
ctgaagaccg ccgcctccga cgtggaggag atgatcacaa aggcagcgaa gaagggacag     180
atgccgtcgc agatcggcgt cctgctccgt gaccagcacg gtatcccccct tgtcaagagt    240 gtcaccggca gcaaaatcct ccgcatcctc aaggccatgg gctggaaccg aaatcccgga     300
ggactgtact ctcatcaaga agccgtggcg ataaggaaca ctttagagga acaagaagga     360
caaagatcna atcaagntc atctngtcaa aacaggttca acgccttgcc cgtatanaac      420
gcnnaagaac ttcancactt gaatnna                                          447

<210> SEQ ID NO 239
<211> LENGTH: 608
<212> TYPE: DNA
<213> ORGANISM: Populus tremula x Populus tremuloides

<400> SEQUENCE: 239
cacagagcca ccaaggagct gagctaaagt gactgcaaaa gaagcagcga atctccacag      60
tcgttgccat gggtcgtatg cacagtaaag gcaagggtat ctcagcatct gctttgccat     120
acaagaggac ctcacctagt tggcttaaga tttctcctca agatgttgac gacaatatct     180
gcaagtttgc aaagaaaggt ttgacaccat ctcaaattgg tgttatcctt cgtgattctc     240
atggtattgc tcaagtgaaa actgttactg gcaaccagat tttgaggata ttgaaggccc     300
atgggcttgc acctgaaatt cctgaggatc tgtaccacct cattaagaaa gcagtttgct     360
atttaggaag catctagaga ggaacaggaa ggataaagat tcccaaattt aggtttgatt     420
ttggtcgaga gcaggatcca ccgcctttgc tcgctattac aagaagacca agaagcttcc     480
accagttctg ggaaatatga atccaccact gccagcaccc ctcgtggcat aggcaaagat     540
atccttggtt tttagttgtc agcacgtcct ttgaactcaa atcttggatg agctgatcag     600
cctttttga                                                              608

<210> SEQ ID NO 240
<211> LENGTH: 701
<212> TYPE: DNA
<213> ORGANISM: Oryza sativa

<400> SEQUENCE: 240
acccttggtg gtttggctcc cccgggaatc gggcttatgg gcgggaagat gggtcagatg      60
tcgtcgcaga ttggcgttgt gctccgtcac agcacggaat ccccctcgtc aagagcatcg     120
ccagtagcaa gattcttcac atcctcaatg cccacggtct tgcaccgaag atcctggaag     180
acctgtactt cctgatcaag aaggctgttg ctattaggaa gcatttggag aggaacagga     240
aggacaagga ctcaagtttc aggcttattc ttgttgagag caggatccac cgcctcgtcc     300
gctactacaa gcgcacaaag aagctcccac ctactttacg gtcttggatt attttttctcg    360
```

```
agttttctac agttttctcc tgcagtagaa tgcttcaaat ggatactctt caaagtcggc    420
ttgatgttga gttccttgtt gctcacatgt gttctgtcaa atttaaggaa tgaattgttg    480
tgctagcaac tttattgaga cgcgctgagg tactgcctat ctttcacatg ttcaacaact    540
gtgcacacaa tttcagtaat actgttcttt tgactaactt gtggcaggct tctgcatctg    600
acaatgcagt gttttttctt attttgtttt ttggattttt accatgtatt gatcgtttaa    660
tgttttgtaa gaagcgtact catccttggt gctaaaaaaa a                        701
```

```
<210> SEQ ID NO 241
<211> LENGTH: 565
<212> TYPE: DNA
<213> ORGANISM: Triticum aestivum
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t

<400> SEQUENCE: 241
```

```
gctaggtttc cctctccgcc gccacagcag cttctcccca tctccctcct cgccgccgcc     60
ctccgctcgc cgctcgccgc catgggacgc atgcacagca acgggaaggg catgtcgtcc    120
tcggtgatcc cctacaagcg ggaggccccg acctgggtca agacgtccgc gccggacgtg    180
gaggagatca tcgtccgcgc cgccaagaag ggccagctgc cgtcgcagat cggcgccctg    240
ctccgcgacg gctacggcat cccgctgtcc aaggccgtca ccggcgccaa gatcgtgcgc    300
ctgctcaagg cgcgcgggct ggcgccggag atgccccgag gacctctact tcctcatcaa    360
gaaggccgtt gcgattcgga agcacctgga agaggaacaa gtcggacgtg gacgccaagt    420
tccgcctcat cctcgtcgag aacaaggtca acgcctcaa ccgctactac cgcctcaaca    480
agaagatgcc gccgcctngg aagtacgagt cacaccgcga agnatctcgt cgctgaatcg    540
gttaacctcg gttctttgac taatt                                          565
```

```
<210> SEQ ID NO 242
<211> LENGTH: 1052
<212> TYPE: DNA
<213> ORGANISM: Oryza sativa

<400> SEQUENCE: 242
```

```
gtggagacga gcgacctgag agagagagag agagaaggca agggaaggag gagaagaagg     60
gggacgaagc ggacgaggcg cgcgcgcgcc atctttgctt tgcttcctct ctcttccctc    120
tcctctcctc tcctccggtc gtcggcctcc ccggccggcc ggcgcctgcc cgtgcttgag    180
gcgcggcggc ggatacgggg ggtgacgaca tggccgacgg gggagagaag tgccgggacg    240
cggccggcga gggcggcggc ggcggcgacc tgtacgccgt gctcgggctc aagaaggagt    300
gctccgacgc cgacctcaag ctcgcgtacc ggaagctcgc catgagatgg catccggaca    360
aatgctcatc ctccagcagt gcaaagcaca tggaggaagc caaggagaag ttccaggaga    420
tccagggcgc ctattccgtc ctctcagact caaacaagcg gttcctctac gacgtggggg    480
tatatgatga tgacgacaat gacgatgaca acctgcaggg gatggggggac ttcattggtg    540 agatggccca gatgatgagc caggcacggc caacgaggca ggagagcttt aaagaactgc    600
agcagctatt cgtagacatg ttccaagctg atcttgattc gggtttctgc aatggaccct    660
caaagtgcta ccatacccag gcccaaagcc agactcgaac atcctcaacc tcccttcga    720
```

```
tgtcaccgtc tccaccgcct ccagtagcta ctgaggcaga atcgccatca tgtaatggta      780
ttaataagcg tggttcatca gcaatggact ctgggaagcc tccaagagcc agcgaagtca      840
gtgctggaca gagtcaatca gggttttgtt tcgggaagag tgatgctaaa caagcggcga      900
agacgcgaag cgggaacacg gccagccgga ggaggaacgg ccggaagcag aaggtgtcgt      960
cgaagcacga cgtctcgtct gaggacgaga tgccaggttc gcagtggcac ggcgtggcct     1020
gacctttgtt cgtgactggt ttggcccttg at                                   1052
```

```
<210> SEQ ID NO 243
<211> LENGTH: 1513
<212> TYPE: DNA
<213> ORGANISM: Hordeum vulgare
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1273)..(1274)
<223> OTHER INFORMATION: n is a, c, g, or t
<220> FEATURE:
<221> NAME/KEY: misc_feature
<222> LOCATION: (1276)..(1278)
<223> OTHER INFORMATION: n is a, c, g, or t
<220> FEATURE:
<221> NAME/KEY: misc_feature
<222> LOCATION: (1281)..(1282)
<223> OTHER INFORMATION: n is a, c, g, or t
<220> FEATURE:
<221> NAME/KEY: misc_feature
<222> LOCATION: (1284)..(1285)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1304)..(1305)
<223> OTHER INFORMATION: n is a, c, g, or t
<220> FEATURE:
<221> NAME/KEY: misc_feature
<222> LOCATION: (1307)..(1311)
<223> OTHER INFORMATION: n is a, c, g, or t
<220> FEATURE:
<221> NAME/KEY: misc_feature
<222> LOCATION: (1364)..(1364)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t

<400> SEQUENCE: 243
cggacgaggg gggcaggcag tgcgtggaga ggagcccaga cagccgagga gagagaaaga       60
gggaaacttc aggagcctcc tcctcctccc ccggcgcacc ctccggccgg cgacgcgcgc      120
ggcatggcca ccggcggcga cggggacccg cggcgcccg gcggcggcga cctgtacgcc       180
gtgctggggc tcagcaagga gtgctccgac gccgacctca aggtcgccta ccggaagctc      240
gccatgaggt ggcatccgga caggtgctcg tcctccagcg gcaccaagca catggaggag      300
gccaaggaga agttccagga gatccagggc gcctattcgg tcctctccga cgccaacaag      360
```

```
cggttcctct acgacgtggg ggtgtaccaa gaagaagaag acagcgacga cagcatgcag      420
gggatggggg acttccttgg tgagatggcc catatgatga gccagacgcg gccagcgagg      480
caggagagct tcgaggagct gcagcagctg tttgtggaca tgttccagtc tgatattgac      540
tcgggatttt gcaatggacc tgccaagggc catcatgacc cgttccaaag acagactcaa      600
acattctcga cctcccttc ctcgccgcca tctccaccac ctccgctagc tacagaggca      660
gaagcagcct catgtaacgg cattaacaag cgtggctcat cagcaatggg ctctgggaag      720
cctccaagag ctgcggaagc gggtgcgggt tacggccagt ctgagttttg ttttgggacg      780
agtgatgcca agcaagcgcc aagggcgcga ggcgggaaca ccagcaggag acgaaacggg      840
cagaagcaga agctgtcgtc gaagcacgat gtctcgtccg aggacgagat gctgagcccg      900
cagcagccca gagtagtatg accctcgatg caaccatctg gtcccttgtc gccttatgtc      960
ctgaccatgt caatggtcac tcggtatcgc actgcagccg atagagcgcc agcgccggaa     1020
gctgttacga gggggggatgc ttcgtcgaag gctatgtagg ccccccttag aaggtttgta     1080
agagaaccta gtgtgtgaga ctcatcgatg ttaccgcatt cttttttctc ggtttgtgac     1140
gctatgttgt tgttgttgtt gttgttgtgg ttgttgttgg gcattgtact ctcgattgat     1200
tcagtgtcca ttgctgttat gatggaagaa gaaagctcct tgttgtggtg aaaaaaaaaa     1260
aaaaaaaana cannannnaa nnannanaaa aaaaaaaana anannannnn naaaaatacg     1320
tgggggggg gccccgcccc aattcccct taaaggggg gagntaaccg ccgttactac      1380
tattttactg ccaccccgc aactgccacc tagtcggcaa tcgacccgt tattttgcct      1440
tcttgcgagt gcgaatgtgt tgctggtcg ttgtatttcg ccgcttgta gcggnttgaa      1500
aaggaaatat ttg                                                       1513
```

<210> SEQ ID NO 244
<211> LENGTH: 1257
<212> TYPE: DNA
<213> ORGANISM: Triticum aestivum

<400> SEQUENCE: 244

```
gcacgaggga gcgacctgag ccgagagaga gagagagaga gggaaggaaa cgccaggaac       60
ctcctcctcc ctcctctccg ctctcctcct cctcctcccc cgcgcatcct cgagcccccc      120
aggccggcgg cgcgggacgc ggcatggcca ccggcgcgcga cggctgcggc ggcggggagc      180
cggcggcgcc cggcggcggc gacctgtacg ccgtgctggg gctcagcaag gagtgctccg      240
acgccgacct caagctcgcc taccggaagc tggccatgag atggcatccg gacagatgct      300
cgtcctccag cggcaccaag cggatggagg aggccaagga gaagttccag gagatccagg      360
gcgcctattc cgtcctctcc gacgccaaca gcggttcct ctacgacgtg ggggtgtacc       420
aagaagaaga agacagcgac gacagcatgc aggggatggg ggacttcctt ggtgagatgg      480
cccatatgat gagccagaca cggccagcga ggcaggagag cttttgaggag ctgcagcagc      540
tgtttgtgga catgtttcag tctgatattg actcggggtt ttgcaataga cctgccaagg      600
gccatcatga cccgttccaa acattctcga cctcccttc ctcgtcgcca tctccaccac       660
ctccagtagc tacagaggca gaagcagcct catgtaacgg cattaacaag cgtggctcat      720
cagcaatggg ctctgggaag cctccaagag ctggggaagc gggtgcgggt tacggccagc      780
ctgagttttg ttttgggacg agcgacgcca agcaagcgcc aaaggcgcga ggcaggaaca      840
ccagcaggag acgaaacggg caaaagcaga agctgtcgtc gaagcacgac gtctcgtccg      900
aggacgagat gctgagcccg cagcagccca gagtagcatg accctcgatg caaccgtctg      960
```

```
gtcccttgtc accttatgtc ctgaccatgt ccttggtcac ccagtatcag tgcagccagc    1020
aagtagagcg ccagcgccgg aagctgttac aaggaggggg gattgcttcg tcgaaggcta    1080
tgtagccccc ccttagaagg tttgtaagag aacctatagc gcgtaagact cgtcgatgtc    1140
accacattgt tctttctcgg tttgtgccgc tgtgttgttg ttgttgttgt tgtaattggg    1200
cattggattc tcgattgatt cagtgttcat tgttgttatg atggagggac aaggctc       1257

<210> SEQ ID NO 245
<211> LENGTH: 1094
<212> TYPE: DNA
<213> ORGANISM: Zea mays

<400> SEQUENCE: 245
agtgcggcga cgcggcggca gagggcggag acctctacgc ggttctcggg ctaaaaaagg      60
agtgctccga ggccgagctt aaggtcgctt accggaagct cgccaagaaa tggcacccgg     120
acaaatgctc gtcctccagc agcgtgaagc acatggagga agccaaggag aagttccaag     180
agatccaggg cgcctattcc gtactctccg acgccaataa acggctcctc tacgatgtgg     240
gagtatatga cgatgaggac gacgaggaaa gcatgcaggg gatgggggac ttcatcggtg     300
agatggccca gatgatgagc caggcgcagc cgacgaggca agaaagcttt gaggagctgc     360
agcagctttt tgtggacatg tttcagtccg atattgattc aggattctgc aataggactg     420
ccaaggccca tcagtttcag gggccagcca aaagtagaac atgctcgacc tcaccttcat     480
catcaccgtc ccctcctcct accacagcaa aggatgcaga ggtgccatca tgtaatggct     540
tcaataagcg gggttcatca gctctggact cagggaagcc tccaaagcct gttgaaggtg     600
gtgcaggtca gaaccaggct ggattctgtt ttggggtgag cgacacgaag gaaacgccga     660
agctgccagg tcagaacgcc agccgaggag ggaacggccg gaaacagaag ctgtcatcca     720
agcacgatgt ttcatctgaa gatgaaacgg cggccggttc gtagcacacc agcagtttga     780
cccattggct tcggtgatat atcattcgtt ggcccttggc tgtgcctagg ggccctagta     840
gctagcagca gcagcaggga cggcacatca tgccagctgc tgtgatctga agaggcgttt     900
agctcatcat atgcctcacc ttaggcctgt ggggatttt ccattgaaac tcgtcgatga     960
tactacatct ttctttctcc atctgtgtcg tttgtgttgt aagacagtga cttctgaagt    1020
ctgatcgtct cggttctttt tattaacatc tgatatacgt tactgcctgt tggtagtagc    1080
gaaagattaa aagg                                                      1094

<210> SEQ ID NO 246
<211> LENGTH: 851
<212> TYPE: DNA
<213> ORGANISM: Triticum aestivum
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 246
attcggcacg aggnaacaag cggttcctct acgacgtagg ggtgtaccaa gnaagaagaa      60
gacagcgacg acagcatgca ggggatgggg gacttccttg gtgagatggc ccatatgatg     120
agccagacac ggccagcgag gcaggagagc tttgaggagc tgcagcagct gtttgtggac     180
atgttccagt ctgacattga ctcgggattt tgcaatggac ctgccaaggg ccatcatgac     240
```

```
ccgttccaaa cattctcgac cttccttcc tcgtcgccat ctccaccacc tccgctagct       300
acagaggcag aagcagcctc atgtaacggc attaacaagc gtggctcatc agcaatgggc       360
tctgggaagc ctccaagaac tggggaagcg ggtgcgggtt acggccagcc tgagttttgt       420 tttggggagga gcgacgccaa gcaagcgcca aggcgcgag gcgggaacac cagcaggaga       480
cgaaacgggc agaagcagaa gccgtcttcg aagcacgatg tctcgtccga ggacgagatg       540
ctgagcccgc agcagcccag agtagtatga ccctcgatgc gaccatctgg tcctttgtca       600
ccttatgtcc tgaccatgtc aatggtcact cagtatcaca ctgcagccgg caagtagagc       660
gccagcgccg gaagctgtta caacgagggg gggttgcttc gtcaaaggct atgtaggccc       720
cccttagaag gtttgtaaaa gaacctagcg tgtaagactc attgatgtta ccgcattctt       780
ctttctcggt ttgtgccgct gtgttgttgt aattgggcat tggattctcg attgattcag       840
tgttcattgt t                                                            851

<210> SEQ ID NO 247
<211> LENGTH: 859
<212> TYPE: DNA
<213> ORGANISM: Zea mays

<400> SEQUENCE: 247
aacaagatat acctcgaccg ctttcaagtc acgattgcct acaaaacata atgttcagaa        60
catcacaatc caagtactat tttcttggta atagttcaat acacacccaa ttttttttaa       120
ttatcatggt atcaacttct ccagttaaaa aaatgaatag cttagaagtc actcactgtc       180
actggtagtg gtagtacaac acaaccggca cagatgggga aagaaaactg tagtatcatc       240
gacgagtttc aatggaaatc cctcttaggc ctgtagacgc tggttcggtt ttcgaagtac       300
ctttcaaccc taaagacctc tcaaaagact aaaggcatat gatgagctaa acgcctcttc       360
agatcacagc agctggcaga ggcgacatga tgtgccctcc ctactgctga catcaccaaa       420
gccaacggtc aaactgctac cgtgctgctg atgctaggaa ccggccgtat catcttcgga       480
tgtaacgtag tgcttgggga acagcttctg tttccggccg ttcctcttcc ggttggcgtt       540
cggacctcgc ggctttggcg tgtcgctcac cccaaaacaa aatccagcct ggctctgacc       600
tgcaccacat tcaacaggcc ttggaggctt tcctgagtcc attgctgatg aaccccgctt       660
attgaagcca ttcatgatg acacctctgc ctcctttact atagtagtag gaggggaccg       720
tggtgagcat gttctacttt tggcttgccc ctgaacctga tggcccttag cagtcccatt       780
gcagaatcct gaatcaatat cagactggaa catgtcgaca aaaagctgct gcagctcctc       840
aaagctttcc tgcctcatc                                                    859

<210> SEQ ID NO 248
<211> LENGTH: 607
<212> TYPE: DNA
<213> ORGANISM: Triticum aestivum
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (561)..(561)
```

```
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (596)..(597)
<223> OTHER INFORMATION: n is a, c, g, or t

<400> SEQUENCE: 248
ccactcccac tccccatatt catatattct gtattcacaa cccacctcac atcactagtt    60
acatgttgca ataacaaact gactaacccg ccgaaccgat ctagcaagct agttggcaaa   120
cttatcgcat ggagccctcg tgctcccatc ccgttgttgt tcttgtgcag tcctctccga   180
tgccaacaag cggttcctct acgacgtggg ggtgtaccag gaagaagaag acagcgacga   240
cagtatgcag gggatggggg acttccttgg tgagatggcc catatgatga gccaggcgcg   300
gccagcgagg caggagagct ttgaggagct gcagcagctg tttgtggaca tgttccagtc   360
tgatattgac tcaggatttt gcaatggacc tgccaagggc catcatgacc cgttccaaac   420
attctcgacc tccccttcct cgtcgccatc tccaccacct ccgctagcta cagaggcaga   480
agcagcctca tgtaacggca ttaacaagcg tggctcatca gcaaangggc tctggggaaa   540
gcctccaaga nccngggggaa ncggtncggg ttacaaccag cctganntttt gttttnngga   600
ccaacga                                                            607

<210> SEQ ID NO 249
<211> LENGTH: 1640
<212> TYPE: DNA
<213> ORGANISM: Zea mays

<400> SEQUENCE: 249
gattcggacg accgggacac ctgcctcctc cccttctccc atctctcccc ctctccctct    60
cgtggccact actgccgctg ccgccctacg ccaggtgtcc aggtcatctc cggcccattc   120
gccggcgacg agcaccccac tagatcgacc gagatatgga cggcctgtgg catctggggg   180
acgagctccg cgggcagccc aaggtggtgg aggaccgcca gtggtcgctc atgacgtcca   240
agctggcaga gatcaccagg tccaggggcg agaggacgaa cgacctcgac tacgccagga   300
tgaacgccgc ccccgacgcc aagcggtggg gcaaggcggc gtcctaccag caccatgacg   360
agggcaggat ggaccaccac gtcggcctca gcctcaagat gaacgatctc aagatgaacg   420
aggccgccgc tgccgccgtc atgaagctcc ccttccgcgg cgtgccctac aacgtcaacc   480
cgatgtaccc caaggggagc aacgccaacg ccaatgtcaa cgcgttcaag atgaatgtcg   540
gggtgaacaa gtactccagc agcgcgaacg ggaaagactc cggcgggaaa agcagtggcg   600
gcagcaacaa caacagcggc ggcggaggca acggcaatgg gaccgccaac ggcagttccg   660
cagttgacaa gcgcttcaag acgttgccga cgagcgagat gctgccgaag aacgaagtcc   720
ttggtgggta catctttgtc tgcaacaacg ataccatgca ggaggacctc aagaggcagc   780
tttttggatt gccagcaaga tatcgtgatt cagtccgggc aattactcct ggcctgcctc   840
ttttcctcta taactacacc actcaccagc ttcatggggt atttgaggct gccagttttg   900
gtgggtctaa tattgatccc actgcatggg aggataagaa gtgtaaaggt gaatctagat   960
tcccagcgca ggtgaggatc cgcgttagga agctgtgcaa gccgttggaa gaggattcct  1020
```

-continued

```
tcaggccagt tttgcaccac tatgatggcc caaagtttcg cctcgagctc tccatcgcgg    1080
agaccctgtc cctgctagac ctatgcgaga aggaaggcat ctgagctgtt ggctgcctcg    1140
tgaggttcta gtaaatatca atcatccttg tatgttctgt ggatggtggt tggcaatgtt    1200
gtttattttt caagcgcaag ctgctgccgg tctcgttttc cctgtcctgg atggaagcaa    1260
agggacctgg tactttgaag gccccccctc aaacataagc tgtgagcctg tcagtgcacg    1320
tgtccgccgt tgtcgtcaag aaccaaacca aatcatgaaa tcttgcgccg acggagagtt    1380
ggagcgtgta tgttttgcta tctctatcta catgtctcag tagagtggat ataccctggg    1440
gtccccaaaa gatgggggcc tgtatgtaac actacgtgta atggttaagg tgaatgtgcc    1500
gtgaggcccc ccaaaagttg gagtgtgtat ttttgttgtc accttgaacc gactttgcgt    1560
atgctttttt ttagtgctgc taccttctgc gctgtgtttg gcttctggtt catgtttttg    1620
taatataagg tggcttgcgc                                                1640
```

<210> SEQ ID NO 250
<211> LENGTH: 1570
<212> TYPE: DNA
<213> ORGANISM: Triticum aestivum

<400> SEQUENCE: 250

```
ccacgcgtcc gggtggactc tgtgtgggcg gagcgaagtg ggagccaacg ccaagccagc      60
cgagccgact cctatcctcc tcttcccctt ccccgcagca gtttcccaa  atccagcgcc    120 ctccccgccg gaatccggcg ccgaatcgag cagagagctt gaactgagct atggacaact    180
tgtggcatct cggagatgag ttccgtgggc aatcaaaggt ggtggaggac cgccaatggt    240
ctctcatgac atcaaagctt gctgagatca caaagtcaaa ggctgagagg atgaatgact    300
ttgagtatgc acggatgaac accgtccctg atgtcaagca atgggataag ctatcctacc    360
accaagaaga caacaagatg gaccacctca atcttggcct gatgaacctg gatcttaaga    420
tgaatgatct caagatgaac gaggctgcca tgaagtaccc tttccgcaac atggcctata    480
acatgaatcc gatgtacccc aagggaaaca acggtaatgt caattcgttc aagatgaatg    540
ttggggtcaa caaatatccc aataatcaga atgggaagga agcaaacggc aaacacaatg    600
gtggtaacaa caacaatgga ggcaacagca caacaactc  tgttgacaag cgcttcaaaa    660
cattgccaac aagcgagatg ctaccgagga atgaagttct tggtggatac atctttgtct    720
gcaacaatga taccatgcag gaggatctca agagacagct ttttggcttg ccagcaagat    780
atcgtgattc agtccgagcc atcactcctg gtctacctct tttcctctac aactacacga    840
cccatcagct acatggggtg tttgaggctg ctagttttgg aggatcaaac attgatccca    900
ctgcttggga agataagaag tgcaaaggtg aatccagatt cccagcacag gtgaggatcc    960
gcattagaag gctttgcaag gccttggaag aggatgcttt caggccagtg ctgcaccact    1020
atgatggtcc taaattccgc ctcgagctct ccatagcaga gacactgtca ctgctagacc    1080
tgtgcaagac agaagacgcc tgatctgctt cggaacatgt ttgtggttgc tctgtggttc    1140
tttttagtaa atatcatccc tgtaagttgt ggaagatgtt tcacaatga  tctgtcccgt    1200 ccgtcgtcca tgaaagcgca agctgttggt tggtggttgc atttccccca gaaaggacct    1260
ggtactcgga agaagtaggc ctctaaagat gtgagcctgt ctgtgtcggt gccgtctgtc    1320
cgtaatctcg gtgatgtgta tgttcttctt catatttatg tatttgtagt gcagtatgcc    1380
cgccgccagc ggggaaaccc cgaaagacgg gggatactgt tgtgatgcat catgaatgcc    1440
ccaaagtgag ggcggttgat gttgggagtg tatcttgttg tctctgtacc ttaccttggt    1500
```

```
ttggaaagtt ggaaccttgc atttgacttg atgctgctgt ttctgtactg ctgccagtgt   1560
ggaaggttaa                                                          1570

<210> SEQ ID NO 251
<211> LENGTH: 1824
<212> TYPE: DNA
<213> ORGANISM: Hordeum vulgare

<400> SEQUENCE: 251
ttcggcacga ggcctcgtgc cgaattcggc acgaggccgt gtgcgcggag cgaagtggga     60
gccgagccaa gccgagtctc ctctccttcc ccttcctcgc agcgccctcc ccgtccgaat    120
tcggggccgg atcgagcagg cggagagctt gaactgagct atggacaact tgtggcatct    180
cggagatgag ttccgtggtc aatcaaaggt ggtggaggac cgccaatggt ctctcatgac    240
atcaaagctg gctgagatca caaagtcaaa ggctgagagg atgaatgact ttgagtatgc    300
aaggatgaac actgtccctg atgtgaagca atgggataag ctatcctacc accaagaaga    360
caacaagatg gaccacctca atcttggcct catgaacctg atcttaagga tgaatgatct    420
caagatgaat gaggctgcca tgaagtaccc tttccgcaac atggcctata acatgaatcc    480
gatgtacccc aagggaaaca atggtaatgt caattcattc aagatgaatg ttggggtcaa    540
caaatatccc aataatcaaa atgggaagga agcaaacggc aaacacaatg gtggtaacaa    600
caacaatgga ggcaacagca acaactctgt tgacaagcgc ttcaaaacat tgccaacaag    660
cgagatgcta ccgaggaatg aagttcttgg tggatacatc tttgtctgca acaatgatac    720
catgcaggag gatctcaaga ggcagctttt tggcttgcca gcaagatatc gtgattcagt    780
ccgagcaatc actcccggtc tacctctttt cctctataac tacacgaccc atcaactcca    840
tggggtgttt gaggctgcta gttttggagg atcaaacatt gatcccaccg cctgggaaga    900
taaaaagtgc aaaggcgaat ccagattccc agcacaggtg agaatccgca ttagaaggct    960
gtgcaaggcc ttgaagagg atgcttttag gccagtgctg caccactatg atggtcctaa   1020
attccgcctt gagctctcca tagcagagac actgtcactg ctagaccttt gcaagtcaga   1080
agacgcctaa tctgcttcgg aacatgggtg tggttgctct gtggttcttt ttagtaaata   1140
tcatccctgt aagttgtgga agatgttttc acaatgttct gttctgtccg tcgtccatga   1200
aagcgcaagc tgttggttgg tggttgcatt tcccccagaa aggacctggt acttggaaga   1260
agtaggcctc taagatgtga gcctgtctct gtgttggtgc cgttcgtccg taatctcggt   1320
gatctgtatg ttctccttat ttatgtgttt gtagtgcagt atgcccgccg ccagcgggga   1380 aaccccccg aaagatgggg gggatactgt tgtgatgcat catgaatgcc ccaaagtgag   1440
ggcggttttt gtatcatcat gctggagtgt atctgttgtc tttgtacctt ggttgggaaa   1500
gttggaacct tgcattttac ttggatgctg tttttgtact gcctgtgttg aagttaaaa   1560 ccttgcaatt ttactggttg ctgctattga gatgctgtcg ctgtacacgc tcgtccatct   1620
tgctttcacg ttcaggaatg tagttatgta cttcctccgt tcacaaatac tccccccgtt   1680
tgtaaatata agtctttcta gagattccac aatatattta ggaacggagg aagtatatct   1740
tatacttctc cgtaccaaaa tataatcaat ttgaactgta aaagcctctt atattctggt   1800
atgaatataa tcaatttgaa ctgt                                          1824

<210> SEQ ID NO 252
<211> LENGTH: 1700
<212> TYPE: DNA
<213> ORGANISM: Oryza sativa
```

<400> SEQUENCE: 252

```
ccatgtgttg accgggaat tcggcattat gggcggggcc ttggcgtaaa ataaaagaga    60
aatctccccc cgtctcgtcg tctcctccgc tccttgcgcc tccccaagac gagtcgcggc   120
tgaacagaag aggggagta ggcggcgatc tccatctggc gactcgcgag cagagcaggg   180
gaggggatcc tgatctggaa gaagctctcc tcttaatttc agcgccttaa ccttaataca   240
agtaccagtt tgagtttgtt tgttcccaag ttggatccgg ccctgggtaa tttctttctt   300
gctgaaggtg gagagactga gctgagctat ggacaacttg tggcatctcg gggatgagtt   360
ccgtgggcag tcgaaggtag tggaggaccg tcagtggtct ctcatgacat cgaagttggc   420
tgagatcaac aagtccaagg cggagaggac gaatgagctt gactatgcgc ggatgaacac   480
catccctgat gtcaagcaat gggataaggt atcctaccac caagatgaga gcaagatgga   540
ccacctcaat cttggcctta tgaatctaga tcttaagatg aacgacatca ggatgaatga   600
cgcagctatg aagaatcctt ccgcgggcat ggcctacaac atgaatcagc tgtaccccaa   660
gggaggcaat ggcaatgtta actcgttcaa gatgaatgtt ggggtcaaca atatttgca   720
tagtccaaat ggcaaagatg tcaatggcaa aaacagtggt gccaacagca atggaagtaa   780
cagcagcggg aacaacagca gcaactctgc tgttgacaaa cgattcaaaa cattgccaac   840
aagtgagatg ctaccaagga atgaagtgct cggtggatat atctttgttt gcaacaatga   900
caccatgcag gaggatctca agaggcagct ttttgggttg ccagcaagat atcgtgattc   960
agtccgagca attattcctg gtctacctct tttcctctat aactacacga cccatcagct  1020
tcatggggta tttgaggctt ctagttttgg aggatctaat attgatccca ctgcatggga  1080
agataagaag tgtaaaggtg aatctagatt cccagcgcag gtgaggatcc gcattagaaa  1140
gctctgcaag cctttggaag aggatgcttt cagaccagtg ctgcaccatt acgatggtcc  1200
aaagtttcgt cttgagctct ccatagctga gaccttatca ctgctagacc tttgtgagaa  1260
agaaggcgtc tgaactgttg aagaggtggt tgctttgagg ctttagtaca tatcgctctt  1320
gtatgttgtg gaaggtggtt cactatgttc tcatgttcgt taagcgcaag ctgttggttg  1380
cccccctgcaa ggacctggta cttgaaggcc tctaatacgt gtgcctgtct gtattgtgcc  1440
gtccgtaatc ttgaaaatgt gtatgttttg ctatttatgt atttttggtag agtacaccca  1500
gaagggaacc ccaaaatggg gggatactgt aatgcatcat aatgccctaa ataagggcag   1560
ttgatgttca gagtgtattc gtgttgtatc ttaaaaacct tgcatttgcc ttaatgctgc   1620
tttgcacttc aaagttgtgt tttgctcaag ttttgcttag tagcaacgta gcatgccttt   1680
tatttactcc tcaaacaaaa                                              1700
```

<210> SEQ ID NO 253
<211> LENGTH: 1546
<212> TYPE: DNA
<213> ORGANISM: Zea mays

<400> SEQUENCE: 253

```
gccacctgcc ttctctcctt ccttccatcc attcctccct gtctccgccc tcttctgact    60
cccgtaggcc gtggtgccgc cgccgactgc tgggactgcc ctacaccaag tgcccaggtc   120
atcttcgggc cattcgccgg cgacgagcac caccaggtgt gccaggttga ccagagctatg   180
gacagcctgt ggcatcttgg ggacgagctc cgcgggcagc ccaaggtggt ggaggaccgc   240
cagtggtctc tcatgacgtc caagctggcg gagatcacca ggtccaaggg cgagaggatg   300
aacaccgtcc ctgacgccaa gcagtgggac aagacgtcct accagcttca cgacgacagc   360
```

```
aggatgggcc acatcaacct cggcctcatg aaccttgatc tcaagatgaa cgaggctgcc    420
gccatgaagc tccccttccg tggcatgccg tataacatga accagatgta cctcaagggg    480
agcaatgcca attccaatgt caatgcgttc aagatgaatg ttggggtcaa caagtactcc    540
aatagtccaa acgggaaaga cgccaatggg aaaaacaatg cggcagtgg cggcaacaac     600 aacaatggga gcgccaacgg cacttctgtg gctgacaagc gcttcaagac attgccgacg    660
agtgagatgc taccgaggaa tgaagtcctt ggtggataca tctttgtctg caacaacgat    720
accatgcagg aggatctcaa gaggcagctt tttggtttgc cagcaagata tcgtgattca    780
gtccgagcaa tcactcctgg cttgcctctt ttcctctata actacacaac ccaccagctt    840
catggggtat ttgaggctgc cagttttggt gggtccaata tcgatcctac tgcatgggag    900
gataagaagt gtaaaggtga atctagattc ccagcgcagg tgaggatctg cattaggaag    960
ctgtgcaagc cgttggaaga ggattccttc aggccagttt tgcaccatta tgatgggcca   1020
aagttccgcc ttgagctctc catcgcgag acattgtcac tgctagacct atgcgggaag    1080
gaaggcatct gagctgtcga ggaggtggtg gtggttgcct tgtgagcttc tagtaaatac   1140
caatcatctt tgtatgtttt gtggatggtg gttggcaacg ttgtttattt atgcgcaagc   1200
tgctgctggt ttcgggatgg aaggaaagac ctggtccctg aaacaagctg cggagagtga   1260
gcctgtcagt gtattgtgtc tggcgtggtc aagaaccaaa tcaatgttgg accgaccgac   1320
tgagagtttg gagtgtgtat gttttgctat tactcttatc tctagtagag tgtgggtata   1380
cctgggcaga atgtgtcccc aaaagttggg ggcctgtctg tgtactgtgt gcgatggacg   1440
ccctaagtaa aaaagggca ggtgatggtc gtgctccagg tttgtgtttt gtactctgtt    1500
gtaccttgaa cctcctttgc gttttgccta atcagagaat gaatcc                  1546

<210> SEQ ID NO 254
<211> LENGTH: 1031
<212> TYPE: DNA
<213> ORGANISM: Triticum aestivum
<220> FEATURE:
<221> NAME/KEY: misc_feature
<222> LOCATION: (14)..(14)
<223> OTHER INFORMATION: n is a, c, g, or t

<400> SEQUENCE: 254
cgtaccggtg gatnccgttg tcggcggagc gaagtgggag ccaacgccaa gccagccgag     60
cggactcctc tcctcctcgc agcagttcgc gattcgcccc caaatccagc gccctccccg    120
ccggaatccg gcgccgaatc ttgcagagag cttgaaccga gctatggaca acttgtggca    180
tctcggagat gagttccgtg ggcaatcaaa ggtggtggag gaccgccaat ggtctctcat    240
gacatcaaag ctggctgaga tcacaaagtc aaaggctgag aggatgaatg actttgagta    300
tgcacggatg aacaccgtcc ctgatgtgaa gcaatgggat aagctatcct accaccaaga    360
agacaacaag atggaccacc tcaatcttgg cctcatgaac ctggatctta agatgaacga    420
tctcaagatg aacgaggctg ccatgaagta cccttttccgc aacatggcct ataacatgaa    480
ccccatgtac cccaagggaa acaacggtaa tgtcaattca ttcaagatga atgtcggggt    540
caacaaatat ccgaataatc agaatgggaa ggaagcaaac ggcaaacaca atggtggtaa    600
caacaacaat ggaggcaaca gcaacaacaa ctctgttgac aagcgcttca aaacattacc    660
aacaagcgag atgctaccaa ggaatgaagt tcttggtgga tacatctttg tctgcaacaa    720
tgataccatg caggaggatc tcaagagaca gctttttggc ttgccagcaa gatatcgtga    780
ttcagtccga gccatcactc ctggtctacc tctttttcctc tacaactaca cgacccatca    840
```

```
gctacatggg gtgtttgagg ctgctagttt tggaggatca acattgatc ccaccgcttg      900 ggaagataag aagtgcaaag gtgaatccag attcccagca caggtgagga tccgcattag      960
aaggctttgc aaggccttgg aagaggatgc ttttaggcca gtgctgcacc actatgatgg     1020
tcctaaattc c                                                          1031

<210> SEQ ID NO 255
<211> LENGTH: 1385
<212> TYPE: DNA
<213> ORGANISM: Oryza sativa

<400> SEQUENCE: 255
gactggactg aaggagtaga aattggcgta aaataattga gaaatctccc cccgtctcgt       60
cgtctcctcc gctccttgcg cctcccaag acgagtcgcg gctgaacaga agaggggag       120 taggcggcga tctccatctg gcgactcgcg agcagagcag gggagggat cctggtggag      180 agactgagct gagctatgga caacttgtgg catctcgggg atgagttccg tgggcagtcg      240
aaggtagtgg aggaccgtca gtggtctctc atgacatcga agttggctga gatcaacaag      300
tccaaggcgg agaggacgaa tgagcttgac tatgcgcgga tgaacaccat ccctgatgtc      360
aagcaatggg ataaggtatc ctaccaccaa gatgagagca gatggaccaa cctcaatctt      420
ggccttatga atctagatct taagatgaac gacatcagga tgaatgacgc agctatgaag      480 aatccttttcc gcggcatggc ctacaacatg aatcagctgt accccaaggg aggcaatggc      540
aatgttaact cgttcaagat gaatgttggg gtcaacaaat atttgcatag tccaaatggc      600
aaagatgtca atggcaaaaa cagtggtgcc aacagcaatg gaagtaacag cagcgggaac      660
aacagcagca actctgctgt tgacaaacga ttcaaaacat tgccaacaag tgagatgcta      720
ccaaggaatg aagtgctcgg tggatatatc tttgtttgca acaatgacac catgcaggag      780
gatctcaaga ggcagctttt tgggttgcca gcaagatatc gtgattcagt ccgagcaatt      840
attcctggtc tacctcttttt cctctataac tacacgaccc atcagcttca tggggtatct      900
gaggcttcta gtttcggcgg ctctaatctc gatcccactg aatgggacga tacgacgtgt      960
aacggtgaat ctagattccc agctcaggtg acgctccgcc ttccaaagct ctgcaagcct     1020
ttggaagacg ctgcttccac accagtgctg caccattacg atggaccaca gtctcgtcta     1080
gacctctcca tagctgacaa cttatcactg ctacacctct gtgcccaaca acgcgtctga     1140
actgttgaag acgtgcttgc ctcgaggctt caccaactat cgctctcgta tgtagagcac     1200
cgaggcccct cacgtacacc ctatcgtcag cgcaaccgac cggtgccccc tgacagaaca     1260
gctacccgac agccccacca ggcagcgtac acaacggccg ccagcaacca aacccacgac     1320
tcacgacaac agcaacgcca accccaacc ccaccaacag cccaacacca cacaaccccc     1380
aagaa                                                                 1385

<210> SEQ ID NO 256
<211> LENGTH: 785
<212> TYPE: DNA
<213> ORGANISM: Oryza sativa

<400> SEQUENCE: 256
ccaagacgag tcgccgttga acagaagagg gggagtaggc ggcgatctcc atctggcgac       60
tcgcgagcag agcaggggag gggatcctga tctggaagaa gctctcctct taatttcagc      120
gccttaacct aatacaagt accagtttga gtttgtttgt tcccaagttg atccggccc        180 tgggtaattt cttttcttgct gaaggtggag agactgagct gagctatgga caacttgtgg      240
```

```
catctcgggg atgagttccg tgggcagtcg aaggtagtgg aggaccgtca gtggtctctc      300
atgacatcga agttggctga gatcaacaag tccaaggcgg agaggacgaa tgagcttgac      360
tatgcgcgga tgaacaccat ccctgatgtc aagcaatggg ataaggtatc ctaccaccaa      420
gatgagagca agatggacca cctcaatctt ggccttatga atctagatct taagatgaac      480
gacatcagga tgaatgacgc agctatgaag aatcctttcc gcggcatggc ctacaacatg      540
aatcagctgt accccaaggg aggcaatggc aatgttaact cgttcaagat gaatgttggg      600
gtcaacaaat atttgcatag tccaaatggc aaagatgtca atggcaaacg attcaaaaca      660
ttgccaacaa gtgagatgct accaaggaat gaagtgctcg gtggatatat ctttgtttgc      720
aacaatgaca ccatgcagga ggatctcaag aggcagcttt ttgggttgcc agcaagatat      780
cgtga                                                                  785

<210> SEQ ID NO 257
<211> LENGTH: 1024
<212> TYPE: DNA
<213> ORGANISM: Gossypium hirsutum

<400> SEQUENCE: 257
cagaagaacg ttggggtcaa cggtgggttc aacaaaggga tctattccaa accagggaac       60
aacaacaata acttcaatgt taatttgaat gggaacaaga gcaaaggaga agaatatcat      120
ggaaccaaga gtgggaagaa gaacagcaac aagaaaaaac aataacaaca acgacaataa      180
caacgaaaac aaggatggga aaagtgctgc tgataaaagg tttaagacac tgccaccatc      240
tgaatcattg ccgagaaatg aaactgtcgg cggctatatt tttgtctgca acaacgatac      300
catggaggag aatctcagaa gacagctctt tggtttgcct ccacgttacc gtgattcagt      360
ccgggcaata actccgggcc tgcctctgtt cctctacaac tactccaccc accaactcca      420
tggtgttttt gaggctgcaa gctttggtgg aacaaacatt gacccaactg cctgggagga      480
caagaaatgc cctggcgaat ctcgattccc tgctcaggtt cgcgttatta caaggaaaat      540
ctgcgagcca cttgaagaag attcattag gccaattctc catcactacg atggtccaaa       600
attccgcctt gaactcaaca tcccagaggc acttcccctg ttggatatat ttgctgatca      660
acaagatact tgtatttctt aagcaacaag atgcttgagc aaaactaaaa cactaggcat      720
atcgatacaa atacagatac acacagagat aatgaagaga agagtttgaa gaataagtag      780
agaaaaatag aaattatatt tgtgaaagtg cctttgttag atgtaaaact tttttttttca      840 caggctttgc tgtgattgtt tttcttttct tttcttttt actgtttggc ttatacataa       900
ataatacctg aaactaagtg ataaacatcg acttattttg ggatgttact taatataagt      960
ttgagatttt gttgtattag aacttgtttt gaagctatga atctaaaact acaattattg     1020
gtct                                                                   1024

<210> SEQ ID NO 258
<211> LENGTH: 943
<212> TYPE: DNA
<213> ORGANISM: Solanum tuberosum

<400> SEQUENCE: 258 aaagggata aataggaaat ttggtaaagg attttttgaa gatgagcata aaagtgtgaa        60
gaagaataac aagagtgtta aagagagtaa caaggatgtt aatagtgaga acagaatgg       120 tgttgataaa aggtttaaga ctttgccacc agcagaatct ttgccaagaa atgagacagt      180
tggtggatat attttttgttt gcaacaatga tactatggct gagaatctca aagggagct      240
```

```
ctttggcttg cccccacgtt acagggactc agttaggcaa ataacacctg gattgcctct      300
ttttctgtac aactactcga cccatcagct tcacggtgtt tttgaggctg caagctttgg      360
tgggtcaaat attgatccat cggcctggga ggacaagaag aaccctggtg aatctcgctt      420
tcctgctcag gtccttgtcg tgacaaggaa agtctgtgaa ccacttgaag aggattcatt      480
caggccaatc cttccacact acgacggccc taaattccgc ctcgagctaa acgttccaga      540
ggctatttct cttctagaca ttttgaaga gaacaagaac taaatgaatg ttcttgtttt       600
acaagcagag aatggacaat ataccattat aaaggaagaa aaaaagagt tgattagaga       660 aaagagtga aaagagttt gcttctagta atactgaaga gagtttgcag agcagaaaaa        720
aaaactatct atctattgta tatagatata tacataaatg cagaatataa tgatctggaa      780
aaacactttt tgtgtggaga caaatattat tatatttact atattgtgta atccagcaag      840
aatttgctgt ataataataa gtgaaatatg agtaaaaaca agttatgttt ggttattact      900
acctattatt tcctctttgc tatatctaaa atgcatttgg tgt                        943
```

<210> SEQ ID NO 259
<211> LENGTH: 1236
<212> TYPE: DNA
<213> ORGANISM: Triticum aestivum
<220> FEATURE:
<221> NAME/KEY: misc_feature
<222> LOCATION: (1185)..(1185)
<223> OTHER INFORMATION: n is a, c, g, or t

<400> SEQUENCE: 259

```
cacacgtgcc gggactggag cacgaggaca ctgacatgga ctgaagcagt agaaaattca       60
agatcacttt tccgtgcact ttttttttacc tcggagccac acagactctc accacatccc     120
aggaaccaga gcagcaagcc ttgtggagct cggctcgagc atggacacca agcatgcgga     180
ttcgttcgac gagcgcgacg tcgtcgtcga cgccggctgc gtccgcgccg tgctcgggga     240
gctggtcctc accttcctct tcgtcttcac cggagtcgcc gccgccatgg ccgccggggt     300
gccggagctg caaggcgcgg ctatgccgat ggcgacgttg gccggggttg ccctcgcgca     360
ggcgctggcg gcggggggtgc tggtgacggc gggcttccac gtgtcgggcg ggcacctcaa     420
cccggcggtg acggtggcgc tgctggcgcg cgggcacatc acggcgttca gggccgtgct     480
gtacgtggcg gcccagctgc tggcctcctc cctcgcctgc atcctcctcc gctacctctc     540
cggcggccag gctactccgg ttccggtcca caccctaggc gcaggcatag gccccatgca     600
agggctggtc atggaggtca tcctcacctt ctccctcctc ttcgtcgtgt acgcgaccat     660
catcgacccg cggaccacgg tgcccggcta cggtccgatg ctcaccggcc tcatcgtcgg     720
tgccaacaca attgccggcg gcaacttctc cggcgcttcc atgaacccag ctaggtcctt     780
cgggcccgcg ttggccactg gggtgtggac caaccactgg gtctactggg tcggcccgct     840
ggtcggcggc cccctcgccg ggttcgtcta tgaaacggtg ttcatggtga cgaagacgca     900
tgagcctcta cttggttggg acttttagaa aagcaggttg ctcgcatact tgcatttata     960
ttttgcgatg tataccagtg tgtataaggc aatcgatgtt gctgatagat ttcaggcaa     1020 tgtgaatcta gctaggtgtt gaaatggttt gtagggagca gcgactaaag tggctgtttt    1080
ttttggttgt taaagctttt gattaaaagg ctaataatca gccgtgtaaa tatatttgtt    1140
tggaagacgt gaatttcaac ccattagagg tgtgattttt ctttngttct attagaggtg    1200
tgattggtgt tgcgaatcag ggacaaacct tttgtg                              1236
```

<210> SEQ ID NO 260

```
<211> LENGTH: 1080
<212> TYPE: DNA
<213> ORGANISM: Triticum aestivum

<400> SEQUENCE: 260
cccacgcgtc cgttactttt aacctcggag ccgcacagac tctcgccaca tcccaagaac     60
cagagcggcg agcctcgtgg agctcagctc gagcatggac accaagcatg cggattcgct    120
cgacgagcgt gacgtcgtcg tcgtcgacgc cggctgcgtc cgcgccgtgc tgggggagct    180
ggtcctcacc ttcctcttcg tcttcaccgg agtcgccgcc gccatggccg ccggggtgcc    240
ggagctgcag ggcgcggcta tgccgatggc gacgctggcc ggggttgccc tcgcgcaggc    300
gctggcggcg ggggtgctgg tgacggcggg gttccatgtg tcgggcgggc acctcaaccc    360
ggcggtgacg gtggcgctgc tggcgcgcgg gcacatcacg gcgttcaggg cggtgctgta    420
cgtggcggcc cagctgctgg cctcctccct cgcctgcatc ctcctccgct acctctccgg    480
cggccaggcc actccggttc cggtgcacac cctgggcaca gcataggcc ccatgcaagg    540
gctggtcatg gagatcatcc tcaccttctc cctcctcttt gtggtgtacg cgaccatcct    600
cgacccgcgg accacggtgc ccggctacgg accgatgctc accggtctca tcgtcggtgc    660
caacaccatt gccggcggca atttctccgg cgcttccatg aaccccgccc ggtccttcgg    720
gcccgcgttg gccactggag tgtggaccaa ccattgggtc tactgggtcg gcccgctggt    780
cggtggcccc ctcgccgggt tcgtctatga gacagtgttt atggtgacga agacgcatga    840
gcctctactt ggttgggact tttagaaaag caggttgctc gcatacttgc atttacattt    900
tgcgatgtat aatggtatgt ataagacaat cgatgtcgct gatagatttt tcaggcgaag    960
tgattctagg tagggtgtca gaaatggttt gtacggagct actacaatgc tgtgtaaata   1020
tatttgtttg gaagatgtga atttcaaccc cttagaggtg tgaaattttt tttgagttct   1080

<210> SEQ ID NO 261
<211> LENGTH: 1139
<212> TYPE: DNA
<213> ORGANISM: Hordeum vulgare
<220> FEATURE:
<221> NAME/KEY: misc_feature
<222> LOCATION: (12)..(12)
<223> OTHER INFORMATION: n is a, c, g, or t

<400> SEQUENCE: 261
ctcgtgccga anttcggcac gagccaactt ttcggtgcgc ttttgcatcg tcctgagctt     60
tcacccctct tccttccttc cttccatccc aagaacaaga gcgacgagtg tggtggagtt    120
cagtcccgcc atggccgcca ccaagcacgc ggattcgttc gacgagcgtg aagtcgccgt    180
cgtcgacacc ggctgcgtcc gcgccgtgct ggggagctg gtcctcacct tcctcttcgt    240
cttcaccgga gtcgccgccg ccatggccgc cggggtgccg gagctgccgg gcgcggctat    300
gccgatggcg acgttggccg gggttgcgct tgcgcaggcg ctggcagcgg ggtgttggt    360
gacggcgggg ttccatgtct ccggcgggca cctcaacccg gcggtgacgg tggcgctgct    420
ggcgcgcggg cacatcacgg cgttccggc ggtgctgtac gtggtggccc agctgctggc    480
ctcctcccte gcctgcatcc tcctccggtg cctcaccggc ggccagccta caccggttcc    540
ggtgcacacc ctgggcgcag gcataggcc catgcaaggc ctggtcatgg agatcatcct    600
caccttctcc ctcctcttcg tcgtgtacgc caccatcctc gacccgcgga ccacggtgcc    660
cggctacgga ccgatgctca ccggccttat tgtcggtgcc aacaccattg cgggcggcaa    720
cttctctggg gcgtccatga accctgctcg gtctttcggg cctgcgttgg ctaccggggt    780
```

| | |
|---|---|
| gtggaccaat cattggatct attgggttgg cccattggtc ggtggtccgt tggccggttt | 840 |
| tgtctatgag atggtcttca tggtgaagaa gacgcacgag cctctgcttg gttgggactt | 900 |
| ttaggaaagc aaattgctcg catacttgta attgcatttt gcaatgtata ccggtgtgta | 960 |
| taagacaatc aatgttgctg atagatttgt ttctagctat atatagtgtt caaatggttt | 1020 |
| gtaaggagca actacaaaag atgttttttt agagggatgg ggttagaagc tttgattaaa | 1080 |
| aggctaataa tcagctgtgt aaatatattt gtttggaaat cactggatct tttgggcca | 1139 |

<210> SEQ ID NO 262
<211> LENGTH: 1369
<212> TYPE: DNA
<213> ORGANISM: Triticum aestivum

<400> SEQUENCE: 262

| | |
|---|---|
| ctcagcctag gccttgtgaa gtcacttatt tgattactgc aggaatatca tttcatacct | 60 |
| ttggtactaa tcgtatcata tgttgccggg accgtaacat ggacagacag cggttacttg | 120 |
| acaaggccta ggctgaggat gccgaaggag gtatggggcc agtctttctc cttggcctta | 180 |
| gtcagcatgg ctctgcccca ggacttttcc gtgcactttt tttacctcgg agccacacgg | 240 |
| actactctca ccacatccca agaagcagag caacgagcct tgtaagcatg acaccaagc | 300 |
| acgcggattc gttcgaggag cgtgacgtcg tcgtcgacgc cggctgcgtc cgcgccgtgc | 360 |
| tgggggagct ggtcctcacc ttcctcttcg tcttcaccgg agtcgccgcc gccatggccg | 420 |
| ccggggttcc ggagctgccg ggcgcggcta tgccgatggc gacgttggcc ggggttgccc | 480 |
| tcgcgcaggc gctggcggcg ggggtgctgg tgacggcggg cttccatgtg tcgggcgggc | 540 |
| acctcaaccc ggcggtgacg gtggcgttgc tggcgcgcgg gcacatcacg gcgttcaggg | 600 |
| cggtgctgta cgtggcggcc cagctgctgg cctcctccct cgcctgcatc ctcctccgct | 660 |
| acctctccgg cggccaggct actccggttc cagtgcacac cctgggcgca ggcataggcc | 720 |
| ccatgcaagg gctggtcatg gaggtcatcc tcaccttctc cctcctcttc gtcgtgtacg | 780 |
| cgaccatcat cgaccctcgg accacggtgc ccggctacgg tccgatgctc accggcctca | 840 |
| tcgtcggtgc caacaccatt gccggaggta acttctccgg tgcgtccatg aaccccgcta | 900 |
| ggtccttttgg tcccgcgttg gccatgggag tgtggaccaa ccactgggtc tactgggtcg | 960 |
| gtccgctggt cggtggcccc ctcgcggggt tcgtctacga gatggtgttc atggtgaaga | 1020 |
| aagacgcacg agcctctgct tggctgggac ttctagaaaa caggttgctc ccatacttgc | 1080 |
| atttacattt tgcgatgtat accagtgtgt ataaggcaat cgatgttgct ggtagatttt | 1140 |
| tcaggcccag tgattctagc tagggtgtcc aaatggtttg tagggaggta ctacggtgga | 1200 |
| tgtttttttt cttgggggag gggggagat aggttttgtt caaagctttg attaaaaggc | 1260 |
| taataatcag ccgtgtaaat atattgggcg cttataggcg ccggcgcgcc ggccgaaccg | 1320 |
| ctcggccggt cgagcccag ccgcccgata tcatgaataa gagccgtcc | 1369 |

<210> SEQ ID NO 263
<211> LENGTH: 1430
<212> TYPE: DNA
<213> ORGANISM: Oryza sativa

<400> SEQUENCE: 263

| | |
|---|---|
| ggcacaaaca gtttcgcttt cttgatagcc atgtcgcagc cacagctttg tttgctagaa | 60 |
| tgagacaccc ctgattcctc agccacatac ttagattaag aaactaatca ccttcctcaa | 120 |
| tcttggttcc taatccgcta taaaaagcag aggaaagcag aggagacagg cagagcagag | 180 |

-continued

| | |
|---|---|
| gagagaaccc caccttggca aaaagaaaag aaaaataata tcatcgcact ttttgctgcc | 240 |
| cttttcatcc cctcggatat tcacgaagca aatctctctg caattctttt cttttttttt | 300 |
| tttgatcttg cggatcttct ccattgagga aaggcgagag ctttgggatc gattccgggc | 360 |
| catggcgaag gaggtggatc cgtgcgacca cggcgaggtc gtcgacgccg ggtgcgtccg | 420 |
| cgccgtgctg gccgagctcg tcctcacctt cgtcttcgtc ttcaccggcg tcgccgccac | 480 |
| catggccgca ggggtgccgg aggtggcggg ggcggcgatg ccgatggcgg cgctggcggg | 540 |
| ggtggcgatc gcgacggcgc tggcggcggg ggtgctggtg acggcggggt tccacgtgtc | 600 |
| cggcgggcac ctgaacccgg cggtgacggt ggcgctgctg gcgcggggc acatcacggc | 660 |
| gttcaggtcg gcgctctacg tcgccgccca gctgctggct tcctccctcg cctgcatcct | 720 |
| cctccgctac ctcaccggcg gcatggcgac cccggtgcac actctgggct cagggatagg | 780 |
| gcccatgcag ggcctggtca tggagatcat cctaaccttc tccctcctct tcgtcgtcta | 840 |
| cgcgaccatc cttgacccgc ggagctcggt ccccgggcttc ggcccgctgc tcacgggcct | 900 |
| catcgtcggt gccaacacca tcgctggtgg caacttctcc ggcgcgtcaa tgaacccggc | 960 |
| ccggtcattt gggccggcgc tggccactgg agtgtggacc caccactgga tctactggct | 1020 |
| cgggccgctg attggcgggc ctctcgctgg gctggtctat gagtcattgt tcttggtcaa | 1080 |
| gaggacccat gagcctctgc tagataattc cttttagtag tctggtctct ttagatggtt | 1140 |
| tcatttgcag aatgcatata ttgccaggta gtaataagat gcttgtgcag cttgtaggcc | 1200 |
| tgtaagggct gtataattat tattttcttt ttgccctcga ggattttatc aacgttgata | 1260 |
| atcagccatg taaaaagatt gtttgggata tgattttttt gttagtataa aatgtagtcc | 1320 |
| ggtagttggt ctgttgtaaa tcggcgaatg ccatgtggtt ttgaaattag aatctatgta | 1380 |
| aacattttca aatgaattca gtaaaattca tttcaaatgg gtaaaaaaaa | 1430 |

<210> SEQ ID NO 264
<211> LENGTH: 618
<212> TYPE: DNA
<213> ORGANISM: Saccharum officinarum
<220> FEATURE:
<221> NAME/KEY: misc_feature
<222> LOCATION: (597)..(597)
<223> OTHER INFORMATION: n is a, c, g, or t

<400> SEQUENCE: 264

| | |
|---|---|
| cccacccgcc tcctcctcct cctcctcctg tcgttcaaaa tatctcgctg cgcttttccg | 60 |
| agtccttttc cctccaagga acaggaacaa ccggcgcttt tacccccacca cccgctttcc | 120 |
| cctccccgcc aggaacagga gcgacaaggc tcctcctcgc aatagttcat tcattcatgg | 180 |
| cgaagctcgt gaacaagctg ctcgattcgt tcgaccacga cgacactacg ccggacgtcg | 240 |
| gctgcgtgcg cgccgtgctg gccgagctcg tcctcacctt cctcttcgtc ttcaccggcg | 300 |
| tctccgccgc catggccgcc gggtccggcg ggaagcccgg cgaggctatg ccgatggcga | 360 |
| cgctggcggc ggtggctatc gcgaacgcgc tggccgccgg cgtcctggtc acggccgggt | 420 |
| tccacgtctc cggcggccac ctcaacccg ccgtgacggt ggggctcatg gtgtgccgcc | 480 |
| acatcaccaa gctccgcgcg gtgctctaca tcgccgcgca gctgctggcc tcctccctcg | 540 |
| cctgcattct cctccgctac ctcagcggcg gcatggtgac cccggtgcac gccctgngcg | 600 |
| ctggcatcaa gcccgatg | 618 |

<210> SEQ ID NO 265
<211> LENGTH: 2695
<212> TYPE: DNA

<213> ORGANISM: Oryza sativa

<400> SEQUENCE: 265

```
ctttgaagtc ctagcctaaa agctcttcta ctcgcataaa gaaagatggt gaagcttgca      60
tttggaagct gcggcgactc tttcagtgcc tcgtccatca aggcctatgt cgcggagttc     120
attgccacac tcctctttgt gttcgccggc gtcggctccg ccattgccta cgggcaactg     180
acaaagggcg gcgcgctaga cccagctggt ctggtggcga tcgccatagc ccatgccttc     240
gcgctgttcg tcggagtttc catggccgcc aacatctccg gtggccactt gaacccgtt      300
gtcaccttcg gcctcgccgt cggtggccac atcaccatcc tcaccggcat cttctactgg     360
gtcgctcagc tgctcggcgc gtccgtcgcg tgtctgctct gcagttctcc acccacggac     420
aggttggcta tcccgacgca cgccatcgcc ggaattagcg agatcgaggg catggtgatg     480
gagattgtga tcacgttcgc gctggtgtac acggggtacg ccacggcggc cgacccgaag     540
aagggttccc tcggcaccgt cgcgcccatg gacatcggct tcatcgtcgg tgccaacatc     600
ctggcggcgg ggccctttag cggcagttcc atgaaccctg cccgctcctt cggcccggcc     660
gtcgcggccg gcaacttcgc cggcaactgg gtgtactggg tcggcccact gatcggtggt     720
ggcctggccg ggctcgtcta cgacgacgtg ttcatcgcct cctaccagcc ggtgatgatc     780
ggattcactg ttattttatg tgaccggtct gaccaggctg tgtatgccgg tcagaccagc     840
ggtgatcgag cggtgactcc atgcctaggg agagtatttg cggtgatgga ccgggagtcg     900
gcttggtgta ggatgcaatc ttacattatg gctgagaatt atgatatttg gagaaaagtt     960
tctcatcctt atgtgattcc tgaagctatt aatactgctg ctgaaaaaac tgcttttgaa    1020
caaaattgca aagctcgcaa tattcttttg agtgggattt ctcgttcgga ttatgatcgt    1080
gttgctcatc ttcaaactgc tcatgagatt tggattgctt tgagtaattt tcatcaagga    1140
acaaataata ttaaagaact tcgtcgtgat cttttcaaaa aggagtatat taaatttgag    1200
atgaaacctg agaagctttt ggatgactat cttttctaggt ttaataaaat tttgagtgat    1260
cttagatctg ttgattcttc ttatgatgct aattatccac aatctgagat ttctcgtcac    1320
tttttgaatg gtcttgacat gtctatttgg gagatgaaag ttacatctat tcaggagtct    1380
gttaacatgt ctactttgac tttggattcg ctttacacaa aattgaaaac tcatgagatg    1440
aatattcttg ctcgtaaagt tgattctaag tctagtgctt tggtttcttc ttcgacttct    1500
ttggatgttg gtgcttcttc atcgaagtct tctgttcttg ctttatttaa tgccatgtcc    1560
gatgatcaac tcgaacagtt cgaggaggag gacttggttt tgttatctaa caaatttttct    1620
cgagctatga aaaatgttag gaacaggaaa agaggagaac cgaatcgttg ttttgagtgt    1680
ggagcacttg atcatcttcg ctcgcattgt cctaagcttg ggagaggcaa gaaggaagat    1740
gatggtagag tcaaagagga tgacgtgaac aagaagaaga acatgaagga aaggagaag    1800
aagaagcatt gtatgcagtg gttaatccaa gaactcataa aagttttga tgaatcggaa    1860
gatgaagatg agggcaaagg taagcaagtt gttgatctag ctttttattgc tcgtaatgca    1920
agttctgatg ttgatgaatc tgatgatgat aatgaagaaa agcttagtta tgatcaatta    1980
gaatatgctg cttacaaatt tgctaagaaa cttcaaacat gttctattgt gcttgatgag    2040
aaggatcata ctattgagat tcttaatgct gaaattgcta gattaaaatc tttgattcct    2100
aatgatgata attgtcaatc ttgtgaagtt ttattttctg aaattaatgc tttgcgagat    2160
gtcaattctg ttaattgcaa gaaattggaa tttgagattg aaaaatctaa aaagttggaa    2220
tcttcttttg ctcttggatt tgctttacat gctcgtgttg ttgatgagtt gattttgaca    2280
```

```
aagaacgttt tgaaaaaaat acaaagttgc tttttgtgca agttctttgg tcaatgcttc    2340
atgtgcaaat aaggcaaaac aaaacaatgg tgttttgatt tctcaagatt gttcaaagtg    2400
tgttttgaat gagttgaagt tgaaagatgc tttagagcgt gttaaacaca tggaagaaat    2460
tattaaacaa gatgaggtgt tttcatgctc aacttgtaga aaacaaaaag gtcttttgga    2520
tgcttgtaaa aattgtgcta ttcttactca ggaggtttct tatttgaaaa gttctttgca    2580
aagattttct gatggtaaaa agaacctcaa catgattctt gatcaatcta acgttagcac    2640
acacaatcgt ggtttaggtt tgattcttta ttcaaaggac cttgatgtcg cctag         2695
```

<210> SEQ ID NO 266
<211> LENGTH: 1083
<212> TYPE: DNA
<213> ORGANISM: Glycine max
<220> FEATURE:
<221> NAME/KEY: misc_feature
<222> LOCATION: (24)..(24)
<223> OTHER INFORMATION: n is a, c, g, or t

<400> SEQUENCE: 266

```
attagttcga ttttgtagta agtnaggtgc caatatggtg aagatagctc ttggtacttt      60
ggatgactct tttagcgctg cctctcttaa agcttatttc gcagagttcc acgcaactct     120
gattttcgtg ttcgctggtg ttggatcagc catcgcttac aacgagctta caaaagatgc     180
agccttggat ccaacggggc tggtggcagt agctgtggca catgcatttg cactgtttgt     240
aggtgtctcc gtcgccgcca acatctcagg tggccatttg aacccagctg tcacttttgg     300
attggccatt ggaggcaaca tcactctcat cactggtttc ttatactgga ttgcccaatt     360
gttgggttct atagtcgcat gcctcctcct caatttgatc accgctaaga gcattccaag     420
ccactcgccg gctaatggtg tgaacgattt gcaagctgta gtgtttgaga ttgttatcac     480
atttgggttg gtttacactg tgtatgcaac tgcagtagac ccaaagaagg ggtcattggg     540
tatcattgca cccattgcta ttgggttcgt tgtgggtgcc aacatcttag cagcaggccc     600
attcagcggc ggttcaatga acccagctcg ctcattcggc ccagctgtgg tcagtggaga     660
cttggctgct aactggatct actgggttgg cccattgatt ggaggaggtt tggctggctt     720
gatttatgga gacgtcttca ttggttccta tgcccctgtc ccagcctctg aaacctaccc     780
ttgagcttca acttcacttg tgtgttcctt caagtttcat ctctgttcac cgtttcatgt     840
catgagcctc ttggcttctt gcattttaaa ctctacttta tctattatcc accgcttgca     900
ataattatgt aaattataat tcgaacttga tacatgaatt gttggaaggt ccccttgttt     960
ttcggttttc gtcctaccaa tgacagcgag ctagctagtg gttttttacgg atcagatctg    1020 cagttcattt ttcaactgta atcaatctcg gccaatattt aatagactaa cataattaaa    1080
aaa                                                                  1083
```

<210> SEQ ID NO 267
<211> LENGTH: 1146
<212> TYPE: DNA
<213> ORGANISM: Triticum aestivum
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t

<400> SEQUENCE: 267

-continued

| | |
|---|---|
| aggaattcgg cacgagggaa acattccgtc tcatcctccc cagctcggtt tttgggccat | 60 |
| tctaagccac catgcctgcc tccatcgcct tcggtcggtt cgatgactcc ttcagcttgg | 120 |
| cctctttcaa ggcctacatc gccgagttca tctccaccct catcttcgtc ttcgccggcg | 180 |
| tcggctctgc catcgcctac tccaaggtga gcggcggcgc gccgcttgac ccatccgggc | 240 |
| tgatcgccgt ggcgatctgc cacgggttcg ggctgttcgt cgcggtcgcc gtcggcgcca | 300 |
| acatctccgg cggccatgtg aaccctgccg tcaccttcgg cctcgccctc ggcggccaga | 360 |
| tcaccatcct caccggcatc ttctactggg ttgcccagct cctcggcgcc atcgtcggcg | 420 |
| ccttcctcgt ccagttctgc accggcgtgg cgacccctac acacgggctt tccggcgtgg | 480 |
| gcgccttcga gggcgtcgtg atggagatca tcgtcacctt cgggctcgtc tacaccgtgt | 540 |
| acgccaccgc cgccgacccc aagaagggt ccctcggcac catcgctcca atcgccatcg | 600 |
| gcttcatcgt cggcgccaac atcctcgtcg ccggcccctt ctccggcggg tccatgaacc | 660 |
| ctgcacgctc cttcggcccc gccgttgcca gcggcgactt caccaacatc tggatctact | 720 |
| gggccggccc gctcatcggc ggtggcctcg ccggcgtcgt ctaccggtac ctgtacatgt | 780 |
| gcgacgacca caccgccgtc gccggcaacg actactaagc cagccatggg aagatcattc | 840 |
| ggtctttggt ttccataatg tcttcggcaa cataagaagt gcgtacgtgg tggtcactct | 900 |
| caggattgtc tggatgatgt gaggaacgtc atgttgtttg gttccgatcg aaagcccgcg | 960 |
| aggctgtggc acttggatga tgcatgtttc tgtatctgta ctgtgatgga tgttgtgaag | 1020 |
| ttgttggggt ttcaagattc ttcagttgag tttccttatg cgattcaata agagcatcat | 1080 |
| tgtttagtgc attcccatgc ccacggccaa acttctgggg tacatngtcg ttnacaacct | 1140 |
| ccactt | 1146 |

<210> SEQ ID NO 268
<211> LENGTH: 1076
<212> TYPE: DNA
<213> ORGANISM: Triticum aestivum
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t

<400> SEQUENCE: 268

| | |
|---|---|
| attcctagga ttacgncgac ccacgcgtcc gtctacctct catcctccca gttctgttcc | 60 |
| tcggccattc tagccaccat gccgggctcc atcgccttcg gtcgcttcga tgactccttc | 120 |
| agcttggcct ctttcaaggc ctacatcgct gagttcatct ccaccctcat cttcgtcttc | 180 |
| gccggcgtcg gctctgccat cgcctacact aaggtgagcg gcggcgcgcc ccttgaccca | 240 |
| tccgggctga ttgccgtggc gatatgccac gggttcgggc tgttcgtcgc ggtcgccatc | 300 |
| ggcgccaaca tctccggcgg ccacgtgaac cctgccgtca ccttcggcct cgccctcggc | 360 |
| ggccagatca ccatcctcac cggcatcttc tattggttg cccagctcct cggtgccatc | 420 |
| gtcggcgcct tcctcgtcca gttctgcacc ggcgtggcga cccctacaca cgggctttcc | 480 |
| ggcgtgggcg cctttgaggg cgtcgtgatg gagatcatcg tcaccttcgg gctcgtctac | 540 |
| accgtgtacg ccaccgccgc cgaccccaag aagggttccc tcggcaccat cgcccccatc | 600 |
| gccatcggct tcatcgtcgg cgccaacatc ctcgttgccg ccccttctc cggcgggtcc | 660 |
| atgaaccctg cacgctcctt cggccccgcc gttgccagcg gcgacttcac caacatctgg | 720 |

```
atctactggg ccggcccgct catcggcggt ggcctcgccg gcgtcgtcta ccggtacgtg      780
tacatgtgcg acgaccacag ctccgtcgcc ggcaacgact actaagccag ccatgggaag      840
agtcgtcggg tccataatgc ctttcggcaa cataaaagtg cgtacgtggt gggcagtctc      900
acgaatggtc tcgatgatgt gaagaaccat cctgttgttt gggtcagatc gaanctgtta      960
cacctgggat atgcatgttc ttttatctgt aaatgtgatg tggtgaagtt gttggggttg     1020
agattcttca gtggagtttc cttatcgatt caatagaaca tattggttag gcatcc         1076

<210> SEQ ID NO 269
<211> LENGTH: 749
<212> TYPE: DNA
<213> ORGANISM: Solanum tuberosum

<400> SEQUENCE: 269
gatcacattg gcaagtgact taaaattgta ctttctttga tttaagcaca ttcttttgtg       60
agagccaaaa aaaatggtg aagattgcct ttggtagcat tggtgactct ttaagtgttg      120
gatcattgaa ggcttactta gctgagttta ttgccactct actctttgta tttgctggtg      180
ttggatctgc tatagcttat aataagttga cttcagatgc agctcttgac ccagctggtc      240
tagtagcaat agctgtggct catgcatttg cattgtttgt tggggtttcc atggcagcca      300
atatctcggg tggacattta atccagctg tcactttggg attggctgtt ggtggtaaca      360
tcaccatctt gactggctta ttctactggg ttgcccaatt acttggctcc acagttgctt      420
gcctcctcct taaatatgtc actaatggtt tggctgttcc aactcacgga gttgctgccg      480
ggatgaatgg agctgaggga gtagttatgg aaatagtcat tacctttgca cttgtctaca      540
ctgtttatgc cacagcagct gtcgttgctg gagacttttc tcagaactgg atttactggg      600
tcggaccact cattggtgga ggattggctg ggtttattta tggagatgtt ttcattggat      660
cccacacccc acttccaacc tcagaagact atgcttagaa caaagaagaa agaagaagtc      720
ttcaacaatg ttttcttttg tgtgttttc                                        749

<210> SEQ ID NO 270
<211> LENGTH: 729
<212> TYPE: DNA
<213> ORGANISM: Saccharum officinarum
<220> FEATURE:
<221> NAME/KEY: misc_feature
<222> LOCATION: (550)..(551)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t

<400> SEQUENCE: 270
cagctagcaa tttctcaagc tcagagcgct aagtcttcca gccgcgaaga gctaagaggg       60
aaagcaagat ggtgaagctc gcgttcggaa gcgtcggcga ctccttcagc gccacctcca      120
tcaaggccta cgtctctgag ttcatcgcca ccctcctctt cgtcttcgcc ggcgtcggtt      180
ccgccatcgc ctacggacaa ctgaccaacg atggcgcgct cgaccctgcc ggtctggtgg      240
cgatcgcgat cgcgcacgcg ctggccctct tcgtgggcgt ctccatcgcc gcgaacatct      300
ccggcggcca cctgaacccg gccgtgacgt tcggcctggc cgtgggcggc cacatcacca      360
tcctcacggg cctcttctac tgggtggccc agctgctggg cgcgtccgtg gcgtgcctgc      420
tcctcaagtt cgtgacccac ggcaaggcga tcccgaccca cggcgtgtcc gggatcagcg      480
agctggaagg cgtggtgttc gagatcgtca tcaccttcgc gctcgtgtac accgtgtacg      540
```

```
ccaccgccgn ncgaccccaa gaagggctcc ctcggcacca tcgcgcccat cgccatcggc    600
ttcatcgtcg gcgccaacat cctcgccgcg gggcccttca gccgcggctc catgaacccg    660
gcccgtcctt cgggcccgnc gtcgcccgcg gcaacttcgc cggcaactgg gtctactggg    720
tccgcccat                                                            729

<210> SEQ ID NO 271
<211> LENGTH: 1269
<212> TYPE: DNA
<213> ORGANISM: Populus tremula x Populus tremuloides
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t

<400> SEQUENCE: 271
gaaatatcat gncgaactac acatngccct gatnacatac nttggnttct atctcatnnt     60
cagtcgcttc tcccatttttc cagagctccc ctttagnnct gttctttcaa agatggctgg   120
aattgccttt ggtcgctttg atgattcttt cagtttaggg tcttttaagg gcctatcttg    180
nctgaattca tctcaacttt gctctttgtt tttgctggtg ttggttcagc catggcttac    240
aataagctga caggtgatgc agctcttgat cctgctgggc tagtagccat tgcggtttgc    300
catggatttg ctctcttcgt tgcagtttct gtaggtgcca acatctccgg tggccatgtt    360
aaccctgctg tcacttttgg cttggctctt ggtggccaaa tcaccatcct cactggcatc    420
ttctactgga ttgcccagct cctgggctcc attgtcgcat gctaccttct caaagttgcc    480
actggaggct tggtaattaa gatcgatata tattttgcct cttattatat attgaatcac    540
tctactggga cgacctccta atacatatat gaaaatctcc atgcattttt ttcttctga    600 actcttcttc ttttatggta agaagtatgt tttcatgaga aatgtgattt atttattaat    660
tttcccttaa gcttgactct ctatatgatt acctggtttc aacaggcagt ccccatccac    720
agtgttgcag ctggagtagg agccattgaa ggagtcgtca tggagatcat catcacatt    780 gccttggttt acactgtcta tgcaactgct gctgacccca agaagggatc cctcggcacc    840
atagctccca tagccatcgg tttcattgtg ggtgccaaca tcttggctgc aggcccattc    900
tctggtggat ccatgaaccc agcccgatca tttggcccag ctgtggctag tggtgatttc    960
```

```
catgacaact ggatctactg ggctgggcct cttgttggtg gtgggattgc tggacttatc    1020 tatgaaacg tgttcatcac tgatcatact cctttgtccg gagacttcta ataacttcac    1080
ttggccacat ttgtctttgt aataaagaaa ggggtagcag attatgctct tctttctttt    1140
ctttgctctc tctctctctt taaacaattt catcaagtct atcttgttgt aaagctttgt    1200
tgtcaaaaac catttgcttt tatgaaaatg aatggagtgt gcagcctcag ccaagtctct    1260
tttggaggc                                                           1269
```

<210> SEQ ID NO 272
<211> LENGTH: 1132
<212> TYPE: DNA
<213> ORGANISM: Solanum tuberosum

<400> SEQUENCE: 272

```
agtgacttaa aattgtactt tctttgattt aagcacattc ttttgtgata gccaaaaaaa    60
aatatggtga agattgcctt tggtagcatt ggtgactctt taagtgttgg atcattgaag    120
gcttacttag ctgagtttat tgccactcta ctctttgtat ttgctggtgt tggatctgct    180
atagcttata ataagttgac ttcagatgca gctcttgacc cagctggtct agtagcaata    240
gctgtggctc atgcatttgc attgtttgtt ggggtttcca tggcagccaa tatctcgggt    300
ggacatttaa atccagctgt cactttggga ttggctgttg gtagaaacat caccatcttg    360
actggcttat tctactgggt tgcccaatta cttggctcca cagttgcttg cctcctcctt    420
aaatatgtca ctaatggttt ggtatattgt ttcactatta acatactatt aagttaatta    480
aatcctatta ttagtctaat tagaggttgg gcgaccatgt tgtactaaag cttataagct    540
gatcaaatta tgatcaattt ttcagctact tttaatcggc taaccaaacg ggctcgttat    600 tggattttg caggctgttc caactcatgg agttgctgct gggatgagtg gagctgaggg    660
agtagttatg gaaatagtca tcacctttgc acttgtttac actgtttatg ccacagcagc    720
agatcccaaa aagggctcac ttggaaccat tgcacccatg gcaattgggt tcattgtggg    780
agccaacatt ttggcagctg gcccattcag tggtgggtca atgaacccag cacgatcatt    840
tgggccagct gttgttgcag agacttttt tcagaactgg atttactggg ttggaccact    900
cattggtgga ggattggctg ggtttatta tggagatgtt ttcattggat ccccccccc    960 ccttccaacc tcagaagatt atgcttagaa caaagaagaa agaagaagtt tttaacaatg    1020
ttttcttttt gtgtgttttc aaaaatgcaa tgttgatttt aatttaagtt ttgtttattg    1080
tgttatgcaa gaagtttgtt tccaatgaaa tatcctgttt ggttcatttt gt           1132
```

<210> SEQ ID NO 273
<211> LENGTH: 713
<212> TYPE: DNA
<213> ORGANISM: Glycine max
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t

<400> SEQUENCE: 273

```
atgtcacagg aggctttcca actccaatcc acagtgtnnc nnntgggtt ggagctgttg    60 aaggagttgt gaccgagatc atcatcacat ttggttggt gtacacagtg tatgccacag    120
cagcagaccc taagaaggga tcattgggaa ccattgcacc aattgccatt ggtttcattg    180
```

```
ttggtgccaa catcttggca gcagggccat ctctggcgg ctcgatgaac ccagcacgct    240
ccttcgggcc tgcagttgtt agtggtgact tccatgacaa ctggatctac tgggttggac    300
ctctcattgg tggtggtttg gctggcctta tctatggcaa tgtcttcatt cgctctgacc    360
atgcacctct ttccagtgaa ttttgatttg gttcaagtca tggcatgtgt aattcatgtt    420
tcttgatgat aaaggagga aaaagcagtt cttgctttc tttctttttc tatctctctt    480
ttttctctct ctccattcta tgcttttttt ttcttctctt aatttatttg taaagtgtgc    540
tactactgtt taatttggtg agaattcaag aggttggtgg tgtgcagaag tgctttatat    600
ataattatct ggggtttact tttttggctt tccttttaat tttggatccc gtgcatgagg    660
actattgtac cactggcatt tatcattatg agaagttca cacttcctaa cct    713

<210> SEQ ID NO 274
<211> LENGTH: 1100
<212> TYPE: DNA
<213> ORGANISM: Solanum tuberosum

<400> SEQUENCE: 274
tttctctcta agtctattat tagtagttaa ttaaattatt ttttatagtg aaaatggctg     60
gcggcgtagc tattggaagt tttagtgatt cattcagcgt tgtgtctctt aaggcctatc    120
ttgctgaatt catctccaca ctcatctttg tcttcgccgg agttggttcc gccattgctt    180
acagcaagtt gacagcaaat gctgcacttg atccggctgg gctcgtagct attgcagttt    240
gccatggatt tgctctattt gtggccgttt cagtttcagc taacatctct ggtggccatg    300
ttaaccctgc tgtcacctgc ggattaacct tcggcggcca tattacctt attactggct    360 ccttctacat gtttgctcaa cttaccggcg ccgctgtagc ttgcttcctc ctcaaattcg    420
tcaccggagg atgtgtaagc ccttcaattt ttacctattt atcgcgtaaa catgaccgat    480
tttatttttt ttagattact aatttcactt tttacgacga tctcaggcta ttccaaccca    540
tggagtggga gctggtgtgg ggataattga aggacttgtg atggaaataa ttatcacatt    600
tggtttagtg tacactgtat tcgcaacagc cgctgacccg aagaagggtt cattgggcac    660
aattgcaccg attgctattg gtttcattgt tggagctaat attttggctg ctggtccatt    720
ttccggcgga tcaatgaacc cagctcgttc atttggacct gcaatggcta ctggtaactt    780
tgagggtttc tggatctact ggattggtcc attagttggt ggtagtttgg ctggtcttat    840
ttacaccaat gtgttcatgc aacaagaaca tgctcctcta tccaatgagt tctaaattga    900
atttgtttga gtttgatttg tgggtctaaa aaaagcccat ttgaatttcg ttttttttt    960 taaaaaaagg gaaggaaaag caatattttt tgttgtttct ttctttgttt tttccggaat   1020
tgttgttttg tttttctagt tattggtttg cagctgtata tgcattatct tttggtgaga   1080
tgttcttgtc atgatgctct                                               1100

<210> SEQ ID NO 275
<211> LENGTH: 1110
<212> TYPE: DNA
<213> ORGANISM: Zea mays
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (982)..(983)
```

```
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t

<400> SEQUENCE: 275
caccagatct tcttctctga attccagtcc aagggccgga ataccgtcag agggagtggg      60 agagggggg  aaaaaagatg gtgaagctcg catttggaag ctttcgcgac tctttgagcg     120
ccgcgtcgct caaggcctat gtggccgagt tcattgccac gctgctcttc gtgttcgccg     180
gcgtcgggtc cgccattgcc tactcgcaat tgacgaaggg cggcgctctg gaccccgccg     240
gcctggtggc catcgccatc gcccatgcgt tcgcgctctt cgtcggcgtc tccatggccg     300
ccaacatctc cggcggccac ctgaaccccg ccgtcacctt cggccccttc gacgcgcgt      360 ccatgaaccc ggcccgctcc ttcggccccg ccgtggcggc cggtaacttc gccggcaact     420
gggtgtactg ggtcggcccc ctcgtcggcg gtggcctggc ggggctcgtc tacgcgacg      480 tgttcatcgc ctcctaccag ccggtcggcc agcaggagta cccatgaaag tccggatgag     540
ctagcccgat cgatccgtct gtgttgattt caccatcgtc gtcgtcgtgt catctggcgc     600
ttcgtgctgt gatcatgttt tgtcctgttt gcatttccca acgtctggtt ttcatttcca     660 ttccaacg gtgccaagat gccgtaagca agcgagagaa gtgttcggtc tgtatctgta       720
taaatgcaat gcacagttcg gcgtttccaa aaaaaaaaa aaaaacctcg ggggggccc       780 cggaccccaa tcccccctat aggagtgaaa ataaaaaacn ccgntgttag cgaccgtctg     840
catgtattac aatatgcgtc tatttatctt cccgcagtat ttaaataacc ctcgcgagca     900
cggggaagga gcaaagagag atcagtaaga gggaggcaag tgcgcgacag aaaagaagaa     960
aggaagatcc cacgcgaaat cnntgaataa aacaactgtn taatttatac atgaattcta    1020
ataggacaaa gcccgcaccc gccgaccata tacattacct cagatgaaaa gggaggcaaa    1080
gagatcagga cagacaagca acaatattaa                                     1110

<210> SEQ ID NO 276
<211> LENGTH: 1110
<212> TYPE: DNA
<213> ORGANISM: Zea mays
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (982)..(983)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t

<400> SEQUENCE: 276
caccagatct tcttctctga attccagtcc aagggccgga ataccgtcag agggagtggg      60 agagggggg  aaaaaagatg gtgaagctcg catttggaag ctttcgcgac tctttgagcg     120
ccgcgtcgct caaggcctat gtggccgagt tcattgccac gctgctcttc gtgttcgccg     180
gcgtcgggtc cgccattgcc tactcgcaat tgacgaaggg cggcgctctg gaccccgccg     240
gcctggtggc catcgccatc gcccatgcgt tcgcgctctt cgtcggcgtc tccatggccg     300
```

| | |
|---|---|
| ccaacatctc cggcggccac ctgaaccccg ccgtcacctt cggcccctc gacggcgcgt | 360 |
| ccatgaaccc ggcccgctcc ttcggccccg ccgtggcggc cggtaacttc gccggcaact | 420 |
| gggtgtactg ggtcggcccc ctcgtcggcg gtggcctggc ggggctcgtc tacggcgacg | 480 |
| tgttcatcgc ctcctaccag ccggtcggcc agcaggagta cccatgaaag tccggatgag | 540 |
| ctagcccgat cgatccgtct gtgttgattt caccatcgtc gtcgtcgtgt catctggcgc | 600 |
| ttcgtgctgt gatcatgttt tgtcctgttt gcatttccca acgtctggtt ttcatttcca | 660 |
| ttcaccaacg gtgccaagat gccgtaagca agcgagagaa gtgttcggtc tgtatctgta | 720 |
| taaatgcaat gcacagttcg gcgtttccaa aaaaaaaaa aaaaacctcg gggggggccc | 780 |
| cggaccccaa tcccccctat aggagtgaaa ataaaaaacn ccgntgttag cgaccgtctg | 840 |
| catgtattac aatatgcgtc tatttatctt cccgcagtat ttaaataacc ctcgcgagca | 900 |
| cggggaagga gcaaagagag atcagtaaga gggaggcaag tgcgcgacag aaaagaagaa | 960 |
| aggaagatcc cacgcgaaat cnntgaataa aacaactgtn taatttatac atgaattcta | 1020 |
| ataggacaaa gcccgcaccc gccgaccata tacattacct cagatgaaaa gggaggcaaa | 1080 |
| gagatcagga cagacaagca acaatattaa | 1110 |

<210> SEQ ID NO 277
<211> LENGTH: 1223
<212> TYPE: DNA
<213> ORGANISM: Oryza sativa

<400> SEQUENCE: 277

| | |
|---|---|
| atcacatcct ctcctcctta tacctctgct cactcagctc tccccgcgc gcgtcaccgt | 60 |
| cgtcgccatg tcgggcaaca tcgccttcgg ccgcttcgat gactccttca gcgcggcctc | 120 |
| cctcaaggcc tacgtcgccg agttcatctc caccctcgtc ttcgtcttcg ccggcgtcgg | 180 |
| ctccgccatc gcctacagtg agtaaatcga tggcaccatg gcgcatgcaa acgtacgatg | 240 |
| aacggtgcga ttaattgtga tttacgatcg aattgcagcc aagttgaccg gcggcgcgcc | 300 |
| gcttgacccg gccgggctgg tcgccgtggc ggtgtgccac gggttcgggc tgttcgtggc | 360 |
| ggtggccatc ggcgccaaca tctccggcgg ccacgtcaac ccggccgtca ccttcggcct | 420 |
| cgccctcggc ggccagatca ccatcctcac cggcgtcttc tactggatcg cccagctcct | 480 |
| cggcgccatc gtcggcgccg tcctcgtcca gttctgcacc ggcgtggtaa gccttctttc | 540 |
| ttgcatgcac ctcaccgcca gagctgagct ctcagcctga tccgtcactc actcactgac | 600 |
| gccgccgtgg gtgccgttg gtttgcaggc gacaccgacg cacgggctgt ccggcgtggg | 660 |
| cgcgttcgag ggcgtggtga tggagatcat cgtcaccttc gggctggtgt acaccgtgta | 720 |
| cgccaccgcc gccgacccca agaagggggtc gctcggcacc atcgcgccca tcgccatcgg | 780 |
| cttcatcgtc ggcgccaaca tcctcgtcgc cggccccttc tccggcggct ccatgaaccc | 840 |
| ggcgcgctcc ttcggccccg ccgtcgcag cggcgactac accaacatct ggatctactg | 900 |
| ggtcggcccc ctcgtcggcg gcggcctcgc cggcctcgtc taccggtacg tctacatgtg | 960 |
| cggcgaccac gccccgttg ccagcagcga gttctaatta cccatttcgc catcggcaac | 1020 |
| acgcataaaa atggtggtca ctccatcgtc agaatcttgt gaggatgtgt tgtgaaggac | 1080 |
| tgatttggtt cagatgggga agaaggcttt tgttgcgagg atgtgacact tgggtgatga | 1140 |
| tcgatccatg tttagtttct tcttgattaa tttgtaatgt gatcagtgtg gagcaagttg | 1200 |
| gatgagatgc atgtttaaga tcg | 1223 |

<210> SEQ ID NO 278

```
<211> LENGTH: 606
<212> TYPE: DNA
<213> ORGANISM: Lycopersicon esculentum

<400> SEQUENCE: 278
ctaacatctc cggtggtcat gttaaccctg cggtcacctg tggattaacc ttcggcggac      60
atattacctt tatcactggc tccttctaca tgcttgctca acttaccggc gccgctgtag     120
cttgcttcct cctcaaattc gtcaccggag gatgtgtaag tccttcaatt tttacgaccg    180 attttatt t gttttagat tactaatttc actttttacg acgatctcag gctattccaa     240
cccatggagt gggagctggt gtgagcatac tagaaggact cgtgatggaa ataataatca    300
catttggttt agtttatact gtgttcgcaa ccgccgctga cccgaagaag ggttcattgg    360
gcacaattgc accgattgca attggtctca ttgttggagc taatattttg gctgccggac    420
cattctccgg tggatcaatg aacccagctc gttcatttgg acctgcaatg gttagtggta    480
actttgaggg tttctggatc tactggattg gtccattagt tggtggtagt ttggctggtc    540
ttatttacac aaatgtgttc atgacacaag aacatgctcc tttatccaat gagttctaaa    600
ttgaat                                                              606

<210> SEQ ID NO 279
<211> LENGTH: 540
<212> TYPE: DNA
<213> ORGANISM: Capsicum annuum

<400> SEQUENCE: 279
attttctctc taattaagtc tattcttctt cctttagctt ctattaaatt tattattctt     60
cttttatagt gatcaaaaaa atggctggca ttgcttttgg acgtgttgat gattcattca    120
gtgctgggtc tcttaaggcc tatcttgctg aattcatctc cactttgctc tttgtcttcg    180
ctggtgttgg ctccgccatt gcttacaaca agttgacagt aaatgctgca cttgacccgg    240
ctgggctcgt agctattgca gtttgccatg gattcggtct cttcgtggct gtttcaattg    300
ctgctaacat ctctggtggt catgttaacc ctgctgtcac cttcggattg gcccttggtg    360
gtcaaattac ccttcttact ggcctttttt tacaccattg ctcaacttt t gggctccatt    420 gtagcttgca tcctcctcaa attcgtcacc ggaggattgg ctattccaac tcatggagtg    480
gcagctggtg tgggtgccat tgaaggagtt gtgatggaaa taattgtcac ctttgctttg    540

<210> SEQ ID NO 280
<211> LENGTH: 1019
<212> TYPE: DNA
<213> ORGANISM: Hordeum vulgare
<220> FEATURE:
<221> NAME/KEY: misc_feature
<222> LOCATION: (994)..(994)
<223> OTHER INFORMATION: n is a, c, g, or t

<400> SEQUENCE: 280
ggccgggtcg gccggtccgc ctcacggcga gcaccgacct actcgaccct tcggccggca     60
tcgcgctcct agccttaatt ggccgggtcg tgttttcggc atcgttactt tgaagaaatt    120
agagtgctca aagcaagcca tcgctctgga tacattagca tgggataaca tcataggatt    180
ccggtcctat tgtgttggcc ttcgggatcg gagtaatgat taatagggac agtcgggggc    240
attcgtattt catagtcaga ggtgaaattc ttggatttat gaaagacgaa caactgcgaa    300
agcatttgcc aaggatgttt tcattaatca agaacgaaag ttgggggctc gaagacgatc    360
agataccgtc ctagtctcaa ccataaacga tgccgaccag ggatcggcgg atgttgctta    420
```

| | |
|---|---|
| taggactcca ccggcacctt cgggctcacc ggcatcggcg cgtgggaggc ggtggtcctg | 480 |
| gagatcgtca tgaccttcgg gctggtgtac acggtgtacg ccaccgccgt cgaccccaag | 540 |
| aagggcagcc tgggcaccat cgcgcccatc gccatcggct tcatcgtcgg cgccaacatc | 600 |
| ctcgtcggcg gcgccttctc cggcgcgtcc atgaacccg ccgtctcctt cggccccgcc | 660 |
| ctcgtcagct gggagtgggg gtaccagtgg gtgtactggg tcggcccct catcggcggc | 720 |
| ggcctcgccg gcgtcatcta cgagctgctc ttcatctccc gcacccacga gcagctcccc | 780 |
| accaccgact actaagctca ccgccgcctg ccccccgccc gccgtccgt ccgtgtggtc | 840 |
| gatcgcgtct ccccttgctt cccagacatg agtcgtttaa gtttgctttg aatgaatgaa | 900 |
| tccatcccat tcccagggtc gatcggtcca tcagtttgtg gtgctgtgaa acctgtgacg | 960 |
| atcgaccctg tcaatttgct tgtgtaaaac ctgnaattcg tccgcccgag aatttcaag | 1019 |

<210> SEQ ID NO 281
<211> LENGTH: 779
<212> TYPE: DNA
<213> ORGANISM: Gossypium hirsutum

<400> SEQUENCE: 281

| | |
|---|---|
| acccgctttt gggttgtcat caggtggggg ggtgtttaac gcattggttt tcgaaatggt | 60 |
| gatgcccttc ggattggtgt acccagtgta cgccccagcc gttgatccca aaagggaag | 120 |
| cttgggaaca atcgccccat tggcaattgg tttcatcgtg ggggccaaca ttttggcagg | 180 |
| aggtgccttc gatggagcct caatgaaccc agctgtttca tttggaccac ccttggttag | 240 |
| ctggacatgg gacaacccct ggatttattg ggtgggaccc cttatcggtg gtgggctcgc | 300 |
| tggtttcatt taggagttca ttttcatcag caacacccag gagcagttcc caaccccga | 360 |
| ttattaagcc taatcagggt ttaattgatt tgtttgtccc tttgaaaccg gattttttcc | 420 |
| gatttcattt gagtttccta tttctttcct tgttttttgt gtttaatttg gggcccgtcg | 480 |
| atttgtttta cttttttttc attccccatc ctttttcatg atcatcatgc atggcagatg | 540 |
| ttgtttacaa ttgcatgccc tgaaaaaatg gtatatgagt gactccctgt aagtttttt | 600 |
| ttttatatta tcaaaacca gcatcagggc tgtaaatgtg actttttcc ttccttttc | 660 |
| cttgttttta tcatgggcat ttcctattca cttttccctt ttcttaagta agattgtaca | 720 |
| ggtggcatgt ttcatttaga cagaatattt aagataatga aaaaaagga gtttttttt | 779 |

<210> SEQ ID NO 282
<211> LENGTH: 1118
<212> TYPE: DNA
<213> ORGANISM: Oryza sativa

<400> SEQUENCE: 282

| | |
|---|---|
| accgccccga atccgccccc aaatctcctc gcgacctcga aaccctagcc tcctccggcc | 60 |
| accgtcgccg gccacggtga gcggccccac ccccccgcag ccatggcctc cccggagggc | 120 |
| tccacgtggg tcttcgactg ccctctgatg gacgacctcg ccgccgccgc cggcttcgac | 180 |
| gccgcccccg ccggaggctt ctactggacg acgcccgctc ctccgcaggc ggcgctacag | 240 |
| ccgccgccgc cgcagcagca gccgtcgccc cctgccaccg cggctccgaa cgcctgtgct | 300 |
| gaaatcaatg gctctgtgga ctgtgaacat ggcaaagaac agccaacaaa taaacgtccg | 360 |
| agatcagaaa gtggcactcg accaagctcc aaagcatgca gggaaaaagt aagaagggac | 420 |

```
aagttgaacg agaggttctt ggaactgggt gctgtcctgg aaccagggaa gacacccaaa      480
atggacaaat cgtctatatt gaacgatgct attcgtgtaa tggctgagct gcgtagtgag      540
gcacagaagt tgaaggaatc aaatgagagt ctccaagaga aaatcaaaga gttgaaggct      600
gagaaaaacg agctgcgtga tgagaagcaa aagctgaagg cagagaaaga gagcctggag      660
cagcagataa agttcctgaa tgctcgacca agcttcgtac cacaccctcc ggttatccca      720
gccagtgcat tcactgctcc tcaagggcaa gctgccgggc agaagctgat gatgcctgtg      780
attggctacc caggatttcc gatgtggcag ttcatgccgc cttctgatgt tgataccaca      840
gatgacacca agtcatgccc tcctgttgca taagtcaaag caaagatcaa tttgcctcgc      900
cttgtaggaa agaggtgaaa ctgccttcca ttcaagccca gtttggtcgt cagtgtttaa      960
actacctagc taatcccagg attaaaccga agcttcgctg tatcgaagta tcaaccggtg     1020
acatgtgaac tgacgaaaga tgacaccgtt gtatattaca tattagtaaa taaattccat     1080
ctgtccaatt aaatgagaat tagaggccaa aaaattat                             1118

<210> SEQ ID NO 283
<211> LENGTH: 1203
<212> TYPE: DNA
<213> ORGANISM: Triticum aestivum

<400> SEQUENCE: 283
cgttccggac tctctcagtt gtccgtactc gttaacctcg tgctccccccc tctgcttgat      60 ccttatctcg gcgccggagc ccacgaccgc ttccccccctt tccctcccct ccccctcacc     120
accccaaccc cgaaatatcc cccaattccg acgcgaccgc gaaaccctag ccccccggca     180
atcttcgctg gacccggaga gccgctccgg cgccatggca tccccggaag gatcaaactg     240
ggtattcgac tgccccctca tggacgacct tgctgccgcc gacttcgccg cggcatccgc     300
aggaggcttc tactggaccc cgccgatgca gccgcagatg cacactcttg cgcaggccgt     360
ctccgccacc ccggctccca atccctgtgc tgaaatcaat agctctgttt cggtggactg     420
ggaccatgcc aaaggacaac cgaaaaataa acgtcctagg tcagaaactg gtgctcaacc     480
tagctccaaa gcatgcaggg agaaagtgag aagggacaag ctaaacgaga ggttcttgga     540
attgggtgct gtcttggatc cggggaaaac acctaaaatc gacaaatgtg ctatattaaa     600
tgatgctatc cgtgcagtaa ctgaattgcg tagtgaagca gagaagttga aggattccaa     660
tgagtctctc caagaagaa ttagagagct aaaggctgag aagaatgagc tacgagatga     720
gaagcaaaag ttgaaggcgg agaaagagag cctggagcag cagattaagt tcatgaatgc     780
ccgtcagagc ctcgtaccac acccttctgt catcccagct gctgcattcg ctgccgccca     840
aggccaagcg gcagggcaca agctgatgat gcctgtaatg agctacccag gatttcccat     900
gtggcagttc atgccgcctt cagatgttga tacctccgat gacccaagt catgccctcc     960 ggttgcataa gccagcaaaa atcatttgcc tcatctatct catggggaag gatggctaaa    1020
aagccgtccg ttaaagtata tcttactagt cgtcagtgtt actatgcaga agccgtttag    1080
tgttactata tgtagttaaa ccaagaaccg aactgaagcg tcgtcgttgt atcacccggg    1140
gacatttgat tatcttgtga caccgttgta tattgttagt aaataaatac catccgttga    1200
agc                                                                  1203

<210> SEQ ID NO 284
<211> LENGTH: 1077
<212> TYPE: DNA
<213> ORGANISM: Hordeum vulgare
```

<400> SEQUENCE: 284

```
gccccaaccc cgaaatatcc cccaactccg acgcgaccgc gaaaccctag tccccggca       60
accttcgctg gacccgggga gccgctccgg cgccatggca tccccggaag gatcaaactg      120
ggtcttcgac tgccccctca tggacgacct tgctgccgcc gacttcgccg cggtacccgc      180
aggaggcttc tactggaacc cgccgatgcc gccgcagatg cacactctgg cgcaggccgt      240
ctccgccacc ccggctccca tccctgtgc tgaaatcaat agctctgttt cggtggactg       300
ggaccatgcc aaaggacaac cgaaaaataa acgtcctaga tcagaaactg gtgctcaacc      360
tagctccaaa gcatgcaggg agaaagttag aagggacaag ctaaatgaga ggttcttgga      420
attgggtgct gtcttggacc cggggaaaac acctaaaatc gacaaatgtg ctatattaaa      480
tgatgctatc cgtgcggtaa ctgaattgcg tagtgaagca gagaagttga aggattcaaa      540
tgagtctctc caagaagaa ttagagagct gaaggctgag aagaatgagc tgcgagatga       600
gaagcaaaag ctgaaggcgg aaaaagagag cctggagcag cagattaagt tcatgaatgc      660
ccgtcagaga ctcgtaccac acccttctgt catcccagct actgcattcg ctgccgccca      720
aggccaagcg gcagggcata agcttatgat gcctgtaatg agctacccag gatttcccat      780
gtggcagttc atgccgcctt cagatgttga tacctcggat gaccctaagt catgccctcc      840
tgttgcataa gccagcgaaa atcatttgcc tcatctatct catggggaag gatggctaaa      900
cagccttccg ttaaagtata ttttagttgt cagtgttact atgtagttaa actaagaacc      960
gaactgaagc atcgtcgttg tatcacctgg ggacatttga ttatcttgtg gcactgctgt     1020
atattgttag taaataaatg ccgtctgtcg aaggaaatgc tgattggacg ccatagc        1077
```

<210> SEQ ID NO 285
<211> LENGTH: 2595
<212> TYPE: DNA
<213> ORGANISM: Oryza sativa

<400> SEQUENCE: 285

```
gaccgccccg aatccgcccc caaatctcct cgcgacctcg aaaccctagc ctcctccggc       60
caccgtcgcc ggccacggtg agcggccca ccccccgca gccatggcct ccccggaggg        120
ctccacgtgg gtcttcgact gccctctgat ggacgacctc gccgccgccg ccggcttcga      180
cgccgccccc gccggaggct tctactggac gacgcccgct cctccgcagg cggcgctaca      240
gccgccgccg ccgcagcagc agcccgtcgc ccctgccacc gcggctccga acgcctggta      300
attgcgggt ttacggcctc cgatcgcgct ccagccagcc ctggctgggc ccggtgccgt       360
ggtctgggt gctacatttt tttttcgtcc tgatttgtcg cggcagcgtg ttagtgcgta       420
agttgagact gggtatatcg tgatcgttgc tattgattgt tcgattggag gtcgatagaa      480
gcgtatcata tcagactatc agtgggattc ggatcagggg attagtcgtg tgtctgaaca     540
tttagaacta gttacatact ccctccgttt tctaaaatat gatgctgttg acttttttaaa    600
atacatctga tcatcttatt caaaaaaatt atataatttt tatttatttt attgtgactt      660
gattcatcat tcatcgtcaa atattcttta ggcatgactt aaaaattttt tatatttgca     720
caaaaatttt gaagatgacg aatagtcaaa cgtttatcag aaagtcaacg acgtcataca      780
ttaaaaaaca gaagtagtat aacctagtag gagccgtcag cctgttttac tgaacagagg      840
gctcaattcc tggttatatt gaattgtcag cttcattttc aaatctatttt atttgtgtgc     900
atacgtaatg tatttaaacc taatttaggg cctcttcatg atttataatt ctcatttaaa     960
ttgtgatgca aatgctgcat agcatagcat atatagtttg ctaagcatgc attgtgtcat    1020
```

```
gtttatctgg tgtcatgtca tgggatagtt gaactgaaga aaacatacac cataattgat    1080
gatgtttatg atgccactat tgtacaagat tcagtttgcc gtgtaatatt acaatataag    1140
aactgataac aagtaaacca aatggtgtca aattggcgtg gtggtgggag ggtggatggt    1200
tgtgatttgc tgtaggtcca actgtctgag ataccagatt ttaaaatttt ttgtatctat    1260
atgcaagtaa attgcattga catgatattt tgagccaggt attgagattt gtcctgagct    1320
ttccagtgga tttttcaatg aatgatctat gaaggatcag aaacggggtg agagaagtgg    1380
ttaatctgta tcacttgggt tccagcacga agcttactgt ggaatggaaa tttattgaag    1440
aacgtgttca tgttaggata ttgtttactg caactctttg atttaagagt attcttttat    1500
ttatgatacc ttgtagtctt gtggtgctag tacattttct ttatgcacca ggaagtcatc    1560
tcatgtgttt ttaaatctgt cctggttttt gacttgtgct tccaccttct ggtgccatag    1620
gttgtggtgt tatgaaccac acagtgcatc ttaactgatg tattgttctg ttgtgttaaa    1680
tttgcttgat tcttttgttg tcattgtata gttttttatg tacttattgc tgtatattat    1740
cgtgacatat ggcatactga agtacaagtt tattttttc actagtgctg aaatcaatgg     1800
ctctgtggac tgtgaacatg gcaaagaaca gccaacaaat aaacgtccga gatcagaaag    1860
tggcactcga ccaagctcca aagcatgcag ggaaaaagta agaagggaca agttgaacga    1920
gaggttcttg gaactgggtg ctgtcctgga accaggaag acacccaaaa tggacaaatc     1980
gtctatattg aacgatgcta ttcgtgtaat ggctgagctg cgtagtgagg cacagaagtt    2040
gaaggaatca aatgagagtc tccaagagaa aatcaaagag ttgaaggctg agaaaaacga    2100
gctgcgtgat gagaagcaaa agctgaaggc agagaaagag agcctggagc agcagataaa    2160
gttcctgaat gctcgaccaa gcttcgtacc acaccctccg gttatcccag ccagtgcatt    2220
cactgctcct caaggtcaag ctgccgggca gaagctgatg atgcctgtga ttggctaccc    2280
aggatttccg atgtggcagt tcatgccgcc ttctgatgtt gataccacag atgacaccaa    2340
gtcatgccct cctgttgcat aagtcaaagc aaagatcaat ttgcctcgcc ttgtaggaaa    2400
gaggtgaaac tgccttccat tcaagcccag tttggtcgtc agtgtttact acctagctaa    2460
acccaggatt aaaccgaagc ttcgctgtat cgaagtatca accggtgaca tgtgaactga    2520
cgaaagatga caccgttgta tattacatat tagtaaataa attccatctg tccaattaaa    2580
tgagaattag atgcc                                                    2595
```